United States Patent
Kolesnikov et al.

(10) Patent No.: US 11,376,260 B2
(45) Date of Patent: Jul. 5, 2022

(54) SERINE/THREONINE KINASE INHIBITORS

(71) Applicant: GENENTECH, INC., South San Francisco, CA (US)

(72) Inventors: Aleksandr Kolesnikov, South San Francisco, CA (US); Steven Do, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 121 days.

(21) Appl. No.: 17/075,380

(22) Filed: Oct. 20, 2020

(65) Prior Publication Data

US 2021/0106593 A1   Apr. 15, 2021

Related U.S. Application Data

(60) Division of application No. 16/680,221, filed on Nov. 11, 2019, now Pat. No. 10,842,799, which is a division of application No. 16/286,955, filed on Feb. 27, 2019, now Pat. No. 10,517,878, which is a division of application No. 15/705,104, filed on Sep. 14, 2017, now Pat. No. 10,278,975, which is a continuation of application No. 14/559,786, filed on Dec. 3, 2014, now Pat. No. 9,867,833.

(60) Provisional application No. 61/912,905, filed on Dec. 6, 2013.

(51) Int. Cl.
| | | |
|---|---|---|
| A61K 31/53 | (2006.01) | |
| A61P 35/00 | (2006.01) | |
| A61P 35/02 | (2006.01) | |
| A61P 43/00 | (2006.01) | |
| C07D 471/16 | (2006.01) | |
| A61K 31/553 | (2006.01) | |
| C07D 498/16 | (2006.01) | |
| A61K 31/519 | (2006.01) | |
| A61K 31/5365 | (2006.01) | |
| A61K 31/542 | (2006.01) | |
| A61K 31/55 | (2006.01) | |
| A61K 45/06 | (2006.01) | |
| C07D 513/16 | (2006.01) | |

(52) U.S. Cl.
CPC .......... *A61K 31/553* (2013.01); *A61K 31/519* (2013.01); *A61K 31/53* (2013.01); *A61K 31/5365* (2013.01); *A61K 31/542* (2013.01); *A61K 31/55* (2013.01); *A61K 45/06* (2013.01); *C07D 471/16* (2013.01); *C07D 498/16* (2013.01); *C07D 513/16* (2013.01)

(58) Field of Classification Search
CPC .......... A61K 31/53; A61P 35/00; A61P 35/02; A61P 43/00; C07D 471/16
See application file for complete search history.

(56) References Cited

U.S. PATENT DOCUMENTS

| | | |
|---|---|---|
| 8,697,715 B2 | 4/2014 | Blake et al. |
| 8,722,657 B2 | 5/2014 | Catron et al. |
| 9,867,833 B2 | 1/2018 | Kolesnikov et al. |
| 10,278,975 B2 | 5/2019 | Kolesnikov et al. |
| 10,517,878 B2 | 12/2019 | Kolesnikov et al. |
| 10,842,799 B2 | 11/2020 | Kolesnikov et al. |
| 2010/0093718 A1 | 4/2010 | Berdini et al. |
| 2013/0338140 A1 | 12/2013 | Blake et al. |
| 2014/0066453 A1 | 3/2014 | Blake et al. |
| 2015/0087664 A1 | 3/2015 | Blake et al. |
| 2015/0111869 A1 | 4/2015 | Belvin et al. |
| 2015/0182537 A1 | 7/2015 | Kolesnikov et al. |
| 2015/0218176 A1 | 8/2015 | Burdick et al. |
| 2018/0000833 A1 | 1/2018 | Kolesnikov et al. |

FOREIGN PATENT DOCUMENTS

| | | |
|---|---|---|
| EP | 2002836 A1 | 12/2008 |
| WO | 2003035039 A1 | 5/2003 |
| WO | 2007030939 A2 | 3/2007 |
| WO | 2012118850 A1 | 9/2012 |
| WO | 2013020062 A1 | 2/2013 |
| WO | 2013130976 A1 | 9/2013 |
| WO | 2014036015 A1 | 3/2014 |
| WO | 2014060395 A1 | 4/2014 |
| WO | 2015032840 A1 | 3/2015 |
| WO | 2015103133 A1 | 7/2015 |
| WO | 2015103137 A1 | 7/2015 |
| WO | 2015154674 A1 | 10/2015 |

OTHER PUBLICATIONS

Kohno, et al., "Pharmacological inhibitors of the ERK signaling pathway: application as anticancer drugs", Prog in Cell Cycle Res 5, 219 (2003).
Patent Cooperation Treaty, International Searching Authority, Search Report and Written Opinion for PCT/US2014/068452, 11 pages, dated Feb. 25, 2015.

*Primary Examiner* — Brenda L Coleman
(74) *Attorney, Agent, or Firm* — Viksnins Harris Padys Malen LLP

(57) ABSTRACT

Compounds having the formula I wherein $R^1$, $X^1$, $X^2$, $X^3$ and $X^4$ as defined herein are inhibitors of ERK kinase. Also disclosed are compositions and methods for treating hyperproliferative disorders.

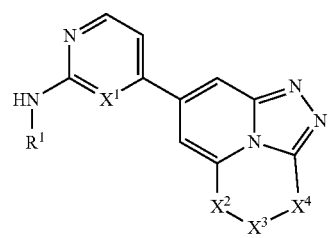

(I)

11 Claims, No Drawings

SERINE/THREONINE KINASE INHIBITORS

RELATED APPLICATIONS

This divisional application claims the benefit of priority of U.S. application Ser. No. 16/680,221, filed 11 Nov. 2019, which claims the benefit of priority of U.S. application Ser. No. 16/286,955 filed 27 Feb. 2019, now U.S. Pat. No. 10,517,878 issued 31 Dec. 2019, which claims the benefit of priority of U.S. application Ser. No. 15/705,104 filed 14 Sep. 2017, now U.S. Pat. No. 10,278,975 issued 7 May 2019, which claims the benefit of priority of U.S. application Ser. No. 14/559,786 filed 3 Dec. 2014, now U.S. Pat. No. 9,867,833 issued 16 Jan. 2018, which claims the benefit of priority of provisional U.S. Application No. 61/912,905 filed 6 Dec. 2013, each of which are hereby incorporated by reference in their entirety.

FIELD ON THE INVENTION

The present invention relates to compounds which inhibit serine/threonine kinases and which are useful for treating hyperproliferative and neoplastic diseases by inhibiting signal transduction pathways which commonly are overactive or overexpressed in cancerous tissue. The present compounds are selective inhibitors of ERK (extracellular-signal regulated kinase). The present invention further relates to methods for treating cancer or hyperproliferative diseases with compounds within the scope of the present invention

BACKGROUND OF THE INVENTION

The processes involved in tumor growth, progression, and metastasis are mediated by signaling pathways that are activated in cancer cells. The ERK pathway plays a central role in regulating mammalian cell growth by relaying extracellular signals from ligand-bound cell surface receptor tyrosine kinase (RTK's) such as erbB family, PDGF, FGF, and VEGF receptor tyrosine kinase. Activation of an RTK induces a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates ERK1/2. When activated, ERK1/2 phosphorylates several downstream targets involved in a multitude of cellular events including cytoskeletal changes and transcriptional activation. The ERK/MAPK pathway is one of the most important for cell proliferation, and it is believed that the ERK/MAPK pathway is frequently activated in many tumors. Ras genes, which are upstream of ERK1/2, are mutated in several cancers including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK1/2 signaling pathway is an attractive pathway for anticancer therapies in a broad spectrum of human tumors. (M. Hohno and J. Pouyssegur, *Prog. in Cell Cycle Res.* 2003 5:219)

Therefore, small-molecular inhibitors of ERK activity (i.e., ERK1 and/or ERK2 activity) would be useful for treating a broad spectrum of cancers, such as, for example, melanoma, pancreatic cancer, thyroid cancer, colorectal cancer, lung cancer, breast cancer, and ovarian cancer. Such a contribution is provided by this invention.

SUMMARY OF THE INVENTION

In one aspect of the present invention there is provided a compound according to formula I, wherein:

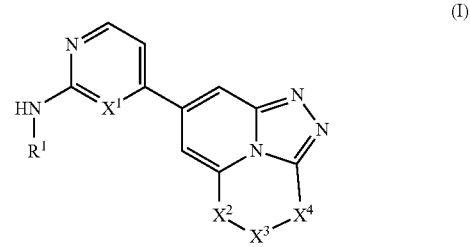

(I)

$X^1$ is N or CH;
$X^2$ is $NR^a$, O or S;
$X^3$ is $(CR^4{}_2)_{1-3}$, $CH_2NR^b$, $C(=O)$, $C(=O)NR^b$ or $C(=O)O$ with the proviso that:
  when $X^3$ is $CH_2NR^b$, the tricyclic moiety of (I) is a 6,7,8,9-tetrahydro-1,2,2a¹,6,8-pentaazabenzo[cd]azulene,
  when $X^3$ is $C(=O)NR^b$, the tricyclic moiety of (I) is a 8,9-dihydro-1,2,2a¹,6,8-pentaazabenzo[cd]azulen-7(6H)-one,
  when $X^3$ is $CH_2C(=O)$, the tricyclic moiety of (I) is a 8,9-dihydro-1,2,2a¹,6-tetraazabenzo[cd]azulen-7(6H)-one, and,
  when $X^3$ is $C(=O)O$, the tricyclic moiety of (I) is a 6H-8-oxa-1,2,2a¹,6-tetraazabenzo[cd]azulen-7(9H)-one;
$X^4$ is $CR^2R^3$ or $NR^3$ with the proviso that when $X^4$ is $NR^3$, $X^2$ is $NR^a$ and $X^3$ is $C(=O)$);
$R^1$ is (i) a 4 to 7 membered saturated or partially unsaturated heterocyclyl moiety or, (ii) a optionally substituted 5- or 6-membered heteroaryl moiety;
$R^2$ is selected from the group consisting of:
  (a) $C_{1-10}$ alkyl,
  (b) $C_{1-10}$ alkenyl,
  (c) $C_{1-10}$ haloalkyl,
  (d) $C_{3-7}$ cycloalkyl or $C_{3-7}$ cycloalkyl-$C_{1-6}$ alkyl,
  (e) $C_{3-7}$ halocycloalkyl or $C_{3-7}$ halocycloalkyl-$C_{1-6}$ alkyl,
  (f) $C_{1-10}$ hydroxyalkyl or $C_{1-10}$ dihydroxyalkyl,
  (g) $C_{1-3}$ alkoxy-$C_{1-6}$ alkyl,
  (h) $C_{1-3}$ alkylthio-$C_{1-6}$ alkyl,
  (i) $C_{1-110}$ cyanoalkyl,
  (j) phenyl, phenyl-$C_{1-3}$ alkyl, phenoxy or benzyloxy-$C_{1-3}$ alkyl,
  (k) heteroaryl, heteroaryl-$C_{1-3}$ alkyl or heteroaryloxy wherein said heteroaryl moiety is selected from the group consisting of pyrazolyl, imidiazolyl, oxazolyl, isoazolyl, thiazolyl, isothiazolyl, pyridinyl, pyrid-2(1H)-one and 1-alkylpyrid-2(1H)-one and each said heteroaryl is independently optionally substituted with one or more groups selected from the group consisting of halogen, hydroxyl, oxide, $C_{1-6}$ alkoxy, $C_{1-6}$ haloalkoxy, cyano, $C_{3-6}$ cycloalkyl and $C_{1-6}$ alkyl wherein said $C_{1-6}$ alkyl is optionally independently substituted with one or more groups independently selected from halogen, oxo, hydroxyl or $C_{1-6}$ alkoxy; and,
  (l) phenylthio or phenylthio-$C_{1-6}$ alkyl;
$R^3$ and $R^4$ is independently in each occurrence hydrogen or $C_{1-3}$ alkyl;
$R^a$ and $R^b$ are independently hydrogen or $C_{1-3}$ alkyl; or, a pharmaceutically salt thereof;

wherein any phenyl moiety is optionally substituted one or more halogen, cyano, hydroxyl, $C_{1-6}$ alkoxy, $C_{1-6}$ haloalkoxy or $C_{1-6}$ alkyl wherein said $C_{1-6}$ alkyl is optionally independently substituted with one or more groups independently selected from halogen, oxo, hydroxyl or $C_{1-6}$ alkoxy; and, wherein each cycloalkyl is independently optionally substituted with one to three groups halogen, $C_{1-6}$ haloalkyl, $C_{1-6}$alkoxy or $C_{1-6}$ haloalkoxy.

The present invention also relates to a method for treating a hyperproliferative disorder by administering a therapeutically effective quantity of a compound according to formula I to a patient in need thereof. The compound of formula I can be administered alone or co-administered with at least one other anti-hyperproliferative or chemotherapeutic compound.

The present invention also relates to a method for inhibiting ERK protein kinase activity in a cell comprising treating a cell with a compound according to formula I in an amount effective to attenuate or eliminate ERK kinase activity.

The present invention also relates to a pharmaceutical composition comprising a compound according to formula I and at least one pharmaceutically acceptable carrier, diluent or excipient.

The present invention also relates to the use of a compound of formula I or a pharmaceutically acceptable salt thereof in the manufacture of a medicament for the treatment of cancer or a hyperproliferative disease.

The present invention also relates to compounds according to formula 1 wherein the compound is selected from:
4-(9-(4-chlorobenzyl)-8,9-dihydro-7H-6-oxa-1,2,2a$^1$-triazabenzo[cd]azulen-4-yl)-N-(1-methyl-1H-pyrazol-5-yl)pyrimidin-2-amine;
(R)-4-(9-(4-chlorobenzyl)-8,9-dihydro-7H-6-oxa-1,2,2a$^1$-triazabenzo[cd]azulen-4-yl)-N-(1-methyl-1H-pyrazol-5-yl)pyrimidin-2-amine;
(S)-4-(9-(4-chlorobenzyl)-8,9-dihydro-7H-6-oxa-1,2,2a$^1$-triazabenzo[cd]azulen-4-yl)-N-(1-methyl-1H-pyrazol-5-yl)pyrimidin-2-amine;
3-benzyl-5-methyl-7-(2-((1-methyl-1H-pyrazol-5-yl)amino)pyrimidin-4-yl)-3H-1,1,2a$^1$,3,5-pentaazaacenaphthylen-4(5H)-one;
9-(4-chlorobenzyl)-6-methyl-4-(2-((1-methyl-1H-pyrazol-5-yl)amino)pyrimidin-4-yl)-8,9-dihydro-1,2,2a$^1$,6-tetraazabenzo[cd]azulen-7(6H)-one;
(S)-9-(4-chlorobenzyl)-6-methyl-4-(2-((1-methyl-1H-pyrazol-5-yl)amino)pyrimidin-4-yl)-8,9-dihydro-1,2,2a$^1$,6-tetraazabenzo[cd]azulen-7(6H)-one;
(R)-9-(4-chlorobenzyl)-6-methyl-4-(24(1-methyl-1H-pyrazol-5-yl)amino)pyrimidin-4-yl)-8,9-dihydro-1,2,2a$^1$,6-tetraazabenzo[cd]azulen-7(6H)-one;
4-(9-((4-chloro-1H-pyrazol-1-yl)methyl)-8,9-dihydro-7H-6-oxa-1,2,2a'-triazabenzo[cd]azulen-4-yl)-N-(1-methyl-1H-pyrazol-5-yl)pyrimidin-2-amine;
(R)-4-(9-((4-chloro-1H-pyrazol-1-yl)methyl)-8,9-dihydro-7H-6-oxa-1,2,2a$^1$-triazabenzo[cd]azulen-4-yl)-N-(1-methyl-1H-pyrazol-5-yl)pyrimidin-2-amine; or
(S)-4-(9-((4-Chloro-1H-pyrazol-1-yl)methyl)-8,9-dihydro-7H-6-oxa-1,2,2a$^1$-triazabenzo[cd]azulen-4-yl)-N-(1-methyl-1H-pyrazol-5-yl)pyrimidin-2-amine;
or a pharmaceutically acceptable salt thereof.

The present invention also relates to pharmaceutical compositions comprising a compound according to formula 1 wherein the compound is selected from:

4-(9-(4-chlorobenzyl)-8,9-dihydro-7H-6-oxa-1,2,2a$^1$-triazabenzo[cd]azulen-4-yl)-N-(1-methyl-1H-pyrazol-5-yl)pyrimidin-2-amine;
(R)-4-(9-(4-chlorobenzyl)-8,9-dihydro-7H-6-oxa-1,2,2a$^1$-triazabenzo[cd]azulen-4-yl)-N-(1-methyl-1H-pyrazol-5-yl)pyrimidin-2-amine;
(S)-4-(9-(4-chlorobenzyl)-8,9-dihydro-7H-6-oxa-1,2,2a$^1$-triazabenzo[cd]azulen-4-yl)-N-(1-methyl-1H-pyrazol-5-yl)pyrimidin-2-amine;
3-benzyl-5-methyl-7-(2-((1-methyl-1H-pyrazol-5-yl)amino)pyrimidin-4-yl)-3H-1,1,2a$^1$,3,5-pentaazaacenaphthylen-4(5H)-one;
9-(4-chlorobenzyl)-6-methyl-4-(2-((1-methyl-1H-pyrazol-5-yl)amino)pyrimidin-4-yl)-8,9-dihydro-1,2,2a$^1$,6-tetraazabenzo[cd]azulen-7(6H)-one;
(S)-9-(4-chlorobenzyl)-6-methyl-4-(2-((1-methyl-1H-pyrazol-5-yl)amino)pyrimidin-4-yl)-8,9-dihydro-1,2,2a$^1$,6-tetraazabenzo[cd]azulen-7(6H)-one;
(R)-9-(4-chlorobenzyl)-6-methyl-4-(24(1-methyl-1H-pyrazol-5-yl)amino)pyrimidin-4-yl)-8,9-dihydro-1,2,2a$^1$,6-tetraazabenzo[cd]azulen-7(6H)-one;
4-(9-((4-chloro-1H-pyrazol-1-yl)methyl)-8,9-dihydro-7H-6-oxa-1,2,2a$^1$-triazabenzo[cd]azulen-4-yl)-N-(1-methyl-1H-pyrazol-5-yl)pyrimidin-2-amine;
(R)-4-(9-((4-chloro-1H-pyrazol-1-yl)methyl)-8,9-dihydro-7H-6-oxa-1,2,2a$^1$-triazabenzo[cd]azulen-4-yl)-N-(1-methyl-1H-pyrazol-5-yl)pyrimidin-2-amine; or
(S)-4-(9-((4-Chloro-1H-pyrazol-1-yl)methyl)-8,9-dihydro-7H-6-oxa-1,2,2a$^1$-triazabenzo[cd]azulen-4-yl)-N-(1-methyl-1H-pyrazol-5-yl)pyrimidin-2-amine;
or a pharmaceutically acceptable salt thereof; and at least one pharmaceutically acceptable carrier, excipient or diluent.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "~~~~" drawn through a bond each refer to the point of attachment of a functional group or other chemical moiety to the rest of the molecule of which it is a part. Thus, for example:

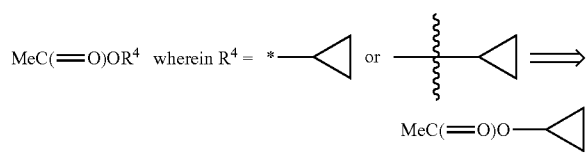

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

Compounds of formula I exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomer usually produces a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ -C(—OH)=CH—), amide/imidic acid (—C(=O)—NH— ⇌ -C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

The compounds of formula I may contain an acidic or basic center and suitable salts are formed from acids or bases may form non-toxic salts which have similar antiviral activity. Examples of salts of inorganic acids include the hydrochloride, hydrobromide, hydroiodide, chloride, bromide, iodide, sulfate, bisulfate, nitrate, phosphate, hydrogen phosphate. Examples of salts of organic acids include acetate, fumarate, pamoate, aspartate, besylate, carbonate, bicarbonate, camsylate, D and L-lactate, D and L-tartrate, esylate, mesylate, malonate, orotate, gluceptate, methylsulfate, stearate, glucuronate, 2-napsylate, tosylate, hibenzate, nicotinate, isethionate, malate, maleate, citrate, gluconate, succinate, saccharate, benzoate, esylate, and pamoate salts. For a review on suitable salts see Berge et al, *J. Pharm. Sci.*, 1977 66:1-19 and G. S. Paulekuhn et al. *J. Med. Chem.* 2007 50:6665.

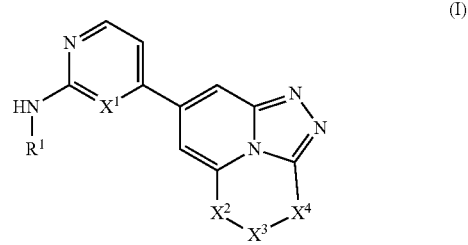

In one embodiment of the present invention there is provided a compound according to formula I wherein $R^1$, $R^2$, $R^3$, $R^4$, $X^1$, $X^2$, $X^3$, $X^4$, $R^a$ and $R^b$ are as defined hereinabove. In all other embodiments provided below, substituents which can be present in each embodiment and which are not explicitly defined retain the broadest definition provided in the Summary of the Invention.

In another embodiment there is provided a compound according to formula I wherein $X^2$ is $NR^a$, $X^3$ is $CH_2$ and $X^4$ is $CR^2R^3$. In one subembodiment there is provided a compound according to formula I wherein $X^1$ is N. In another subembodiment there is provided a compound according to formula I wherein $X^1$ is CH.

In another embodiment there is provided a compound according to formula I wherein $X^2$ is $NR^a$, $X^3$ is C(=O) and $X^4$ is $CR^2R^3$. In one subembodiment there is provided a compound according to formula I wherein $X^1$ is N. In another subembodiment there is provided a compound according to formula I wherein $X^1$ is CH.

In another embodiment there is provided a compound according to formula I wherein $X^2$ is $NR^a$, $X^3$ is $(CH_2)_2$ and $X^4$ is $CR^2R^3$. In one subembodiment there is provided a compound according to formula I wherein $X^1$ is N. In another subembodiment there is provided a compound according to formula I wherein $X^1$ is CH.

In another embodiment there is provided a compound according to formula I wherein $X^2$ is $NR^a$, $X^3$ is $CH_2NR^b$ and $X^4$ is $CR^2R^3$. In one subembodiment there is provided a compound according to formula I wherein $X^1$ is N. In another subembodiment there is provided a compound according to formula I wherein $X^1$ is CH.

In another embodiment there is provided a compound according to formula I wherein $X^2$ is $NR^a$, $X^3$ is $C(=O)CH_2$ and $X^4$ is $CR^2R^3$. In one subembodiment there is provided a compound according to formula I wherein $X^1$ is N. In another subembodiment there is provided a compound according to formula I wherein $X^1$ is CH.

In another embodiment there is provided a compound according to formula I wherein $X^2$ is $NR^a$, $X^3$ is $C(=O)NR^b$ and $X^4$ is $CR^2R^3$. In one subembodiment there is provided a compound according to formula I wherein $X^1$ is N. In another subembodiment there is provided a compound according to formula I wherein $X^1$ is CH.

In another embodiment there is provided a compound according to formula I wherein $X^2$ is O, $X^3$ is $CH_2$ and $X^4$ is $CR^2R^3$. In one subembodiment there is provided a compound according to formula I wherein $X^1$ is N. In another subembodiment there is provided a compound according to formula I wherein $X^1$ is CH.

In another embodiment there is provided a compound according to formula I wherein $X^2$ is O, $X^3$ is $(CH_2)_2$ and $X^4$ is $CR^2R^3$. In one subembodiment there is provided a compound according to formula I wherein $X^1$ is N. In another subembodiment there is provided a compound according to formula I wherein $X^1$ is CH.

In another embodiment there is provided a compound according to formula I wherein $X^2$ is $NR^a$, $X^3$ is $C(=O)$ and $X^4$ is $NR^3$. In one subembodiment there is provided a compound according to formula I wherein $X^1$ is N. In another subembodiment there is provided a compound according to formula I wherein $X^1$ is CH.

In another embodiment there is provided a compound according to formula I wherein $R^2$ is optionally substituted phenyl-$C_{1-3}$ alkyl and $R^3$ is hydrogen. In one subembodiment $X^2$ is $NR^a$, $X^3$ is $CH_2$ and $X^4$ is $CR^2R^3$. In another subembodiment $X^2$ is $NR^a$, $X^3$ is $C(=O)$ and $X^4$ is $CR^2R^3$. In another subembodiment $X^2$ is $NR^a$, $X^3$ is $(CH_2)_2$ and $X^4$ is $CR^2R^3$. In another subembodiment wherein $X^2$ is $NR^a$, $X^3$ is $CH_2NR^b$ and $X^4$ is $CR^2R^3$. In another subembodiment $X^2$ is $NR^a$, $X^3$ is $C(=O)CH_2$ and $X^4$ is $CR^2R^3$. In another subembodiment $X^2$ is $NR^a$, $X^3$ is $C(=O)NR^b$ and $X^4$ is $CR^2R^3$. In another subembodiment $X^2$ is O, $X^3$ is $CH_2$ and $X^4$ is $CR^2R^3$. In another subembodiment $X^2$ is O, $X^3$ is $(CH_2)_2$ and $X^4$ is $CR^2R^3$. In any of the above subembodiments $X^1$ can either N or CH.

In another embodiment there is provided a compound according to formula I wherein $R^2$ is optionally substituted heteroaryl-$C_{1-3}$ alkyl and $R^3$ is hydrogen. In one subembodiment $X^2$ is $NR^a$, $X^3$ is $CH_2$ and $X^4$ is $CR^2R^3$. In another subembodiment $X^2$ is $NR^a$, $X^3$ is $C(=O)$ and $X^4$ is $CR^2R^3$. In another subembodiment $X^2$ is $NR^a$, $X^3$ is $(CH_2)_2$ and $X^4$ is $CR^2R^3$. In another subembodiment wherein $X^2$ is $NR^a$, $X^3$ is $CH_2NR^b$ and $X^4$ is $CR^2R^3$. In another subembodiment $X^2$ is $NR^a$, $X^3$ is $C(=O)CH_2$ and $X^4$ is $CR^2R^3$. In another subembodiment $X^2$ is $NR^a$, $X^3$ is $C(=O)NR^b$ and $X^4$ is $CR^2R^3$. In another subembodiment $X^2$ is O, $X^3$ is $CH_2$ and $X^4$ is $CR^2R^3$. In another subembodiment $X^2$ is O, $X^3$ is $(CH_2)_2$ and $X^4$ is $CR^2R^3$. In any of the above subembodiments $X^1$ can either N or CH.

In another embodiment there is provided a compound according to formula I wherein $R^2$ is optionally substituted phenoxy or heteroaryloxy and $R^3$ is hydrogen. In one subembodiment $X^2$ is $NR^a$, $X^3$ is $CH_2$ and $X^4$ is $CR^2R^3$. In another subembodiment $X^2$ is $NR^a$, $X^3$ is $C(=O)$ and $X^4$ is $CR^2R^3$. In another subembodiment $X^2$ is $NR^a$, $X^3$ is $(CH_2)_2$ and $X^4$ is $CR^2R^3$. In another subembodiment wherein $X^2$ is $NR^a$, $X^3$ is $CH_2NR^b$ and $X^4$ is $CR^2R^3$. In another subembodiment $X^2$ is $NR^a$, $X^3$ is $C(=O)CH_2$ and $X^4$ is $CR^2R^3$. In another subembodiment $X^2$ is $NR^a$, $X^3$ is $C(=O)NR^b$ and $X^4$ is $CR^2R^3$. In another subembodiment $X^2$ is O, $X^3$ is $CH_2$ and $X^4$ is $CR^2R^3$. In another subembodiment $X^2$ is O, $X^3$ is $(CH_2)_2$ and $X^4$ is $CR^2R^3$. In any of the above subembodiments $X^1$ can either N or CH.

In another embodiment of the present invention there is provided a compound according to formula I wherein $CR^2R^3$ is in the (S) configuration. In another embodiment of the present invention there is provided a compound according to formula I wherein $CR^2R^3$ is in the (R) configuration. In yet another embodiment of the present invention there is provided a compound according to formula I wherein there are equal portions of (R) and (S) isomers (i.e., a racemic mixture). In yet another embodiment of the present invention there is provided a compound according to formula I wherein there are enriched in either the (R) or (S) isomer. In yet another embodiment of the present invention the $R^2$ substituent is in the β-configuration. In yet another embodiment of the present invention the $R^2$ substituent is in the α-configuration.

In another embodiment of the present invention there is provided a compound according to formula I wherein $X^2$ is O, $X^3$ is $CH_2$ or $(CH_2)_2$ and $R^1$ is tetrahydropyranyl, tetrahydrofuranyl, oxetanyl or optionally substituted pyrazolyl. In one subembodiment. $R^2$ is optionally substituted phenyl-$C_{1-3}$ alkyl and $R^3$ is hydrogen. In another subembodiment $R^2$ is optionally substituted benzyl and $R^3$ is hydrogen. In another subembodiment $R^2$ is substituted heteroaryl-methyl and $R^3$ is hydrogen. In another subembodiment $R^2$ is optionally substituted phenoxy or heteraryloxy and $R^3$ is hydrogen. In another subembodiment $R^2$ is optionally substituted phenoxy and $R^3$ is hydrogen.

In another embodiment of the present invention there is provided a compound according to formula I wherein $X^2$ is O, $X^3$ is $(CH_2)_2$ and $R^1$ is optionally substituted pyrazolyl. In one subembodiment. $R^2$ is optionally substituted phenyl-$C_{1-3}$ alkyl and $R^3$ is hydrogen. In another subembodiment $R^2$ is optionally substituted benzyl and $R^3$ is hydrogen. In another subembodiment $R^2$ is substituted heteroaryl-methyl and $R^3$ is hydrogen. In another subembodiment $R^2$ is optionally substituted phenoxy or heteraryloxy and $R^3$ is hydrogen. In another subembodiment $R^2$ is optionally substituted phenoxy and $R^3$ is hydrogen In another embodiment of the present invention there is provided a compound according to formula I wherein $X^2$ is O, $X^3$ is $CH_2$ and $R^1$ is optionally substituted pyrazolyl. In one subembodiment. $R^2$ is optionally substituted phenyl-$C_{1-3}$ alkyl and $R^3$ is hydrogen. In another subembodiment $R^2$ is optionally substituted benzyl and $R^3$ is hydrogen. In another subembodiment $R^2$ is substituted heteroaryl-methyl and $R^3$ is hydrogen. In another subembodiment $R^2$ is optionally substituted phenoxy or heteraryloxy and $R^3$ is hydrogen. In another subembodiment $R^2$ is optionally substituted phenoxy and $R^3$ is hydrogen.

In another embodiment of the present invention there is provided a compound according to formula I wherein $X^2$ is O, $X^3$ is $CH_2$ and $R^1$ is 1-methyl-1H-pyrazol-5-yl). In one subembodiment. $R^2$ is optionally substituted phenyl-$C_{1-3}$ alkyl and $R^3$ is hydrogen. In another subembodiment $R^2$ is optionally substituted benzyl and $R^3$ is hydrogen. In another subembodiment $R^2$ is benzyl and $R^3$ is hydrogen. In another subembodiment $R^2$ is substituted heteroaryl-methyl and $R^3$ is hydrogen. In another subembodiment $R^2$ is optionally substituted phenoxy or heteraryloxy and $R^3$ is hydrogen. In another subembodiment $R^2$ is optionally substituted phenoxy and $R^3$ is hydrogen.

In another embodiment of the present invention there is provided a compound according to formula I wherein $X^2$ is O, $X^3$ is $(CH_2)_2$ and $R^1$ is 1-methyl-1H-pyrazol-5-yl). In one subembodiment. $R^2$ is optionally substituted phenyl-$C_{1-3}$ alkyl and $R^3$ is hydrogen. In another subembodiment $R^2$ is optionally substituted benzyl and $R^3$ is hydrogen. In another subembodiment $R^2$ is benzyl and $R^3$ is hydrogen. In another subembodiment $R^2$ is substituted heteroaryl-methyl and $R^3$ is hydrogen. In another subembodiment $R^2$ is optionally substituted (1H-pyrazol-1-yl)methyl and $R^3$ is hydrogen. In another subembodiment $R^2$ is (4-chloro-1H-pyrazol-1-yl)methyl and $R^3$ is hydrogen. In another subembodiment $R^2$(4-trifluoromethyl-1H-pyrazol-1-yl)methyl and $R^3$ is hydrogen. In another subembodiment $R^2$ is (4-cyclopropyl-1H-pyrazol-1-yl)methyl and $R^3$ is hydrogen. In another subembodiment $R^2$ is optionally substituted phenoxy or heteraryloxy and $R^3$ is hydrogen. In another subembodiment $R^2$ is optionally substituted phenoxy and $R^3$ is hydrogen.

In another embodiment of the present invention there is provided a compound selected from compounds I-1 to I-109 in TABLE 1.

In another embodiment of the present invention there is provided a method of treating or ameliorating the severity of a hyperproliferative disorder in a patient in need thereof comprising administering to the patient a compound according to formula I wherein $R^1$, $R^2$, $R^3$, $R^4$, $X^1$, $X^2$, $X^3$, $X^4$, $R^a$ and $R^b$ are as defined hereinabove.

In another embodiment of the present invention there is provided a compound wherein $R^1$, $R^2$, $R^3$, $R^4$, $X^1$, $X^2$, $X^3$, $X^4$, $R^a$ and $R^b$ are as defined hereinabove for use as a medicament.

In another embodiment of the present invention there is provided a a compound wherein $R^1$, $R^2$, $R^3$, $R^4$, $X^1$, $X^2$, $X^3$, $X^4$, $R^a$ and $R^b$ are as defined hereinabove for use in therapy.

In another embodiment of the present invention there is provided a pharmaceutical composition for use in the treatment of a hyperproliferative disease containing a compound according to formula I wherein $R^1$, $R^2$, $R^3$, $R^4$, $X^1$, $X^2$, $X^3$, $X^4$, $R^a$ and $R^b$ are as defined hereinabove are as defined hereinabove and at least one pharmaceutically acceptable carrier, excipient or diluent.

In another embodiment of the present invention there is provided a method of inhibiting ERK protein kinase activity in a cell comprising treating the cell with a compound according to formula wherein $R^1$, $R^2$, $R^3$, $R^4$, $X^1$, $X^2$, $X^3$, $X^4$, $R^a$ and $R^b$ are as defined hereinabove are as defined hereinabove and at least one pharmaceutically acceptable carrier, excipient or diluent In another embodiment of the present invention there is provided a method of inhibiting ERK protein kinase activity in a patient in need thereof comprising administering to the patient a compound according to formula I wherein $R^1$, $R^2$, $R^3$, $R^4$, $X^1$, $X^2$, $X^3$, $X^4$, $R^a$ and $R^b$ are as defined hereinabove and at least one pharmaceutically acceptable carrier, excipient or diluent.

In another embodiment of the present invention there is provided a method of treating or ameliorating the severity of a hyperproliferative disorder in a patient in need thereof comprising administering to the patient a compound according to formula I wherein $R^1$, $R^2$, $R^3$, $R^4$, $X^1$, $X^2$, $X^3$, $X^4$, $R^a$ and $R^b$ are as defined hereinabove and at least one pharmaceutically acceptable carrier, excipient or diluent.

In another embodiment of the present invention there is provided a method of treating or ameliorating the severity of a hyperproliferative disorder selected from the group consisting of adenoma, bladder cancer, brain cancer, breast cancer, colon cancer, epidermal carcinoma, follicular carcinoma, cancer of the genitourinary tract, glioblastoma, Hodgkin's disease, head and neck cancers, hepatoma, keratoacanthoma, kidney cancer, large cell carcinoma, leukemias, lung adenocarcinoma, lung cancer, lymphoid disorders, melanoma and non-melanoma skin cancer, myelodysplastic syndrome, neuroblastoma, non-Hodgkins lymphoma, ovarian cancer, papillary carcinoma, pancreatic cancer, prostate cancer, rectal cancer, sarcoma, small cell carcinoma, testicular cancer, tetracarcinomas, thyroid cancer, and undifferentiated carcinoma in a patient in need thereof comprising administering to the patient a compound according to formula I wherein $R^1$, $R^2$, $R^3$, $R^4$, $X^1$, $X^2$, $X^3$, $X^4$, $R^a$ and $R^b$ are as defined hereinabove and at least one pharmaceutically acceptable carrier, excipient or diluent.

In another embodiment of the present invention there is provided a method of treating or ameliorating the severity of a hyperproliferative disorder selected from the group consisting of melanoma, pancreatic cancer, thyroid cancer colorectal cancer, lung cancer, breast cancer and ovarian cancer in a patient in need thereof comprising administering to the patient a compound according to formula I wherein $R^1$, $R^2$, $R^3$, $R^4$, $X^1$, $X^2$, $X^3$, $X^4$, $R^a$ and $R^b$ are as defined hereinabove and at least one pharmaceutically acceptable carrier, excipient or diluent.

In another embodiment of the present invention there is provided a method of treating or ameliorating the severity of a hyperproliferative disorder selected from the group consisting of acute myelogenous leukemia, chronic myelomonocytic leukemia, chronic myelogenous leukemia, multiple myeloma and myeloid leukemia in a patient in need thereof comprising administering to the patient a compound according to formula I wherein $R^1$, $R^2$, $R^3$, $R^4$, $X^1$, $X^2$, $X^3$, $X^4$, $R^a$ and $R^b$ are as defined hereinabove and at least one pharmaceutically acceptable carrier, excipient or diluent.

In another embodiment of the present invention there is provided a method of treating or ameliorating the severity of a hyperproliferative disorder in a patient in need thereof comprising co-administering to the patient a compound according to formula I wherein $R^1$, $R^2$, $R^3$, $R^4$, $X^1$, $X^2$, $X^3$, $X^4$, $R^a$ and $R^b$ are as defined hereinabove and at least one other chemotherapeutic agent used.

Another embodiment of the present invention provides the use a compound of formula I wherein $R^1$, $R^2$, $R^3$, $R^4$, $X^1$, $X^2$, $X^3$, $X^4$, $R^a$ and $R^b$ are as defined hereinabove in the manufacture of a medicament for the treatment of a hyperproliferative disease.

Another embodiment of the present invention provides a pharmaceutical composition comprising a compound of formula I wherein $R^1$, $R^2$, $R^3$, $R^4$, $X^1$, $X^2$, $X^3$, $X^4$, $R^a$ and $R^b$ are as defined hereinabove for use in the treatment of a hyperproliferative disease.

In another embodiment $R^1$ is selected from optionally substituted heteroaryl or heteroaryl-$C_{1-6}$ alkyl, wherein said heteroaryl is selected from the group consisting of isoxazole, pyridinyl, pyridone, pyrimidinyl, pyrazinyl, pyrazole, thiazolyl, triazolyl, N—$C_{1-6}$ alkyl-pyrazolyl and N—$C_{1-6}$ alkyl triazolyl or heterocyclyl wherein said heterocyclyl is selected from the group consisting of tetrahydropyranyl, tetrahydrofuranyl, oxetanyl, piperidinyl, pyrrolidinyl, morpholinyl and N—$C_{1-6}$ alkyl-piperidinyl. In one subembodiment, $R^1$ is selected from 1-methyl-1H-pyrazol-4-yl, 1-methyl-1H-pyrazol-3-yl, 2-ethyl-2H-pyrazol-3-yl, 2-methyl-2H-pyrazol-3-yl, 2-isopropyl-2H-pyrazol-3-yl, 1-methyl-1H-pyrazol-5-yl, 1-ethyl-1H-pyrazol-5-yl, 4-methylthiazol-2-yl, 1-methyl-1H-[1,2,4]triazol-3-yl, 2-methyl-2H-[1,2,3]-triazol-4-yl, 1-methyl-1H-[1,2,4]-triazol-5-yl, 1,3-dimethyl-1H-pyrazol-4-yl, 1,3,5-trimethyl-1H-pyrazol-4-yl, 1-methyl-1H-tetrazol-5-yl, 2-methyl-2H-tetrazol-5-yl, 5-methyl-1,3,4-thiadizol-2-yl, oxetan-3-yl, 3-methyloxetan-3-yl, tetrahydropyran-4-yl, tetrahydro-2H-pyran-4-yl, tetrahydropyran-3-yl, 2-methyl-tetrahydropyran-4-yl, 2,2-dimethyl-tetrahydropyran-4-yl, 2-hydroxymethyltetrahydropyran-4-yl, 3-fluorotetrahydropyran-4-yl and tetrahydrofuran-3-yl. In another subembodiment, $R^1$ is selected from oxetan-3-yl, tetrahydropyran-4-yl, 1-methyl-1H-pyrazol-5-yl, 1-methyl-1H-pyrazol-4-yl, 2-methyl-2H-1,2,3-triazol-4-yl and 1-methyl-1H-1,2,4-triazol-5-yl. In yet another subembodiment, $R^1$ is selected from 1-methyl-1H-pyrazol-5-yl and 1-methyl-1H-pyrazol-4-yl.

In another embodiment $R^2$ is (a) $C_{1-10}$ alkyl, e.g., selected from methyl, ethyl, 2-methylbutyl, 2,3-dimethylbutyl, 2,2-dimethylbutyl, 2-ethylbutyl, 3-methylpentyl, 2-methylpentyl, isopentyl, neopentyl, isobutyl, 3,3-dimethylbutyl, butyl, propyl, trifluoromethyl, 4-methylpentyl, 3-methylbutan-2-yl; (b) $C_{1-10}$ alkenyl; (c) $C_{1-10}$ haloalkyl, e.g., 2-fluorobutyl, 4,4,4-trifluoro-2-methylbutyl, 3,3,3-trifluoro-2-methylpropyl, 2,2,2-trifluoroethyl, 3,3,3-trifluoropropyl, 2-fluoro-2-methylpropyl, 3,3,3-trifluoro-2-(trifluoromethyl)propyl, 1,1-difluoropropyl, 3-fluoro-3-methylbutyl, 2,2-difluoropropyl, 2-(trifluoromethyl)butyl, 3-fluoro-2-(fluoromethyl)propyl; (d) $C_{3-7}$ cycloalkyl or $C_{3-7}$ cycloalkyl-$C_{1-6}$ alkyl, e.g., cyclopropyl, cyclohexyl, cyclohexymethyl, (1-(1-(trifluoromethyl)cyclopropyl)methyl, (1-isopropylcyclopropyl)methyl, (1-ethylcyclopropyl)methyl, (cyclopentylmethyl, cyclohexylmethyl, (1-(trifluoromethyl)cyclobutyl)methyl, cyclopropylmethyl, cyclobutylmethyl, and cyclohexylethyl; (e) $C_{3-7}$ halocycloalkyl or $C_{3-7}$ halocycloalkyl-$C_{1-6}$ alkyl, e.g., (2,2-difluorocyclopropyl)methyl, (3,3-difluorocyclobutyl) methyl, (4,4-difluorocyclohexyl)methyl; (f) $C_{1-10}$ hydroxyalkyl or $C_{1-10}$ dihydroxyalkyl, e.g., 1-hydroxy-3-methylbutyl, 1-hydroxy-2-methylpropyl, 2-hydroxy-2-methylpropyl, 2-hydroxyethyl, 1-hydroxy-2-methylbutyl, 2-hydroxy-3-methylbutyl, 2-hydroxybutyl, 3-hydroxy-2-methylpropyl, 1-hydroxy-2-methylpropyl, 1-hydroxy-2-methylpropyl, 2-hydroxy-2-methylpropyl, 2-hydroxyethyl, 1-hydroxy-2-methylbutyl, 2-hydroxy-3-methylbutyl, 2-hydroxybutyl and 1-hydroxybutyl; (g) $C_{1-3}$ alkoxy-$C_{1-6}$ alkyl, e.g., 2-methoxy-3-methylbutyl, 2-ethoxybutyl, 3-methoxy-2-methylpropyl, 3,3,3-trifluoro-2-methoxypropyl, 2-ethoxyethyl, tert-butoxymethyl, isopropoxymethyl, 2-methoxyethyl, isobutoxymethyl, methoxymethyl, 1-methoxy-2-methylpropyl, 2-methoxybutyl, 2-methoxypropyl, 3-hydroxy-2-methylpropyl, 2-methoxy-2-methylpropyl, 2-(2-fluoroethoxy)propyl, 2-(cyclopropylmethoxy)propyl, benzyloxymethyl; (h) $C_{1-3}$ alkylthio-$C_{1-6}$ alkyl, e.g., 1,2-(methylthio)butyl, 2-(methylthio)ethyl, 2-(methylthio)propyl, (isopropylthio)methyl, (tert-butylthio)methyl and (isobutylthio)methyl; (j) $C_{1-10}$ cyanoalkyl, e.g., 2-cyano-2-methylpropyl, and 2-butanenitrile (j) phenyl, phenyl-$C_{1-3}$ alkyl, phenoxy or benzyloxy-$C_{1-3}$ alkyl, e.g., 4-chlorophenyl, 3-chlorophenyl, 2-chlorophenyl, 4-fluroophenyl, 3-fluorophenyl, 2-chlorophenyl, 4-methoxyphenyl, 3-fluoro-4-methoxypheny; 4-chloro-3-fluorophenyl, benzyl, 2-fluorobenzyl, 2-chlorobenzyl, 2-methoxybenzyl, 2-(trifluoromethyl)benzyl, 2-methylbenzyl, 3-bromobenzyl, 3-chlorobenzyl, 3-fluorobenzyl, 3-cyclopropylbenzyl, 3-cyclobutylbenzyl, 3-(trifluoromethyl)benzyl, 3-methoxybenzyl, 3-(difluoromethoxy)benzyl, 3-(trifluoromethoxy)benzyl, 3-cyanobenzyl, 4-chlorobenzyl, 4-fluorobenzyl, 4-(trifluoromethyl)benzyl, 4-methoxybenzyl, 4-(difluoromethoxy)benzyl, 4-(methylthio)benzyl, 4-methylbenzyl, 4-(trifluoromethoxy)benzyl, 4-ethoxybenzyl, 2,3-difluorobenzyl, 2,3-dichlorobenzyl, 2-fluoro-4-methoxybenzyl, 2-chloro-4-fluorobenzyl, 2,4-dichlorobenzyl, 2,4-difluorobenzyl, 2-fluoro-4-(trifluoromethyl)benzyl, 2,5-difluorobenzyl, 2-chloro-6-fluorobenzyl, 2,6-difluorobenzyl, 3-fluoro-4-methoxybenzyl, 3-fluoro-4-(trifluoromethoxy)benzyl, 3,4-difluorobenzyl, 3-chloro-4-fluorobenzyl, 3-chloro-4-methoxybenzyl, 3-chloro-5-fluorobenzyl, 3-fluoro-5-(trifluoromethyl)benzyl, 3,5-difluorobenzyl, 3,5-difluorobenzyl, 4-chloro-2-fluorobenzyl, 4-(difluoromethoxy)-2-fluorobenzyl, 4-chloro-3-fluorobenzyl, 4-fluoro-3-methoxybenzyl, 2,3-difluoro-4-methoxybenzyl, 2,3,4-trifluorobenzyl, 2,4,5-trifluorobenzyl, 3,5-difluoro-4-methoxybenzyl, 4-ethoxy-2,3-difluorobenzyl, phenethyl, 3-chlorophenethyl, 4-chlorophenethyl, 1-(4-chlorophenyl) ethyl, 1-methoxy-2-phenylethyl, 1-(4-chlorophenyl)-2-methylpropyl, 1-phenylethyl, 2-(4-chlorophenyl)propan-2-yl, (4-chlorophenyl)difluoromethyl, 1-methoxy-1-phenylethyl, difluoro(3-fluoro-4-methoxyphenyl)methyl, 3-fluoro-4-methoxyphenethyl, 2-chlorophenethyl, 2-(4-fluorophenyl)-2-methylpropyl, 2-(4-methoxyphenyl)-2-methylpropyl, 2-methoxy-2-(4-methoxyphenyl)ethyl, 3,3,3-trifluoro-2-(4-methoxyphenyl)propyl, 3,3,3-trifluoro-2-(4-fluorophenyl)propyl, 2-(4-chlorophenyl)-2-methoxyethyl, 2-(4-chlorophenyl)-2-hydroxyethyl, 3,3,3-trifluoro-2-(4-methoxyphenyl)propyl, 2-hydroxy-2-(4-methoxyphenyl) ethyl, phenoxy, 2-fluoro-phenoxy, 3-fluorophenoxy, 4-fluorophenoxy, 3,4-difluorophenoxy and 3-methylphenoxy; (k) heteroaryl, heteroaryl-$C_{1-3}$ alkyl or heteroaryloxy, 1H-pyrazol-1-yl 1H-pyrazol-3-yl, 1H-pyrazol-4-yl, 1-($C_{1-3}$ alkyl)-1H-pyrazol-3-yl, e.g., 1-methyl-1H-pyrazol-3-yl, 1-($C_{1-3}$ alkyl)-1H-pyrazol-4-yl, e.g., 1-methyl-1H-pyrazol-4-yl, thiazol-2-yl, thiazol-4-yl, thiazol-5-yl, isothiazol-3-yl, isothiazol-4-yl, isothiazol-5-yl, oxazol-2-yl, oxazol-4-yl, oxazol-5-yl, isoxazol-3-yl, isoxazol-4-yl, isoxazol-5-yl, (thiazol-2-yl)-$C_{1-3}$ alkyl, (thiazol-4-yl)-$C_{1-3}$ alkyl, (thiazol-5-yl)-$C_{1-3}$ alkyl, (isothiazol-3-yl)-$C_{1-3}$ alkyl, (isothiazol-4-yl)-$C_{1-3}$ alkyl, (isothiazol-5-yl)-$C_{1-3}$ alkyl, (oxazol-2-yl)-$C_{1-3}$ alkyl, (oxazol-4-yl)-$C_{1-3}$ alkyl, (oxazol-5-yl)-$C_{1-3}$ alkyl, (isoxazol-3-yl)-$C_{1-3}$ alkyl, (isoxazol-4-yl)-$C_{1-3}$ alkyl, (isoxazol-5-yl)-$C_{1-3}$ alkyl 1H-imidazol-2-yl, (1H-imidazol-2-yl)-$C_{1-3}$ alkyl, (1-($C_{1-3}$ alkyl)-1H-imidazol-2-yl)-$C_{1-3}$ alkyl, 1H-imidazol-5-yl, 1-($C_{1-3}$ alkyl)-1H-imidazol-5-yl, and (1-($C_{1-3}$ alkyl)-1H-imidazol-5-yl)-$C_{1-3}$ alky; thiophen-2-ylmethyl, thiazol-2-ylmethyl, (1-methylpyrazol-3-yl)methyl, (1-methylpyrazol-4-yl)methyl, (1-methylimidazol-2-yl)methyl, (1-cyclopropyl-3,5-dimethylpyrazol-4-yl)methyl, (1,3-dimethylpyrazol-5-yl)methyl, (3-cyclopropylpyrazol-1-yl)methyl, (4-methylthiazol-2-yl)methyl, (5-methylthiazol-2-yl)methyl, (5-chlorothiophen-2-yl)methyl, (5-cyclopropylthiophen-2-yl)methyl, (5-cyanothiophen-2-yl)methyl, 2-(1,2,4-triazol-5-yl)ethyl, 2-(4-(trifluoromethyl)pyrazol-1-yl)ethyl, pyridinyl such as pyridine-2-yl, pyridine-3-yl pyridine-4-yl, 1-(pyridin-2(1H)-one), (1-methyl-2-oxo-1,2-dihydropyridin-4-yl)methyl, pyridin-4-ylmethyl, 5-chloropyridin-2-yl)methyl, (2-methoxypyridin-3-yl) methyl, (6-methoxypyridin-3-yl)methyl, (6-methoxypyridin-2-yl)methyl or 5-(pyridin-2(1H)-one), (5-fluoro-3-pyridyl)oxy, (5-chloro-3-pyridinyl)oxy; and (l) phenylthio or phenylthio-$C_{1-6}$ alkyl.

In one subembodiment $R^2$ is benzyl, 2-fluorobenzyl, 2-chlorobenzyl, 2-methoxybenzyl, 2-(trifluoromethyl)benzyl, 2-methylbenzyl, 3-bromobenzyl, 3-chlorobenzyl, 3-fluorobenzyl, 3-cyclopropylbenzyl, 3-(trifluoromethyl) benzyl, 3-methoxybenzyl, 3-(difluoromethoxy)benzyl, 3-(trifluoromethoxy)benzyl, 3-cyanobenzyl, 4-chlorobenzyl, 4-fluorobenzyl, 4-(trifluoromethyl)benzyl, 4-methoxybenzyl, 4-(difluoromethoxy)benzyl, 4-(methylthio)benzyl, 4-methylbenzyl, 4-(trifluoromethoxy)benzyl, 4-ethoxybenzyl, 2,3-difluorobenzyl, 2,3-dichlorobenzyl, 2-fluoro-4-methoxybenzyl, 2-chloro-4-fluorobenzyl, 2,4-dichlorobenzyl, 2,4-difluorobenzyl, 2-fluoro-4-(trifluoromethyl)benzyl, 2,5-difluorobenzyl, 2-chloro-6-fluorobenzyl, 2,6-difluorobenzyl, 3-fluoro-4-methoxybenzyl, 3-fluoro-4-(trifluoromethoxy)benzyl, 3,4-difluorobenzyl, 3-chloro-4-fluorobenzyl, 3-chloro-4-methoxybenzyl, 3-chloro-5-fluorobenzyl, 3-fluoro-5-(trifluoromethyl)benzyl, 3,5-difluorobenzyl, 3,5-difluorobenzyl, 4-chloro-2-fluorobenzyl, 4-(difluoromethoxy)-2-fluorobenzyl, 4-chloro-3-fluorobenzyl, 4-fluoro-3-methoxybenzyl, 2,3-difluoro-4-methoxybenzyl, 2,3,4-trifluorobenzyl, 2,4,5-trifluorobenzyl, 3,5-difluoro-4-methoxybenzyl, 4-ethoxy-2,3-difluorobenzyl. In another subembodiment one or both hydrogen atoms on the benzylic methylene group are replaced by deuterium.

In another subembodiment $R^2$ is benzyl, 3-fluoro-4-chlorophenyl, 4-fluorobenzyl, 4-methoxybenzyl, 3-fluoro-4-methoxybenzyl, 4-chloro-3-fluorophenyl, 3,4-difluorobenzyl, 2-fluoro-4-methoxybenzyl, 2-chlorobenzyl.

In another subembodiment $R^2$ is 1-($C_{1-3}$ alkyl)-1H-pyrazol-3-yl, e.g., 1-methyl-1H-pyrazol-3-yl, 1-($C_{1-3}$ alkyl)-1H-pyrazol-4-yl, e.g., 1-methyl-H-pyrazol-4-yl, (thiazol-2-yl)-$C_{1-3}$ alkyl, (thiazol-4-yl)-$C_{1-3}$ alkyl, (thiazol-5-yl)-$C_{1-3}$ alkyl, (isothiazol-3-yl)-$C_{1-3}$ alkyl, (isothiazol-4-yl)-$C_{1-3}$ alkyl, (isothiazol-5-yl)-$C_{1-3}$ alkyl, (oxazol-2-yl)-$C_{1-3}$ alkyl, (oxazol-4-yl)-$C_{1-3}$ alkyl, (oxazol-5-yl)-$C_{1-3}$ alkyl, (isoxazol-3-yl)-$C_{1-3}$ alkyl, (isoxazol-4-yl)-$C_{1-3}$ alkyl, (isoxazol-5-yl)-$C_{1-3}$ alkyl (1H-imidazol-2-yl)-$C_{1-3}$ alkyl, (1-($C_{1-3}$ alkyl)-1H-imidazol-2-yl)-$C_{1-3}$ alkyl, 1-($C_{1-3}$ alkyl)-1H-imidazol-5-yl, and (1-($C_{1-3}$ alkyl)-1H-imidazol-5-yl)-$C_{1-3}$ alkyl, thiophen-2-ylmethyl, thiazol-2-ylmethyl, (1-methylpyrazol-3-yl)methyl, (1-methylpyrazol-4-yl)methyl, (1-methylimidazol-2-yl)methyl, (1-cyclopropyl-3,5-dimethylpyrazol-4-yl)methyl, (1,3-dimethylpyrazol-5-yl)methyl, (3-cyclopropylpyrazol-1-yl)methyl, (4-methylthiazol-2-yl)methyl, (5-methylthiazol-2-yl)methyl, (5-chlorothiophen-2-yl)methyl, (5-cyanothiophen-2-yl)methyl, 2-(1,2,4-triazol-5-yl)ethyl, 2-(4-(trifluoromethyl)pyrazol-1-yl)ethyl, (3-methylisoxazol-5-yl)methyl, (isoxazol-5-yl)methyl, (isoxazol-4-yl)methyl, (isoxazol-3-yl)methyl, (oxazol-2-yl)methyl, (oxazol-4-yl)methyl, (oxazol-5-yl)methyl.

In one subembodiment $R^2$ is (4-chloro-1H-pyrazol-1-yl)methyl, (4-trifluoromethyl-1H-pyrazol-1-yl)methyl, (4-cyclopropyl-1H-pyrazol-1-yl)methyl, (4-methylthiazol-2-yl)methyl, (3-methylisoxazol-5-yl)methyl and (1-methyl-1H-pyrazol-5-yl)methyl.

In another subembodiment $R^2$ is phenoxy, 2-fluoro-phenoxy, 3-fluorophenoxy, 4-fluorophenoxy, 3,4-difluorophenoxy and 3-methylphenoxy, (5-chloro-3-pyridyl)oxy, (5-fluoro-3-pyridyl)oxy, (1-methylpyrazol-4-yl)oxy.

In another subembodiment $R^2$ is (4-chloro-1H-pyrazol-1-yl)methyl, (4-trifluoromethyl-1H-pyrazol-1-yl)methyl, (4-cyclopropyl-1H-pyrazol-1-yl)methyl.

In another subembodiment $R^2$ is 2-butanenitrile, n-propyl, isopropyl, isobutyl, 2-methylbutylcyclopropylmethyl, 2,2,2-trifluoroethyl, 3,3,3-trifluoropropyl.

In one embodiment of the present invention there is provided a compound of formula Ia

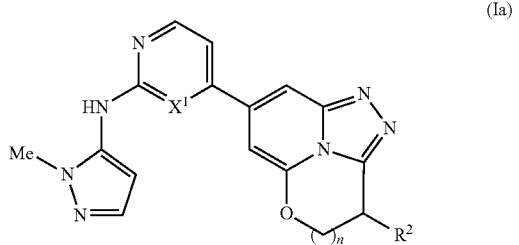

(Ia)

wherein $X^1$ is N, n is 1 and $R^2$ is optionally substituted benzyl. In a subembodiment $R^2$ is benzyl. In another subembodiment $R^2$ is 4-chlorobenzyl. In another subembodiment $R^2$ is 2-chlorobenzyl. In another subembodiment $R^2$ is 4-fluorobenzyl. In another subembodiment $R^2$ is 3,4-difluorobenzyl. In another subembodiment $R^2$ is 3-fluoro-4-chlorobenzyl. In another subembodiment $R^2$ is 3-fluoro-3-methoxybenzyl. In another subembodiment $R^2$ is (4-trifluoromethyl-1H-pyrazol-1-yl)methyl. In another subembodiment $R^2$ is (4-chloro-1H-pyrazol-1-yl)methyl. In another subembodiment $R^2$ is (3-methylisoxazol-5-yl)methyl. In another subembodiment $R^2$ is (4-methylthiazol-2-yl)methyl. In another subembodiment $R^2$ is phenoxy. In another subembodiment $R^2$ is 2-chloro-phenoxy. In another subembodiment $R^2$ is 4-fluoro-phenoxy.

In another embodiment of the present invention there is provided a compound of formula Ia wherein $X^1$ is C, n is 1 and $R^2$ is optionally substituted benzyl. In a subembodiment $R^2$ is benzyl. In another subembodiment $R^2$ is 4-chlorobenzyl. In another subembodiment $R^2$ is 2-chlorobenzyl. In another subembodiment $R^2$ is 4-fluorobenzyl. In another subembodiment $R^2$ is 3,4-difluorobenzyl. In another subembodiment $R^2$ is 3-fluoro-4-chlorobenzyl. In another subembodiment $R^2$ is 3-fluoro-3-methoxybenzyl. In another subembodiment $R^2$ is (4-trifluoromethyl-1H-pyrazol-1-yl)methyl. In another subembodiment $R^2$ is (4-chloro-1H-pyrazol-1-yl)methyl. In another subembodiment $R^2$ is (3-methylisoxazol-5-yl)methyl. In another subembodiment $R^2$ is (4-methylthiazol-2-yl)methyl. In another subembodiment $R^2$ is phenoxy. In another subembodiment $R^2$ is 2-chloro-phenoxy. In another subembodiment $R^2$ is 4-fluoro-phenoxy.

In another embodiment of the present invention there is provided a compound of formula Ia wherein $X^1$ is N, n is 2 and $R^2$ is optionally substituted benzyl. In a subembodiment $R^2$ is benzyl. In another subembodiment $R^2$ is 4-chlorobenzyl. In another subembodiment $R^2$ is 2-chlorobenzyl. In another subembodiment $R^2$ is 4-fluorobenzyl. In another subembodiment $R^2$ is 3,4-difluorobenzyl. In another subembodiment $R^2$ is 3-fluoro-4-chlorobenzyl. In another subembodiment $R^2$ is 3-fluoro-3-methoxybenzyl. In another subembodiment $R^2$ is (4-trifluoromethyl-1H-pyrazol-1-yl)methyl. In another subembodiment $R^2$ is (4-chloro-1H-pyrazol-1-yl)methyl. In another subembodiment $R^2$ is (3-methylisoxazol-5-yl)methyl. In another subembodiment $R^2$ is (4-methylthiazol-2-yl)methyl. In another subembodiment $R^2$ is phenoxy. In another subembodiment $R^2$ is 2-chloro-phenoxy. In another subembodiment $R^2$ is 4-fluoro-phenoxy.

In another embodiment of the present invention there is provided a compound of formula Ia wherein $X^1$ is C, n is 2 and $R^2$ is optionally substituted benzyl. In a subembodiment $R^2$ is benzyl. In another subembodiment $R^2$ is 4-chlorobenzyl. In another subembodiment $R^2$ is 2-chlorobenzyl. In another subembodiment $R^2$ is 4-fluorobenzyl. In another subembodiment $R^2$ is 3,4-difluorobenzyl. In another subembodiment $R^2$ is 3-fluoro-4-chlorobenzyl. In another subembodiment $R^2$ is 3-fluoro-3-methoxybenzyl. In another subembodiment $R^2$ is (4-trifluoromethyl-1H-pyrazol-1-yl)methyl. In another subembodiment $R^2$ is (4-chloro-1H-pyrazol-1-yl)methyl. In another subembodiment $R^2$ is (3-methylisoxazol-5-yl)methyl. In another subembodiment $R^2$ is (4-methylthiazol-2-yl)methyl. In another subembodiment $R^2$ is phenoxy. In another subembodiment $R^2$ is 2-chloro-phenoxy. In another subembodiment $R^2$ is 4-fluoro-phenoxy.

In one embodiment of the present invention there is provided a compound of formula Ib (Ib)

wherein $X^1$ is N, n is 1 and $R^2$ is optionally substituted benzyl. In a subembodiment $R^2$ is benzyl. In another subembodiment $R^2$ is 4-chlorobenzyl. In another subembodiment $R^2$ is 2-chlorobenzyl. In another subembodiment $R^2$ is 4-fluorobenzyl. In another subembodiment $R^2$ is 3,4-difluorobenzyl. In another subembodiment $R^2$ is 3-fluoro-4-chlorobenzyl. In another subembodiment $R^2$ is 3-fluoro-3-methoxybenzyl. In another subembodiment $R^2$ is (4-trifluoromethyl-1H-pyrazol-1-yl)methyl. In another subembodiment $R^2$ is (4-chloro-1H-pyrazol-1-yl)methyl. In another subembodiment $R^2$ is (3-methylisoxazol-5-yl)methyl. In another subembodiment $R^2$ is (4-methylthiazol-2-yl)methyl. In another subembodiment $R^2$ is phenoxy. In another subembodiment $R^2$ is 2-chloro-phenoxy. In another subembodiment $R^2$ is 4-fluoro-phenoxy.

In another embodiment of the present invention there is provided a compound of formula Ib wherein $X^1$ is C, n is 1 and $R^2$ is optionally substituted benzyl. In a subembodiment $R^2$ is benzyl. In another subembodiment $R^2$ is 4-chlorobenzyl. In another subembodiment $R^2$ is 2-chlorobenzyl. In another subembodiment $R^2$ is 4-fluorobenzyl. In another subembodiment $R^2$ is 3,4-difluorobenzyl. In another subembodiment $R^2$ is 3-fluoro-4-chlorobenzyl. In another subembodiment $R^2$ is 3-fluoro-3-methoxybenzyl. In another subembodiment $R^2$ is (4-trifluoromethyl-1H-pyrazol-1-yl)methyl. In another subembodiment $R^2$ is (4-chloro-1H-pyrazol-1-yl)methyl. In another subembodiment $R^2$ is (3-methylisoxazol-5-yl)methyl. In another subembodiment $R^2$ is (4-methylthiazol-2-yl)methyl. In another subembodiment $R^2$ is phenoxy. In another subembodiment $R^2$ is 2-chloro-phenoxy. In another subembodiment $R^2$ is 4-fluoro-phenoxy.

In another embodiment of the present invention there is provided a compound of formula Ib wherein $X^1$ is N, n is 2 and $R^2$ is optionally substituted benzyl. In a subembodiment $R^2$ is benzyl. In another subembodiment $R^2$ is 4-chlorobenzyl. In another subembodiment $R^2$ is 2-chlorobenzyl. In another subembodiment $R^2$ is 4-fluorobenzyl. In another subembodiment $R^2$ is 3,4-difluorobenzyl. In another subembodiment $R^2$ is 3-fluoro-4-chlorobenzyl. In another subembodiment $R^2$ is 3-fluoro-3-methoxybenzyl. In another subembodiment $R^2$ is (4-trifluoromethyl-1H-pyrazol-1-yl)methyl. In another subembodiment $R^2$ is (4-chloro-1H-pyrazol-1-yl)methyl. In another subembodiment $R^2$ is (3-methylisoxazol-5-yl)methyl. In another subembodiment $R^2$ is (4-methylthiazol-2-yl)methyl. In another subembodiment $R^2$ is phenoxy. In another subembodiment $R^2$ is 2-chloro-phenoxy. In another subembodiment $R^2$ is 4-fluoro-phenoxy.

In another embodiment of the present invention there is provided a compound of formula Ib wherein $X^1$ is C, n is 2 and $R^2$ is optionally substituted benzyl. In a subembodiment $R^2$ is benzyl. In another subembodiment $R^2$ is 4-chlorobenzyl. In another subembodiment $R^2$ is 2-chlorobenzyl. In another subembodiment $R^2$ is 4-fluorobenzyl. In another subembodiment $R^2$ is 3,4-difluorobenzyl. In another subembodiment $R^2$ is 3-fluoro-4-chlorobenzyl. In another subembodiment $R^2$ is 3-fluoro-3-methoxybenzyl. In another subembodiment $R^2$ is (4-trifluoromethyl-1H-pyrazol-1-yl)methyl. In another subembodiment $R^2$ is (4-chloro-1H-pyrazol-1-yl)methyl. In another subembodiment $R^2$ is (3-methylisoxazol-5-yl)methyl. In another subembodiment $R^2$ is (4-methylthiazol-2-yl)methyl. In another subembodiment $R^2$ is phenoxy. In another subembodiment $R^2$ is 2-chloro-phenoxy. In another subembodiment $R^2$ is 4-fluoro-phenoxy.

In one embodiment of the present invention there is provided a compound of formula Ic (Ic)

wherein $X^1$ is N and $R^2$ is optionally substituted benzyl. In a subembodiment $R^2$ is benzyl. In another subembodiment $R^2$ is 4-chlorobenzyl. In another subembodiment $R^2$ is 2-chlorobenzyl. In another subembodiment $R^2$ is 4-fluorobenzyl. In another subembodiment $R^2$ is 3,4-difluorobenzyl. In another subembodiment $R^2$ is 3-fluoro-4-chlorobenzyl. In another subembodiment $R^2$ is 3-fluoro-3-methoxybenzyl. In another subembodiment $R^2$ is (4-trifluoromethyl-1H-pyrazol-1-yl)methyl. In another subembodiment $R^2$ is (4-chloro-1H-pyrazol-1-yl)methyl. In another subembodiment $R^2$ is (3-methylisoxazol-5-yl)methyl. In another subembodiment $R^2$ is (4-methylthiazol-2-yl)methyl. In another subembodiment $R^2$ is phenoxy. In another subembodiment $R^2$ is 2-chloro-phenoxy. In another subembodiment $R^2$ is 4-fluoro-phenoxy.

In another embodiment of the present invention there is provided a compound of formula Ib wherein $X^1$ is C and $R^2$ is optionally substituted benzyl. In a subembodiment $R^2$ is benzyl. In another subembodiment $R^2$ is 4-chlorobenzyl. In another subembodiment $R^2$ is 2-chlorobenzyl. In another subembodiment $R^2$ is 4-fluorobenzyl. In another subembodiment $R^2$ is 3,4-difluorobenzyl. In another subembodiment $R^2$ is 3-fluoro-4-chlorobenzyl. In another subembodiment $R^2$ is 3-fluoro-3-methoxybenzyl. In another subembodiment $R^2$ is (4-trifluoromethyl-1H-pyrazol-1-yl)methyl. In another subembodiment $R^2$ is (4-chloro-1H-pyrazol-1-yl)methyl. In another subembodiment $R^2$ is (3-methylisoxazol-5-yl)methyl. In another subembodiment $R^2$ is (4-methylthiazol-2-yl)methyl. In another subembodiment $R^2$ is phenoxy. In another subembodiment $R^2$ is 2-chloro-phenoxy. In another subembodiment $R^2$ is 4-fluoro-phenoxy.

In another embodiment of the present invention there is provided a compound of formula Ib wherein $X^1$ is N and $R^2$ is optionally substituted benzyl. In a subembodiment $R^2$ is benzyl. In another subembodiment $R^2$ is 4-chlorobenzyl. In another subembodiment R² is 2-chlorobenzyl. In another subembodiment R² is 4-fluorobenzyl. In another subembodiment R² is 3,4-difluorobenzyl. In another subembodiment R² is 3-fluoro-4-chlorobenzyl. In another subembodiment R² is 3-fluoro-3-methoxybenzyl. In another subembodiment R² is (4-trifluoromethyl-1H-pyrazol-1-yl)methyl. In another subembodiment R² is (4-chloro-1H-pyrazol-1-yl)methyl. In another subembodiment R² is (3-methylisoxazol-5-yl)methyl. In another subembodiment R² is (4-methylthiazol-2-yl)methyl. In another subembodiment R² is phenoxy. In another subembodiment R² is 2-chloro-phenoxy. In another subembodiment R² is 4-fluoro-phenoxy.

In another embodiment of the present invention there is provided a compound of formula Ib wherein X¹ is C and R² is optionally substituted benzyl. In a subembodiment R² is benzyl. In another subembodiment R² is 4-chlorobenzyl. In another subembodiment R² is 2-chlorobenzyl. In another subembodiment R² is 4-fluorobenzyl. In another subembodiment R² is 3,4-difluorobenzyl. In another subembodiment R² is 3-fluoro-4-chlorobenzyl. In another subembodiment R² is 3-fluoro-3-methoxybenzyl. In another subembodiment R² is (4-trifluoromethyl-1H-pyrazol-1-yl)methyl. In another subembodiment R² is (4-chloro-1H-pyrazol-1-yl)methyl. In another subembodiment R² is (3-methylisoxazol-5-yl)methyl. In another subembodiment R² is (4-methylthiazol-2-yl)methyl. In another subembodiment R² is phenoxy. In another subembodiment R² is 2-chloro-phenoxy. In another subembodiment R² is 4-fluoro-phenoxy.

The term "alkyl" as used herein alone or in combination with other groups, denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-6}$ alkyl" as used herein refers to an alkyl composed of 1 to 6 carbons. Examples of alkyl groups include, but are not limited to, methyl, ethyl, propyl, i-propyl, n-butyl, i-butyl, t-butyl, neopentyl, hexyl, and octyl.

The term "alkenyl" as used herein denotes an unsubstituted hydrocarbon chain radical having from 2 to 10 carbon atoms having one or two olefinic double bonds. "$C_{2-10}$ alkenyl" as used herein refers to an alkenyl composed of 2 to 10 carbons. Examples are vinyl, 1-propenyl, 2-propenyl (allyl) or 2-butenyl (crotyl).

The term "cycloalkyl" denotes a monovalent saturated monocyclic or bicyclic hydrocarbon group of 3 to 10 ring carbon atoms Fused cycloalkyl groups can have one (i.e., spirocyclic), two (i.e., bicyclic) or more (i.e., polycyclic) carbon atoms in common. Particular cycloalkyl groups are monocyclic. "$C_{3-7}$ cycloalkyl" as used herein refers to a cycloalkyl composed of 3 to 7 carbons in the carbocyclic ring. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl.

The term "cycloalkylalkyl" as used herein refers to the radical R'R"—, wherein R' is a cycloalkyl radical, and R" is an alkylene radical as defined herein with the understanding that the attachment point of the cycloalkylalkyl moiety will be on the alkylene radical. Examples of cycloalkylalkyl radicals include, but are not limited to, cyclopropylmethyl, cyclohexylmethyl, cyclopentylethyl. $C_{3-7}$ cycloalkyl-$C_{1-3}$ alkyl refers to the radical R'R" where R' is $C_{3-7}$ cycloalkyl and R" is $C_{1-3}$ alkylene as defined herein.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH₂CH(i-Pr)CH₂—), unless otherwise indicated. "$C_{0-4}$ alkylene" refers to a linear or branched saturated divalent hydrocarbon radical comprising 1-4 carbon atoms or, in the case of $C_0$, the alkylene radical is omitted. "$(CH_2)_{0-4}$" refers to a linear saturated divalent hydrocarbon radical comprising 0-4 carbon atoms or, in the case of $C_0$, the alkylene radical is omitted. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "haloalkyl" as used herein denotes an alkyl group as defined above wherein at least one hydrogen atom is substituted by a halogen. Examples are 1-fluoromethyl, 1-chloromethyl, 1-bromomethyl, 1-iodomethyl, difluoromethyl, trifluoromethyl, trichloromethyl, 1-fluoroethyl, 1-chloroethyl, 2-fluoroethyl, 2-chloroethyl, 2-bromoethyl, 2,2-dichloroethyl, 3-bromopropyl or 2,2,2-trifluoroethyl.

The term "alkoxy" as used herein means an —O-alkyl group, wherein alkyl is as defined above, such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "haloalkoxy" as used herein refers to a group —OR where R is haloalkyl as defined herein. The term "haloalkylthio" as used herein refers to a group —SR where R is haloalkyl as defined herein.

The terms "hydroxyalkyl" and "alkoxyalkyl" as used herein denotes alkyl radical as herein defined wherein one to three hydrogen atoms on different carbon atoms is/are replaced by hydroxyl or alkoxy groups respectively. A $C_{1-3}$ alkoxy-$C_{1-6}$ alkyl moiety refers to a $C_{1-6}$ alkyl substituent in which 1 to 3 hydrogen atoms are replaced by a $C_{1-3}$ alkoxy and the point of attachment of the alkoxy is the oxygen atom.

The term "alkylthio" or "alkylsulfanyl" means an —S-alkyl group, wherein alkyl is as defined above such as meththio, ethylthio, n-propylthio, i-propylthio, n-butylthio, hexylthio, including their isomers. "Lower alkylthio" or "lower thioalkyl" as used herein denotes an alkylthio group with a "lower alkyl" group as previously defined. "$C_{1-10}$ alkylthio" as used herein refers to an —S-alkyl wherein alkyl is $C_{1-10}$. "Arylthio" means an —S-aryl group, wherein aryl is as defined herein. "Phenylthio" is an "arylthio" moiety wherein aryl is phenyl. The term "alkylthioalkyl" or "phenylthioalkyl" as used herein denotes the radical R'R" where R' is a alkylthio or phenylthio radical respectively and R" is alkylene as defined herein and the attachment point of the alkylthioalkyl radical will be on the alkylene radical. $C_{1-3}$ alkthio-$C_{1-6}$ alkyl denotes a group wherein the alkyl portion is comprised of 1-6 carbon atoms and the alkthio group is 1-3 carbons.

The term "cyanoalkyl" refers to an alkyl group as defined herein wherein one or more hydrogen atoms are replaced with a cyano group.

The term "halogen" or "halo" as used herein means fluorine, chlorine, bromine, or iodine. The term "halo", "halogen", and "halide" are used interchangeably herein and denote fluoro, chloro, bromo, or iodo.

The term "oxide" as used herein refers to a heteroaryl N-oxide.

The term "halocycloalkyl" as used herein denotes a cycloalkyl group as defined above wherein at least one hydrogen atom is substituted by a halogen. Examples are 3,3-difluorocyclopentyl, 4,4-difluorocyclohexyl.

The term "halocycloalkylalkyl" as used herein refers to the radical R'R"—, wherein R' is a halocycloalkyl radical as defined herein, and R" is an alkylene radical as defined herein with the understanding that the attachment point of the halocycloalkylalkyl moiety will be on the alkylene radical. Examples of cycloalkylalkyl radicals include, but are not limited to, 2-fluorocyclopropyl, 4,4-difluorocyclohexylmethyl. $C_{3-7}$ halocycloalkyl-$C_{1-3}$ alkyl refers to the radical R'R" where R' is $C_{3-7}$ halocycloalkyl and R" is $C_{1-3}$ alkylene as defined herein.

The terms "heterocycle" and "heterocyclic" include four to seven membered saturated or partially unsaturated rings containing one, two or three heteroatoms selected from the group consisting of O, N, S, S(═O) and S(═O)$_2$. These terms include bicyclic rings such as 2-oxabicyclo[2.2.1] heptane. In certain instances, these terms may be specifically further limited, such as, "five to six membered heterocyclic" only including five and six membered rings.

The term "heterocycloalkyl" (or "heterocyclylalkyl") denotes the radical of the formula R'R", wherein R' is a heterocyclic radical as defined herein, and R" is an alkylene radical as defined herein, and the attachment point of the heterocycloalkyl radical will be on the alkylene radical. Examples of heterocycloalkyl radicals include, but are not limited to, 1-piperazinylmethyl, 2-morpholinomethyl, and the like The term "aryl" as used herein denotes a monovalent aromatic carbocyclic radical containing 6 to 15 carbon atoms consisting of one individual ring, or one or more fused rings in which at least one ring is aromatic in nature. An aryl group can optionally be substituted with one or more, preferably one to three substituents. Alternatively two adjacent atoms of the aryl ring may be substituted with a methylenedioxy or ethylenedioxy group. Examples of aryl radicals include phenyl, naphthyl, indanyl, 3,4-methylenedioxyphenyl, 1,2,3,4-tetrahydroquinolin-7-yl, 1,2,3,4-tetrahydroisoquinoline-7-yl, and the like.

The term "aryloxy" as used herein denotes an O-aryl group, wherein aryl is as defined above. An aryloxy group can be unsubstituted or substituted with one or three suitable substituents. The term "phenoxy" refers to an aryloxy group wherein the aryl moiety is a phenyl ring. The term "benzyloxy" refers to a group PhCH$_2$O— and "or benzyloxy-$C_{1-3}$ alkyl" refers to a $C_1$ to $C_3$ alkyl group wherein one hydrogen is replaced by a benzyloxy group.

The term heteroaryloxy as used herein means an —O-(heteroaryl) group which is attached to the remainder of the molecule by an oxygen atom. For example a (pyridyl)oxy group can be attached at the 2, 3 or 4 positions of the pyridine.

The term "heteroaryl" includes five to six membered aromatic rings containing one, two, three or four heteroatoms selected from the group consisting of O, N and S. In certain instances, these terms may be specifically further limited, such as, five to six membered heteroaryl, wherein the heteroaryl contains one or two nitrogen heteroatoms. As well known to those skilled in the art, heteroaryl rings have less aromatic character than their all-carbon counter parts. Thus, for the purposes of the invention, a heteroaryl group need only have some degree of aromatic character.

The term "heteroarylalkyl" or "heteroaralkyl" means the radical of the formula R'R", wherein R' is an optionally substituted heteroaryl radical as defined herein, and R" is an alkylene radical as defined herein with the understanding that the attachment point of the heteroaryl radical will be on the alkylene radical and the attachment may be anywhere on the heteroaryl ring. Examples of heteroarylalky radicals include, but are not limited to, 2-imidazolylmethyl, 3-pyrrolylethyl, 4-pyridinylmethyl and 5-pyrimidinylmethyl.

The term heteroaryloxy as used herein means an —O-(heteroaryl) group which is attached to the remainder of the molecule by an oxygen atom. A (pyridyl)oxy group is an heteroaryloxy wherein the heteroaryl moiety 2-, 3- or 4-pyridinyl.

The term "oxo" as used herein refers to a doubly bonded oxygen such as "C═O" (i.e., a carbonyl group when the oxo is attached to a carbon) wherein it is understood that this is equivalent to two hydroxyl groups attached to the same carbon are equivalent The terms "6,7,8,9-tetrahydro-1,2,2a$^1$,6,8-pentaazabenzo[cd]azulene" (i), 8,9-dihydro-1,2,2a$^1$,6,8-pentaazabenzo[cd]azulen-7(6H)-one (ii), 6H-8-oxa-1,2,2a$^1$,6-tetraazabenzo[cd]azulen-7(9H)-one (iii) and 3,4-dihydro-5-oxa-1,2,2a$^1$-triazaacenaphthylene (iv) and 8,9-dihydro-1,2,2a$^1$,6-tetraazabenzo[cd]azulen-7(6H)-one (v) were generated with ChemBioDraw Ultra 12.0 and denote the following:

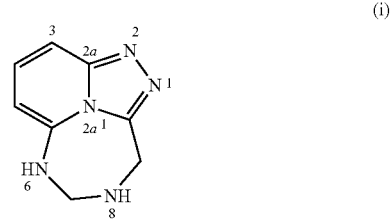

(i)

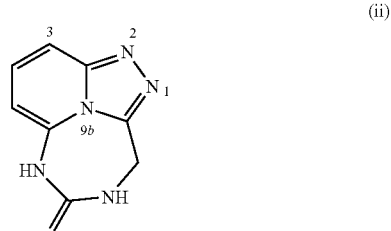

(ii)

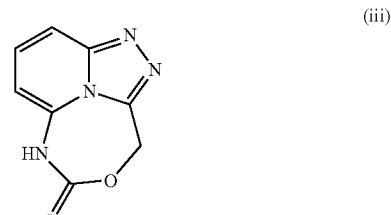

(iii)

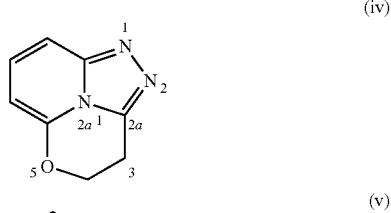

(iv)

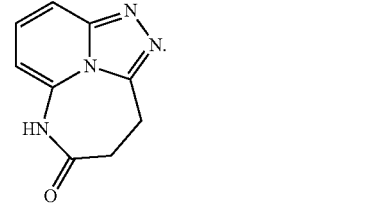

(v)

The terms "treat" and "treatment" refer to therapeutic treatment wherein the object is to slow down (lessen) an undesired physiological change or disorder, such as the spread of cancer. For purposes of this invention, beneficial or desired clinical results include, but are not limited to, alleviation of symptoms, limiting the extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer. Examples of chemotherapeutic agents include erlotinib (TARCEVA®, Genentech/OSI Pharm.), bortezomib (VELCADE®, Millennium Pharm.), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew Chem. Intl. Ed. Engl.* 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Raf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; (ix) anti-angiogenic agents such as bevacizumab (AVASTIN®), Genentech); and (x) pharmaceutically acceptable salts, acids and derivatives of any of the above.

Commonly used abbreviations include: acetyl (Ac), aqueous (aq.), atmospheres (Atm), tert-butoxycarbonyl (Boc), di-tert-butyl pyrocarbonate or Boc anhydride (BOC$_2$O), benzyl (Bn), benzotriazol-1-yloxy-tris-(dimethylamino)phosphonium hexafluorophosphate (BOP), butyl (Bu), benzoyl (Bz), Chemical Abstracts Registration Number (CASRN), benzyloxycarbonyl (CBZ or Z), carbonyl diimidazole (CDI), dibenzylideneacetone (DBA), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether (Et$_2$O), O-(7-azabenzotriazole-1-yl)-N, N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), methanol (MeOH), melting point (mp), MeSO$_2$— (mesyl or Ms), methyl (Me), acetonitrile (MeCN), m-chloroperbenzoic acid (MCPBA), mass spectrum (ms), methyl tert-butyl ether (MTBE), N-methylmorpholine (NMM), N-methylpyrrolidone (NMP), petroleum ether (pet ether, i.e. hydrocarbons), phenyl (Ph), propyl (Pr), iso-propyl (i-Pr), pounds per square inch (psi), bromo-tris-pyrrolidinophosphonium hexafluorophosphate (PyBrOP), pyridine (pyr), room temperature (rt or RT), satd. (saturated), tert-butyldimethylsilyl or t-BuMe2Si (TBDMS), triethylamine (TEA or Et$_3$N), triflate or CF$_3$SO$_2$— (Tf), trifluoroacetic acid (TFA), O-benzotriazol-1-yl-N,N,N',N'-tetramethyluronium tetrafluoroborate (TBTU), thin layer chromatography (TLC), tetrahydrofuran (THF), tetramethylethylenediamine (TMEDA), trimethylsilyl or Me$_3$Si (TMS), 2-(trimethylsilyl)ethoxymethyl (SEM), p-toluenesulfonic acid monohydrate (TsOH or pTsOH), 4-Me-C$_6$H$_4$SO$_2$— or tosyl (Ts), N-urethane-N-carboxyanhydride (UNCA). Conventional nomenclature including the prefixes normal (n), iso (i-), secondary (sec-), tertiary (tert- or -t) and neo- have their customary meaning when used with an alkyl moiety. (J. Rigaudy and D. P. Klesney, Nomenclature in Organic Chemistry, IUPAC 1979 Pergamon Press, Oxford.).

Compounds and Preparation

Examples of representative compounds within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In addition, if the stereochemistry of a structure or a portion of a structure is not indicated with, for example, bold or dashed lines, the structure or portion of the structure is to be interpreted as encompassing all stereoisomers of it. The following numbering system is used herein.

TABLE I

| STRUCTURE | MS[1] | R S[2] | ERK[3] IC$_{50}$ (μM) | NAME[4] |
|---|---|---|---|---|
| I-1 | 410 410 | R S | 0.1790 0.0011 | N-(1-methyl-1H-pyrazol-5-yl)-4-(3-phenyl-4,5-dihydro-3H-1,2,2a[1],5-tetraazaacenaphthylen-7-yl)pyrimidin-2-amine |

TABLE I-continued

| | STRUCTURE | MS[1] | R S[2] | ERK[3] IC$_{50}$ (μM) | NAME[4] |
|---|---|---|---|---|---|
| I-2 | 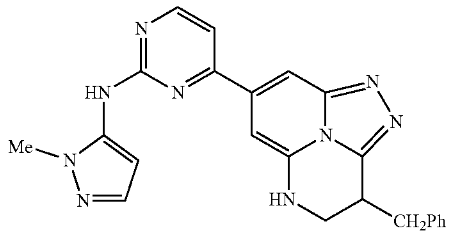 | 424<br>424 | R<br>S | 0.00038<br>0.00002 | N-(1-methyl-1H-pyrazol-5-yl)-4-(3-phenyl-4,5-dihydro-3H-1,2,2a[1],5-tetraazaacenaphthylen-7-yl)pyrimidin-2-amine |
| I-3 | 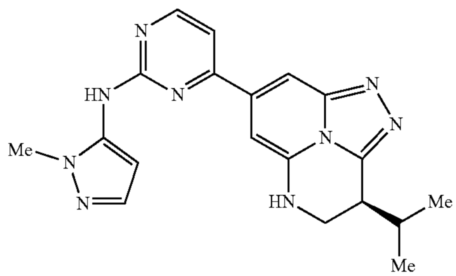 [SMILES: CC(C)[C@H]1CNc2cc(-c3ccnc(Nc4ccnn4C)n3)cc3nnc1n23] | 376 | | 0.000039 | S-4-(3-isopropyl-4,5-dihydro-3H-1,2,2a[1],5-tetraazaacenaphthylen-7-yl)-N-(1-methyl-1H-pyrazol-5-yl)pyrimidin-2-amine |
| I-4 | 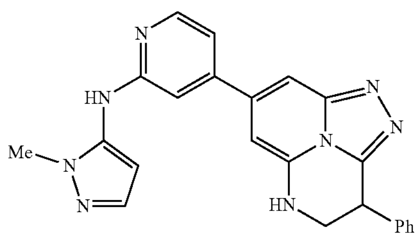 [SMILES: Cn1nccc1Nc1cc(-c2cc3n4c(nnc4c2)C(c2ccccc2)CN3)ccn1] | 409<br>409 | S<br>R | <0.000020<br>0.0431 | N-(1-methyl-1H-pyrazol-5-yl)-4-(3-phenyl-4,5-dihydro-3H-1,2,2a[1],5-tetraazaacenaphthylen-7-yl)pyridin-2-amine |
| I-5 | 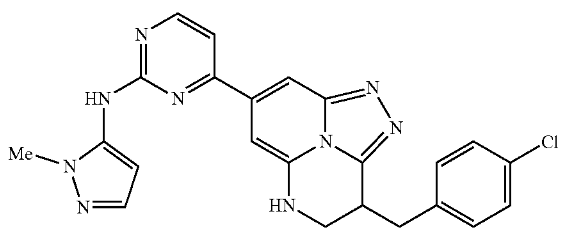 [SMILES: Cn1nccc1Nc1nccc(-c2cc3n4c(nnc4c2)C(Cc2ccc(Cl)cc2)CN3)n1] | 458<br>458 | S<br>R | <0.000020<br>0.000408 | 4-(3-(4-chlorobenzyl)-4,5-dihydro-3H-1,2,2a[1],5-tetraazaacenaphthylen-7-yl)-N-(1-methyl-1H-pyrazol-5-yl)pyrimidin-2-amine |
| I-6 | 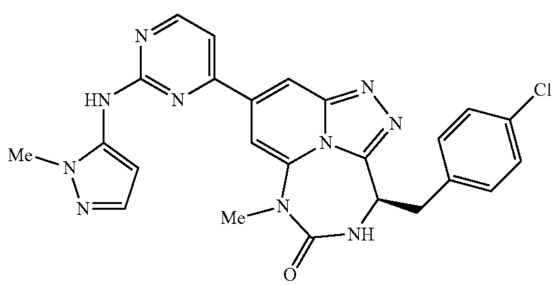 [SMILES: CN1C(=O)N[C@H](Cc2ccc(Cl)cc2)c2nnc3cc(-c4ccnc(Nc5ccnn5C)n4)cc1n23] | 501 | R | 0.000023 | (R)-9-(4-chlorobenzyl)-6-methyl-4-(2-((1-methyl-1H-pyrazol-5-yl)amino)pyrimidin-4-yl)-8,9-dihydro-1,2,2a[1],6,8-pentaazabenzo[cd]azulen-7(6H)-one |
| I-7 | 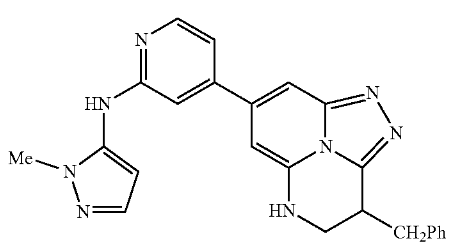 | 423<br>423 | S<br>R | <0.000020<br>0.000707 | 4-(3-benzyl-4,5-dihydro-3H-1,2,2a[1],5-tetraazaacenaphthylen-7-yl)-N-(1-methyl-1H-pyrazol-5-yl)pyridin-2-amine |

TABLE I-continued

| STRUCTURE | MS[1] | R S[2] | ERK[3] IC$_{50}$ (μM) | NAME[4] |
|---|---|---|---|---|
| I-8 | 457<br>457 | S<br>R | <0.000020<br>0.00155 | 4-(3-(4-chlorobenzyl)-4,5-dihydro-3H-1,2,2a[1],5-tetraazaacenaphthylen-7-yl)-N-(1-methyl-1H-pyrazol-5-yl)pyridin-2-amine |
| I-9 | 438<br>438 | S<br>R | <0.000020<br>0.00504 | 4-(3-benzyl-5-methyl-4,5-dihydro-3H-1,2,2a[1],5-tetraazaacenaphthylen-7-yl)-N-(1-methyl-1H-pyrazol-5-yl)pyrimidin-2-amine |
| I-10 | 390<br>390 | S<br>R | <0.000020<br>0.002747 | 4-(3-isobutyl-4,5-dihydro-3H-1,2,2a[1],5-tetraazaacenaphthylen-7-yl)-N-(1-methyl-1H-pyrazol-5-yl)pyrimidin-2-amine |
| I-11 | 454<br>454 | S<br>R | <0.000020<br>0.000514 | 4-(3-(4-methoxybenzyl)-4,5-dihydro-3H-1,2,2a[1],5-tetraazaacenaphthylen-7-yl)-N-(1-methyl-1H-pyrazol-5-yl)pyrimidin-2-amine |
| I-12 | 472<br>472 | S<br>R | <0.000020<br>0.000311 | 4-(3-(3-fluoro-4-methoxybenzyl)-4,5-dihydro-3H-1,2,2a[1],5-tetraazaacenaphthylen-7-yl)-N-(1-methyl-1H-pyrazol-5-yl)pyrimidin-2-amine |
| I-13 | 471<br>471 | S<br>R | <0.000020<br>0.0086 | 4-(3-(4-chlorobenzyl)-5-methyl-4,5-dihydro-3H-1,2,2a[1],5-tetraazaacenaphthylen-7-yl)-N-(1-methyl-1H-pyrazol-5-yl)pyridin-2-amine |

TABLE I-continued

| STRUCTURE | MS[1] | R S[2] | ERK[3] IC$_{50}$ (μM) | NAME[4] |
|---|---|---|---|---|
| I-14 | 476<br>476 | S<br>R | <0.000020<br>0.0000441 | 4-(3-(4-chloro-3-fluorobenzyl)-4,5-dihydro-3H-1,2,2a[1],5-tetraazaacenaphthylen-7-yl)-N-(1-methyl-1H-pyrazol-5-yl)pyrimidin-2-amine |
| I-15 | 425.2<br>425.2 | R<br>S | 0.000020<br>0.00224 | 4-(3-benzyl-3,4-dihydro-5-oxa-1,2,2a[1]-triazaacenaphthylen-7-yl)-N-(1-methyl-1H-pyrazol-5-yl)pyrimidin-2-amine |
| I-16 | 441.2<br>441.2 | R<br>S | <0.000020<br>0.000661 | 4-(3-benzyl-3,4-dihydro-5-thia-1,2,2a[1]-triazaacenaphthylen-7-yl)-N-(1-methyl-1H-pyrazol-5-yl)pyrimidin-2-amine |
| I-17 | 452.3<br>452.2 | S<br>R | <0.000020<br>0.00339 | 4-(3-benzyl-5-ethyl-4,5-dihydro-3H-1,2,2a[1],5-tetraazaacenaphthylen-7-yl)-N-(1-methyl-1H-pyrazol-5-yl)pyrimidin-2-amine |
| I-18 | 467.2<br>467.3 | R<br>S | 0.000036<br>0.0558 | 4-(3-(4-methoxybenzyl)-5-methyl-4,5-dihydro-3H-1,2,2a[1],5-tetraazaacenaphthylen-7-yl)-N-(1-methyl-1H-pyrazol-5-yl)pyridin-2-amine |
| I-19 | 447.3 | R | 0.00115 | (R)-9-isobutyl-6,8-dimethyl-4-(2-((1-methyl-1H-pyrazol-5-yl)amino)pyrimidin-4-yl)-8,9-dihydro-1,2,2a[1],6,8-pentaazabenzo[cd]azulen-7(6H)-one |

TABLE I-continued

| STRUCTURE | MS[1] | R S[2] | ERK[3] IC$_{50}$ (μM) | NAME[4] |
|---|---|---|---|---|
| I-20 | 403.2<br>403.2 | S<br>R | 0.000316<br>0.0487 | 4-(3-isobutyl-5-methyl-4,5-dihydro-3H-1,2,2a[1],5-tetraazaacenaphthylen-7-yl)-N-(1-methyl-1H-pyrazol-5-yl)pyridin-2-amine |
| I-21 | 442.2<br>442.2 | S<br>R | <0.000020<br>0.000731 | 4-(3-(4-fluorobenzyl)-4,5-dihydro-3H-1,2,2a[1],5-tetraazaacenaphthylen-7-yl)-N-(1-methyl-1H-pyrazol-5-yl)pyrimidin-2-amine |
| I-22 | 500.2<br>500.2 | S<br>R | <0.000020<br>0.0882 | 9-(4-chlorobenzyl)-6-methyl-4-(2-((1-methyl-1H-pyrazol-5-yl)amino)pyrimidin-4-yl)-8,9-dihydro-1,2,2a[1],6-tetraazabenzo[cd]azulen-7(6H)-one |
| I-23 | 433.2 | R | 0.00112 | (R)-9-isobutyl-8-methyl-4-(2-((1-methyl-1H-pyrazol-5-yl)amino)pyrimidin-4-yl)-8,9-dihydro-1,2,2a[1],6,8-pentaazabenzo[cd]azulen-7(6H)-one |
| I-24 | 455.2<br>455.1 | S<br>R | <0.000020<br>0.001847 | 4-(3-((6-methoxypyridin-3-yl)methyl)-4,5-dihydro-3H-1,2,2a[1],5-tetraazaacenaphthylen-7-yl)-N-(1-methyl-1H-pyrazol-5-yl)pyrimidin-2-amine |

TABLE I-continued

| STRUCTURE | MS[1] | R S[2] | ERK[3] IC$_{50}$ (μM) | NAME[4] |
|---|---|---|---|---|
| I-25 | 432.2 | R | 0.00428 | (R)-9-isobutyl-6-methyl-4-(2-((1-methyl-1H-pyrazol-5-yl)amino)pyridin-4-yl)-8,9-dihydro-1,2,2a[1],6,8-pentaazabenzo[cd]azulen-7(6H)-one |
| I-26 | 496.2 | R | 0.00039 | (R)-9-(4-methoxybenzyl)-6-methyl-4-(2-((1-methyl-1H-pyrazol-5-yl)amino)pyridin-4-yl)-8,9-dihydro-1,2,2a[1],6,8-pentaazabenzo[cd]azulen-7(6H)-one |
| I-27 | 455.2 455.2 | S R | 0.000030 0.0023 | 4-(3-((6-methoxypyridin-2-yl)methyl)-4,5-dihydro-3H-1,2,2a[1],5-tetraazaacenaphthylen-7-yl)-N-(1-methyl-1H-pyrazol-5-yl)pyrimidin-2-amine |
| I-28 | 453.2 | | 0.000020 | 3-benzyl-5-methyl-7-(2-((1-methyl-1H-pyrazol-5-yl)amino)pyrimidin-4-yl)-3H-1,2,2a[1],3,5-pentaazaacenaphthylen-4(5H)-one |
| I-29 | 469.2 469.2 | S R | <0.00002 0.000109 | 4-(9-((benzyloxy)methyl)-8,9-dihydro-7H-6-oxa-1,2,2a[1]-triazabenzo[cd]azulen-4-yl)-N-(1-methyl-1H-pyrazol-5-yl)pyrimidin-2-amine |

TABLE I-continued

| STRUCTURE | MS[1] | R S[2] | ERK[3] IC$_{50}$ (μM) | NAME[4] |
|---|---|---|---|---|
| I-30 | 472 472 | R S | 0.00255 <0.00002 | 4-(9-(2-chlorobenzyl)-8,9-dihydro-7H-6-oxa-1,2,2a[1]-triazabenzo[cd]azulen-4-yl)-N-(1-methyl-1H-pyrazol-5-yl)pyridin-2-amine |
| I-31 | 456.2 456.2 | S R | <0.000020 0.00135 | 4-(3-(4-fluorobenzyl)-5-methyl-4,5-dihydro-3H-1,2,2a[1],5-tetraazaacenaphthylen-7-yl)-N-(1-methyl-1H-pyrazol-5-yl)pyrimidin-2-amine |
| I-32 | 490.2 490.2 | S S | <0.00002 0.00060 | 4-(3-(4-chloro-3-fluorobenzyl)-5-methyl-4,5-dihydro-3H-1,2,2a[1],5-tetraazaacenaphthylen-7-yl)-N-(1-methyl-1H-pyrazol-5-yl)pyrimidin-2-amine |
| I-33 | 439.2 439.2 | | 0.00117 0.0629 | 4-(3-benzyl-3-methyl-3,4-dihydro-5-oxa-1,2,2a[1]-triazaacenaphthylen-7-yl)-N-(1-methyl-1H-pyrazol-5-yl)pyrimidin-2-amine |
| I-34 | 486.1 486.1 | S R | | 9-(4-chlorobenzyl)-4-(2-((1-methyl-1H-pyrazol-5-yl)amino)pyrimidin-4-yl)-8,9-dihydro-1,2,2a[1],6-tetraazabenzo[cd]azulen-7(6H)-one |
| I-35 | 485.1 | R | 0.000173 | (R)-9-(4-fluorobenzyl)-6-methyl-4-(2-((1-methyl-1H-pyrazol-5-yl)amino)pyrimidin-4-yl)-8,9-dihydro-1,2,2a[1],6,8-pentaazabenzo[cd]azulen-7(6H)-one |

TABLE I-continued

| STRUCTURE | MS[1] | R S[2] | ERK[3] IC$_{50}$ (μM) | NAME[4] |
|---|---|---|---|---|
| I-36 | 473.1<br>473.1 | S<br>R | <0.000020<br>0.00069 | 4-(9-(4-chlorobenzyl)-8,9-dihydro-7H-6-oxa-1,2,2a[1]-triazabenzo[cd]azulen-4-yl)-N-(1-methyl-1H-pyrazol-5-yl)pyrimidin-2-amine |
| I-37 | 438.2<br>438.2 | | 0.00532<br>0.0757 | 4-(3-benzyl-3-methyl-3,4-dihydro-5-oxa-1,2,2a[1]-triazaacenaphthylen-7-yl)-N-(1-methyl-1H-pyrazol-5-yl)pyridin-2-amine |
| I-38 | 424.2<br>424.2 | R<br>S | 0.000020<br>0.00434 | 4-(3-benzyl-3,4-dihydro-5-oxa-1,2,2a[1]-triazaacenaphthylen-7-yl)-N-(1-methyl-1H-pyrazol-5-yl)pyridin-2-amine |
| I-39 | 485.1 | R | 0.000215 | (R)-9-(3-fluorobenzyl)-6-methyl-4-(2-((1-methyl-1H-pyrazol-5-yl)amino)pyrimidin-4-yl)-8,9-dihydro-1,2,2a[1],6,8-pentaazabenzo[cd]azulen-7(6H)-one |
| I-40 | 499.2<br>499.2 | S<br>R | <0.000020<br>0.00135 | 9-(4-chlorobenzyl)-6-methyl-4-(2-((1-methyl-1H-pyrazol-5-yl)amino)pyridin-4-yl)-8,9-dihydro-1,2,2a[1],6-tetraazabenzo[cd]azulen-7(6H)-one |

TABLE I-continued

| | STRUCTURE | MS[1] | R S[2] | ERK[3] IC$_{50}$ (μM) | NAME[4] |
|---|---|---|---|---|---|
| I-41 | 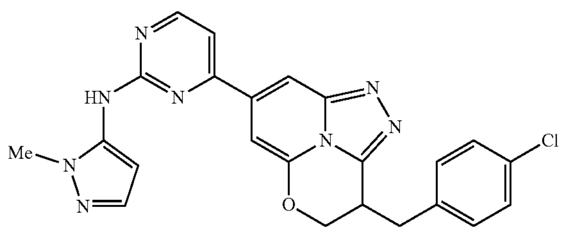 [SMILES: Cn1nccc1Nc1nccc(-c2cc3n4c(nnc4c2)C(Cc2ccc(Cl)cc2)CO3)n1] | 459.2 459.2 | R S | <0.000020 0.000783 | 4-(3-(4-chlorobenzyl)-3,4-dihydro-5-oxa-1,2,2a[1]-triazaacenaphthylen-7-yl)-N-(1-methyl-1H-pyrazol-5-yl)pyrimidin-2-amine |
| I-42 | 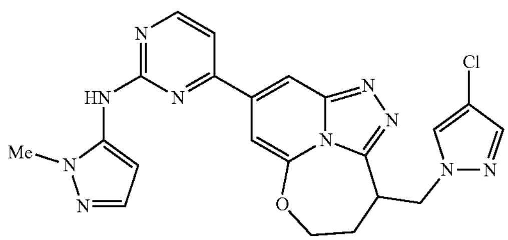 [SMILES: Cn1nccc1Nc1nccc(-c2cc3n4c(nnc4c2)C(Cn2cc(Cl)cn2)CCO3)n1] | 463.1 462 | R S | 0.000079 0.000131 | S-4-(9-((4-chloro-1H-pyrazol-1-yl)methyl)-8,9-dihydro-7H-6-oxa-1,2,2a[1]-triazabenzo[cd]azulen-4-yl)-N-(1-methyl-1H-pyrazol-5-yl)pyrimidin-2-amine |
| I-43 | 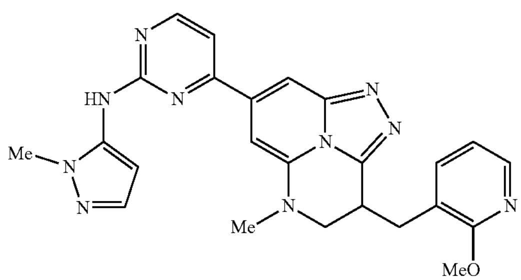 [SMILES: COc1ncccc1CC1CN(C)c2cc(-c3ccnc(Nc4ccnn4C)n3)cc3nnc1n23] | 469.2 469.2 | S R | 0.00133 0.12 | 4-(3-((2-methoxypyridin-3-yl)methyl)-5-methyl-4,5-dihydro-3H-1,2,2a[1],5-tetraazaacenaphthylen-7-yl)-N-(1-methyl-1H-pyrazol-5-yl)pyrimidin-2-amine |
| I-44 | 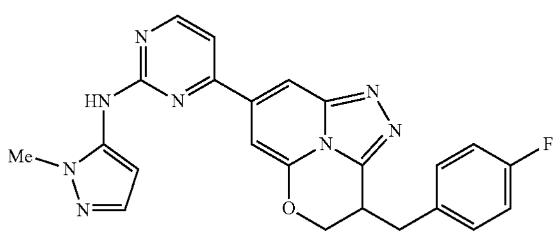 [SMILES: Cn1nccc1Nc1nccc(-c2cc3n4c(nnc4c2)C(Cc2ccc(F)cc2)CO3)n1] | 443.2 443.2 | R S | <0.00002 0.005 | 4-(3-(4-fluorobenzyl)-3,4-dihydro-5-oxa-1,2,2a[1]-triazaacenaphthylen-7-yl)-N-(1-methyl-1H-pyrazol-5-yl)pyrimidin-2-amine |
| I-45 | 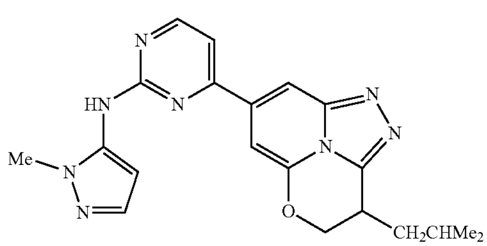 | 391.2 391.2 | R S | <0.00002 0.0209 | 4-(3-isobutyl-3,4-dihydro-5-oxa-1,2,2a[1]-triazaacenaphthylen-7-yl)-N-(1-methyl-1H-pyrazol-5-yl)pyrimidin-2-amine |
| I-46 | 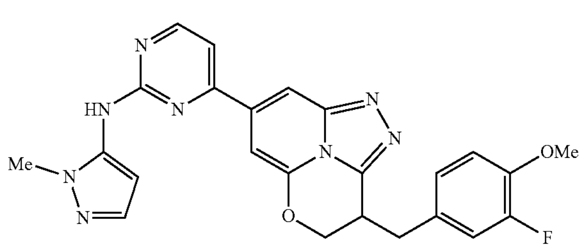 [SMILES: COc1ccc(CC2COc3cc(-c4ccnc(Nc5ccnn5C)n4)cc4nnc2n34)cc1F] | 473.2 473.2 | R S | <0.00002 0.00247 | 4-(3-(3-fluoro-4-methoxybenzyl)-3,4-dihydro-5-oxa-1,2,2a[1]-triazaacenaphthylen-7-yl)-N-(1-methyl-1H-pyrazol-5-yl)pyrimidin-2-amine |

TABLE I-continued

| | STRUCTURE | MS[1] | R S[2] | ERK[3] IC$_{50}$ (μM) | NAME[4] |
|---|---|---|---|---|---|
| I-47 | 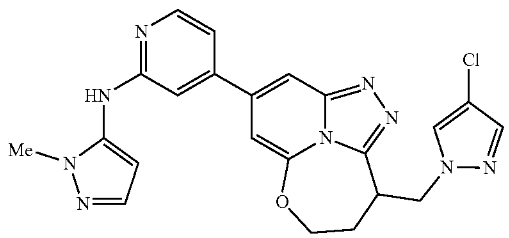 [SMILES: Cn1nccc1Nc1cc(-c2cc3n4c(nnc4c2)C(Cn2cc(Cl)cn2)CCO3)ccn1] | 462.2 462.2 | R S | <0.00002 0.000465 | 4-(9-((4-chloro-1H-pyrazol-1-yl)methyl)-8,9-dihydro-7H-6-oxa-1,2,2a[1]-triazabenzo[cd]azulen-4-yl)-N-(1-methyl-1H-pyrazol-5-yl)pyridin-2-amine |
| I-48 | 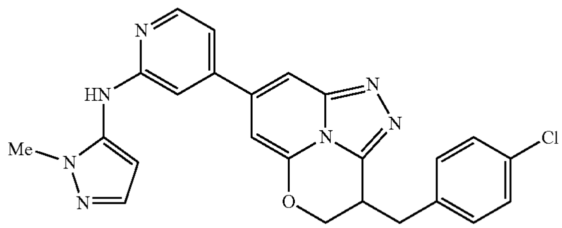 [SMILES: Cn1nccc1Nc1cc(-c2cc3n4c(nnc4c2)C(Cc2ccc(Cl)cc2)CO3)ccn1] | 458.2 458.2 | R S | <0.000020 0.0123 | 4-(3-(4-chlorobenzyl)-3,4-dihydro-5-oxa-1,2,2a[1]-triazaacenaphthylen-7-yl)-N-(1-methyl-1H-pyrazol-5-yl)pyridin-2-amine |
| I-49 | 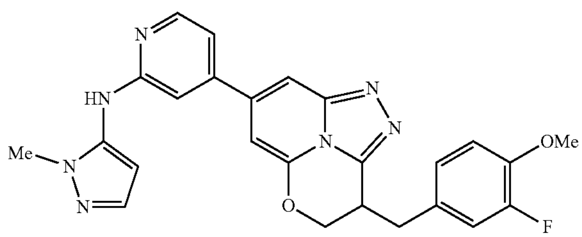 [SMILES: COc1ccc(CC2COc3cc(-c4ccnc(Nc5ccnn5C)c4)cc4nnc2n34)cc1F] | 472.2 472.2 | R S | <0.000020 0.00622 | 4-(3-(3-fluoro-4-methoxybenzyl)-3,4-dihydro-5-oxa-1,2,2a[1]-triazaacenaphthylen-7-yl)-N-(1-methyl-1H-pyrazol-5-yl)pyridin-2-amine |
| I-50 | 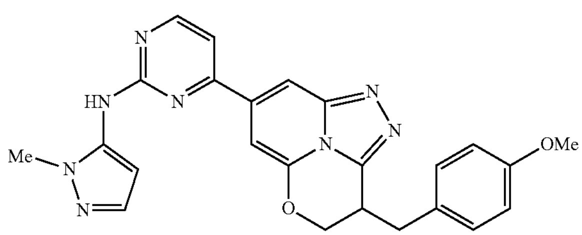 [SMILES: COc1ccc(CC2COc3cc(-c4ccnc(Nc5ccnn5C)n4)cc4nnc2n34)cc1] | 455.2 455.2 | R S | 0.000020 0.0071184 | 4-(3-(4-methoxybenzyl)-3,4-dihydro-5-oxa-1,2,2a[1]-triazaacenaphthylen-7-yl)-N-1-methyl-1H-yl)pyrimidin-2-amine |
| I-51 | 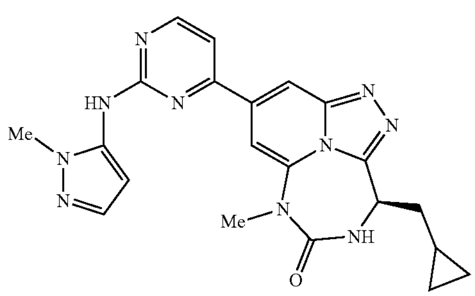 [SMILES: CN1C(=O)N[C@H](CC2CC2)c2nnc3cc(-c4ccnc(Nc5ccnn5C)n4)cc1n23] | 430.9 | | 0.00234 | (R)-9-(cyclopropylmethyl)-6-methyl-4-(2-((1-methyl-1H-pyrazol-5-yl)amino)pyrimidin-4-yl)-8,9-dihydro-1,2,2a[1],6,8-pentaazabenzo[cd]azulen-7(6H)-one |
| I-52 | 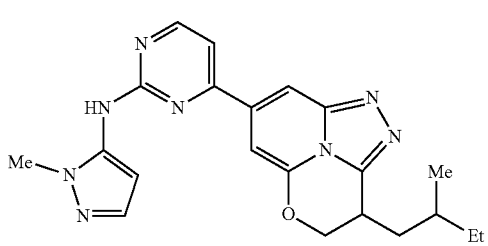 [SMILES: CCC(C)CC1COc2cc(-c3ccnc(Nc4ccnn4C)n3)cc3nnc1n23] | 405.2 405.2 | R S | <0.000020 0.0934 | N-(1-methyl-1H-pyrazol-5-yl)-4-(3-(2-methylbutyl)-3,4-dihydro-5-oxa-1,2,2a[1]-triazaacenaphthylen-7-yl)pyrimidin-2-amine |

TABLE I-continued

| STRUCTURE | MS[1] | R S[2] | ERK[3] IC$_{50}$ (μM) | NAME[4] |
|---|---|---|---|---|
| I-53 | 461.2 461.2 | R S | <0.000020 0.0113 | 4-(3-(3,4-difluorobenzyl)-3,4-dihydro-5-oxa-1,2,2a[1]-triazaacenaphthylen-7-yl)-N-(1-methyl-1H-pyrazol-5-yl)pyrimidin-2-amine |
| I-54 | 460.2 460.2 | R S | 0.00003 0.0223 | 4-(3-(3,4-difluorobenzyl)-3,4-dihydro-5-oxa-1,2,2a[1]-triazaacenaphthylen-7-yl)-N-(1-methyl-1H-pyrazol-5-yl)pyridin-2-amine |
| I-55 | 458.2 458.2 | S R | 0.0125 <0.000020 | 4-(3-(4-chlorobenzyl)-3,4-dihydro-5-oxa-1,2,2a[1]-triazaacenaphthylen-7-yl)-N-(1-methyl-1H-pyrazol-5-yl)pyridin-2-amine |
| I-56 | 469.2 469.2 | R S | <0.000020 0.00139 | 4-(9-((4-cyclopropyl-1H-pyrazol-1-yl)methyl)-8,9-dihydro-7H-6-oxa-1,2,2a[1]-triazabenzo[cd]azulen-4-yl)-N-(1-methyl-1H-pyrazol-5-yl)pyrimidin-2-amine |
| I-57 | 442.2 442.2 | R S | <0.000020 0.0114 | 4-(3-(4-fluorobenzyl)-3,4-dihydro-5-oxa-1,2,2a[1]-triazaacenaphthylen-7-yl)-N-(1-methyl-1H-pyrazol-5-yl)pyridin-2-amine |
| I-58 | 457.2 457.2 | R S | <0.000020 0.000311 | 4-(9-(4-fluorobenzyl)-8,9-dihydro-7H-6-oxa-1,2,2a[1]-triazabenzo[cd]azulen-4-yl)-N-(1-methyl-1H-pyrazol-5-yl)pyrimidin-2-amine |

TABLE I-continued

| STRUCTURE | MS[1] | R S[2] | ERK[3] IC$_{50}$ (μM) | NAME[4] |
|---|---|---|---|---|
| I-59 | 487.2<br>487.2 | R<br>S | <0.000020<br>0.00186 | 4-(9-(3-fluoro-4-methoxybenzyl)-8,9-dihydro-7H-6-oxa-1,2,2a[1]-triazabenzo[cd]azulen-4-yl)-N-(1-methyl-1H-pyrazol-5-yl)pyrimidin-2-amine |
| I-60 | 472<br>472 | R<br>S | 0.00255<br><0.000020 | 4-(9-(2-chlorobenzyl)-8,9-dihydro-7H-6-oxa-1,2,2a[1]-triazabenzo[cd]azulen-4-yl)-N-(1-methyl-1H-pyrazol-5-yl)pyridin-2-amine |
| I-61 | 465.1<br>465.1 | R<br>S | 0.000073<br>0.00583 | 9-benzyl-6-methyl-4-(2-((1-methyl-1H-pyrazol-5-yl)amino)pyridin-4-yl)-8,9-dihydro-1,2,2a[1],6-tetraazabenzo[cd]azulen-7(6H)-one |
| I-62 | 496.2<br>496.2 | R<br>S | <0.000020<br>0.044 | 9-(4-methoxybenzyl)-6-methyl-4-(2-((1-methyl-1H-pyrazol-5-yl)amino)pyrimidin-4-yl)-8,9-dihydro-1,2,2a[1],6-tetraazabenzo[cd]azulen-7(6H)-one |
| I-63 | 495.2<br>495.1 | R<br>S | <0.000020<br>0.00717 | 9-(4-methoxybenzyl)-6-methyl-4-(2-((1-methyl-1H-pyrazol-5-yl)amino)pyridin-4-yl)-8,9-dihydro-1,2,2a[1],6-tetraazabenzo[cd]azulen-7(6H)-one |

TABLE I-continued

| | STRUCTURE | MS[1] | R S[2] | ERK[3] IC$_{50}$ (μM) | NAME[4] |
|---|---|---|---|---|---|
| I-64 | 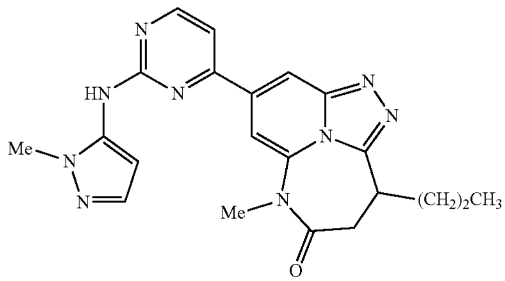 | 418.0 417.9 | S R | 0.000149 0.183 | 6-methyl-4-(2-((1-methyl-1H-pyrazol-5-yl)amino)pyrimidin-4-yl)-9-propyl-8,9-dihydro-1,2,2a[1],6-tetraazabenzo[cd]azulen-7(6H)-one |
| I-65 | 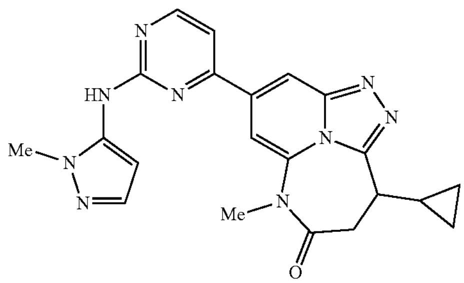 [SMILES: CN1C(=O)CC(C2CC2)c2nnc3cc(-c4ccnc(Nc5ccnn5C)n4)cc1n23] | 415.9 415.9 | R S | 0.00066 0.119 | 9-cyclopropyl-6-methyl-4-(2-((1-methyl-1H-pyrazol-5-yl)amino)pyrimidin-4-yl)-8,9-dihydro-1,2,2a[1],6-tetraazabenzo[cd]azulen-7(6H)-one |
| I-66 | 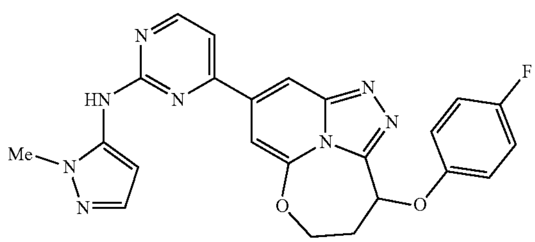 [SMILES: Cn1nccc1Nc1nccc(-c2cc3n4c(nnc4c2)C(Oc2ccc(F)cc2)CCO3)n1] | 459.2 459.2 | S R | 0.000020 0.00295 | 4-(9-(4-fluorophenoxy)-8,9-dihydro-7H-6-oxa-1,2,2a[1]-triazabenzo[cd]azulen-4-yl)-N-(1-methyl-1H-pyrazol-5-yl)pyrimidin-2-amine |
| I-67 | 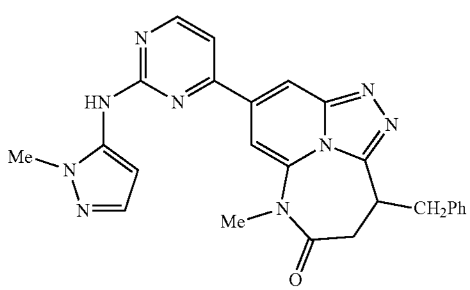 | 466.0 466.0 | S S | <0.000020 0.00649 | 9-benzyl-6-methyl-4-(2-((1-methyl-1H-pyrazol-5-yl)amino)pyrimidin-4-yl)-8,9-dihydro-1,2,2a[1],6-tetraazabenzo[cd]azulen-7(6H)-one |
| I-68 | 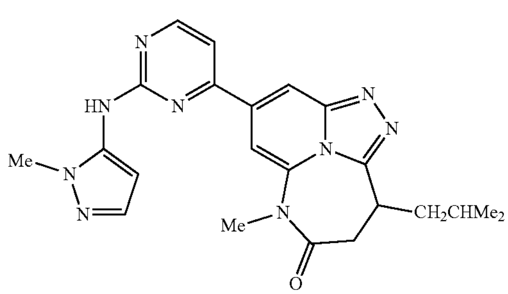 | 432.0 432.0 | R S | 0.000132 0.052 | 9-isobutyl-6-methyl-4-(2-((1-methyl-1H-pyrazol-5-yl)amino)pyrimidin-4-yl)-8,9-dihydro-1,2,2a[1],6-tetraazabenzo[cd]azulen-7(6H)-one |

TABLE I-continued

| | STRUCTURE | MS[1] | R S[2] | ERK[3] IC$_{50}$ (μM) | NAME[4] |
|---|---|---|---|---|---|
| I-69 | 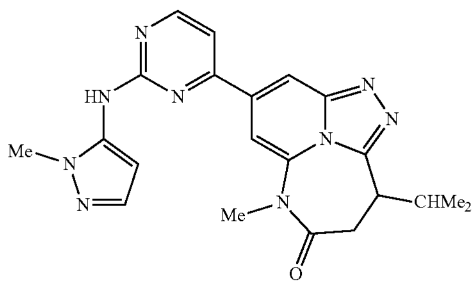 | 417.9 417.9 | R S | 0.000512 0.369 | 9-isopropyl-6-methyl-4-(2-((1-methyl-1H-pyrazol-5-yl)amino)pyrimidin-4-yl)-8,9-dihydro-1,2,2a[1],6-tetraazabenzo[cd]azulen-7(6H)-one |
| I-70 | 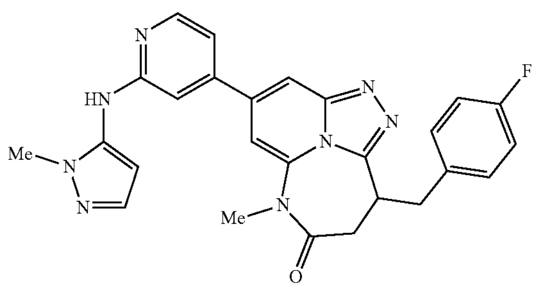 [SMILES: CN1C(=O)CC(Cc2ccc(F)cc2)c2nnc3cc(-c4ccnc(Nc5ccnn5C)c4)cc1n23] | 483.2 482.9 | R S | 0.000316 0.0172 | 9-(4-fluorobenzyl)-6-methyl-4-(2-((1-methyl-1H-pyrazol-5-yl)amino)pyridin-4-yl)-8,9-dihydro-1,2,2a[1],6-tetraazabenzo[cd]azulen-7(6H)-one |
| I-71 | 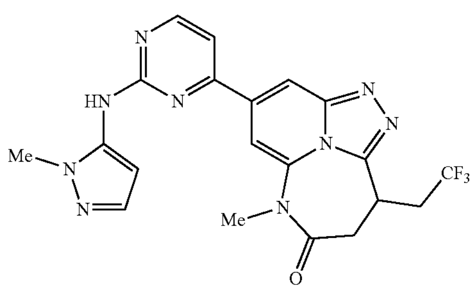 [SMILES: CN1C(=O)CC(CC(F)(F)F)c2nnc3cc(-c4ccnc(Nc5ccnn5C)n4)cc1n23] | 457.9 457.9 | R S | 0.000655 0.189 | 6-methyl-4-(2-((1-methyl-1H-pyrazol-5-yl)amino)pyrimidin-4-yl)-9-(2,2,2-trifluoroethyl)-8,9-dihydro-1,2,2a[1],6-tetraazabenzo[cd]azulen-7(6H)-one |
| I-72 | 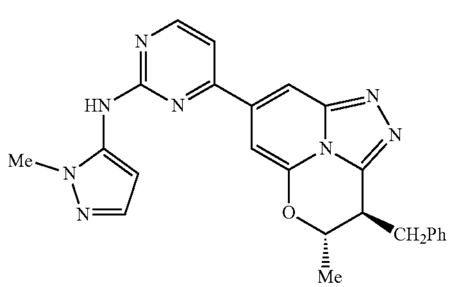 | 439.2 439.2 | 3R 4S 3S 4R | <0.000020 0.00155 | 4-(3-benzyl-4-methyl-3,4-dihydro-5-oxa-1,2,2a[1]-triazaacenaphthylen-7-yl)-N-(1-methyl-1H-pyrazol-5-yl)pyrimidin-2-amine |
| I-73 | 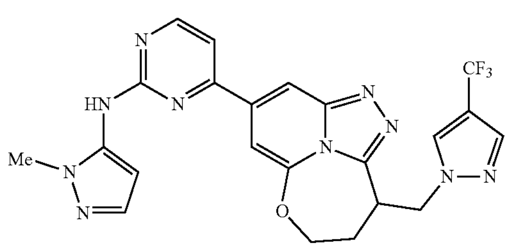 [SMILES: Cn1nccc1Nc1nccc(-c2cc3n4c(nnc4c2)C(Cn2cc(C(F)(F)F)cn2)CCO3)n1] | 497.2 497.2 | R S | <0.000020 | N-(1-methyl-1H-pyrazol-5-yl)-4-(9-((4-(trifluoromethyl)-1H-pyrazol-1-yl)methyl)-8,9-dihydro-7H-6-oxa-1,2,2a[1]-triazabenzo[cd]azulen-4-yl)pyrimidin-2-amine |

TABLE I-continued

| STRUCTURE | | MS[1] | R S[2] | ERK[3] IC$_{50}$ (μM) | NAME[4] |
|---|---|---|---|---|---|
| I-74 | 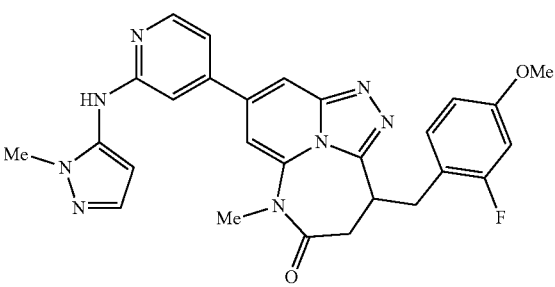 [SMILES: COc1ccc(CC2CC(=O)N(C)c3cc(-c4ccnc(Nc5ccnn5C)c4)cc4nnc2n34)c(F)c1] | 513.1 513.0 | R S | <0.000020 0.00285 | 9-(2-fluoro-4-methoxybenzyl)-6-methyl-4-(2-((1-methyl-1H-pyrazol-5-yl)amino)pyridin-4-yl)-8,9-dihydro-1,2,2a[1],6-tetraazabenzo[cd]azulen-7(6H)-one |
| I-75 | 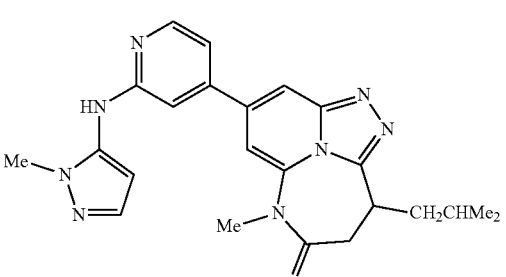 | 431.1 431.1 | R S | 0.00322 0.718 | 9-isobutyl-6-methyl-4-(2-((1-methyl-1H-pyrazol-5-yl)amino)pyridin-4-yl)-8,9-dihydro-1,2,2a[1],6-tetraazabenzo[cd]azulen-7(6H)-one |
| I-76 | 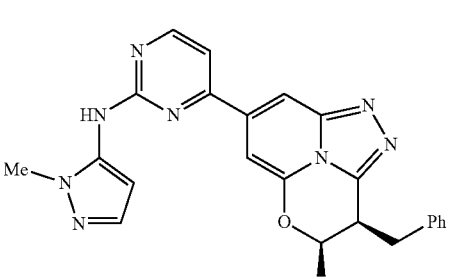 | 439.2 439.2 | 3R 4R 3S 4S | <0.000020 0.00047 | 4-(3-benzyl-4-methyl-3,4-dihydro-5-oxa-1,2,2a[1]-triazaacenaphthylen-7-yl)-N-(1-methyl-1H-pyrazol-5-yl)pyrimidin-2-amine |
| I-77 | 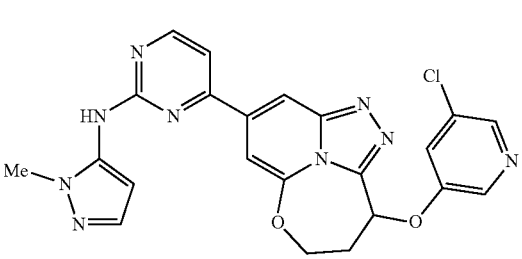 [SMILES: Cn1nccc1Nc1nccc(-c2cc3n4c(nnc4c2)C(Oc2cncc(Cl)c2)CCO3)n1] | 476.1 476.1 | R S | 0.000311 <0.000020 | 4-(9-((5-chloropyridin-3-yl)oxy)-8,9-dihydro-7H-6-oxa-1,2,2a[1]-triazabenzo[cd]azulen-4-yl)-N-(1-methyl-1H-pyrazol-5-yl)pyrimidin-2-amine |
| I-78 | 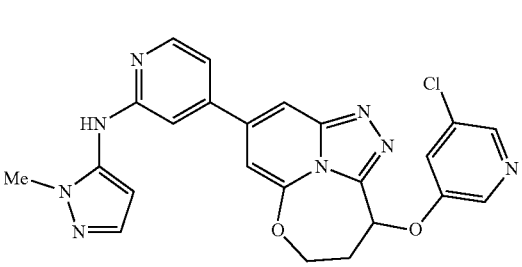 [SMILES: Cn1nccc1Nc1cc(-c2cc3n4c(nnc4c2)C(Oc2cncc(Cl)c2)CCO3)ccn1] | 475.1 475.1 | R S | 0.00461 <0.000020 | 4-(9-((5-chloropyridin-3-yl)oxy)-8,9-dihydro-7H-6-oxa-1,2,2a[1]-triazabenzo[cd]azulen-4-yl)-N-(1-methyl-1H-pyrazol-5-yl)pyridin-2-amine |

TABLE I-continued

| STRUCTURE | MS[1] | R S[2] | ERK[3] IC$_{50}$ (μM) | NAME[4] |
|---|---|---|---|---|
| I-79 | 484.0 484.0 | R S | 0.017 | 9-(4-fluorobenzyl)-6-methyl-4-(2-((1-methyl-1H-pyrazol-5-yl)amino)pyrimidin-4-yl)-8,9-dihydro-1,2,2a[1],6-tetraazabenzo[cd]azulen-7(6H)-one |
| I-80 | 458.8 | | <0.000020 | (S)-9-(3-chlorobenzyl)-6-methyl-4-(2-((1-methyl-1H-pyrazol-5-yl)amino)pyrimidin-4-yl)-8,9-dihydro-1,2,2a[1],6-tetraazabenzo[cd]azulen-7(6H)-one |
| I-81 | 454.9 | R | <0.000020 | 4-(3-(3-methoxybenzyl)-3,4-dihydro-5-oxa-1,2,2a[1]-triazaacenaphthylen-7-yl)-N-(1-methyl-1H-pyrazol-5-yl)pyrimidin-2-amine |
| I-82 | 476.9 476.8 | R S | 0.0006 0.0124 | 4-(3-(3-chloro-4-fluorobenzyl)-3,4-dihydro-5-oxa-1,2,2a[1]-triazaacenaphthylen-7-yl)-N-(1-methyl-1H-pyrazol-5-yl)pyrimidin-2-amine |
| I-83 | 475.9 | R | 0.000111 | 4-(3-(3-chloro-4-fluorobenzyl)-3,4-dihydro-5-oxa-1,2,2a[1]-triazaacenaphthylen-7-yl)-N-(1-methyl-1H-pyrazol-5-yl)pyridin-2-amine |

TABLE I-continued

| STRUCTURE | MS[1] | R S[2] | ERK[3] IC$_{50}$ (μM) | NAME[4] |
|---|---|---|---|---|
| I-84 | 500.9 500.9 | R S | 0.000102 0.0327 | 9-((5-chloropyridin-2-yl)methyl)-6-methyl-4-(2-((1-methyl-1H-pyrazol-5-yl)amino)pyrimidin-4-yl)-8,9-dihydro-1,2,2a[1],6-tetraazabenzo[cd]azulen-7(6H)-one |
| I-85 | 514.0 514.0 | R S | <0.000020 0.0259 | 9-(2-fluoro-4-methoxybenzyl)-6-methyl-4-(2-((1-methyl-1H-pyrazol-5-yl)amino)pyrimidin-4-yl)-8,9-dihydro-1,2,2a[1],6-tetraazabenzo[cd]azulen-7(6H)-one |
| I-86 | 457.2 457.2 | R S | 0.009 0.212 | 6-methyl-4-(2-((1-methyl-1H-pyrazol-5-yl)amino)pyridin-4-yl)-9-(2,2,2-trifluoroethyl)-8,9-dihydro-1,2,2a[1],6-tetraazabenzo[cd]azulen-7(6H)-one |
| I-87 | 417.3 417.2 | R S | 0.00694 1 | 9-isopropyl-6-methyl-4-(2-((1-methyl-1H-pyrazol-5-yl)amino)pyridin-4-yl)-8,9-dihydro-1,2,2a[1],6-tetraazabenzo[cd]azulen-7(6H)-one |
| I-88 | 458.8 458.8 | S R | 0.00636 <0.000020 | 4-(3-(3-chlorobenzyl)-3,4-dihydro-5-oxa-1,2,2a[1]-triazaacenaphthylen-7-yl)-N-(1-methyl-1H-pyrazol-5-yl)pyrimidin-2-amine |

TABLE I-continued

| | STRUCTURE | MS[1] | R S[2] | ERK[3] IC$_{50}$ (μM) | NAME[4] |
|---|---|---|---|---|---|
| I-89 | 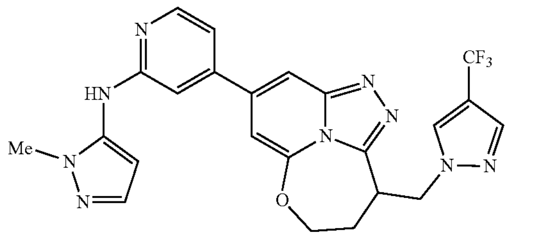 | 496.2 496.2 | R S | <0.000020 0.00231 | N-(1-methyl-1H-pyrazol-5-yl)-4-(9-((4-(trifluoromethyl)-1H-pyrazol-1-yl)methyl)-8,9-dihydro-7H-6-oxa-1,2,2a[1]-triazabenzo[cd]azulen-4-yl)pyridin-2-amine |
| I-90 | 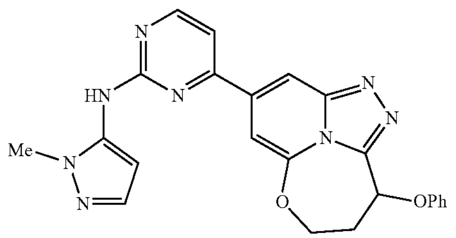 | 441.2 441.2 | S R | <0.000020 0.000942 | N-(1-methyl-1H-pyrazol-5-yl)-4-(9-phenoxy-8,9-dihydro-7H-6-oxa-1,2,2a[1]-triazabenzo[cd]azulen-4-yl)pyrimidin-2-amine |
| I-91 | 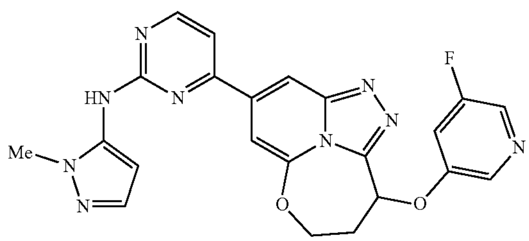 [SMILES: Cn1nccc1Nc1nccc(-c2cc3n4c(nnc4c2)C(Oc2cncc(F)c2)CCO3)n1] | 460.2 460.2 | S R | 0.000035 0.0258 | 4-(9-((5-fluoropyridin-3-yl)oxy)-8,9-dihydro-7H-6-oxa-1,2,2a[1]-triazabenzo[cd]azulen-4-yl)-N-(1-methyl-1H-pyrazol-5-yl)pyrimidin-2-amine |
| I-92 | 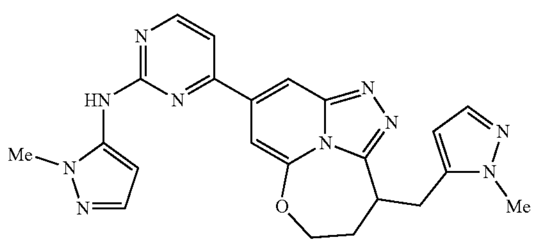 [SMILES: Cn1nccc1CC1CCOc2cc(-c3ccnc(Nc4ccnn4C)n3)cc3nnc1n23] | 443.2 443.2 | R S | 0.00242 0.000085 | N-(1-methyl-1H-pyrazol-5-yl)-4-(9-((1-methyl-1H-pyrazol-5-yl)methyl)-8,9-dihydro-7H-6-oxa-1,2,2a[1]-triazabenzo[cd]azulen-4-yl)pyrimidin-2-amine |
| I-93 | 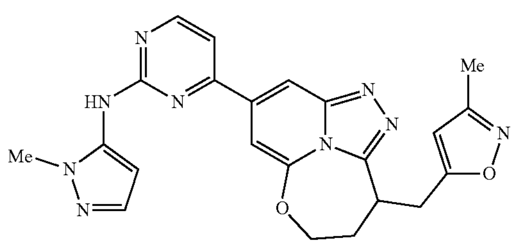 [SMILES: Cc1cc(CC2CCOc3cc(-c4ccnc(Nc5ccnn5C)n4)cc4nnc2n34)on1] | 444 444 | S R | 0.0182 <0.000020 | N-(1-methyl-1H-pyrazol-5-yl)-4-(9-((3-methylisoxazol-5-yl)methyl)-8,9-dihydro-7H-6-oxa-1,2,2a[1]-triazabenzo[cd]azulen-4-yl)pyrimidin-2-amine |
| I-94 | 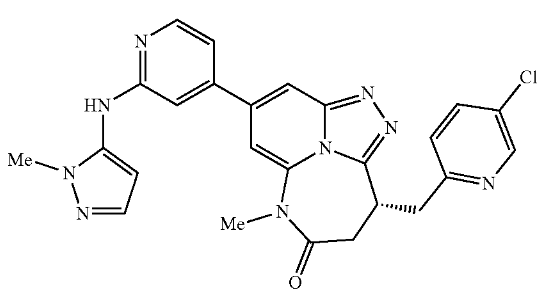 [SMILES: CN1C(=O)C[C@@H](Cc2ccc(Cl)cn2)c2nnc3cc(-c4ccnc(Nc5ccnn5C)c4)cc1n23] | 499.9 | R | 0.598 | (R)-9-((5-chloropyridin-2-yl)methyl)-6-methyl-4-(2-((1-methyl-1H-pyrazol-5-yl)amino)pyridin-4-yl)-8,9-dihydro-1,2,2a[1],6-tetraazabenzo[cd]azulen-7(6H)-one |

TABLE I-continued

| STRUCTURE | MS[1] | R S[2] | ERK[3] IC$_{50}$ (μM) | NAME[4] |
|---|---|---|---|---|
| I-95 | 374.8 | | 0.000751 | 4-(3-cyclopropyl-3,4-dihydro-5-oxa-1,2,2a[1]-triazaacenaphthylen-7-yl)-N-(1-methyl-1H-pyrazol-5-yl)pyrimidin-2-amine |
| I-96 | 457.9 | | 0.000149 | 4-(3-(3-chlorobenzyl)-3,4-dihydro-5-oxa-1,2,2a[1]-triazaacenaphthylen-7-yl)-N-(1-methyl-1H-pyrazol-5-yl)pyridin-2-amine |
| I-97 | 453.9 453.9 | R S | <0.000020 0.000794 | 4-(3-(3-methoxybenzyl)-3,4-dihydro-5-oxa-1,2,2a[1]-triazaacenaphthylen-7-yl)-N-(1-methyl-1H-pyrazol-5-yl)pyridin-2-amine |
| I-98 | 487.0 | | 0.000273 | 3-(4-chlorobenzyl)-5-methyl-7-(2-((1-methyl-1H-pyrazol-5-yl)amino)pyrimidin-4-yl)-3H-1,2,2a[1],3,5-pentaazaacenaphthylen-4(5H)-one |
| I-99 | 488.9 | | 0.000113 | 3-(3,5-difluorobenzyl)-5-methyl-7-(2-((1-methyl-1H-pyrazol-5-yl)amino)pyrimidin-4-yl)-3H-1,2,2a[1],3,5-pentaazaacenaphthylen-4(5H)-one |

TABLE I-continued

| | STRUCTURE | MS[1] | R S[2] | ERK[3] IC$_{50}$ (µM) | NAME[4] |
|---|---|---|---|---|---|
| I-100 | 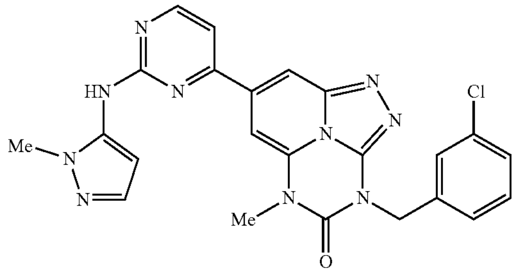 [SMILES: CN1C(=O)N(Cc2cccc(Cl)c2)c2nnc3cc(-c4ccnc(Nc5ccnn5C)n4)cc1n23] | 486.9 | | <0.000020 | 3-(3-chlorobenzyl)-5-methyl-7-(2-((1-methyl-1H-pyrazol-5-yl)amino)pyrimidin-4-yl)-3H-1,2,2a[1],3,5-pentaazaacenaphthylen-4(5H)-one |
| I-101 | 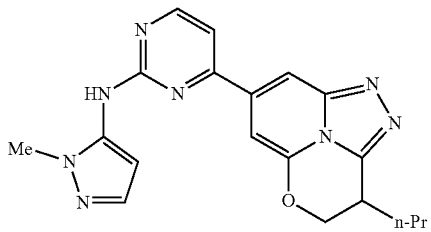 | 377 377 | S R | 0.0195 0.000038 | N-(1-methyl-1H-pyrazol-5-yl)-4-(3-propyl-3,4-dihydro-5-oxa-1,2,2a[1]-triazaacenaphthylen-7-yl)pyrimidin-2-amine |
| I-102 | 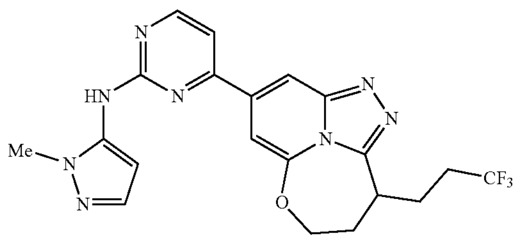 [SMILES: Cn1nccc1Nc1nccc(-c2cc3n4c(nnc4c2)C(CCC(F)(F)F)CCO3)n1] | 445 445 | R S | 0.0017 0.000025 | N-(1-methyl-1H-pyrazol-5-yl)-4-(9-(3,3,3-trifluoropropyl)-8,9-dihydro-7H-6-oxa-1,2,2a[1]-triazabenzo[cd]azulen-4-yl)pyrimidin-2-amine |
| I-103 | 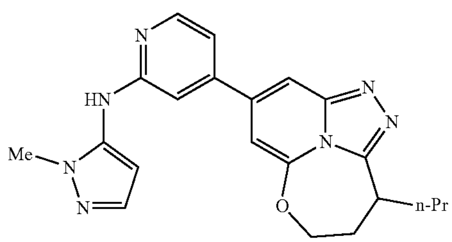 | 390 390 | R S | 0.00277 0.000026 | N-(1-methyl-1H-pyrazol-5-yl)-4-(9-propyl-8,9-dihydro-7H-6-oxa-1,2,2a[1]-triazabenzo[cd]azulen-4-yl)pyridin-2-amine |
| I-104 | 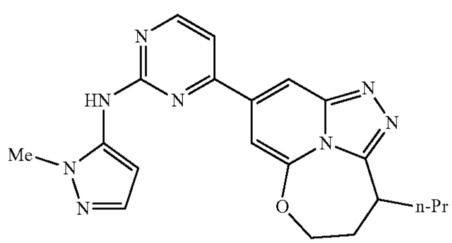 | 391 391 | R S | 0.0023 <0.00002 | N-(1-methyl-1H-pyrazol-5-yl)-4-(9-propyl-8,9-dihydro-7H-6-oxa-1,2,2a[1]-triazabenzo[cd]azulen-4-yl)pyrimidin-2-amine |
| I-105 | 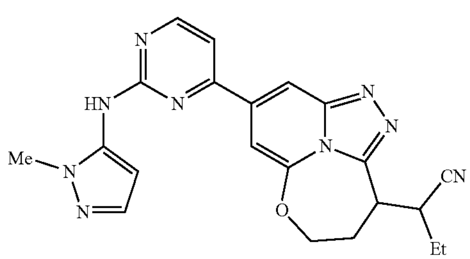 [SMILES: CCC(C#N)C1CCOc2cc(-c3ccnc(Nc4ccnn4C)n3)cc3nnc1n23] | 416 416 | S S | <0.00002 0.000082 | (S)-2-[4-(2-((1-methyl-1H-pyrazol-5-yl)amino)pyrimidin-4-yl)]-8,9-dihydro-7H-6-oxa-1,2,2a[1]-triazabenzo[cd]azulen-9-yl)butanenitrile |

TABLE I-continued

| STRUCTURE | MS[1] | R S[2] | ERK[3] IC$_{50}$ (μM) | NAME[4] |
|---|---|---|---|---|
| I-106 | 431<br>431 | S<br>R | 0.000168<br>0.000088 | N-(1-methyl-1H-pyrazol-5-yl)-4-(9-(2,2,2-trifluoroethyl)-8,9-dihydro-7H-6-oxa-1,2,2a[1]-triazabenzo[cd]azulen-4-yl)pyrimidin-2-amine |
| I-107 | 405<br>405 | R<br>S | 0.00185<br>0.000023 | 4-(9-isobutyl-8,9-dihydro-7H-6-oxa-1,2,2a[1]-triazabenzo[cd]azulen-4-yl)-N-(1-methyl-1H-pyrazol-5-yl)pyrimidin-2-amine |
| I-108 | 459<br>459 | R<br>S | 0.00295<br><0.000020 | 4-(9-(4-fluorophenoxy)-8,9-dihydro-7H-6-oxa-1,2,2a[1]-triazabenzo[cd]azulen-4-yl)-N-(1-methyl-1H-pyrazol-5-yl)pyrimidin-2-amine |
| I-109 | 460<br>460 | S<br>R | 0.000103<br><0.000020 | N-(1-methyl-1H-pyrazol-5-yl)-4-(9-((4-methylthiazol-2-yl)methyl)-8,9-dihydro-7H-6-oxa-1,2,2a[1]-triazabenzo[cd]azulen-4-yl)pyrimidin-2-amine |
| I-110 | 466<br>466 | R<br>S | <0.000020<br>0.00014 | 4-(9-((4-chloro-1H-pyrazol-1-yl)methyl)-8,9-dihydro-7H-6-oxa-1,2,2a[1]-triazabenzo[cd]azulen-4-yl)-N-(tetrahydro-2H-pyran-4-yl)pyrimidin-2-amine |
| I-111 | 477<br>477 | S<br>R | <0.000020<br>0.0026 | 4-(9-(3,4-difluorophenoxy)-8,9-dihydro-7H-6-oxa-1,2,2a[1]-triazabenzo[cd]azulen-4-yl)-N-(1-methyl-1H-pyrazol-5-yl)pyrimidin-2-amine |

1. MS [M + H]$^+$
2. Configuration of CR$^2$R$^3$
3. ERK Inhibitor Assay-Biological Example 1
4. Name generated by ChemBioDraw Ultra 12.0

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's *Reagents for Organic Synthesis*; Wiley & Sons: New York, Volumes 1-21; R. C. LaRock, *Comprehensive Organic Transformations*, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, or, about 20° C.

Some compounds in following schemes are depicted with generalized substituents; however, one skilled in the art will immediately appreciate that the nature of the R groups can varied to afford the various compounds contemplated in this invention. Moreover, the reaction conditions are exemplary and alternative conditions are well known. The reaction sequences in the following examples are not meant to limit the scope of the invention as set forth in the claims.

SCHEME A

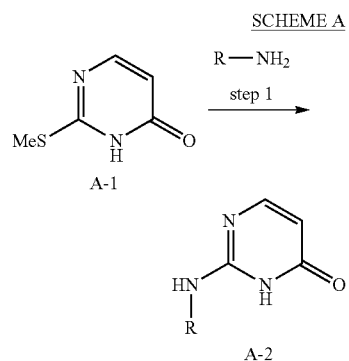

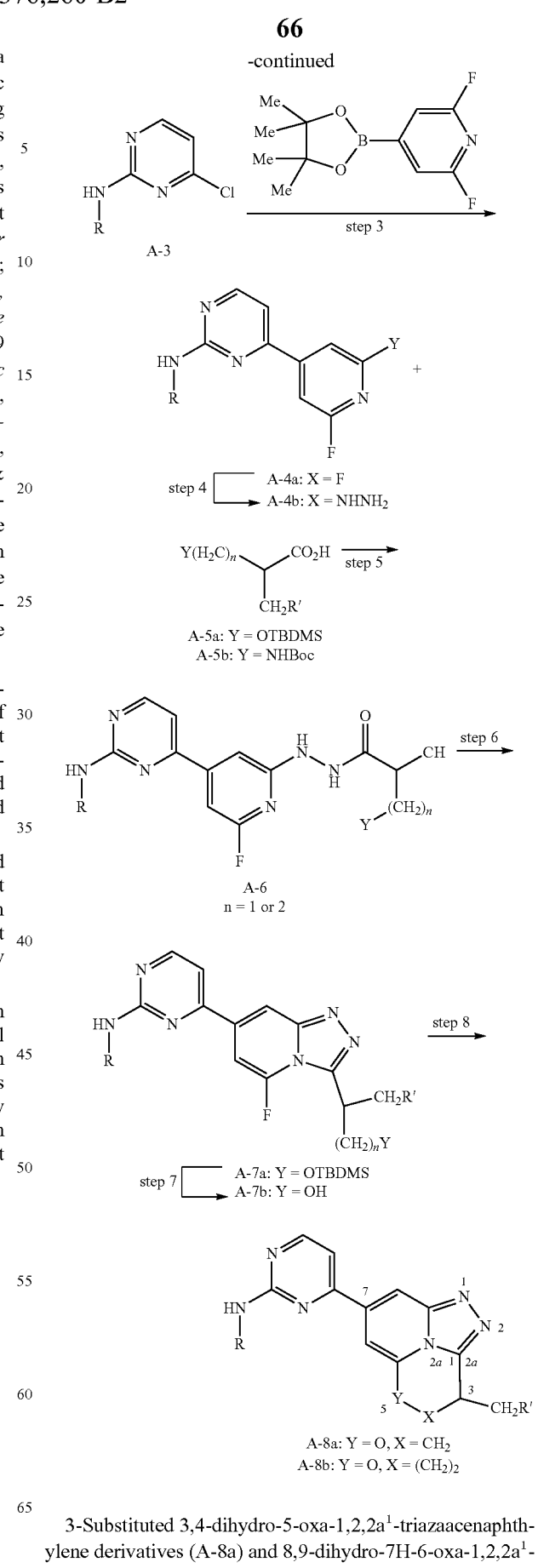

3-Substituted 3,4-dihydro-5-oxa-1,2,2a[1]-triazaacenaphthylene derivatives (A-8a) and 8,9-dihydro-7H-6-oxa-1,2,2a[1]- triazabenzo[cd]azulenes) (A-8b) can be prepared by condensation of 4-(2-fluoro-6-hydrazinylpyridin-4-yl) pyrimidin-2-amine derivative (A-4b) with a suitably protected β- or γ-hydroxyacid in the presence of a condensation catalyst. While HATU is convenient, protocols for condensation of amines and carboxylic acids have been extensively optimized for peptide synthesis and other equivalent procedures would be familiar to one skilled in the art.

The conventional synthesis of triazolopyridines involves the dehydration of a 2-hydrazidopyridine using refluxing phosphorus oxychloride, concentrated HCl or refluxing HOAc which are relatively harsh conditions incompatible with many functional groups. Modified Mitsunobu conditions have been successfully applied to synthesis of triazolopyridines and triazolopyrimidines (J. Y. Roberge et al., Arkivoc 2007 (xii):132-147). Cyclization with $Cl_2PPh_3$ has been reported to afford [1,2,4]triazolo[4,3-a]pyridines in good yield. (H. Warmhoff and M. Zahran, Synthesis 1987 876; J. M. Cid et al., J. Med. Chem. 2012 55:8770). Herein we use the in situ formation of triphenylphosphine dibromide to drive dehydrative cyclization of the acyl hydrazine intermediate to afford A-6. Desilylation of the primary alcohol and treatment with base results in displacement of the fluoride to afford oxa-triazaacenaphthalene A-8.

Hydroxy acids are prepared as disclosed in SCHEME B. The requisite β-hydroxy acids are readily available by alkylation of the diethyl malonate with benzyl halides, alkyl halides and the like to afford substituted malonate diesters. Selective hydrolysis affords the half ester which is reduced with $LiBH_4$ to afford an α-substituted β-hydroxy acid B-3. The requisite γ-hydroxy acids were prepared by alkylation of butryolactone and subsequent saponification and silylation liberated hydroxyl group. Alternatively 2-bromobutyrolactone can be converted to diethyl (2-oxo-tetrahydro-furan-3-yl)-phosphonate and condensed with the requisite aldehyde to afford an olefin which can be hydrogenated to afford B-5. 3-Aryloxy and 2-heteroaryloxy-4-hydroxy-butanoic acids were prepared by a Williamson ether synthesis using 2-bromobutyrolactone and appropriate phenol.

A variation (SCHEME C) of the intra-molecular cyclization of A-7b utilizes a 2-step process comprising converting the primary alcohol to the corresponding bromide (or other leaving group) and adding a bivalent nucleophile such as $Na_2S$ to displace the bromide and fluoride atom and introduce the new ring.

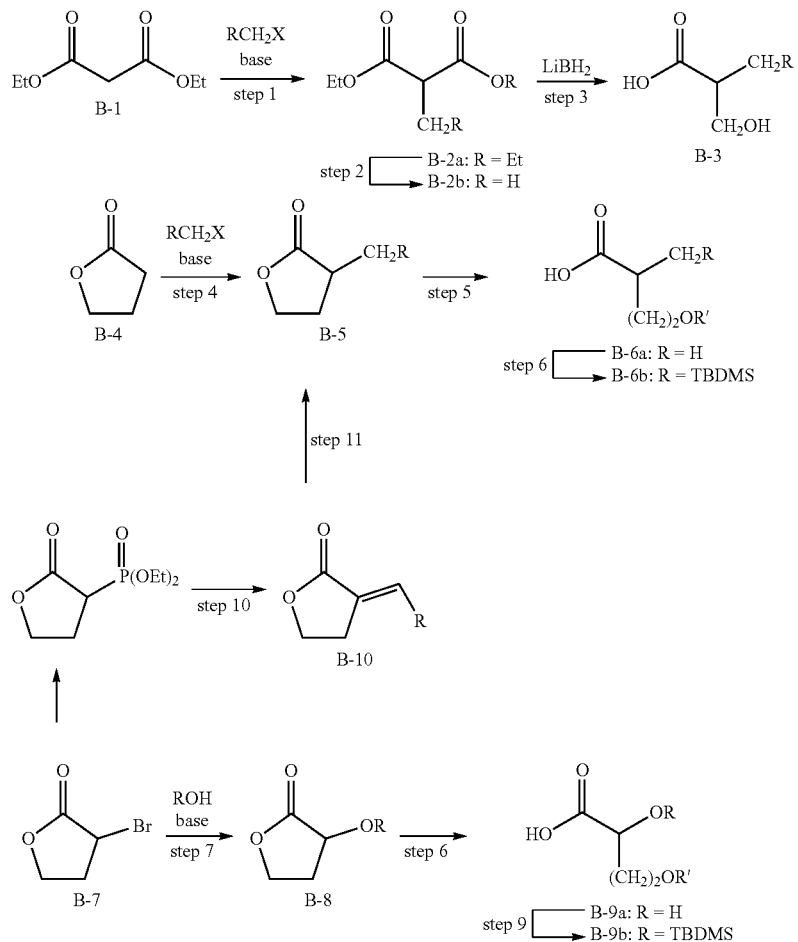

SCHEME B

SCHEME C

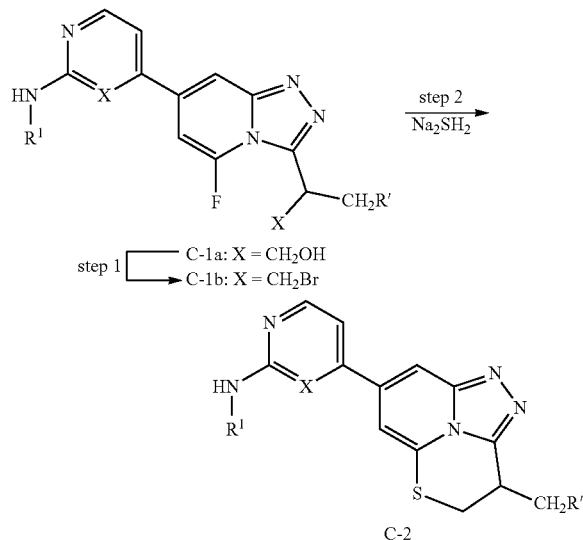

A two-step process to form tricyclic F-lactams comprises synthesis of a 5-fluorotriazolopyridine core with a substituted propanoic acid side chain followed by displacement of the fluoride with ammonia or a primary amine followed by condensation of the amine with the pendant carboxylic acid SCHEMED. The requisite starting material D-1 is prepared by a process analogous sequence depicted in SCHEME A wherein the N-protected β- or γ-amino acid is replaced by a 4-tert-butyl 2-substituted-succinate. Displacement of the fluoride by ammonia or a primary amine affords D-2a (R'''=H or Me respectively). The tert-butyl ester is hydrolyzed and the resulting amino acid D-2b cyclized to D-3. One skilled in the art will appreciate that the corresponding δ-lactam can be prepared analogously from a substituted malonic acid.

SCHEME D

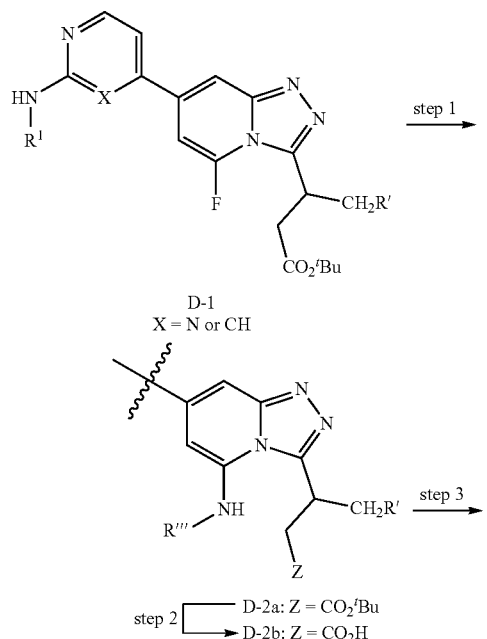

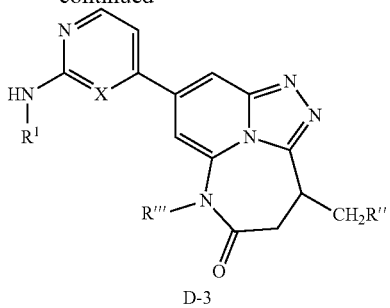

3,5-Dihydro-1,2,3,5,8b-pentaaza-acenaphthylen-4-one (E-5) and 8,9-dihydro-6H-1,2,6,8,9b-pentaaza-benzo[cd]azulen-7-one (E-6) are prepared as depicted in SCHEME E. The six-member ureas are prepared by condensation of the hydrazine A-4b with an isocyanate to afford E-2 which is cyclized as to afford the triazolopyridine E-3 which is treated with ammonia or a primary amine to afford E-4. Cyclization with carbonyl diimidazole affords the urea. The sequence allows selective introduction of substituents on each nitrogen of the urea. The seven-member ureas E-8 are prepared by condensation with an N-protected α-amino acid which is subjected to condensation with the hydrazine and cyclization to afford E-6 which is converted to the urea by displacement of the fluoride as described above. When compounds wherein R'' is methyl are desired, the requisite N-methyl N-Boc-α-amino acids are commercially available or readily prepared.

SCHEME E

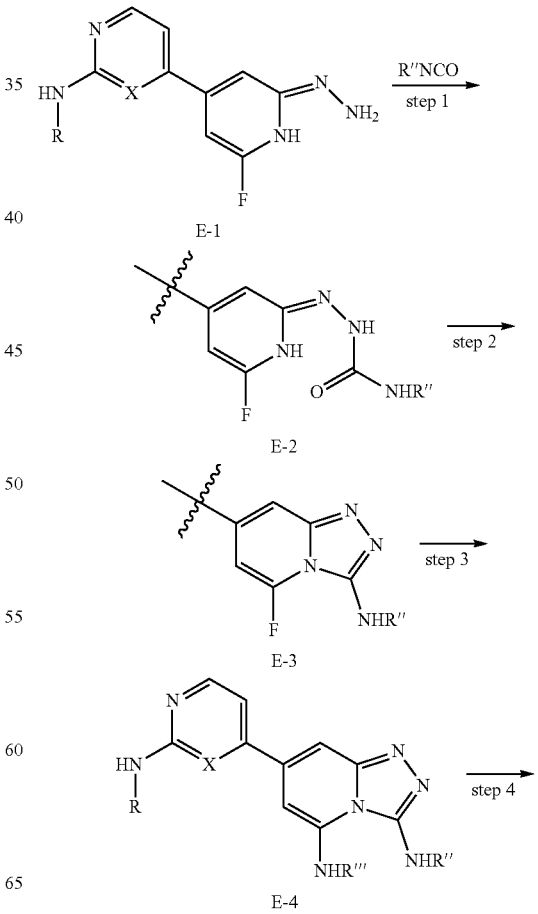

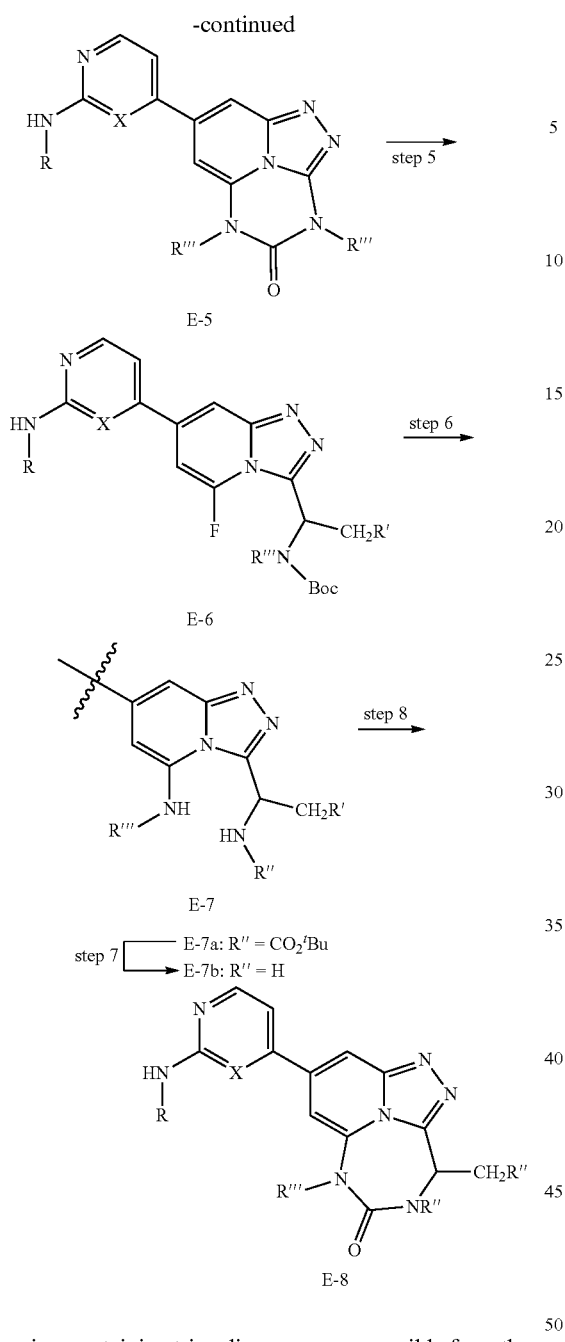

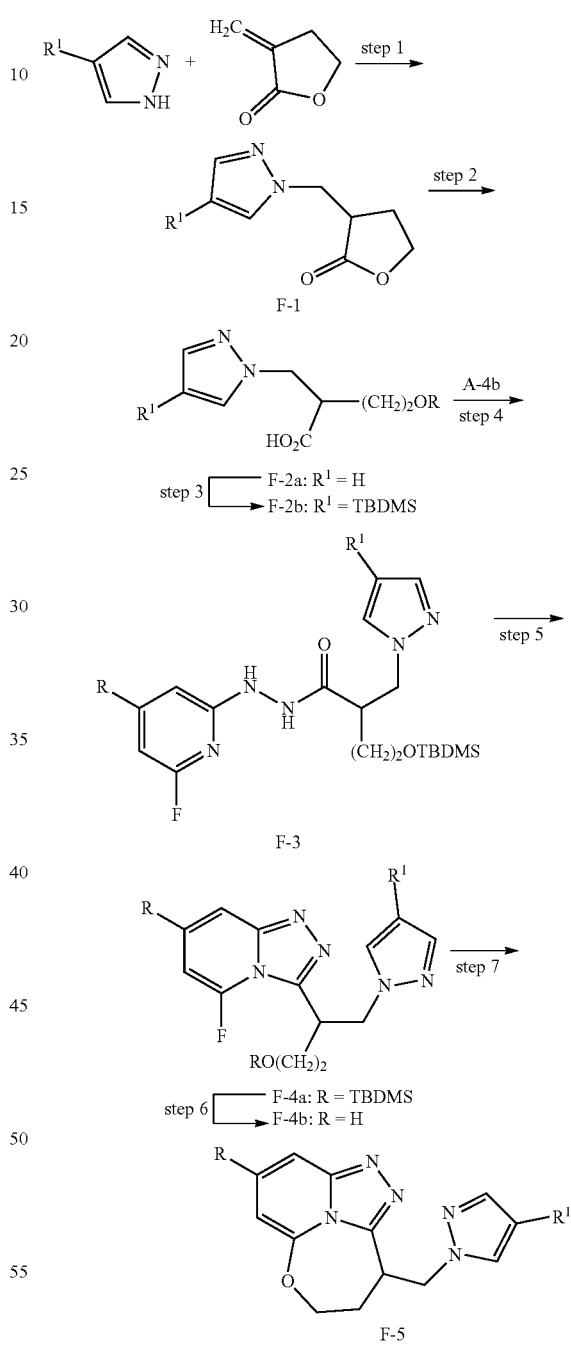

[1,2,4]triazolo[4,3-a]pyridine core, deprotection and finally displacement of the fluoride to introduce the oxepine proceeds as described above.

Oxepine-containing tricyclic cores are accessible from the corresponding γ-hydroxy carboxyl acids. Compounds containing a 1-pyrazolyl or 1-imidazolyl linkage can be prepared by Michael Addition of a nucleophile to 3-methylenedihydrofuran-2(3H)-one (SCHEME F, step 1). Alkylation of γ-butyrolactone with alkyl halides or benzyl halides affords useful 2-substituted-4-hyroxybutanoic acid intermediates. Alternatively 2-bromo-γ-butyrolactone can be displaced with phenols (SCHEME G, step 1) to afford analogs wherein substituent at C-9 is attached with an ether linkage. One skilled in the art will quickly appreciate that addition of an alcohol or phenol to 3-methylenedihydrofuran-2(3H)-one will afford ether containing side chains (TABLE I, I-29) After protection of the hydroxyl group, condensation with the hydrazone, cyclization to form the 9-Aryloxy- or heteroaryloxy-)-8,9-dihydro-7H-6-oxa-1,2,2a$^1$-triazabenzo[cd]azulen-4-yl analogs are prepared from optionally substituted 2-aryloxy-3-hydroxybutanoic derivatives or optionally substituted 2-heteroaryloxy-3-hydroxybutanoic derivatives as depicted in SCHEME G.

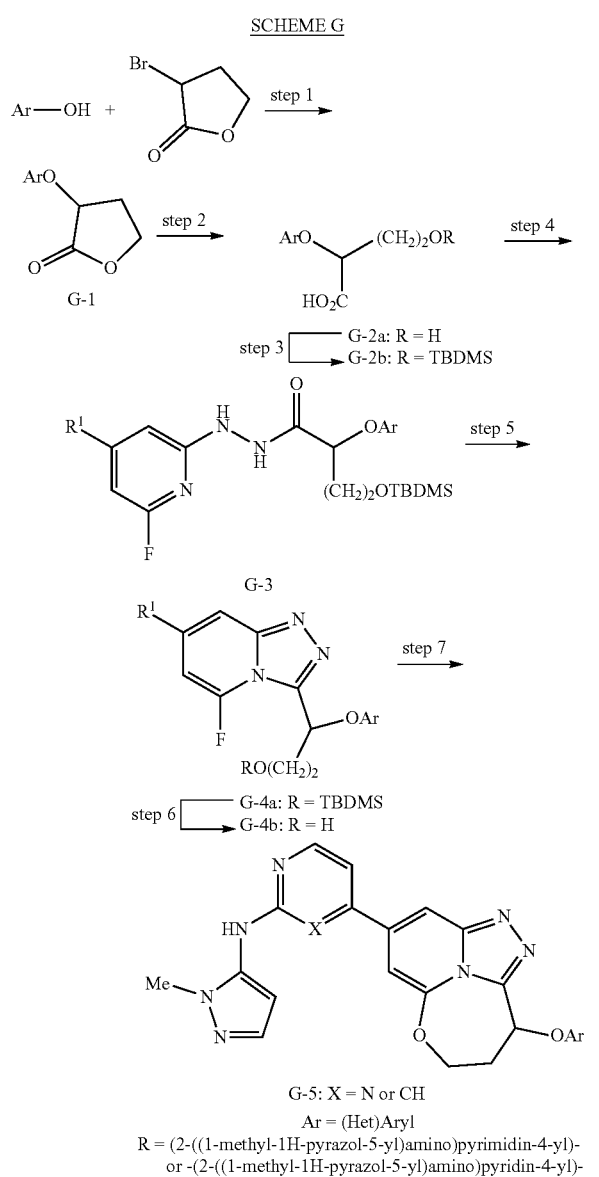

SCHEME G

G-5: X = N or CH
Ar = (Het)Aryl
R = (2-((1-methyl-1H-pyrazol-5-yl)amino)pyrimidin-4-yl)-
or -(2-((1-methyl-1H-pyrazol-5-yl)amino)pyridin-4-yl)-

Biological Activity

Determination of the activity of ERK activity of a compound of formula I is possible by a number of direct and indirect detection methods. Certain exemplary compounds described herein were assayed for their ERK inhibition assay (Biological Example 1). The range of ERK binding activities was less than 1 nM (nanomolar) to about 10 M (micromolar). A cell-based function assay (Biological Example 2) was used to determine the effect of ERK inhibitors on down-stream signaling by assaying phosphorylation of P90RSK.

The cytotoxic or cytostatic activity of formula I exemplary compounds was measured by establishing a proliferating mammalian tumor cell line in a cell culture medium, adding a formula I compound, culturing the cells for a period from about 6 h to about 5 d; and measuring cell viability (Biological Example 2). Cell-based in vitro assays were used to measure viability, i.e. proliferation ($IC_{50}$), cytotoxicity ($EC_{50}$).

Dosage & Administration

The present invention provides pharmaceutical compositions or medicaments containing the compounds of the invention and at least one therapeutically inert carrier, diluent or excipient, as well as methods of using the compounds of the invention to prepare such compositions and medicaments. In one example, compounds of Formula I with the desired degree of purity may be formulated by mixing with physiologically acceptable carriers, i.e., carriers that are non-toxic to recipients at the dosages and concentrations employed into a dosage form at ambient temperature and at the appropriate pH. The pH of the formulation depends mainly on the particular use and the concentration of compound, but typically ranges anywhere from about 3 to about 8. In one example, a compound of Formula I is formulated in an acetate buffer, at pH 5. In another embodiment, the compounds of Formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the severity of the disorder, the particular patient being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit ERK activity. Typically such amount may be below the amount that is toxic to normal cells, or the patient as a whole.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Sustained-release preparations may be prepared. Suitable examples of sustained-release preparations include semipermeable matrices of solid hydrophobic polymers containing a compound of Formula I, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides, copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

A dose to treat human patients may range from about 0.1 mg to about 1000 mg of a compound of formula I. A typical dose may be about 1 mg to about 300 mg of the compound. A dose may be administered once a day (QD), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal, epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, H. C., et al., Ansel's *Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, R. C., *Handbook of Pharmaceutical Excipients*, Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

For oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

An example of a suitable oral dosage form is a tablet containing about 25 mg, 50 mg, 100 mg, 250 mg or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such as sodium chloride, if desired. The solution may be filtered, e.g., using a 0.2 micron filter, to remove impurities and contaminants.

In one embodiment, the pharmaceutical composition also includes at least one additional anti-proliferative agent.

An embodiment, therefore, includes a pharmaceutical composition comprising a compound of Formula I, or a stereoisomer, tautomer or pharmaceutically acceptable salt thereof. A further embodiment includes a pharmaceutical composition comprising a compound of Formula I, or a stereoisomer, tautomer or pharmaceutically acceptable salt thereof, together with a pharmaceutically acceptable carrier or excipient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of formula I may be employed alone or in combination with other therapeutic agents for the treatment of a disease or disorder described herein, such as a hyperproliferative disorder (e.g., cancer). In certain embodiments, a compound of formula I is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of formula I such that they do not adversely affect each other. The combination therapy may provide "synergy" and prove "synergistic", i.e., the effect achieved when the active ingredients used together is greater than the sum of the effects that results from using the compounds separately.

The combination therapy may be administered as a simultaneous or sequential regimen. When administered sequentially, the combination may be administered in two or more administrations. The combined administration includes co-administration, using separate formulations or a single pharmaceutical formulation, and consecutive administration in either order, wherein preferably there is a time period while both (or all) active agents simultaneously exert their biological activities.

Suitable dosages for any of the above co-administered agents are those presently used and may be lowered due to the combined action (synergy) of the newly identified agent and other chemotherapeutic agents or treatments.

Combination therapies according to the present invention thus comprise the administration of at least one compound of formula I, or a stereoisomer, geometric isomer, tautomer, or pharmaceutically acceptable salt and the use of at least one other cancer treatment method. The amounts of the compound(s) of formula I and the other pharmaceutically active chemotherapeutic agent(s) and the relative timings of administration will be selected in order to achieve the desired combined therapeutic effect.

Articles of Manufacture

In another embodiment of the invention, an article of manufacture, or "kit", containing materials useful for the treatment of the diseases and disorders described above is provided. In one embodiment, the kit comprises a container comprising a compound of formula I, or a stereoisomer, tautomer, or pharmaceutically acceptable salt thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of formula I or a formulation thereof which is effective for treating the condition and may have a sterile access port (for example, the container may be an intravenous solution bag or a vial having a stopper pierceable by a hypodermic injection needle). At least one active agent in the composition is a compound of formula I. Alternatively, or additionally, the article of manufacture may further comprise a second container comprising a pharmaceutical diluent, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In another embodiment, the kits are suitable for the delivery of solid oral forms of a compound of formula I, such as tablets or capsules. Such a kit can include a number of unit dosages. An example of such a kit is a "blister pack". Blister packs are well known in the packaging industry and are widely used for packaging pharmaceutical unit dosage forms.

According to one embodiment, a kit may comprise (a) a first container with a compound of formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof. The referential examples that follow illustrate procedures which prepare the amines required to assemble the ERK inhibitors encompassed in the present invention.

The following chromatography methods protocols were used to resolve racemic mixtures. Analytical chromatography was carried out on a Waters Inc. UPC2 SFC (Supercritical Fluid Chromatography). Sample concentrations typically were ca. 0.2 mg/mL and 2 μL samples were injected onto a Chiral Technologies Inc. Chiralpak AS-H 5 micron (2.1×50 mm) column. The sample was eluted with a $CO_2$/MeOH (containing 0.1% aq. $NH_3$) gradient (5 to 60% MeOH over 2 min) at a flow rate of 4 mL/min. The column temperature was maintained at 40° C. and the back pressure was 120 Bar. The peaks were detect with a UV diode array detector and characterized with a Single Quad Mass Spec. Detector (SQD).

Preparative SCF was carried out with a Waters Inc.—Thar 350 SFC. Sample concentrations typically were ca. 30 mg/mL in MeOH and 1500 μL samples were injected onto a—Chiral Technologies Inc. Chiralpak AS-H 5 micron (30× 250 mm). The sample was eluted with isocratic eluent containing 70% $CO_2$ and 30% MeOH (containing 0.1% aq. $NH_3$) gradient a flow rate of 150 mL/min. The column temperature was maintained at 20° C. and the back pressure was 100 Bar. The peaks were detect with a UV detector at 240 nm.

Referential Example 1

4-(2-fluoro-6-hydrazino-4-pyridyl-N-(2-methylpyrazol-3-yl)pyridine-2-amine

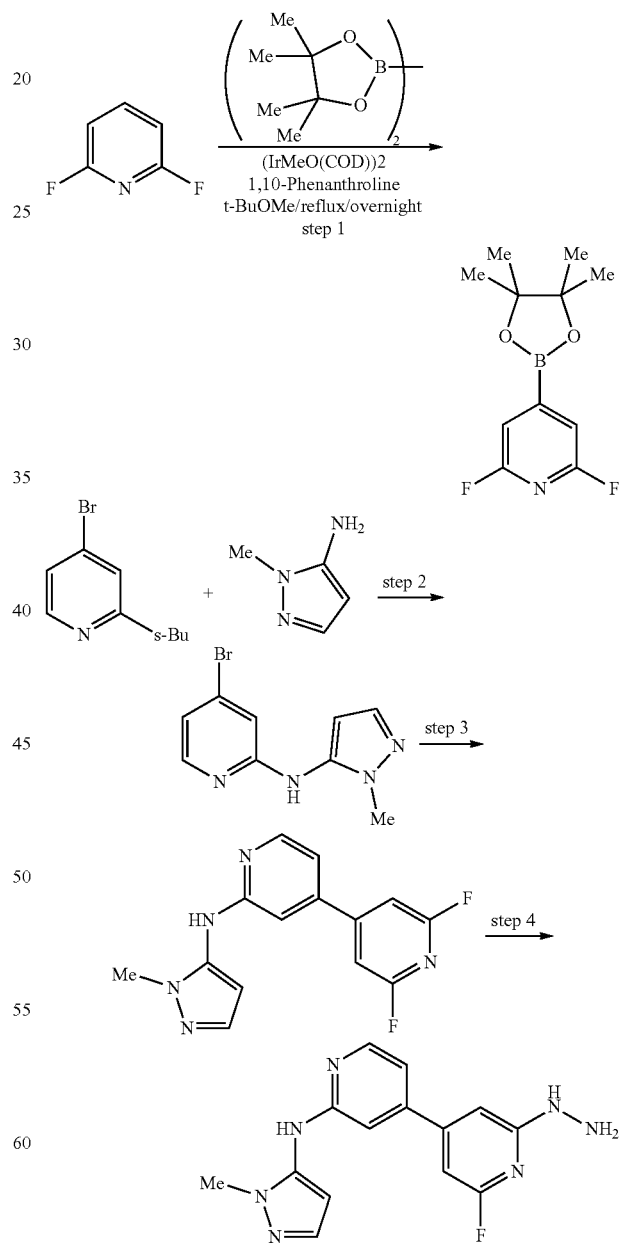

step 1: To the mixture of 2,6-difluoropyridine (100 g, 0.869 mol) in MTBE (1.0 L) was added bis(pinacolato)

diboron (250 g, 0.984 mol), bis(1,5-cyclooctadiene)di-μ-methoxydiiridium(I) (5.00 g) and 1,10-phenanthroline (5.00 g). The mixture was stirred at 70° C. for 4 h under nitrogen gas. The mixture was evaporated to give a brown solid which was dissolved in pet ether, filtered and the solvent evaporated. The crude product which was purified by $SiO_2$ chromatography eluting with pet ether to afford 2,6-difluoro-4-(4,4,5,5-tetramethyl-1,3,2-dioxaborolan-2-yl)pyridine (80.0 g, 38.3%) as white solid. $^1$H NMR: $CDCl_3$ 400 MHz: δ 7.09 (s, 2H), 1.28 (s, 12H).

step 2: A solution of 4-bromo-2-fluoropyridine (210 g, 1.2 mol), 1-methyl-1H-pyrazol-5-ylamine (140 g, 1.44 mol) and sodium tert-butoxide (230 g, 2.4 mol) in DMSO (4 L) was heated to 125° C. overnight. The reaction was quenched with water and extracted with EtOAc. The combined organic layers were dried ($Na_2SO_4$), filtered and concentrated in vacuo. The crude product was purified by $SiO_2$ chromatography eluting with an EtOAc/pet ether gradient (the product eluted with 50% EtOAc) to afford 190 g of 4-bromo-N-(1-methyl-1H-pyrazol-5-yl)pyridin-2-amine as a yellow solid. $^1$H NMR $CDCl_3$ 400 MHz; 67.90 (d, J=5.2 Hz, 1H), 7.40-7.50 (m, 1H), 6.87 (dd, J=5.2, 1.6 Hz, 1H), 6.56 (d, J=0.8 Hz, 1H), 6.09 (d, J=1.6 Hz, 1H), 3.61-3.77 (m, 3H).

step 3: A solution of 4-bromo-N-(2-methylpyrazol-3-yl)pyridin-2-amine (120 g, 0.476 mol), 2,6-difluoro-4-(4,4,5,5-tetramethyl-1,3,2-dioxaborolan-2-yl)pyridine (1.5 equiv, 172 g, 0.714 mol), cesium carbonate (310 g, 0.952 mol) and (dppf)Pd(II)Cl$_2$ (0.10 equiv, 172 g, 0.0476 mol) in MeCN (1 L) and water (500 mL) was degassed. The reaction mixture was heated at 95° C. for 4 h. The reaction was filtered thru CELITE® (Johns Manville Co.). The crude product was purified by $SiO_2$ chromatography eluting with a MeOH/DCM gradient (the product eluted with 10% MeOH) to afford 74 g of 4-(2,6-difluoro-4-pyridyl)-N-(2-methylpyrazol-3-yl)pyridin-2-amine as a yellow solid). $^1$H NMR $CDCl_3$ 400 MHz; δ 8.30 (d, J=5.2 Hz, 1H), 7.54 (d, J=2.0 Hz, 1H), 6.96 (dd, J=5.2, 2.0 Hz, 1H), 6.66 (s, 1H), 6.94 (s, 2H), 6.63 (d, J=0.8 Hz, 1H), 6.20 (d, J=2 Hz, 1H), 3.79 (s, 3H).

step 4: To a solution of 4-(2,6-difluoro-4-pyridyl)-N-(2-methylpyrazol-3-yl)pyridin-2-amine (640 mg, 2.228 mmol) in EtOH (2700 mg, 3.4 mL, 58 mmol) was added hydrazine (0.196 mL, 197.7 mg, 65% aqueous solution). The reaction was heated at 70° C. for 6 h. The reaction precipitate was filtered to afford 468 mg of 4-(2-fluoro-6-hydrazino-4-pyridyl-N-(2-methylpyrazol-3-yl)pyridine-2-amine which was used without further purification.

Referential Example 2

4-(2-fluoro-6-hydrazinylpyridin-4-yl)-N-(1-methyl-1H-pyrazol-5-yl)pyrimidin-2-amine

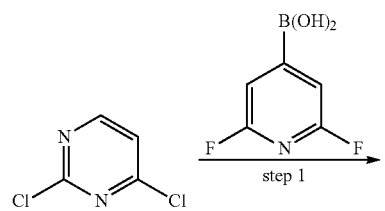

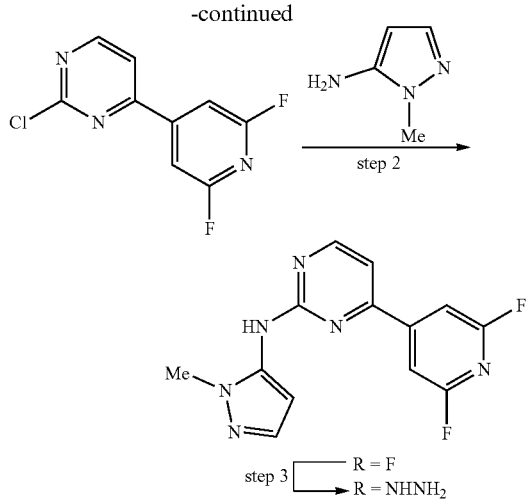

Method A step 1: A vial was charged with 2,4-dichloropyrimidine (1.4 equiv, 1312.6 mg, 8.8106 mmol), (2,6-difluoro-4-pyridyl)boronic acid (1 g, 6.29 mmol), Pd(dppf)Cl$_2$ (0.07 equiv, 325.60 mg, 0.44053 mmol), and Cs$_2$CO$_3$ (1.4 equiv, 2870.7 mg, 0.697 mL, 8.81 mmol) in MeCN (14 mL) and H$_2$O (6 mL), degassed with N$_2$, sealed and heated at 95° C. for 3 h. The solution was cooled, diluted with water and extracted with EtOAc (2×20 mL). The combined extracts were dried (Na$_2$SO$_4$), filtered and concentrated on CELITE®. The product was purified by SiO$_2$ chromatography (ISCO 24 g column) eluting with an EtOAc/heptane gradient (0 to 30% EtOAc) to afford 905 mg of 2-chloro-4-(2,6-difluoropyridin-4-yl)pyrimidine as an off white solid.

step 2: A vial was charged with 2-chloro-4-(2,6-difluoro-4-pyridyl)pyrimidine (905 mg, 3.9763 mmol), 2-methylpyrazol-3-amine (1.1 equiv, 424.8 mg, 4.3739 mmol), Cs$_2$CO$_3$ (1.5 equiv, 1943.4 mg, 5.9644 mmol), Xantphos (0.20 equiv, 460.16 mg, 0.79525 mmol), and Pd$_2$(dba)$_3$ (0.10 equiv, 364.12 mg, 0.39763 mmol) in dioxane (12 mL), degassed with N$_2$, sealed and heated at ° C. for 2 h. Additional Pd$_2$(dba)3 (180 mg) and Xantphos (230 mg) were added and heating continued for 2 h. The solution was filtered through CELITE®, partitioned between water (100 mL) and EtOAc (2×50 mL). The combined organic extracts were dried (Na$_2$SO$_4$), filtered, concentrated on CELITE®. The crude product was purified by SiO$_2$ chromatography (ISCO 24 g column) eluting with an EtOAc/heptane gradient (0 to 50% EtOAc) to afford 455 mg of 4-(2,6-difluoro-4-pyridyl)-N-(2-methylpyrazol-3-yl)pyrimidin-2-amine as a yellow solid which was used without additional purification.

step 3: To a suspension of 4-(2,6-difluoro-4-pyridyl)-N-(2-methylpyrazol-3-yl)pyrimidin-2-amine (455 mg, 1.263 mmol) in EtOH (10 mL) was added dropwise hydrazine (3.0 equiv, 0.123 mL, 3.788 mmol). The resulting dark mixture was heated at 70° C. for 8 h. The solution was cooled and concentrated in vacuo. The resulting solid was triturated with H$_2$O and dried to afford 254 mg of 4-(2-fluoro-6-hydrazinylpyridin-4-yl)-N-(1-methyl-1H-pyrazol-5-yl)pyrimidin-2-amine.

Method B step 1: 2-Methylsulfanyl-1H-pyrimidin-6-one (143 mg, 1.0058 mmol) and 2-methylpyrazol-3-amine (2.0 equiv, 2.0115 mmol) was neat at 150° C. for 24 h. The melt was dissolved in DCM and loaded on a SiO$_2$ column (12 g)

eluting with a MeOH/DCM gradient (0 to 8% MeOH) to afford 100 mg of 2-(2-methyl-2H-pyrazol-3-ylamino)-3H-pyrimidin-4-one.

step 2: A mixture of 2-[(2-methylpyrazol-3-yl)amino]-1H-pyrimidin-6-one (1 g, 5.2304 mmol) and $POCl_3$ (10 mL, 106.2 mmol) in MeCN (10 mL) was heated in an open flask with condenser at 100° C. for 2 h. The mixture was concentrated in vacuum, the residue partitioned between EtOAc and sat. aq. $NaHCO_3$. The organic extracts were washed with water, brine, dried ($MgSO_4$), filtered and concentrated. The residue was purified on a $SiO_2$ column (24 g) eluting with an EtOAc/heptane gradient (0 to 50% EtOAc) to afford 720 mg of (4-chloro-pyrimidin-2-yl)-(2-methyl-2H-pyrazol-3-yl)-amine. $^1$H NMR: $CDCl_3$ 400 MHz; δ 8.28 (d, J=5.2 Hz, 1H), 7.48 (d, J=1.6 Hz, 1H), 7.10 (brs, 1H), 6.82 (d, J=5.2 Hz, 1H), 6.30 (d, J=1.2 Hz, 1H), 3.79 (s, 3H).

step 3: A vial was charged with (2,6-difluoro-4-pyridyl) boronic acid (1.20 equiv, 9.16 mmol), 4-chloro-N-(2-methylpyrazol-3-yl)pyrimidin-2-amine (1.60 g, 7.63 mmol), (dppf)$PdCl_2$ (0.08 equiv, 0.611 mmol) and 1 M aq. $Cs_2CO_3$ (1.50 equiv, 11.4 mmol, 1.0 mol/L) in MeCN (22 mL), degassed, sealed and heated at 95° C. for 1.5 h. The mixture was partitioned between EtOAc and $H_2O$. The organic layer was separated, washed with brine, dried ($MgSO_4$), filtered and concentrated. The residue was dry loaded on a 40 g $SiO_2$ column and eluted with 0-100% EtOAc in heptane to afford 1.742 g of 4-(2,6-difluoro-4-pyridyl)-N-(2-methylpyrazol-3-yl)pyrimidin-2-amine. $^1$H NMR: $CDCl_3$ 400 MHz; δ 8.62 (d, J=5.6 Hz, 1H), 755 (d, J=1.6 Hz, 1H), 7.43 (s, 2H), 7.23 (d, J=5.6 Hz, 1H), 6.95 (brs, 1H), 6.36 (d, J=2.0 Hz, 1H), 3.84 (s, 3H); LCMS: (M+H$^+$): 289.0 step 4: To a suspension of 4-(2,6-difluoro-4-pyridyl)-N-(2-methylpyrazol-3-yl)pyrimidin-2-amine (455 mg, 455 mg, 1.263 mmol) in EtOH (10 mL) was added dropwise hydrazine (3.0 equiv, 123.9 mg, 0.123 mL, 3.788 mmol). The resulting dark mixture was heated at 70° C. for 8 h. The reaction mixture was cooled, concentrated in vacuo and triturated with water. The solid was collected by filtration, washed with small amount of EtOH, dried to afford 254 mg of 4-(2-fluoro-6-hydrazinylpyridin-4-yl)-N-(1-methyl-1H-pyrazol-5-yl)pyrimidin-2-amine.

Referential Example 3

3-((tert-butyldimethylsilyl)oxy)-2-((3-methylisoxazol-5-yl)methyl)propanoic Acid

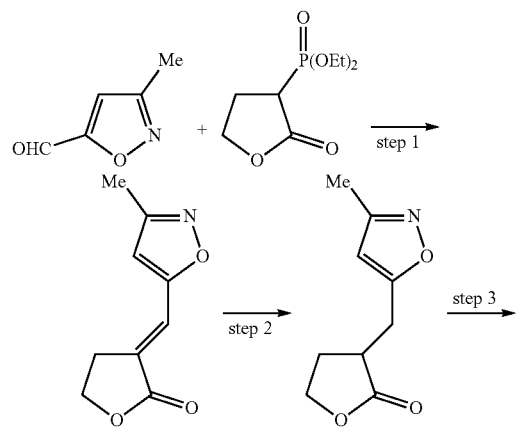

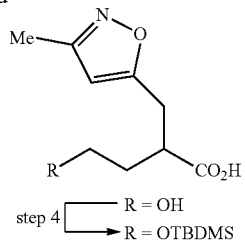

step 1: To the stirred solution of 4-methylthiazole-2-carbaldehyde 1.8 g, 14.2 mmol) in DCM (50 mL) was added 3-(triphenylphosphoranylidene)dihydrofuran-2(3H)-one (9.8 g, 28.4 mmol, CASRN 34372-07-5). The mixture was stirred at about 26° C. for 1 h. The reaction mixture was concentrated and purified by $SiO_2$ chromatography eluting with pet ether/EtOAc gradient (5 to 13% EtOAc) to afford (Z)-3-((4-methylthiazol-2-yl)methylene)dihydrofuran-2(3H)-one (1.35 g, yield 50%) as a white solid.

step 2: To a solution of compound (Z)-3-((4-methylthiazol-2-yl)methylene)dihydrofuran-2(3H)-one (1.35 g, 6.9 mmol) in MeOH (15 mL) was added Pd/C (10%, 100 mg). The mixture was stirred under $H_2$ (30 psi) at about 26° C. for 16 h. The catalyst was filtered off and the filtrate was concentrated to afford compound 3-((4-methylthiazol-2-yl)methyl)dihydrofuran-2(3H)-one (1.3 g, yield 95%) as a yellowish oil.

The lactone ring can be hydrolyzed under basic conditions and the hydroxyl group of the resulting hydroxyl acid can be silylated with tert-butyldimethylshlorosilane as described in experiment 1.

Example 1

(R)-4-(3-benzyl-3,4-dihydro-5-oxa-1,2,2a$^1$-triazaacenaphthylen-7-yl)-N-(1-methyl-1H-pyrazol-5-yl)pyrimidin-2-amine (I-15)

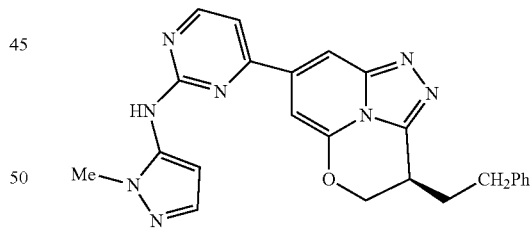

2-Benzyl-3-((tert-butyldimethylsilyl)oxy)propanoic acid-tert-Butyldimethylchlorosilane (4.4 g, 2.5 equiv, 28.5 mmol) in DCM (20 mL) was added dropwise to a mixture of 2-benzyl-3-hydroxy-propanoic acid (2.419 g, 11.41 mmol, CASRN 6811-98-9) and imidazole (9.0 g, 57.05 mmol, 5.0 equiv) in DMF (25 mL) cooled to 0 to 5° C. The mixture was stirred for 24 h, concentrated in vacuo and the residue partitioned between water and $Et_2O$. The organic extracts were washed sequentially with water, 1% aqueous citric acid, water, dried ($Na_2SO_4$), filtered and concentrated in vacuo to afford 4.09 g of oil residue which was used in the next procedure without purification.

The residue was added to a mixture of $K_2CO_3$ (3.5 g, 2.5 equiv, 25 mmol) in water (50 mL) and MeOH (100 mL). The mixture was stirred for 24 h, concentrated in vacuo, diluted with water (120 mL) and twice extracted with Et$_2$O. The organic extracts were discarded and the aqueous solution was acidified to pH 4 with citric acid. The mixture then was extracted with Et$_2$O, the organic layer washed with water, brine, dried (Na$_2$SO$_4$), filtered and concentrated in vacuo to afford 10.23 g of 2-benzyl-3-((tert-butyldimethylsilyl)oxy) propanoic acid. MS: m/z 295 step 5 (SCHEME A): HATU (224 mg, 1.15 equiv, 0.5783 mmol) was added portionwise to a mixture of 6-fluoro-4-[2-[(2-methylpyrazol-3-yl)amino]pyrimidin-4-yl]-1H-pyridin-2-one hydrazone (151 mg, 0.5028 mmol), 2-benzyl-3-[tert-butyl(dimethyl)silyl]oxy-propanoic acid (163 mg, 1.10 equiv, 0.5531 mmol) and TEA (0.21 mL, 3.0 equiv, 1.508 mmol) in DMF (3 mL). The mixture was stirred for 1 h. The reaction mixture was concentrated in vacuo, the residue partitioned between water and EtOAc. The organic extracts were washed with water, 1% aq. citric acid, aq. NaHCO$_3$, brine, dried (MgSO$_4$), filtered and concentrated in vacuo to afford crude 2-benzyl-3-((tert-butyldimethylsilyl)oxy)-N'-(6-fluoro-4-(2-((1-methyl-1H-pyrazol-5-yl)amino)pyrimidin-4-yl)pyridin-2(1H)-ylidene)propanehydrazide (329 mg, 96%) which was used in the next step without further purification. MS: m/z 577.

step 6—Triphenylphosphine dibromide (460 mg, 1.055 mmol, 2.5 eq) was added to a mixture of 2-benzyl-3-((tert-butyldimethylsilyl)oxy)-N'-(6-fluoro-4-(2-((1-methyl-H-pyrazol-5-yl)amino)pyrimidin-4-yl)pyridin-2(1H)-ylidene) propanehydrazide (242 mg, 0.42 mmol) and DIPEA (0.46 mL, 2.635 mmol, 6.25 eq) in MeCN (6 mL) and the solution was heated at 60-80° C. in a sealed vial for 1 h. The mixture was cooled to RT and then stirred with water (5 mL) for 20 min. The mixture was concentrated to a small volume and partitioned between water and EtOAc. The organic extracts were washed sequentially with 1% aq. citric acid, water, brine, then dried (Na$_2$SO$_4$), filtered and concentrated in vacuo. The residue was purified on a 12 g SiO$_2$ column eluting with a EtOAc/heptane gradient (0 to 100% EtOAc) to afford 212 mg (90%) of 4-(3-(1-(((tert-butyldimethylsilyl)oxy)-3-phenylpropan-2-yl)-5-fluoro-[1,2,4]triazolo[4,3-a]pyridin-7-yl)-N-(1-methyl-1H-pyrazol-5-yl)pyrimidin-2-amine. MS: m/z 559.

step 7: BF$_3$·Et$_2$O (0.18 mL, 1.43 mmol, 8.0 eq.) was added to a solution of 4-(3-(1-((tert-butyldimethylsilyl)oxy)-3-phenylpropan-2-yl)-5-fluoro-[1,2,4]triazolo[4,3-a]pyridin-7-yl)-N-(1-methyl-1H-pyrazol-5-yl)pyrimidin-2-amine (100 mg, 0.18 mmol) in DCM (6 mL). The mixture was stirred for 4 h, concentrated in vacuo and the residue partitioned between aq. NaHCO$_3$ and EtOAc. The organic extracts were washed with brine, dried (Na$_2$SO$_4$), filtered and concentrated in vacuo. The residue was triturated with hexane/Et$_2$O mixture (2:1) and filtered to afford 64 mg (80%) of 2-(5-fluoro-7-(2-(((1-methyl-H-pyrazol-5-yl) amino)pyrimidin-4-yl)-[1,2,4]triazolo[4,3-a]pyridin-3-yl)-3-phenylpropan-1-ol. MS: m/z 445.

step 8: Method A: Sodium hydride (288 mg, 7.2 mmol, 20 eq, 60% dispersion in mineral oil) was added portionwise to a solution of 2-(5-fluoro-7-(2-((1-methyl-H-pyrazol-5-yl) amino)pyrimidin-4-yl)-[1,2,4]triazolo[4,3-a]pyridin-3-yl)-3-phenylpropan-1-ol (160 mg, 0.36 mmol) in THF (20 mL). The mixture was stirred for 20 min at RT and then heated in a sealed vial at 85° C. for 2 h. The mixture was cooled to RT, quenched with sat. aq. NH$_4$Cl and extracted with MeTHF. The organic extracts were washed with water, brine, dried (MgSO$_4$), filtered and concentrated in vacuo. The residue was purified on a 12 g SiO$_2$ column eluting MeOH/DCM gradient (0 to 8% MeOH) to afford 40 mg (26%) of racemic 4-(3-benzyl-3,4-dihydro-5-oxa-1,2,2a$^1$-triazaacenaphthylen-7-yl)-N-(1-methyl-1H-pyrazol-5-yl)pyrimidin-2-amine (I-17).

step 8: Method B: Sodium bis-(trimethylsilyl)amide in THF (1 M, 0.11 mL, 0.11 mmol) was added in one portion to a vigorously stirred solution of 2-(5-fluoro-7-(2-((1-methyl-1H-pyrazol-5-yl)amino)pyrimidin-4-yl)-[1,2,4]triazolo[4,3-a]pyridin-3-yl)-3-phenylpropan-1-ol (22 mg, 0.05 mmol) in DMF (1.0 mL) at 80° C. Immediately after addition the mixture was quenched with 5% aq. KHSO$_4$ then partitioned between water and EtOAc. The organic extracts were washed with water, brine, dried (MgSO$_4$), filtered and concentrated in vacuo. The crude product was purified on a 4 g SiO$_2$ column eluting with a MeOH/DCM gradient (0-8% MeOH) to afford 9.3 mg (44%) of racemic 4-(3-benzyl-3,4-dihydro-5-oxa-1,2,2a$^1$-triazaacenaphthylen-7-yl)-N-(1-methyl-1H-pyrazol-5-yl)pyrimidin-2-amine. MS: m/z 425

40 mg of the racemic mixture was resolved by SFC chromatography on a chiral support.

(R)-4-(3-benzyl-3,4-dihydro-5-oxa-1,2,2a$^1$-triazaacenaphthylen-7-yl)-N-(1-methyl-H-pyrazol-5-yl)pyrimidin-2-amine ((R)-I-15): 8.3 mg. $^1$H NMR (400 MHz, DMSO-d6) δ 9.54 (s, 1H), 8.59 (d, J=5.2 Hz, 1H), 8.17 (d, J=1.1 Hz, 1H), 7.63-7.58 (m, 1H), 7.40 (d, J=1.9 Hz, 1H), 7.33-7.30 (m, 4H), 7.27-7.21 (m, 1H), 6.95 (d, J=1.1 Hz, 1H), 6.29 (d, J=2.0 Hz, 1H), 4.56 (dd, J=11.0, 4.4 Hz, 1H), 4.42 (dd, J=11.0, 6.2 Hz, 1H), 4.08-3.99 (m, 1H), 3.71 (s, 3H), 3.35 (dd, J=14.0, 6.1 Hz, 1H), 3.03 (dd, J=14.0, 8.3 Hz, 1H); MS: m/z 425; and, (S)-4-(3-benzyl-3,4-dihydro-5-oxa-1,2,2a$^1$-triazaacenaphthylen-7-yl)-N-(1-methyl-H-pyrazol-5-yl)pyrimidin-2-amine ((S)-I-15): 8.7 mg $^1$H NMR (400 MHz, DMSO-d6) δ 9.54 (s, 1H), 8.59 (d, J=5.2 Hz, 1H), 8.17 (d, J=1.2 Hz, 1H), 7.66-7.60 (m, 1H), 7.40 (d, J=1.9 Hz, 1H), 7.35-7.30 (m, 4H), 7.28-7.22 (m, 1H), 6.95 (d, J=1.1 Hz, 1H), 6.29 (d, J=1.9 Hz, 1H), 4.56 (dd, J=11.0, 4.5 Hz, 1H), 4.42 (dd, J=11.0, 6.1 Hz, 1H), 4.07-3.99 (m, 1H), 3.71 (s, 3H), 3.35 (dd, J=14.1, 6.2 Hz, 1H), 3.03 (dd, J=14.0, 8.3 Hz, 1H); MS: m/z 425.

4-(3-Benzyl-3,4-dihydro-5-oxa-1,2,2a$^1$-triazaacenaphthylen-7-yl)-N-(1-methyl-1H-pyrazol-5-yl)pyridin-2-amine (I-38) can be prepared analogously except in step 5, (6'-fluoro-2'-hydrazino-[4,4']bipyridinyl-2-yl)-(2-methyl-2H-pyrazol-3-yl)-amine replaced [4-(2-fluoro-6-hydrazino-pyridin-4-yl)-pyrimidin-2-yl]-(2-methyl-2H-pyrazol-3-yl)-amine.

4-(3-(4-Chlorobenzyl)-3,4-dihydro-5-oxa-1,2,2a$^1$-triazaacenaphthylen-7-yl)-N-(1-methyl-1H-pyrazol-5-yl)pyrimidin-2-amine (I-41) can be prepared analogously except in step 5, 3-(tert-butyl-dimethyl-silanyloxy)-2-(4-chloro-benzyl)-propionic acid replaced 2-benzyl-3-[tert-butyl(dimethyl)silyl]oxy-propanoic acid.

4-(3-(4-Fluorobenzyl)-3,4-dihydro-5-oxa-1,2,2a$^1$-triazaacenaphthylen-7-yl)-N-(1-methyl-1H-pyrazol-5-yl)pyrimidin-2-amine (I-44) can be prepared analogously except in step 5, 3-(tert-butyl-dimethyl-silanyloxy)-2-(4-fluoro-benzyl)-propionic acid replaced 2-benzyl-3-[tert-butyl(dimethyl)silyl]oxy-propanoic acid.

4-(3-(3-Fluoro-4-methoxybenzyl)-3,4-dihydro-5-oxa-1,2,2a$^1$-triazaacenaphthylen-7-yl)-N-(1-methyl-1H-pyrazol-5-yl)pyrimidin-2-amine (I-46) can be prepared analogously except in step 5, 3-(tert-butyl-dimethyl-silanyloxy)-2-(3-fluoro-4-methoxy-benzyl)-propionic acid replaced 2-benzyl-3-[tert-butyl(dimethyl)silyl]oxy-propanoic acid.

4-(3-(4-chlorobenzyl)-3,4-dihydro-5-oxa-1,2,2a$^1$-triazaacenaphthylen-7-yl)-N-(1-methyl-1H-pyrazol-5-yl)pyridin-2-amine (I-48) can be prepared analogously except in step 5, 3-(tert-butyl-dimethyl-silanyloxy)-2-(4-chloro-benzyl)-propionic acid replaced 2-benzyl-3-[tert-butyl(dimethyl)silyl]oxy-propanoic acid and (6'-fluoro-2'-hydrazino-[4,4']bipyridinyl-2-yl)-(2-methyl-2H-pyrazol-3-yl)-amine replaced [4-(2-fluoro-6-hydrazino-pyridin-4-yl)-pyrimidin-2-yl]-(2-methyl-2H-pyrazol-3-yl)-amine.

4-(3-(3-fluoro-4-methoxybenzyl)-3,4-dihydro-5-oxa-1,2,2a$^1$-triazaacenaphthylen-7-yl)-N-(1-methyl-1H-pyrazol-5-yl)pyridin-2-amine (I-49) can be prepared analogously except in step 5, 3-(tert-butyl-dimethyl-silanyloxy)-2-(3-fluoro-4-methoxy-benzyl)-propionic acid replaced 2-benzyl-3-[tert-butyl(dimethyl)silyl]oxy-propanoic acid and (6'-fluoro-2'-hydrazino-[4,4']bipyridinyl-2-yl)-(2-methyl-2H-pyrazol-3-yl)-amine replaced [4-(2-fluoro-6-hydrazino-pyridin-4-yl)-pyrimidin-2-yl]-(2-methyl-2H-pyrazol-3-yl)-amine.

N-(1-Methyl-1H-pyrazol-5-yl)-4-(3-(2-methylbutyl)-3,4-dihydro-5-oxa-1,2,2a$^1$-triazaacenaphthylen-7-yl)pyrimidin-2-amine (I-52) can be prepared analogously except in step 5, 2-(((tert-butyldimethylsilyl)oxy)methyl)-4-methylhexanoic acid replaced 2-benzyl-3-[tert-butyl(dimethyl)silyl]oxy-propanoic acid.

4-(3-(4-chlorobenzyl)-3,4-dihydro-5-oxa-1,2,2a$^1$-triazaacenaphthylen-7-yl)-N-(1-methyl-1H-pyrazol-5-yl)pyridin-2-amine (I-55) can be prepared analogously except in step 5, 3-(tert-butyl-dimethyl-silanyloxy) 2-(4-chlorobenzyl)-propionic acid replaced 2-benzyl-3-[tert-butyl(dimethyl)silyl]oxy-propanoic acid and (6'-fluoro-2'-hydrazino-[4,4']bipyridinyl-2-yl)-(2-methyl-2H-pyrazol-3-yl)-amine replaced [4-(2-fluoro-6-hydrazino-pyridin-4-yl)-pyrimidin-2-yl]-(2-methyl-2H-pyrazol-3-yl)-amine 4-(3-(3-Methoxybenzyl)-3,4-dihydro-5-oxa-1,2,2a$^1$-triazaacenaphthylen-7-yl)-N-(1-methyl-1H-pyrazol-5-yl)pyrimidin-2-amine (I-81) can be prepared analogously except in step 5, 3-(tert-butyl-dimethyl-silanyloxy)-2-(3-methoxy-benzyl)-propionic acid replaced 2-benzyl-3-[tert-butyl(dimethyl)silyl]oxy-propanoic acid.

4-(3-(3-chloro-4-fluorobenzyl)-3,4-dihydro-5-oxa-1,2,2a$^1$-1-triazaacenaphthylen-7-yl)-N-(1-methyl-1H-pyrazol-5-yl)pyrimidin-2-amine (I-82) can be prepared analogously except in step 5, 3-(tert-butyl-dimethyl-silanyloxy)-2-(3-chloro-4-fluorobenzyl)-propionic acid replaced 2-benzyl-3-[tert-butyl(dimethyl)silyl]oxy-propanoic acid.

4-(3-(3-Chloro-4-fluorobenzyl)-3,4-dihydro-5-oxa-1,2,2a$^1$-triazaacenaphthylen-7-yl)-N-(1-methyl-1H-pyrazol-5-yl)pyridin-2-amine (I-83) can be prepared analogously except in step 5, 3-(tert-butyl-dimethyl-silanyloxy)-2-(3-chloro-4-fluorobenzyl)-propionic acid replaced 2-benzyl-3-[tert-butyl(dimethyl)silyl]oxy-propanoic acid and (6'-fluoro-2'-hydrazino-[4,4']bipyridinyl-2-yl)-(2-methyl-2H-pyrazol-3-yl)-amine replaced [4-(2-fluoro-6-hydrazino-pyridin-4-yl)-pyrimidin-2-yl]-(2-methyl-2H-pyrazol-3-yl)-amine.

4-(3-(3-Chlorobenzyl)-3,4-dihydro-5-oxa-1,2,2a$^1$-triazaacenaphthylen-7-yl)-N-(1-methyl-1H-pyrazol-5-yl)pyrimidin-2-amine (I-88) can be prepared analogously except in step 5, 3-(tert-butyl-dimethyl-silanyloxy)-2-(3-chloro-benzyl)-propionic acid replaced 3-(tert-butyl-dimethyl-silanyloxy)-2-phenyl-propionic acid.

4-(3-Cyclopropyl-3,4-dihydro-5-oxa-1,2,2a$^1$-triazaacenaphthylen-7-yl)-N-(1-methyl-1H-pyrazol-5-yl)pyrimidin-2-amine (I-95) can be prepared analogously except in step 5, 3-((tert-butyldimethylsilyl)oxy)-2-cyclopropylpropanoic acid replaced 2-benzyl-3-[tert-butyl(dimethyl)silyl]oxy-propanoic acid.

4-(3-(3-Chlorobenzyl)-3,4-dihydro-5-oxa-1,2,2a$^1$-triazaacenaphthylen-7-yl)-N-(1-methyl-1H-pyrazol-5-yl)pyridin-2-amine (I-96) can be prepared analogously except in step 5, 3-(tert-butyl-dimethyl-silanyloxy)-2-(3-chloro-benzyl)-propionic acid replaced 2-benzyl-3-[tert-butyl(dimethyl)silyl]oxy-propanoic acid and (6'-fluoro-2'-hydrazino-[4,4']bipyridinyl-2-yl)-(2-methyl-2H-pyrazol-3-yl)-amine replaced [4-(2-fluoro-6-hydrazino-pyridin-4-yl)-pyrimidin-2-yl]-(2-methyl-2H-pyrazol-3-yl)-amine.

4-(3-(3-Methoxybenzyl)-3,4-dihydro-5-oxa-1,2,2a$^1$-triazaacenaphthylen-7-yl)-N-(1-methyl-1H-pyrazol-5-yl)pyridin-2-amine (I-97) can be prepared analogously except in step 5, 3-(tert-butyl-dimethyl-silanyloxy)-2-(3-methoxybenzyl)-propionic acid replaced 2-benzyl-3-[tert-butyl(dimethyl)silyl]oxy-propanoic acid and (6'-fluoro-2'-hydrazino-[4,4']bipyridinyl-2-yl)-(2-methyl-2H-pyrazol-3-yl)-amine replaced [4-(2-fluoro-6-hydrazino-pyridin-4-yl)-pyrimidin-2-yl]-(2-methyl-2H-pyrazol-3-yl)-amine.

N-(1-methyl-1H-pyrazol-5-yl)-4-(3-propyl-3,4-dihydro-5-oxa-1,2,2a$^1$-triazaacenaphthylen-7-yl)pyrimidin-2-amine (I-101) can be prepared was prepared analogously except in step 5, 2-(tert-butyl-dimethyl-silanyloxymethyl)-pentanoic acid replaced 2-benzyl-3-[tert-butyl(dimethyl)silyl]oxy-propanoic acid.

Example 2

4-(3-(4-fluorobenzyl)-3,4-dihydro-5-oxa-1,2,2a$^1$-triazaacenaphthylen-7-yl)-N-(1-methyl-1H-pyrazol-5-yl)pyrimidin-2-amine (I-44)

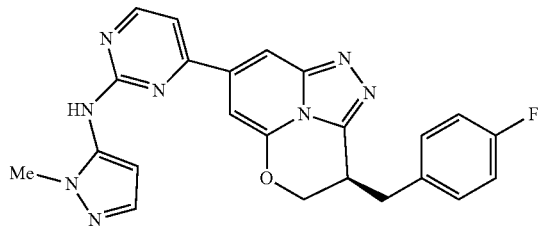 [SMILES: Cn1nccc1Nc1nccc(-c2cc3n4c(nnc4c2)[C@@H](Cc2ccc(F)cc2)CO3)n1]

step 1: To a solution of dimethyl 2-(4-fluorobenzyl) malonate (1 g, 4.037 mmol) in THF (10 mL) and water (10 mL) was added LiOH (106.36 mg 4.44 mmol) and the resulting solution was stirred at RT overnight. The solution was diluted with water and washed with EtOAc (30 mL). The aqueous phase was acidified with 1N HCl, extracted with EtOAc (2×30 mL). The combined extracts were dried (Na$_2$SO$_4$), filtered and concentrated in vacuo to afford 818 mg (89.5%) of the monoester as clear oil which was used without additional purification: MS m/z 226.

step 2: To an ice cold solution of 2-[(4-fluorophenyl)methyl]-3-methoxy-3-oxo-propanoic acid (818 mg, 3.61 mmol) in IPA (10 mL) under N$_2$ was added dropwise LiBH$_4$ in THF (2M, 3.61 mL, 7.23 mmol) and the resulting solution stirred at 0° C. for 5 h. It was quenched by dropwise addition of 1N HCl, with cooling (gas evolution!) until the solution was acidic. The organic solvent was removed in vacuo. The aqueous residue was extracted with EtOAc (3×30 mL). The combined extracts were washed with brine, dried (MgSO$_4$), filtered, and concentrated in vacuo, to afford 740 mg (100%) of 2-[(4-fluorophenyl)methyl]-3-hydroxy-propanoic acid as clear gum which was used with further purification: MS m/z 198.

step 3: A mixture of 2-[(4-fluorophenyl)methyl]-3-hydroxy-propanoic acid (748 mg, 3.77 mmol), tert-butyl-chloro-dimethyl-silane (3.41 g, 22.64 mmol), and imidazole (3.08 g, 45.29 mmol) in DMF (10 mL) was stirred at RT overnight. It was diluted with water and extracted with EtOAc (3×30 mL). The combined extracts were dried (Na$_2$SO$_4$), filtered and concentrated on CELITE®. The crude product was purified by SiO$_2$ chromatography (ISCO 24 g column) eluting with an EtOAc/heptane gradient (0 to 50% EtOAc) to afford 516 mg (43.7%) of 2-[[tert-butyl (dimethyl)silyl]oxymethyl]-3-(4-fluorophenyl)propanoic acid as clear syrup: MS m/z 312.

HATU mediated condensation of 2-[[tert-butyl(dimethyl) silyl]oxymethyl]-3-(4-fluorophenyl)propanoic acid and 6-fluoro-4-[2-[(2-methylpyrazol-3-yl)amino]pyrimidin-4-yl]-1H-pyridin-2-one hydrazine (step 4), Ph$_3$P.Br$_2$ mediated cyclization of the acyl hydrazine (step 5) and BF$_3$—OEt$_2$ desilylation of the alcohol (step 6) were carried out in accord with step 5, 6 and 7 of Example 1.

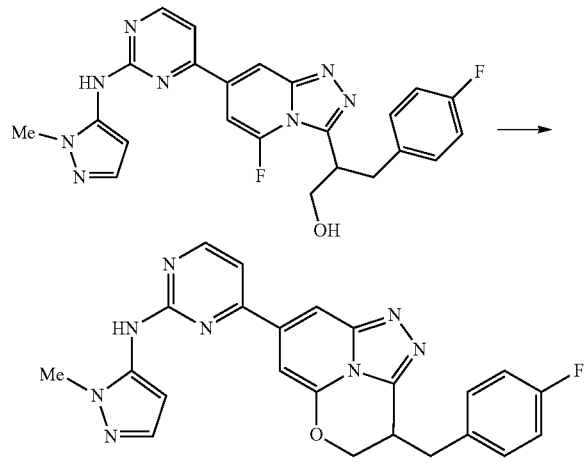

step 7: To a solution of 2-[5-fluoro-7-[2-[(2-methylpyrazol-3-yl)amino]pyrimidin-4-yl]-[1,2,4]triazolo[4,3-a]pyridin-3-yl]-3-(4-fluorophenyl)propan-1-ol (93 mg, 0.20 mmol) in THF (20 mL) was added DBU (0.45 mL, 3.01 mmol) and the resulting solution was stirred at RT for 15 min, then heated at 75° C. for 4 h. Additional DBU (0.45 mL) was added and the solution was heated at 65° C. overnight. The solution was concentrated on CELITE®. The crude product was purified by SiO$_2$ chromatography (ISCO 12 g column) eluting with a MeOH/DCM gradient (0 to 8% MeOH) to afford 32.5 mg (36.5%) of I-44 as yellow solid.

The racemic product was resolved by SFC chromatography on a chiral column to afford:

(R)-4-(3-(4-fluorobenzyl)-3,4-dihydro-5-oxa-1,2,2a$^1$-triazaacenaphthylen-7-yl)-N-(1-methyl-1H-pyrazol-5-yl)pyrimidin-2-amine: 1H NMR (400 MHz, DMSO-d6) δ 9.55 (s, 1H), 8.59 (d, J=5.2 Hz, 1H), 8.17 (d, J=1.1 Hz, 1H), 7.63 (d, J=5.3 Hz, 1H), 7.43-7.29 (m, 3H), 7.19-7.08 (m, 2H), 6.95 (d, J=1.2 Hz, 1H), 6.29 (d, J=1.9 Hz, 1H), 4.58 (dd, J=11.0, 4.4 Hz, 1H), 4.43 (dd, J=11.0, 6.0 Hz, 1H), 4.08-3.97 (m, 1H), 3.71 (s, 3H), 3.36-3.21 (m, 1H), 3.05 (dd, J=14.0, 7.9 Hz, 1H); MS: m/z 442.

(S)-4-(3-(4-fluorobenzyl)-3,4-dihydro-5-oxa-1,2,2a$^1$-triazaacenaphthylen-7-yl)-N-(1-methyl-1H-pyrazol-5-yl)pyrimidin-2-amine: 1H NMR (400 MHz, DMSO-d6) δ 9.55 (s, 1H), 8.59 (d, J=5.2 Hz, 1H), 8.17 (d, J=1.1 Hz, 1H), 7.63 (d, J=5.2 Hz, 1H), 7.43-7.29 (m, 3H), 7.19-7.08 (m, 2H), 6.95 (d, J=1.2 Hz, 1H), 6.29 (d, J=1.9 Hz, 1H), 4.58 (dd, J=11.0, 4.4 Hz, 1H), 4.43 (dd, J=11.0, 6.1 Hz, 1H), 4.08-3.97 (m, 1H), 3.71 (s, 3H), 3.36-3.25 (m, 1H), 3.05 (dd, J=14.1, 7.9 Hz, 1H); MS: m/z 442.

4-(3-(4-methoxybenzyl)-3,4-dihydro-5-oxa-1,2,2a$^1$-triazaacenaphthylen-7-yl)-N-(1-methyl-1H-pyrazol-5-yl)pyrimidin-2-amine (I-50) was prepared analogously except dimethyl 2-(4-methoxybenzyl)malonate replaced dimethyl 2-(4-fluorobenzyl)malonate (R)-4-(3-(4-methoxybenzyl)-3,4-dihydro-5-oxa-1,2,2a$^1$-triazaacenaphthylen-7-yl)-N-(1-methyl-1H-pyrazol-5-yl) pyrimidin-2-amine: $^1$H NMR (400 MHz, DMSO-d6) δ 9.55 (s, 1H), 8.59 (d, J=5.1 Hz, 1H), 8.17 (d, J=1.2 Hz, 1H), 7.63 (d, J=5.2 Hz, 1H), 7.40 (d, J=1.9 Hz, 1H), 7.27-7.18 (m, 2H), 6.95 (d, J=1.1 Hz, 1H), 6.92-6.84 (m, 2H), 6.29 (d, J=1.9 Hz, 1H), 4.55 (dd, J=11.0, 4.4 Hz, 1H), 4.40 (dd, J=11.0, 6.1 Hz, 1H), 4.03-3.92 (m, 1H), 3.72 (d, J=11.5 Hz, 6H), 3.34-3.23 (m, 1H), 2.97 (dd, J=14.1, 8.4 Hz, 1H); MS: m/z 454.

(S)-4-(3-(4-methoxybenzyl)-3,4-dihydro-5-oxa-1,2,2a$^1$-triazaacenaphthylen-7-yl)-N-(1-methyl-1H-pyrazol-5-yl) pyrimidin-2-amine: $^1$H NMR (400 MHz, DMSO-d6) δ 9.55 (s, 1H), 8.59 (d, J=5.2 Hz, 1H), 8.17 (d, J=1.1 Hz, 1H), 7.63 (d, J=5.2 Hz, 1H), 7.40 (d, J=1.9 Hz, 1H), 7.27-7.18 (m, 2H), 6.95 (d, J=1.1 Hz, 1H), 6.92-6.84 (m, 2H), 6.29 (d, J=1.9 Hz, 1H), 4.55 (dd, J=11.0, 4.4 Hz, 1H), 4.40 (dd, J=11.0, 6.1 Hz, 1H), 4.03-3.92 (m, 1H), 3.72 (d, J=11.5 Hz, 6H), 3.35-3.23 (m, 1H), 2.97 (dd, J=14.1, 8.4 Hz, 1H); MS: m/z 454.

4-(3-(3,4-difluorobenzyl)-3,4-dihydro-5-oxa-1,2,2a$^1$-triazaacenaphthylen-7-yl)-N-(1-methyl-1H-pyrazol-5-yl)pyrimidin-2-amine (I-53) was prepared analogously except dimethyl 2-(3,4-difluorobenzyl)malonate replaced dimethyl 2-(4-fluorobenzyl)malonate.

(R)-4-(3-(3,4-difluorobenzyl)-3,4-dihydro-5-oxa-1,2,2a$^1$-triazaacenaphthylen-7-yl)-N-(1-methyl-1H-pyrazol-5-yl) pyrimidin-2-amine: $^1$H NMR (400 MHz, DMSO-d6) δ 9.55 (s, 1H), 8.59 (d, J=5.2 Hz, 1H), 8.17 (d, J=1.1 Hz, 1H), 7.64 (d, J=5.2 Hz, 1H), 7.49-7.30 (m, 3H), 7.18-7.11 (m, 1H), 6.97 (d, J=1.2 Hz, 1H), 6.29 (d, J=1.9 Hz, 1H), 4.61 (dd, J=11.0, 4.4 Hz, 1H), 4.45 (dd, J=11.0, 6.0 Hz, 1H), 4.12-4.00 (m, 1H), 3.71 (s, 3H), 3.27 (d, J=7.4 Hz, 1H), 3.08 (dd, J=14.1, 7.4 Hz, 1H); MS: m/z 460.

(S)-4-(3-(3,4-difluorobenzyl)-3,4-dihydro-5-oxa-1,2,2a$^1$-triazaacenaphthylen-7-yl)-N-(1-methyl-1H-pyrazol-5-yl) pyrimidin-2-amine: $^1$H NMR (400 MHz, DMSO-d6) δ 9.55 (s, 1H), 8.59 (d, J=5.2 Hz, 1H), 8.17 (d, J=1.2 Hz, 1H), 7.64 (d, J=5.2 Hz, 1H), 7.49-7.30 (m, 3H), 7.19-7.10 (m, 1H), 6.97 (d, J=1.2 Hz, 1H), 6.29 (d, J=1.9 Hz, 1H), 4.61 (dd, J=11.0, 4.4 Hz, 1H), 4.45 (dd, J=11.0, 6.0 Hz, 1H), 4.12-4.00 (m, 1H), 3.71 (s, 3H), 3.27 (q, J=13.4, 9.1 Hz, 3H), 3.08 (dd, J=14.1, 7.4 Hz, 1H); MS: m/z 460.

4-(3-(3,4-difluorobenzyl)-3,4-dihydro-5-oxa-1,2,2a$^1$-triazaacenaphthylen-7-yl)-N-(1-methyl-1H-pyrazol-5-yl)pyridin-2-amine (I-54) was prepared analogously except in step 1, dimethyl 2-(4-fluorobenzyl)malonate was replaced with dimethyl 2-(3,4-difluorobenzyl)malonate and in step 4, 6-fluoro-4-[2-[(2-methylpyrazol-3-yl)amino]pyrimidin-4-yl]-1H-pyridin-2-one hydrazine was replaced by 2'-fluoro-6'-hydrazinyl-N-(1-methyl-1H-pyrazol-5-yl)-[4,4'-bipyridin]-2-amine.

(R)-4-(3-(3,4-difluorobenzyl)-3,4-dihydro-5-oxa-1,2,2a$^1$-triazaacenaphthylen-7-yl)-N-(1-methyl-1H-pyrazol-5-yl) pyridin-2-amine: $^1$H NMR (400 MHz, DMSO-d6) δ 9.55 (s, 1H), 8.59 (d, J=5.2 Hz, 1H), 8.17 (d, J=1.1 Hz, 1H), 7.64 (d, J=5.2 Hz, 1H), 7.49-7.30 (m, 3H), 7.18-7.11 (m, 1H), 6.97 (d, J=1.2 Hz, 1H), 6.29 (d, J=1.9 Hz, 1H), 4.61 (dd, J=11.0, 4.4 Hz, 1H), 4.45 (dd, J=11.0, 6.0 Hz, 1H), 4.12-4.00 (m, 1H), 3.71 (s, 3H), 3.27 (d, J=7.4 Hz, 1H), 3.08 (dd, J=14.1, 7.4 Hz, 1H); MS: m/z 459.

(S)-4-(3-(3,4-difluorobenzyl)-3,4-dihydro-5-oxa-1,2,2a$^1$-triazaacenaphthylen-7-yl)-N-(1-methyl-1H-pyrazol-5-yl) pyridin-2-amine: $^1$H NMR (400 MHz, DMSO-d6) δ 9.55 (s, 1H), 8.59 (d, J=5.2 Hz, 1H), 8.17 (d, J=1.2 Hz, 1H), 7.64 (d, J=5.2 Hz, 1H), 7.49-7.30 (m, 3H), 7.19-7.10 (m, 1H), 6.97 (d, J=1.2 Hz, 1H), 6.29 (d, J=1.9 Hz, 1H), 4.61 (dd, J=11.0, 4.4 Hz, 1H), 4.45 (dd, J=11.0, 6.0 Hz, 1H), 4.12-4.00 (m, 1H), 3.71 (s, 3H), 3.27 (q, J=13.4, 9.1 Hz, 3H), 3.08 (dd, J=14.1, 7.4 Hz, 1H); MS: m/z 459.

4-(3-(4-methoxybenzyl)-3,4-dihydro-5-oxa-1,2,2a$^1$-triazaacenaphthylen-7-yl)-N-(1-methyl-1H-pyrazol-5-yl)pyridin-2-amine was prepared analogously except in step 1, dimethyl 2-(4-fluorobenzyl)malonate was replaced with dimethyl 2-(4-methoxybenzyl)malonate and in step 4, 6-fluoro-4-[2-[(2-methylpyrazol-3-yl)amino]pyrimidin-4-yl]-1H-pyridin-2-one hydrazine was replaced by 2'-fluoro-6'-hydrazinyl-N-(1-methyl-H-pyrazol-5-yl)-[4,4'-bipyridin]-2-amine.

(R)-4-(3-(4-methoxybenzyl)-3,4-dihydro-5-oxa-1,2,2a$^1$-triazaacenaphthylen-7-yl)-N-(1-methyl-1H-pyrazol-5-yl)pyridin-2-amine: $^1$H NMR (400 MHz, DMSO-d6) δ 8.87 (s, 1H), 8.21 (d, J=5.3 Hz, 1H), 7.66 (d, J=1.2 Hz, 1H), 7.35 (d, J=1.9 Hz, 1H), 7.26-7.13 (m, 3H), 7.09-7.03 (m, 1H), 6.93-6.84 (m, 2H), 6.59 (d, J=1.2 Hz, 1H), 6.28 (d, J=1.9 Hz, 1H), 4.55 (dd, J=11.0, 4.4 Hz, 1H), 4.40 (dd, J=11.0, 6.2 Hz, 1H), 4.02-3.91 (m, 1H), 3.71 (d, J=18.6 Hz, 6H), 3.35-3.22 (m, 1H), 2.97 (dd, J=14.1, 8.4 Hz, 1H); MS: m/z 453.

(S)-4-(3-(4-methoxybenzyl)-3,4-dihydro-5-oxa-1,2,2a$^1$-triazaacenaphthylen-7-yl)-N-(1-methyl-1H-pyrazol-5-yl)pyridin-2-amine: $^1$H NMR (400 MHz, DMSO-d6) δ 8.87 (s, 1H), 8.21 (d, J=5.4 Hz, 1H), 7.66 (s, 1H), 7.35 (s, 1H), 7.23 (d, J=8.1 Hz, 2H), 7.17 (d, J=5.3 Hz, 1H), 7.06 (s, 1H), 6.88 (d, J=8.0 Hz, 2H), 6.59 (s, 1H), 6.28 (s, 1H), 4.54 (d, J=4.4 Hz, 1H), 4.40 (t, J=5.4 Hz, 1H), 3.96 (s, 1H), 3.71 (d, J=18.7 Hz, 6H), 3.01-2.93 (m, 1H); MS: m/z 453.

Example 3

4-(3-isobutyl-4,5-dihydro-3H-1,2,2a$^1$,5-tetraazaacenaphthylen-7-yl)-N-(1-methyl-1H-pyrazol-5-yl)pyrimidin-2-amine (I-10)

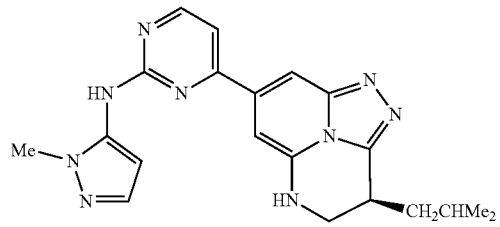

step 5 (SCHEME A): HATU (338 mg, 0.88 mmol) was added to a mixture of 6-fluoro-4-[2-[(2-methylpyrazol-3-yl)amino]pyrimidin-4-yl]-1H-pyridin-2-one hydrazone (218 mg, 0.72 mmol), 2-isobutyl-3-(Boc-amino)propanoic acid (218 mg, 0.88 mmol) and TEA (0.36 mL, 2.54 mmol) in DMF (6 mL). The mixture was stirred for 2 h, concentrated in vacuo and the residue was partitioned between water and EtOAc. The combined organic extracts were washed sequentially with water, 1% aq. citric acid, sat. aq. NaHCO$_3$, water, brine, then dried (MgS$_4$), filtered and concentrated in vacuo. The residue was purified on a 12 g SiO$_2$ column eluting with an EtOAc/heptane gradient (0 to 90% EtOAc) to afford 217 mg (52%) of tert-butyl N-[2-[[[(Z)-[6-fluoro-4-[2-[(2-methylpyrazol-3-yl)amino]pyrimidin-4-yl]-1H-pyridin-2-ylidene]amino]carbamoyl]-4-methyl-pentyl]carbamate. MS: m/z 577.

step 6: A mixture of tert-butyl N-[2-[[[(Z)-[6-fluoro-4-[2-[(2-methylpyrazol-3-yl)amino]pyrimidin-4-yl]-1H-pyridin-2-ylidene]amino]carbamoyl]-4-methyl-pentyl]carbamate (217 mg, 0.38 mmol), DIPEA (0.57 mL, 3.26 mmol) and Ph$_3$P.Br$_2$ (611 mg, 1.45 mmol) in MeCN (5 mL) was heated in a sealed vial at 80° C. for 30 min. The mixture was cooled to RT, mixed with water (5 mL) and stirred for 20 min. The mixture was then partitioned between EtOAc and water. The organic extracts were washed with sat. aq. NaHCO$_3$, 1% aq. citric acid, brine, dried (Na$_2$SO$_4$), filtered and concentrated in vacuo. The residue was purified on a 12 g SiO$_2$ column eluting with MeOH/DCM gradient (0 to 7% MeOH) to afford 130 mg (70%) of tert-butyl (2-(5-fluoro-7-(2-((1-methyl-1H-pyrazol-5-yl)amino)pyrimidin-4-yl)-[1,2,4]triazolo[4,3-a]pyridin-3-yl)-4-methylpentyl)carbamate. MS: m/z 510.

step 7: A mixture of tert-butyl N-[2-[5-fluoro-7-[2-[(2-methylpyrazol-3-yl)amino]pyrimidin-4-yl]-[1,2,4]triazolo[4,3-a]pyridin-3-yl]-4-methyl-pentyl]carbamate (130 mg, 0.26 mmol) in TFA (3 mL, 39.68 mmol) and DCM (3 mL) was stirred for 1 h. The mixture was concentrated in vacuo, the residue triturated with Et$_2$O and the Et$_2$O decanted. The semi-solid residue of 4-(3-(1-amino-4-methylpentan-2-yl)-5-fluoro-[1,2,4]triazolo[4,3-a]pyridin-7-yl)-N-(1-methyl-1H-pyrazol-5-yl)pyrimidin-2-amine bis-trifluoroacetate (168 mg) was used without further purification. MS: m/z 410.

step 8: A mixture of 4-(3-(1-amino-4-methylpentan-2-yl)-5-fluoro-[1,2,4]triazolo[4,3-a]pyridin-7-yl)-N-(1-methyl-1H-pyrazol-5-yl)pyrimidin-2-amine bis-trifluoroacetate (168 mg, 0.26 mmol) in pyridine (8 mL) was heated at 110° C. for 30 min. The mixture was concentrated in vacuo and the residue recrystallized from EtOAc/MeOH mixture to afford 86 mg (87%) of racemic 4-(3-isobutyl-4,5-dihydro-3H-1,2,2a$^1$,5-tetraazaacenaphthylen-7-yl)-N-(1-methyl-1H-pyrazol-5-yl)pyrimidin-2-amine (I-10). MS: m/z 390.

The racemic mixture was resolved by chiral chromatography to afford:

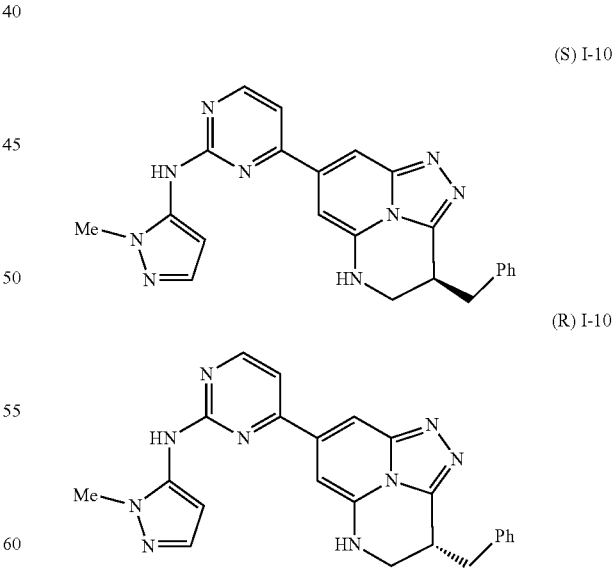

(S)-4-(3-isobutyl-4,5-dihydro-3H-1,2,2a$^1$,5-tetraazaacenaphthylen-7-yl)-N-(1-methyl-1H-pyrazol-5-yl)pyrimidin-2-amine (S)-I-10, 34 mg. $^1$H NMR (400 MHz, DMSO-d$_6$) δ 9.49 (s, 1H), 8.55 (d, J=5.2 Hz, 1H), 7.83 (d, J=2.1 Hz, 1H), 7.66 (d, J=1.2 Hz, 1H), 7.48 (d, J=5.3 Hz, 1H), 7.38 (d, J=1.9

Hz, 1H), 6.53 (d, J=1.2 Hz, 1H), 6.30 (d, J=1.9 Hz, 1H), 3.71 (s, 3H), 3.62 (ddd, J=11.8, 5.0, 2.4 Hz, 1H), 3.49 (dd, J=7.0, 5.0 Hz, 1H), 3.22 (ddd, J=11.9, 6.7, 1.8 Hz, 1H), 1.95 (dq, J=13.4, 6.7 Hz, 1H), 1.81 (dt, J=14.2, 7.2 Hz, 1H), 1.49 (dt, J=13.6, 7.2 Hz, 1H), 1.02 (d, J=6.5 Hz, 3H), 0.96 (d, J=6.6 Hz, 3H). MS: m/z 390.

(R)-4-(3-isobutyl-4,5-dihydro-3H-1,2,2a$^1$,5-tetraazaacenaphthylen-7-yl)-N-(1-methyl-1H-pyrazol-5-yl)pyrimidin-2-amine (R)-I-10: 34 mg. MS: m/z 390.

N-(1-methyl-1H-pyrazol-5-yl)-4-(3-phenyl-4,5-dihydro-3H-1,2,2a$^1$,5-tetraazaacenaphthylen-7-yl)pyrimidin-2-amine (I-1) can be prepared analogously except in step 5, (R,S)-2-isobutyl-3-(Boc-amino)propanoic acid was replaced with 3-((tert-butoxycarbonyl)amino)-2-phenylpropanoic acid (CASRN 67098-56-0).

(R)—N-(1-methyl-1H-pyrazol-5-yl)-4-(3-phenyl-4,5-dihydro-3H-1,2,2a$^1$,5-tetraazaacenaphthylen-7-yl)pyrimidin-2-amine ((R) I-1). $^1$H NMR (400 MHz, DMSO-d6): δ 9.51 (s, 1H), 8.57 (d, J=5.2 Hz, 1H), 7.99 (s, 1H), 7.74 (d, J=1.2 Hz, 1H), 7.52 (d, J=5.3 Hz, 1H), 7.38-7.23 (m, 6H), 6.61 (d, J=1.2 Hz, 1H), 6.31 (d, J=2.0 Hz, 1H), 4.84 (dd, J=6.5, 5.0 Hz, 1H), 3.81 (dd, J=10.3, 5.4 Hz, 1H), 3.72 (s, 3H), 3.59-3.49 (m, 1H). MS: m/z 410

(S)—N-(1-methyl-1H-pyrazol-5-yl)-4-(3-phenyl-4,5-dihydro-3H-1,2,2a$^1$,5-tetraazaacenaphthylen-7-yl)pyrimidin-2-amine ((S) I-1). $^1$H NMR (400 MHz, DMSO-d6) δ 9.51 (s, 1H), 8.57 (d, J=5.1 Hz, 1H), 7.99 (d, J=2.5 Hz, 1H), 7.74 (d, J=1.2 Hz, 1H), 7.52 (d, J=5.3 Hz, 1H), 7.39-7.25 (m, 6H), 6.61 (d, J=1.3 Hz, 1H), 6.31 (d, J=1.9 Hz, 1H), 4.84 (dd, J=6.5, 5.0 Hz, 1H), 3.81 (dd, J=10.4, 5.2 Hz, 1H), 3.72 (s, 3H), 3.59-3.50 (m, 1H). MS: m/z 410.

4-(3-benzyl-4,5-dihydro-3H-1,2,2a$^1$,5-tetraazaacenaphthylen-7-yl)-N-(1-methyl-H-pyrazol-5-yl)pyrimidin-2-amine (I-2) can be prepared analogously except in step 5, 2-isobutyl-3-(Boc-amino)propanoic acid was replaced with N-Boc 3-amino-2-benzylpropionic acid (CAS Reg No. 67098-56-0).

(R)-4-(3-benzyl-4,5-dihydro-3H-1,2,2a$^1$,5-tetraazaacenaphthylen-7-yl)-N-(1-methyl-1H-pyrazol-5-yl)pyrimidin-2-amine ((R) I-2). $^1$H NMR (400 MHz, DMSO-d6) δ 9.49 (s, 1H), 8.55 (d, J=5.2 Hz, 1H), 7.78 (d, J=2.1 Hz, 1H), 7.70 (d, J=1.2 Hz, 1H), 7.50 (d, J=5.2 Hz, 1H), 7.38 (d, J=1.9 Hz, 1H), 7.36-7.31 (m, 4H), 7.29-7.22 (m, 1H), 6.54 (d, J=1.2 Hz, 1H), 6.30 (d, J=1.9 Hz, 1H), 3.77 (ddd, J=9.6, 4.9, 2.0 Hz, 1H), 3.71 (s, 2H), 3.46-3.35 (m, 2H), 3.24-3.16 (m, 1H), 2.91 (dd, J=13.8, 9.5 Hz, 1H). MS: 424.

(S)-4-(3-benzyl-4,5-dihydro-3H-1,2,2a$^1$,5-tetraazaacenaphthylen-7-yl)-N-(1-methyl-1H-pyrazol-5-yl)pyrimidin-2-amine ((S) I-2). $^1$H NMR (400 MHz, DMSO-d6) δ 9.49 (s, 1H), 8.55 (d, J=5.2 Hz, 1H), 7.78 (d, J=2.4 Hz, 1H), 7.70 (d, J=1.2 Hz, 1H), 7.50 (d, J=5.2 Hz, 1H), 7.38 (d, J=1.9 Hz, 1H), 7.34 (d, J=4.4 Hz, 3H), 7.28-7.22 (m, 1H), 6.54 (d, J=1.2 Hz, 1H), 6.30 (d, J=1.9 Hz, 1H), 3.77 (ddd, J=9.5, 4.8, 2.0 Hz, 1H), 3.71 (s, 3H), 3.47-3.35 (m, 2H), 3.24-3.16 (m, 1H), 2.91 (dd, J=13.8, 9.5 Hz, 1H). MS: m/z 424.

(S)-4-(3-isopropyl-4,5-dihydro-3H-1,2,2a$^1$,5-tetraazaacenaphthylen-7-yl)-N-(1-methyl-1H-pyrazol-5-yl)pyrimidin-2-amine (I-3) can be prepared analogously except in step 5, 2-isobutyl-3-(Boc-amino)propanoic acid was replaced with (2S)-2-[[[(1,1-dimethylethoxy)carbonyl]amino]methyl]-3-methyl-butanoic acid, (CASRN 1233517-91-3). $^1$H NMR (400 MHz, DMSO-d$_6$) δ 9.58 (s, 1H), 8.61 (d, J=5.1 Hz, 1H), 8.33 (s, 1H), 7.65 (d, J=1.2 Hz, 1H), 7.53 (d, J=5.2 Hz, 1H), 7.39 (d, J=2.0 Hz, 1H), 6.76 (d, J=1.1 Hz, 1H), 6.30 (d, J=1.9 Hz, 1H), 3.72 (s, 3H), 3.64 (ddd, J=12.3, 5.3, 2.3 Hz, 1H), 2.21 (dq, J=13.4, 6.7 Hz, 1H), 1.11-1.03 (m, 6H). MS: m/z 376.

4-(3-(4-chlorobenzyl)-4,5-dihydro-3H-1,2,2a$^1$,5-tetraazaacenaphthylen-7-yl)-N-(1-methyl-1H-pyrazol-5-yl)pyrimidin-2-amine (I-5) can be prepared analogously except in step 5, (R,S)-2-isobutyl-3-(Boc-amino)propanoic acid was replaced with 2-[(tert-butoxycarbonylamino)methyl]-3-(4-chloro-phenyl)propanoic acid.

4-(3-(4-methoxybenzyl)-4,5-dihydro-3H-1,2,2a$^1$,5-tetraazaacenaphthylen-7-yl)-N-(1-methyl-1H-pyrazol-5-yl)pyrimidin-2-amine (I-11) can be prepared analogously except in step 5, (R,S)-2-isobutyl-3-(Boc-amino)propanoic acid was replaced with 2-[(tert-butoxycarbonylamino)methyl]-3-(4-methoxyphenyl)propanoic acid (CASRN 683218-95-3).

4-(3-(3-fluoro-4-methoxybenzyl)-4,5-dihydro-3H-1,2,2a$^1$,5-tetraazaacenaphthylen-7-yl)-N-(1-methyl-1H-pyrazol-5-yl)pyrimidin-2-amine (I-12) can be prepared analogously except in step 5, (R,S)-2-isobutyl-3-(Boc-amino)propanoic acid was replaced with 2-[(tert-butoxycarbonylamino)methyl]-3-(3-fluoro-4-methoxyphenyl)propanoic acid.

4-(3-(4-chloro-3-fluorobenzyl)-4,5-dihydro-3H-1,2,2a$^1$,5-tetraazaacenaphthylen-7-yl)-N-(1-methyl-1H-pyrazol-5-yl)pyrimidin-2-amine (I-14) can be prepared analogously except in step 5, (R,S)-2-isobutyl-3-(Boc-amino)propanoic acid was replaced with 2-[(tert-butoxycarbonylamino)methyl]-3-(4-chloro-3-fluoro-phenyl)propanoicacid (CASRN1001179-21-0).

4-(3-(4-fluorobenzyl)-4,5-dihydro-3H-1,2,2a$^1$,5-tetraazaacenaphthylen-7-yl)-N-(1-methyl-1H-pyrazol-5-yl)pyrimidin-2-amine (I-21) can be prepared analogously except in step 5, (R,S)-2-isobutyl-3-(Boc-amino)propanoic acid was replaced with 2-[(tert-butoxycarbonylamino)methyl]-3-(4-fluoro-phenyl)propanoic acid (CAS Reg No. 1255099-58-1).

Example 4

4-(3-benzyl-3,4-dihydro-5-thia-1,1,2a$^1$-triazaacenaphthylen-7-yl)-N-(1-methyl-1H-pyrazol-5-yl)pyrimidin-2-amine (I-16)

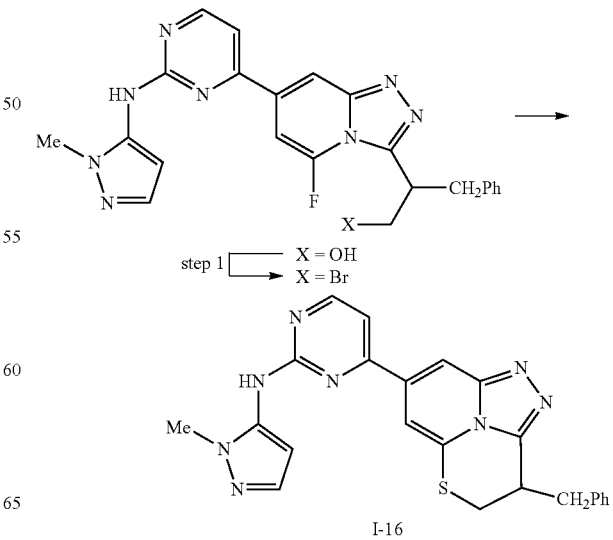

I-16

(SCHEME C) step 1: A mixture of 2-[5-fluoro-7-[2-[(2-methylpyrazol-3-yl)amino]pyrimidin-4-yl]-[1,2,4]triazolo[4,3-a]pyridin-3-yl]-3-phenyl-propan-1-ol (85 mg, 0.1912 mmol), Ph$_3$P.Br$_2$ (282.5 mg, 3.5 equiv, 0.6693 mmol) and DIPEA (0.267 mL, 8.0 equiv, 1.530 mmol) in MeCN (15 mL) was heated in a sealed vial at 80° C. for 3 h. The mixture was partitioned between water and EtOAc. The organic extracts were washed sequentially with water, aq. citric acid, water, brine, dried (MgSO$_4$) and concentrated. The residue was purified on a 12 g SiO$_2$ column eluting with a MeOH/DCM gradient (0 to 7% MeOH) to afford 62 mg of 4-[3-(1-benzyl-2-bromo-ethyl)-5-fluoro-[1,2,4]triazolo[4,3-a]pyridin-7-yl]-N-(2-methylpyrazol-3-yl)pyrimidin-2-amine step 2: A mixture of 4-[3-(1-benzyl-2-bromo-ethyl)-5-fluoro-[1,2,4]triazolo[4,3-a]pyridin-7-yl]-N-(2-methylpyrazol-3-yl)pyrimidin-2-amine (62 mg, 0.1222 mmol) and sulfanylsodium hydrate (45.7 mg, 5.0 equiv, 0.6110 mmol) in DMF (3 mL) was stirred for 1 h. The mixture was concentrated in vacuo the residue partitioned between sat'd. NaHCO$_3$ and MeTHF. The organic extracts were washed sequentially with water, brine, dried (MgSO$_4$), filtered and concentrated. The residue was purified on a 4 g SiO$_2$ column eluting with a MeOH/DCM gradient (0 to 7% MeOH) to afford 40 mg of I-16. The racemic product was resolved by SFC chromatography on a chiral column.

Intramolecular cyclization of bromoethyl derivatives with a secondary amine also affords a procedure to prepare analogs with a tertiary amine in the tricycle.

Racemic 4-(3-benzyl-5-ethyl-4,5-dihydro-3H-1,1,2a$^1$,5-tetraazaacenaphthylen-7-yl)-N-(1-methyl-1H-pyrazol-5-yl)pyrimidin-2-amine (I-17)

A mixture of 4-[3-(1-benzyl-2-bromo-ethyl)-5-fluoro-[1,2,4]triazolo[4,3-a]pyridin-7-yl]-N-(2-methylpyrazol-3-yl)pyrimidin-2-amine (47 mg, 0.093 mmol) and EtNH$_2$ (0.12 mL, 1.86 mmol) in THF was heated in a sealed vial at 75° C. for 3 h. The mixture was concentrated in vacuo and the residue purified on a 4 g SiO$_2$ column eluting with a MeOH/DCM gradient (0 to 8% MeOH) to afford 28 mg of racemic 4-(3-benzyl-5-ethyl-4,5-dihydro-3H-1,1,2a$^1$,5-tetraazaacenaphthylen-7-yl)-N-(1-methyl-1H-pyrazol-5-yl)pyrimidin-2-amine as a yellow foam. MS: m/z 452. The racemic product was resolved by chiral SFC chromatography.

(S)-4-(3-benzyl-5-ethyl-4,5-dihydro-3H-1,1,2a$^1$,5-tetraazaacenaphthylen-7-yl)-N-(1-methyl-1H-pyrazol-5-yl)pyrimidin-2-amine (11 mg) ((S) I-17): $^1$H NMR (400 MHz, DMSO-d$_6$) δ 9.52 (s, 1H), 8.57 (d, J=5.1 Hz, 1H), 7.76 (s, 1H), 7.63 (d, J=5.2 Hz, 1H), 7.38 (d, J=1.9 Hz, 1H), 7.33 (m, 4H), 7.29-7.22 (m, 1H), 6.59 (s, 1H), 6.31 (d, J=1.9 Hz, 1H), 3.87 (dq, J=10.6, 5.7 Hz, 1H), 3.71 (s, 3H), 3.58-3.30 (m, 5H), 2.93 (dd, J=13.9, 9.1 Hz, 1H), 1.18 (t, J=7.0 Hz, 3H); MS: m/z 452.

(R)-4-(3-benzyl-5-ethyl-4,5-dihydro-3H-1,1,2a$^1$,5-tetraazaacenaphthylen-7-yl)-N-(1-methyl-1H-pyrazol-5-yl)pyrimidin-2-amine (11 mg) ((R) I-17): $^1$H NMR (400 MHz, DMSO-d$_6$) δ 9.52 (s, 1H), 8.57 (d, J=5.2 Hz, 1H), 7.76 (d, J=1.1 Hz, 1H), 7.63 (d, J=5.2 Hz, 1H), 7.38 (d, J=1.9 Hz, 1H), 7.35-7.30 (m, 4H), 7.28-7.21 (m, 1H), 6.59 (d, J=1.1 Hz, 1H), 6.31 (d, J=1.9 Hz, 1H), 3.87 (dq, J=10.8, 5.7 Hz, 1H), 3.71 (s, 3H), 3.58-3.30 (m, 5H), 2.93 (dd, J=13.9, 9.1 Hz, 1H), 1.18 (t, J=7.0 Hz, 3H); MS: m/z 452

Example 5

4-(9-(4-chlorobenzyl)-8,9-dihydro-7H-6-oxa-1,2,2a$^1$-triazabenzo[cd]azulen-4-yl)-N-(1-methyl-1H-pyrazol-5-yl)pyrimidin-2-amine (I-36)

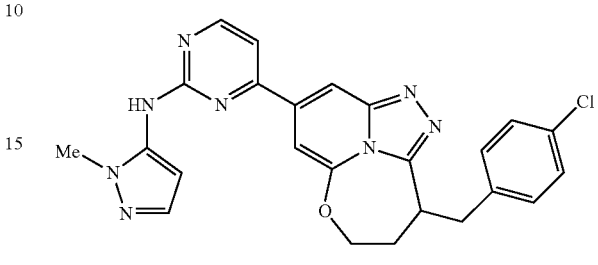

I-36

A solution of O$^4$-tert-butyl O$^1$-methyl 2-[(4-chlorophenyl)methyl]butanedioate (330 mg, 1.055 mmol) in DCM (4.0 mL) and TFA (2.0 mL) was stirred at RT for 18 h. The reaction was concentrated and diluted in water then extracted with EtOAc. The combined organic layers were dried (Na$_2$SO$_4$), filtered and concentrated in vacuo. The crude 3-[(4-chlorophenyl)methyl]-4-methoxy-4-oxo-butanoic was used in the next step without further purification.

step 2: To a solution of 3-[(4-chlorophenyl)methyl]-4-methoxy-4-oxo-butanoic acid (270 mg, 1.0519 mmol) in THF (9.0 mL) at 0° C. was added BH$_3$.SMe$_2$ (1400 mg, 1.6 mL, 3.165 mmol). The reaction mixture was stirred at RT for 18 h. The reaction was quenched with water and extracted with EtOAc. The combined extracts were dried (Na$_2$SO$_4$), filtered and concentrated in vacuo to afford methyl 2-[(4-chlorophenyl)methyl]-4-hydroxy-butanoate. The crude product was used with further purification.

step 3: A solution of methyl 2-[(4-chlorophenyl)methyl]-4-hydroxy-butanoate (256 mg, 1.0548 mmol), tert-butyldimethylchlorosilane (655.7 mg, 4.220 mmol) and imidazole (574.6 mg, 0.558 mL, 8.440 mmol) in DMF (5.0 mL) was stirred at RT for 18 h. The reaction was quenched with water and extracted with EtOAc. The combined extracts were dried (Na$_2$SO$_4$), filtered and concentrated in vacuo. The crude product was purified by SiO$_2$ chromatography eluting with a EtOAc/heptane gradient (the product eluted with 10% EtOAc).

step 4: To a solution of methyl 4-[tert-butyl(dimethyl)silyl]oxy-2-[(4-chlorophenyl)methyl]butanoate (376 mg, 1.053 mmol) in THF (4.0 mL) and water (4.0 mL) was added LiOH.H$_2$O (86 mg, 2.0 mmol). The reaction mixture was stirred at RT overnight. The reaction was concentrated, then diluted with water and extracted with EtOAc. The combined organic extracts were dried (Na$_2$SO$_4$), filtered and concentrated in vacuo. The crude product was used with further purification.

step 5: To a solution of 4-(tert-butyl-dimethyl-silanyloxy)-2-(4-chloro-benzyl)-butyric (1.2 equiv, 313.5 mg, 0.9990 mmol), HATU (1.2 equiv, 387.6 mg, 0.9990 mmol) and DIPEA (2 equiv, 215.2 mg, 0.290 mL, 1.665 mmol) in DMF (3 mL) was added 4-(2-fluoro-6-hydrazino-4-pyridyl)-N-(2-methylpyrazol-3-yl)pyrimidin-2-amine (250 mg, 0.8325 mmol). The resulting dark mixture was stirred at RT for 3 h. The reaction was quenched with 1N NaHCO$_3$, diluted with more water and extracted with EtOAc (3×10 mL). The combined extracts were dried (Na$_2$SO$_4$), filtered and concentrated on CELITE® in vacuo. The crude product was purified by SiO$_2$ chromatography (ISCO, 12 g column) eluting with a MeOH/DCM gradient (0 to 5% MeOH) to afford 283 mg of of 4-[tert-butyl(dimethyl)silyl]oxy-2-[(4-chlorophenyl)methyl]-N'-[6-fluoro-4-[2-[(2-methylpyrazol-3-yl)amino]pyrimidin-4-yl]-2-pyridyl]butanehydrazide as a yellow solid.

step 6: To a solution of 4-[tert-butyl(dimethyl)silyl]oxy-2-[(4-chlorophenyl)methyl]-N'-[6-fluoro-4-[2-[(2-methylpyrazol-3-yl)amino]pyrimidin-4-yl]-2-pyridyl]butanehydrazide (198 mg, 0.3167 mmol) in MeCN (12.0 mL) was added DIPEA (372.1 mg, 0.501 mL, 2.850 mmol) and Ph$_3$P.Cl$_2$ (323.0 mg, 0.9501 mmol). The reaction was stirred at RT for 1 h. The reaction was quenched with water then extracted with EtOAc. The combined organic extracts were dried (Na$_2$SO$_4$), filtered and concentrated in vacuo. The crude product was purified by SiO$_2$ chromatography eluting with a MeOH/DCM gradient (the product eluted with 5% MeOH).

step 7: To a solution of 4-[3-[3-[tert-butyl(dimethyl)silyl]oxy-1-[(4-chlorophenyl)methyl]propyl]-5-fluoro-[1,2,4]triazolo[4,3-a]pyridin-7-yl]-N-(2-methylpyrazol-3-yl)pyrimidin-2-amine (110 mg, 0.1812 mmol) in DCM (10.0 mL) was added BF$_3$—OEt$_2$ (123.6 mg, 0.1102 mL, 0.8709 mmol). The reaction was stirred at RT for 18 h. The crude product was concentrated and purified by SiO$_2$ chromatography eluting with a MeOH/DCM gradient (the product eluted with 10% MeOH).

step 8: To a solution of 4-(4-chlorophenyl)-3-[5-fluoro-7-[2-[(2-methylpyrazol-3-yl)amino]pyrimidin-4-yl]-[1,2,4]triazolo[4,3-a]pyridin-3-yl]butan-1-ol (70 mg, 0.1420 mmol) in THF (15.0 mL) was added NaH (34.08 mg, 0.8521 mmol, 60% mineral oil dispersion). The reaction was stirred at RT for 20 min then heated to 60° C. for 1 h. The reaction was quenched with water and extracted with EtOAc. The combined organic extracts were dried (Na$_2$SO$_4$), filtered and concentrated in vacuo. The crude product was purified by SiO$_2$ chromatography eluting with a MeOH/DCM gradient (the product eluted with 5% MeOH) and finally resolved by chiral SFC.

(S) I-36: $^1$H NMR (400 MHz, DMSO) δ 9.58-9.47 (s, 1H), 8.63-8.53 (d, J=5.2 Hz, 1H), 8.29-8.19 (d, J=1.4 Hz, 1H), 7.69-7.59 (d, J=5.3 Hz, 1H), 7.43-7.27 (m, 5H), 7.07-6.98 (d, J=1.5 Hz, 1H), 6.34-6.23 (d, J=1.9 Hz, 1H), 4.67-4.56 (ddd, J=12.2, 6.6, 4.0 Hz, 1H), 4.53-4.39 (ddd, J=12.1, 7.9, 3.9 Hz, 1H), 3.95-3.80 (tt, J=9.9, 5.3 Hz, 1H), 3.74-3.67 (s, 3H), 3.66-3.57 (dd, J=13.7, 5.2 Hz, 1H), 3.19-3.07 (dd, J=13.8, 8.9 Hz, 1H), 2.28-2.14 (dt, J=15.6, 5.3 Hz, 1H), 2.12-1.95 (ddd, J=18.9, 9.4, 4.3 Hz, 1H).

(R) I-36: $^1$H NMR (400 MHz, DMSO) δ 9.59-9.46 (s, 1H), 8.62-8.54 (d, J=5.2 Hz, 1H), 8.28-8.19 (d, J=1.5 Hz, 1H), 7.67-7.60 (d, J=5.2 Hz, 1H), 7.43-7.26 (m, 5H), 7.05-6.96 (d, J=1.5 Hz, 1H), 6.33-6.20 (d, J=1.9 Hz, 1H), 4.67-4.56 (ddd, J=12.4, 6.7, 4.0 Hz, 1H), 4.52-4.41 (ddd, J=12.0, 7.8, 3.8 Hz, 1H), 3.95-3.81 (tt, J=9.7, 5.3 Hz, 1H), 3.75-3.67 (s, 3H), 3.66-3.57 (dd, J=13.8, 5.3 Hz, 1H), 3.17-3.08 (dd, J=13.8, 8.9 Hz, 1H), 2.28-2.14 (m, 1H), 2.13-1.95 (m, 1H).

4-(9-(4-Fluorobenzyl)-8,9-dihydro-7H-6-oxa-1,1,2a$^1$-triazabenzo[cd]azulen-4-yl)-N-(1-methyl-1H-pyrazol-5-yl)pyrimidin-2-amine (I-58) can be prepared analogously except in step 1, O$^4$-tert-butyl O$^1$-methyl 2-[(4-chlorophenyl)methyl]butanedioate was replaced with O$^4$-tert-butyl O$^1$-methyl 2-[(4-fluorophenyl)methyl]butanedioate.

4-(9-(3-Fluoro-4-methoxybenzyl)-8,9-dihydro-7H-6-oxa-1,1,2a$^1$-triazabenzo[cd]azulen-4-yl)-N-(1-methyl-1H-pyrazol-5-yl)pyrimidin-2-amine (I-59) can be prepared analogously except in step 1, O$^4$-tert-butyl O$^1$-methyl 2-[(4-chlorophenyl)methyl]butanedioate was replaced with O$^4$-tert-butyl O$^1$-methyl 2-[(3-fluoro-4-methoxy-phenyl)methyl]butanedioate.

4-(9-((Benzyloxy)methyl)-8,9-dihydro-7H-6-oxa-1,2,2a$^1$-triazabenzo[cd]azulen-4-yl)-N-(1-methyl-1H-pyrazol-5-yl)pyrimidin-2-amine (I-29) can be prepared analogously except in step 1, O$^4$-tert-butyl O$^1$-methyl 2-[(4-chlorophenyl)methyl]butanedioate was replaced with 2-benzyloxymethyl-4-(tert-butyl-dimethyl-silanyloxy)-butyric acid.

4-(9-(2-Chlorobenzyl)-8,9-dihydro-7H-6-oxa-1,2,2a$^1$-triazabenzo[cd]azulen-4-yl)-N-(1-methyl-1H-pyrazol-5-yl)pyridin-2-amine (I-30) can be prepared analogously except in step 5, 4-(tert-butyl-dimethyl-silanyloxy)-2-(4-chlorobenzyl)-butyric was replaced with 4-(tert-butyl-dimethyl-silanyloxy)-2-(2-chloro-benzyl)-butyric acid and (6'-fluoro-2'-hydrazino-[4,4']bipyridinyl-2-yl)-(2-methyl-2H-pyrazol-3-yl)-amine replaced [4-(2-fluoro-6-hydrazino-pyridin-4-yl)-pyrimidin-2-yl]-(2-methyl-2H-pyrazol-3-yl)-amine.

N-(1-Methyl-1H-pyrazol-5-yl)-4-(9-(3,3,3-trifluoropropyl)-8,9-dihydro-7H-6-oxa-1,2,2a$^1$-triazabenzo[cd]azulen-4-yl)pyrimidin-2-amine (I-102) can be prepared analogously except in step 5, 2-(tert-butyl-dimethyl-silanyloxymethyl)-5,5,5-trifluoro-pentanoic acid replaced 4-(tert-butyl-dimethyl-silanyloxy)-2-(4-chloro-benzyl)-butyric.

N-(1-Methyl-1H-pyrazol-5-yl)-4-(9-propyl-8,9-dihydro-7H-6-oxa-1,2,2a$^1$-triazabenzo[cd]azulen-4-yl)pyridin-2-amine (I-103) can be prepared analogously except in step 5, 2-(tert-butyl-dimethyl-silanyloxymethyl)-pentanoic acid replaced 4-(tert-butyl-dimethyl-silanyloxy)-2-(4-chlorobenzyl)-butyric and (6'-fluoro-2'-hydrazino-[4,4']bipyridinyl-2-yl)-(2-methyl-2H-pyrazol-3-yl)-amine replaced [4-(2-fluoro-6-hydrazino-pyridin-4-yl)-pyrimidin-2-yl]-(2-methyl-2H-pyrazol-3-yl)-amine.

N-(1-Methyl-1H-pyrazol-5-yl)-4-(9-propyl-8,9-dihydro-7H-6-oxa-1,2,2a$^1$-triazabenzo[cd]azulen-4-yl)pyrimidin-2-amine (I-104) can be prepared analogously except in step 5, 2-(tert-butyl-dimethyl-silanyloxymethyl)-pentanoic acid replaced 4-(tert-butyl-dimethyl-silanyloxy)-2-(4-chlorobenzyl)-butyric.

N-(1-Methyl-1H-pyrazol-5-yl)-4-(9-(2,2,2-trifluoroethyl)-8,9-dihydro-7H-6-oxa-1,2,2a$^1$-triazabenzo[cd]azulen-4-yl)pyrimidin-2-amine (I-106) can be prepared analogously except in step 5, 2-[2-(tert-Butyl-dimethyl-silanyloxy)-ethyl]-4,4,4-trifluoro-butyric acid acid replaced 4-(tert-butyl-dimethyl-silanyloxy)-2-(4-chloro-benzyl)-butyric.

4-(9-Isobutyl-8,9-dihydro-7H-6-oxa-1,2,2a$^1$-triazabenzo[cd]azulen-4-yl)-N-(1-methyl-1H-pyrazol-5-yl)pyrimidin-2-amine (I-107) can be prepared analogously except in step 5, 2-[2-(tert-butyl-dimethyl-silanyloxy)-ethyl]-4-methyl-pentanoic acid replaced 4-(tert-butyl-dimethyl-silanyloxy)-2-(4-chloro-benzyl)-butyric.

Example 6

N-(1-methyl-1H-pyrazol-5-yl)-4-(3-phenyl-4,5-dihydro-3H-1,1,2a$^1$,5-tetraazaacenaphthylen-7-yl)pyridin-2-amine (I-4)

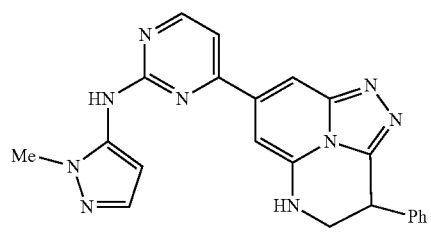

I-4 step 1: To a solution of 4-(2-fluoro-6-hydrazino-4-pyridyl)-N-(2-methylpyrazol-3-yl)pyridin-2-amine (referential example 1, 128 mg, 0.4277 mmol) in DMF (6.0 mL) was added DIPEA (111.7 mg, 0.150 mL, 0.8553 mmol), 3-tert-butoxycarbonylamino-2-phenyl propionic acid (151 mg, 0.5560 mmol) and HATU (234.7 mg, 0.5987 mmol). The reaction mixture was stirred at RT 2 h. The reaction was quenched with water and extracted with EtOAc. The combined organic layers were dried (Na₂SO₄), filtered and concentrated in vacuo. The crude product was purified by SiO₂ chromatography eluting with a MeON/DCM gradient (the product eluted with 10% MeOH) to afford 203 mg of tert-butyl N-[3-[2-[6-fluoro-4-[2-[(2-methylpyrazol-3-yl)amino]-4-pyridyl]-2-pyridyl]hydrazino]-3-oxo-2-phenyl-propyl]carbamate.

step 2: To a mixture of tert-butyl N-[3-[2-[6-fluoro-4-[2-[(2-methylpyrazol-3-yl)amino]-4-pyridyl]-2-pyridyl]hydrazino]-3-oxo-2-phenyl-propyl]carbamate (203 mg, 0.3714 mmol), Ph₃P (147.6 mg, 0.5571 mmol) and TMSN₃ (45.04 mg, 0.0521 mL, 0.3714 mmol) in THF (3.5 mL) was added DEAD (114.1 mg, 0.10 mL, 0.5571 mmol). The reaction was stirred 15 min then concentrated. The crude product was purified by SiO₂ eluting with a MeOH/DCM gradient (eluted with 7% MeOH) to afford 87 mg of tert-butyl N-[2-[5-fluoro-7-[2-[(2-methylpyrazol-3-yl)amino]-4-pyridyl]-[1,2,4]triazolo[4,3-a]pyridin-3-yl]-2-phenyl-ethyl]carbamate.

step 3: To a solution of tert-butyl N-[2-[5-fluoro-7-[2-[(2-methylpyrazol-3-yl)amino]-4-pyridyl]-[1,2,4]triazolo[4,3-a]pyridin-3-yl]-2-phenyl-ethyl]carbamate (86 mg, 0.1627 mmol) in DCM (1.5 mL) was added TFA (0.3 mL). The reaction was stirred for 30 min. The reaction was concentrated and washed with ether. The crude product was used without further purification.

step 4: A solution of 4-[3-(2-amino-1-phenyl-ethyl)-5-fluoro-[1,2,4]triazolo[4,3-a]pyridin-7-yl]-N-(2-methylpyrazol-3-yl)pyridin-2-amine (70 mg, 0.1634 mmol) in pyridine (6.0 mL) was heated at 100° C. for 30 min. The reaction was concentrated and purified by reverse phase HPLC and the racemic mixture resolved by chiral chromatography.

Peak 1 (S) I-4: ¹H NMR (400 MHz, DMSO-d₆) δ 8.91-8.85 (s, 1H), 8.23-8.18 (d, J=5.3 Hz, 1H), 7.96-7.89 (t, J=2.1 Hz, 1H), 7.39-7.24 (m, 6H), 7.15-7.10 (dd, J=5.4, 1.6 Hz, 1H), 7.04-6.99 (d, J=1.4 Hz, 1H), 6.30-6.25 (d, J=1.9 Hz, 1H), 6.16-6.11 (d, J=1.3 Hz, 1H), 4.87-4.79 (dd, J=6.6, 5.0 Hz, 1H), 3.85-3.77 (ddd, J=11.8, 5.0, 2.2 Hz, 1H), 3.73-3.67 (s, 3H), 3.60-3.52 (ddd, J=12.0, 6.7, 2.0 Hz, 1H).

Peak 2 (R)-I-4: ¹H NMR (400 MHz, DMSO-d₆) δ 8.90-8.86 (s, 1H), 8.22-8.18 (d, J=5.4 Hz, 1H), 7.95-7.89 (t, J=2.2 Hz, 1H), 7.39-7.23 (m, 6H), 7.14-7.11 (dd, J=5.3, 1.6 Hz, 1H), 7.04-7.00 (d, J=1.5 Hz, 1H), 6.29-6.25 (d, J=1.9 Hz, 1H), 6.15-6.11 (d, J=1.3 Hz, 1H), 4.86-4.80 (dd, J=6.5, 5.0 Hz, 1H), 3.85-3.78 (ddd, J=12.0, 5.0, 2.3 Hz, 1H), 3.73-3.67 (s, 3H), 3.60-3.52 (ddd, J=12.0, 6.7, 2.0 Hz, 1H).

4-(3-benzyl-4,5-dihydro-3H-1,2,2a¹,5-tetraazaacenaphthylen-7-yl)-N-(1-methyl-1H-pyrazol-5-yl)pyridin-2-amine (I-7) 3-tert-butoxycarbonylamino-2-phenyl propionic acid can be prepared analogously except in step 1, 3-tert-butoxycarbonylamino-2-phenyl propionic acid was replaced with α-[[[(1,1-dimethylethoxy)carbonyl]amino]methyl]-benzyl-3-propanoic acid (CASRN 26250-90-8).

4-(3-(4-chlorobenzyl)-4,5-dihydro-3H-1,2,2a¹,5-tetraazaacenaphthylen-7-yl)-N-(1-methyl-1H-pyrazol-5-yl)pyridin-2-amine (I-8) can be prepared analogously except in step 1, 3-tert-butoxycarbonylamino-2-phenyl propionic acid was replaced with 2-(B0c-aminomethyl)-3-(4-chlorophenyl)-propanoic acid (CASRN 626220-65-3)

Example 7

4-(9-((4-chloro-1H-pyrazol-1-yl)methyl)-8,9-dihydro-7H-6-oxa-1,2,2a¹-triazabenzo[cd]azulen-4-yl)-N-(1-methyl-1H-pyrazol-5-yl)pyrimidin-2-amine (I-42)

I-42

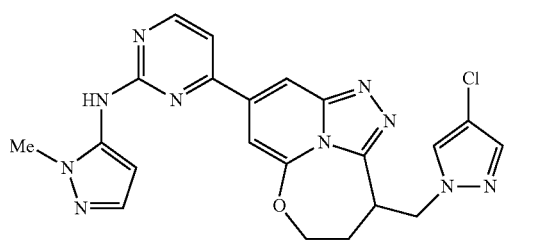

step 1 (SCHEME F): A mixture of 4-chloropyrazole (2.66 g, 24.6 mmol), 3-methylenedihydro-2(3H)-furanone (2.16 g, 22 mmol) and 1,8-diazabicyclo[5.4.0]undec-7-ene (335 mg, 2.2 mmol) in MeCN (30 mL) was stirred overnight. The mixture was concentrated in vacuo. The residue partitioned between ether and 1% aq. citric acid. The organic extracts were washed with water, brine, dried (MgSO₄), filtered and concentrated in vacuo to afford 4.9 g of a crude 3-((4-chloro-1H-pyrazol-1-yl)methyl)dihydrofuran-2(3H)-one which was used in the next step without further purification. MS: m/z 201 step 2: A mixture of 3-[(4-chloropyrazol-1-yl)methyl]tetrahydrofuran-2-one (4.9 g, 22 mmol) and aq. LiOH (1.0 M, 44 mL, 44 mmol) in THF (10 mL) was stirred in a sealed vial at 50° C. for 2 h. The mixture was cooled down to RT, neutralized with 4 N aq. HCl (11 mL, 44 mmol), adjusted to pH 4 and concentrated to dryness in a high vacuum to afford a mixture of 2-((4-chloro-1H-pyrazol-1-yl)methyl)-4-hydroxybutanoic acid and lithium chloride which was used in the next step without further purification. MS: m/z 219 step 3: tert-Butyl-chloro-dimethyl-silane (11.61 g, 77 mmol) in DCM (20 mL) was added dropwise to a crude mixture of 2-[(4-chloropyrazol-1-yl)methyl]-4-hydroxy-butanoic acid and LiCl from step 2 followed by imidazole (13.480 g, 198 mmol) in DMF (30 mL). The mixture was stirred for 36 h then concentrated in vacuo. The residue was partitioned between a EtOAc/Et₂O mixture and water. The organic extracts were washed sequentially with 1% aq. citric acid, water, brine, dried (MgSO₄), filtered and concentrated in vacuo to afford 4-((tert-butyldimethylsilyl)oxy)-2-((4-chloro-1H-pyrazol-1-yl)methyl)butanoic acid as an oily residue (5.01 g, 68%) which was used in the next step without further purification. MS: m/z 333.

step 4: HATU (2.52 g, 6.49 mmol) was added to a mixture of 4-[tert-butyl(dimethyl)silyl]oxy-2-[(4-chloropyrazol-1-yl)methyl]butanoic acid (2.0 g, 5.41 mmol), [4-(2-hydrazino-pyridin-4-yl)-pyrimidin-2-yl]-(2-methyl-2H-pyrazol-3-yl)-amine (1.52 g, 5.41 mmol) and TEA (1.13 mL, 8.11 mmol) in DMF (20 mL). The mixture was stirred for 30 min, concentrated in vacuo and the residue partitioned between EtOAc and water. The combined organic extracts were washed sequentially with water, aq. NaHCO₃, 1% aq. citric acid, water, brine, dried (MgSO₄), filtered and concentrated in vacuo. The residue was purified on a 40 g SiO$_2$ column eluting with an EtOAc/heptane gradient (0 to 70% EtOAc) to afford 2.457 g (74%) of 4-((tert-butyldimethylsilyl)oxy)-2-((4-chloro-1H-pyrazol-1-yl)methyl)-N'-(6-fluoro-2'-((1-methyl-1H-pyrazol-5-yl)amino)-[4,4'-bipyridin]-2(1H)-ylidene)butanehydrazide. MS: m/z 614 step 5: Ph$_3$P.Br$_2$ (5.07 g, 12 mmol) was added portionwise to a mixture of 4-[tert-butyl(dimethyl)silyl]oxy-2-[(4-chloropyrazol-1-yl)methyl]-n-[(z)-[6-fluoro-4-[2-[(2-methylpyrazol-3-yl)amino]-4-pyridyl]-1h-pyridin-2-ylidene]amino]butanamide (2457 mg, 4 mmol) and DIPEA (5.60 mL, 32 mmol) in MeCN (20 mL) under inert atmosphere. The mixture was stirred at RT for 2 h. Water (5 mL) was added to the above mixture and after stirring for 20 min the mixture was concentrated in vacuo. The residue was partitioned between water and EtOAc. The organic extracts were washed sequentially with water, 1% aq. citric acid, water, brine, dried (MgSO$_4$), filtered and concentrated in vacuo to afford a mixture of 4-(3-(4-((tert-butyldimethylsilyl)oxy)-1-(4-chloro-1H-pyrazol-1-yl)butan-2-yl)-5-fluoro-[1,2,4]triazolo[4,3-a]pyridin-7-yl)-N-(1-methyl-1H-pyrazol-5-yl)pyridin-2-amine and triphenylphosphine oxide which was used in the next step without separation. MS: m/z 596 step 6 & 7: TBAF in THF (1M, 10 mL, 10 mmol) was added to a solution of 4-(3-(4-((tert-butyldimethylsilyl)oxy)-1-(4-chloro-1H-pyrazol-1-yl)butan-2-yl)-5-fluoro-[1,2,4]triazolo[4,3-a]pyridin-7-yl)-N-(1-methyl-1H-pyrazol-5-yl)pyridin-2-amine (4.0 mmol) in THF (30 mL). The mixture was stirred for 3 h, concentrated and the residue partitioned between MeTHF and water. The organic extracts were washed 3 times with water, brine, dried (MgSO$_4$), filtered and concentrated in vacuo. The residue was purified on an 80 g SiO$_2$ column eluting with a MeOH/DCM gradient (0 to 8% MeOH) to afford 1.40 g (76%) of racemic 4-(9-((4-chloro-1H-pyrazol-1-yl)methyl)-8,9-dihydro-7H-6-oxa-1,2,2a$^1$-triazabenzo[cd]azulen-4-yl)-N-(1-methyl-1H-pyrazol-5-yl)pyridin-2-amine (I-42) as a yellow foam. MS: m/z 462 The racemic product was resolved by chiral SFC chromatography.

(R)-4-(9-((4-chloro-1H-pyrazol-1-yl)methyl)-8,9-dihydro-7H-6-oxa-1,2,2a$^1$-triazabenzo[cd]azulen-4-yl)-N-(1-methyl-1H-pyrazol-5-yl)pyrimidin-2-amine ((R) I-42): 35 mg. $^1$H NMR (400 MHz, DMSO-d6) δ 9.53 (s, 1H), 8.59 (d, J=5.2 Hz, 1H), 8.25 (d, J=1.4 Hz, 1H), 8.03 (s, 1H), 7.65 (d, J=5.2 Hz, 1H), 7.55 (s, 1H), 7.40 (d, J=1.9 Hz, 1H), 7.03 (d, J=1.4 Hz, 1H), 6.29 (d, J=1.9 Hz, 1H), 4.91 (dd, J=13.8, 5.4 Hz, 1H), 4.69-4.58 (m, 2H), 4.50 (ddd, J=12.0, 8.0, 3.5 Hz, 1H), 4.12 (tt, J=8.4, 5.5 Hz, 1H), 3.72 (s, 3H), 2.25-2.03 (m, 2H). MS: m/z 463.

(S)-4-(9-((4-Chloro-1H-pyrazol-1-yl)methyl)-8,9-dihydro-7H-6-oxa-1,2,2a$^1$-triazabenzo[cd]azulen-4-yl)-N-(1-methyl-1H-pyrazol-5-yl)pyrimidin-2-amine ((S) I-42): 39 mg. $^1$H NMR (400 MHz, DMSO-d6) δ 9.55 (s, 1H), 8.59 (d, J=5.2 Hz, 1H), 8.26 (d, J=1.4 Hz, 1H), 8.04 (s, 1H), 7.65 (d, J=5.2 Hz, 1H), 7.56 (s, 1H), 7.40 (d, J=1.9 Hz, 1H), 7.03 (d, J=1.4 Hz, 1H), 6.29 (d, J=1.8 Hz, 1H), 4.91 (dd, J=13.8, 5.4 Hz, 1H), 4.69-4.56 (m, 2H), 4.50 (ddd, J=12.1, 8.0, 3.5 Hz, 1H), 4.12 (tt, J=8.3, 5.5 Hz, 1H), 3.71 (s, 3H), 2.24-2.02 (m, 2H). MS: m/z 463.

(R)-4-(9-((4-chloro-1H-pyrazol-1-yl)methyl)-8,9-dihydro-7H-6-oxa-1,2,2a$^1$-triazabenzo[cd]azulen-4-yl)-N-(1-methyl-1H-pyrazol-5-yl)pyridin-2-amine ((R) I-47) can be prepared analogously except in step 4, [4-(2-hydrazino-pyridin-4-yl)-pyrimidin-2-yl]-(2-methyl-2H-pyrazol-3-yl)-amine was replaced with (2'-hydrazino-[4,4']bipyridinyl-2-yl)-(2-methyl-2H-pyrazol-3-yl)-amine. The racemic mixture could be resolved by chiral SFC chromatography. $^1$H NMR (400 MHz, DMSO-d$_6$) δ 8.86 (s, 1H), 8.21 (d, J=5.3 Hz, 1H), 8.04 (d, J=0.7 Hz, 1H), 7.79 (d, J=1.5 Hz, 1H), 7.56 (d, J=0.7 Hz, 1H), 7.35 (d, J=1.8 Hz, 1H), 7.21 (dd, J=5.4, 1.6 Hz, 1H), 7.10 (d, J=2.1 Hz, 1H), 6.66 (d, J=1.5 Hz, 1H), 6.29 (d, J=1.9 Hz, 1H), 4.91 (dd, J=13.8, 5.3 Hz, 1H), 4.63 (ddt, J=9.6, 8.3, 4.1 Hz, 2H), 4.50 (ddd, J=12.1, 8.1, 3.5 Hz, 1H), 4.11 (tt, J=8.6, 5.5 Hz, 1H), 3.69 (s, 3H), 2.24-2.03 (m, 2H); MS: m/z 462.

N-(1-Methyl-1H-pyrazol-5-yl)-4-(9-((4-(trifluoromethyl)-1H-pyrazol-1-yl)methyl)-8,9-dihydro-7H-6-oxa-1,2,2a$^1$-triazabenzo[cd]azulen-4-yl)pyrimidin-2-amine (I-73) can be prepared analogously except in step 1, 4-trifluoromethylpyrazole was used in place of 4-chloropyrazole to afford racemic I-73 which was resolved by chromatography on a chiral support.

(S)—N-(1-methyl-1H-pyrazol-5-yl)-4-(9-((4-(trifluoromethyl)-1H-pyrazol-1-yl)methyl)-8,9-dihydro-7H-6-oxa-1,2,2a$^1$-triazabenzo[cd]azulen-4-yl)pyrimidin-2-amine ((S) I-73). $^1$H NMR (400 MHz, DMSO-d$_6$) δ 9.54 (s, 1H), 8.59 (d, J=5.2 Hz, 1H), 8.46 (s, 1H), 8.26 (d, J=1.4 Hz, 1H), 7.91 (s, 1H), 7.65 (d, J=5.2 Hz, 1H), 7.40 (d, J=1.9 Hz, 1H), 7.03 (d, J=1.4 Hz, 1H), 6.29 (d, J=1.9 Hz, 1H), 5.01 (dd, J=13.8, 5.5 Hz, 1H), 4.76-4.60 (m, 2H), 4.51 (ddd, J=12.0, 7.8, 3.8 Hz, 1H), 4.18 (tt, J=8.5, 5.7 Hz, 1H), 3.71 (s, 3H, 2.26-2.08 (m, 2H). MS: m/z 497.

(R)—N-(1-methyl-1H-pyrazol-5-yl)-4-(9-((4-(trifluoromethyl)-1H-pyrazol-1-yl)methyl)-8,9-dihydro-7H-6-oxa-1,2,2a$^1$-triazabenzo[cd]azulen-4-yl)pyrimidin-2-amine ((R) I-73). $^1$H NMR (400 MHz, DMSO-d$_6$) δ 9.54 (s, 1H), 8.59 (d, J=5.2 Hz, 1H), 8.46 (s, 1H), 8.26 (d, J=1.4 Hz, 1H), 7.91 (s, 1H), 7.65 (d, J=5.2 Hz, 1H), 7.40 (d, J=1.9 Hz, 1H), 7.03 (d, J=1.4 Hz, 1H), 6.29 (d, J=1.9 Hz, 1H), 5.01 (dd, J=13.8, 5.5 Hz, 1H), 4.75-4.60 (m, 2H), 4.51 (ddd, J=12.1, 7.8, 3.8 Hz, 1H), 4.19 (tt, J=8.5, 5.6 Hz, 1H), 3.71 (s, 3H), 2.25-2.08 (m, 2H). MS: m/z 497.

N-(1-Methyl-1H-pyrazol-5-yl)-4-(9-((4-(trifluoromethyl)-1H-pyrazol-1-yl)methyl)-8,9-dihydro-7H-6-oxa-1,2,2a$^1$-triazabenzo[cd]azulen-4-yl)pyridin-2-amine (I-89) can be prepared analogously except in step 1, 4-trifluoromethylpyrazole was used in place of 4-chloropyrazole and in step 4 4-(2-fluoro-6-hydrazino-4-pyridyl-N-(2-methylpyrazol-3-yl)pyridine-2-amine was used in place of 4-(2-fluoro-6-hydrazinylpyridin-4-yl)-N-(1-methyl-H-pyrazol-5-yl)pyrimidin-2-amine.

(R)—N-(1-methyl-1H-pyrazol-5-yl)-4-(9-((4-(trifluoromethyl)-1H-pyrazol-1-yl)methyl)-8,9-dihydro-7H-6-oxa-1,2,2a$^1$-triazabenzo[cd]azulen-4-yl)pyridin-2-amine ((R) I-89) $^1$H NMR (400 MHz, DMSO-d$_6$) δ 8.85 (s, 1H), 8.46 (s, 1H), 8.21 (d, J=5.3 Hz, 1H), 7.91 (s, 1H), 7.79 (d, J=1.5 Hz, 1H), 7.35 (d, J=1.9 Hz, 1H), 7.21 (dd, J=5.4, 1.6 Hz, 1H), 7.09 (d, J=1.6 Hz, 1H), 6.66 (d, J=1.5 Hz, 1H), 6.28 (d, J=1.8 Hz, 1H), 5.01 (dd, J=13.8, 5.5 Hz, 1H), 4.76-4.60 (m, 2H), 4.52 (ddd, J=12.1, 7.9, 3.8 Hz, 1H), 4.23-4.11 (m, 1H), 3.69 (s, 3H), 2.28-2.04 (m, 2H). MS: m/z 496

(S)—N-(1-methyl-1H-pyrazol-5-yl)-4-(9-((4-(trifluoromethyl)-1H-pyrazol-1-yl)methyl)-8,9-dihydro-7H-6-oxa-1,2,2a$^1$-triazabenzo[cd]azulen-4-yl)pyridin-2-amine ((S) I-89) $^1$H NMR (400 MHz, DMSO d$_6$) δ 8.84 (s, 1H), 8.45 (s, 1H), 8.21 (d, J=5.3 Hz, 1H), 7.91 (s, 1H), 7.79 (d, J=1.5 Hz, 1H), 7.35 (d, J=1.9 Hz, 1H), 7.21 (dd, J=5.4, 1.6 Hz, 1H), 7.09 (d, J=1.6 Hz, 1H), 6.66 (d, J=1.5 Hz, 1H), 6.28 (d, J=1.8 Hz, 1H), 5.01 (dd, J=13.8, 5.5 Hz, 1H), 4.78-4.59 (m, 2H), 4.52 (ddd, J=12.1, 7.9, 3.8 Hz, 1H), 4.17 (tt, J=8.6, 5.7 Hz, 1H), 3.69 (s, 3H), 2.28-205 (m, 2H). MS: m/z 496

4-(9-((4-cyclopropyl-1H-pyrazol-1-yl)methyl)-8,9-dihydro-7H-6-oxa-1,2,2a$^1$-triazabenzo[cd]azulen-4-yl)-N-(1-methyl-1H-pyrazol-5-yl)pyrimidin-2-amine (I-56) can be prepared analogously except in step 1, 4-cyclopropyl-pyrazole was used in place of 4-chloropyrazole to afford racemic I-56 which was resolved by chromatography on a chiral support.

(R)-4-(9-((4-cyclopropyl-1H-pyrazol-1-yl)methyl)-8,9-dihydro-7H-6-oxa-1,2,2a$^1$-triazabenzo[cd]azulen-4-yl)-N-(1-methyl-1H-pyrazol-5-yl)pyrimidin-2-amine ((R) I-56) $^1$H NMR (400 MHz, DMSO-d6) δ 9.55 (s, 1H), 8.59 (d, J=5.2 Hz, 1H), 8.26 (d, J=1.4 Hz, 1H), 7.65 (d, J=5.2 Hz, 1H), 7.51 (t, J=0.6 Hz, 1H), 7.40 (d, J=1.9 Hz, 1H), 7.24 (d, J=0.8 Hz, 1H), 7.02 (d, J=1.4 Hz, 1H), 6.29 (d, J=1.9 Hz, 1H), 4.85 (dd, J=13.8, 4.9 Hz, 1H), 4.68-4.41 (m, 3H), 4.07 (tt, J=8.8, 5.3 Hz, 1H), 3.71 (s, 3H), 2.22-1.96 (m, 2H), 1.66 (tt, J=8.4, 5.1 Hz, 1H), 0.86-0.71 (m, 2H), 0.50-0.36 (m, 2H). MS: m/z 496 MS: m/z 469

(S)-4-(9-((4-cyclopropyl-1H-pyrazol-1-yl)methyl)-8,9-dihydro-7H-6-oxa-1,2,2a$^1$-triazabenzo[cd]azulen-4-yl)-N-(1-methyl-1H-pyrazol-5-yl)pyrimidin-2-amine ((S) I-56) $^1$H NMR (400 MHz, DMSO-d6) δ 9.55 (s, 1H), 8.59 (d, J=5.2 Hz, 1H), 8.26 (d, J=1.4 Hz, 1H), 7.65 (d, J=5.2 Hz, 1H), 7.51 (t, J=0.6 Hz, 1H), 7.40 (d, J=1.9 Hz, 1H), 7.24 (d, J=0.8 Hz, 1H), 7.02 (d, J=1.4 Hz, 1H), 6.29 (d, J=1.9 Hz, 1H), 4.85 (dd, J=13.8, 4.9 Hz, 1H), 4.68-4.41 (m, 3H), 4.07 (tt, J=8.8, 5.3 Hz, 1H), 3.71 (s, 3H), 2.22-1.96 (m, 2H), 1.66 (tt, J=8.4, 5.1 Hz, 1H), 0.86-0.71 (m, 2H), 0.50-0.36 (m, 2H). MS: m/z 469.

N-(1-Methyl-1H-pyrazol-5-yl)-4-(9-((1-methyl-1H-pyrazol-5-yl)methyl)-8,9-dihydro-7H-6-oxa-1,2,2a$^1$-triazabenzo[cd]azulen-4-yl)pyrimidin-2-amine (I-92) can be prepared analogously except in step 4, 4-[tert-butyl(dimethyl)silyl]oxy-2-[(4-chloropyrazol-1-yl)methyl]butanoic acid was replaced with 4-(tert-butyl-dimethyl-silanyloxy)-2-(3-methyl-isoxazol-5-ylmethyl)-butyric acid.

N-(1-methyl-1H-pyrazol-5-yl)-4-(9-((3-methylisoxazol-5-yl)methyl)-8,9-dihydro-7H-6-oxa-1,2,2a$^1$-triazabenzo[cd]azulen-4-yl)pyrimidin-2-amine (I-93) can be prepared analogously except in step 4, 4-[tert-butyl(dimethyl)silyl]oxy-2-[(4-chloropyrazol-1-yl)methyl]butanoic acid was replaced with 4-(tert-butyl-dimethyl-silanyloxy)-2-(3-methyl-isoxazol-5-ylmethyl)-butyric acid.

N-(1-methyl-1H-pyrazol-5-yl)-4-(9-((4-methylthiazol-2-yl)methyl)-8,9-dihydro-7H-6-oxa-1,2,2a$^1$-triazabenzo[cd]azulen-4-yl)pyrimidin-2-amine (I-109) can be prepared analogously except in step 4, 4-[tert-butyl(dimethyl)silyl]oxy-2-[(4-chloropyrazol-1-yl)methyl]butanoic acid was replaced with 4-(tert-Butyl-dimethyl-silanyloxy)-2-(4-methyl-thiazol-2-ylmethyl)-butyric acid.

Example 8

4-(3-(4-chloro-3-fluorobenzyl)-5-methyl-4,5-dihydro-3H-1,2,2a$^1$,5-tetraazaacenaphthylen-7-yl)-N-(1-methyl-1H-pyrazol-5-yl)pyrimidin-2-amine (I-32)

I-32

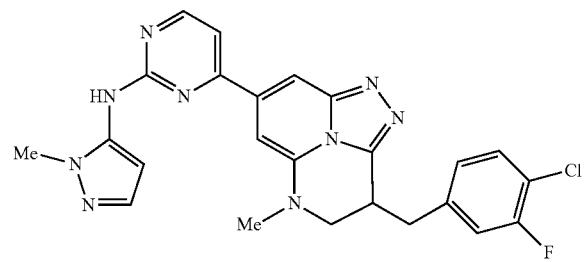

step 1 To a solution of 2-[(tert-butoxycarbonylamino)methyl]-3-(4-chloro-3-fluoro-phenyl)propanoic acid (268 mg, 0.8077 mmol) in THF (6 mL) cooled in ice bath was added MeI (10 equiv, 1.146 g, 0.5030 mL, 8.077 mmol) followed by portion wise addition of NaH (4 equiv, 129.2 mg, 3.231 mmol, 60% mineral oil dispersion). The resulting mixture was stirred overnight at RT. The reaction was quenched with sat'd. NaHCO$_3$, diluted with water (10 mL) and washed with EtOAc. The aqueous layer was acidified with 1N HCl, extracted with EtOAc (3×10 mL). The combined extracts were dried (Na$_2$SO$_4$), filtered and concentrated in vacuo. The crude product was used without further purification.

step 2: To a solution of 2-[[tert-butoxycarbonyl(methyl)amino]methyl]-3-(4-chloro-3-fluoro-phenyl)propanoic acid (1.3 equiv, 149.7 mg, 0.4329 mmol) in DMF (2 mL) was added HATU (1.5 equiv, 193.8 mg, 0.4995 mmol) and 4-(2-fluoro-6-hydrazino-4-pyridyl)-N-(2-methylpyrazol-3-yl)pyrimidin-2-amine (100 mg, 0.3330 mmol) followed by DIPEA (2 equiv, 86.08 mg, 0.116 mL, 0.6660 mmol) and the resulting solution stirred at RT for 2 h. The solution was diluted with water, extracted with EtOAc (2×15 mL), dried (Na$_2$SO$_4$), filtered, concentrated on CELITE®. The crude product was purified by SiO$_2$ chromatography (ISCO, 12 g column) eluting with a MeOH/DCM gradient (0 to 5% MeOH) to afford 194 mg of tert-butyl N-[2-[(4-chloro-3-fluoro-phenyl)methyl]-3-[2-[6-fluoro-4-[2-[(2-methylpyrazol-3-yl)amino]pyrimidin-4-yl]-2-pyridyl]hydrazino]-3-oxo-propyl]-N-methyl-carbamate as a yellow solid which was used without further purification.

step 3: To a solution of tert-butyl N-[2-[(4-chloro-3-fluoro-phenyl)methyl]-3-[2-[6-fluoro-4-[2-[(2-methylpyrazol-3-yl)amino]pyrimidin-4-yl]-2-pyridyl]hydrazino]-3-oxo-propyl]-N-methyl-carbamate (190 mg, 0.3025 mmol) in THF (5 mL) was added Ph$_3$.Br$_2$ (3 equiv, 390.9 mg, 0.9075 mmol) followed by DIPEA (5 equiv, 0.264 mL, 1.512 mmol) and the reaction heated at 70° C. for 2 h. The reaction mixture was diluted with water, extracted with EtOAc (3×10 mL). The combined EtOAc extracts were washed with 0.5% citric acid, dried (Na$_2$SO$_4$), filtered and concentrated on CELITE®. The crude product was purified by SiO$_2$ chromatography (ISCO, 12 g column) eluting with a MeOH/DCM gradient (0 to 5% MeOH) to afford 200 mg of tert-butyl N-[3-(4-chloro-3-fluoro-phenyl)-2-[5-fluoro-7-[2-[(2-methylpyrazol-3-yl)amino]pyrimidin-4-yl]-[1,2,4]triazolo[4,3-a]pyridin-3-yl]propyl]-N-methyl-carbamat as a yellow oil.

step 4: To a solution of tert-butyl N-[3-(4-chloro-3-fluoro-phenyl)-2-[5-fluoro-7-[2-[(2-methylpyrazol-3-yl)amino]pyrimidin-4-yl]-[1,2,4]triazolo[4,3-a]pyridin-3-yl]propyl]-N-methyl-carbamate (200 mg, 200 mg, 0.3278 mmol) in DCM (3 mL) was added TFA (0.8 mL) and the solution stirred at RT for 45 min. The reaction mixture was concentrated in vacuo and used without further purification.

step 5: A solution of 4-[3-[1-[(4-chloro-3-fluoro-phenyl)methyl]-2-(methylamino)ethyl]-5-fluoro-[1,2,4]triazolo[4,3-a]pyridin-7-yl]-N-(2-methylpyrazol-3-yl)pyrimidin-2-amine (170 mg, 0.3334 mmol) in pyridine (4 mL) was heated at 100° C. for 1 h, cooled and concentrated in vacuo to afford I-32. The product was purified by rHPLC and resolved on a chiral SFC column.

4-(3-benzyl-5-methyl-4,5-dihydro-3H-1,2,2a$^1$,5-tetraazaacenaphthylen-7-yl)-N-(1-methyl-1H-pyrazol-5-yl)pyrimidin-2-amine (I-9) can be prepared analogously except step 1 was omitted and in step 2, 2-[[tert-butoxycarbonyl (methyl)amino]methyl]-3-(4-chloro-3-fluoro-phenyl)propanoic acid was replaced with N-Boc-N-methyl-phenylalanine (CASRN 64623-83-8).

4-(3-(4-chlorobenzyl)-5-methyl-4,5-dihydro-3H-1,2,2a$^1$,5-tetraazaacenaphthylen-7-yl)-N-(1-methyl-1H-pyrazol-5-yl)pyridin-2-amine (I-13) can be prepared analogously except in step 1, 2-[[tert-butoxycarbonyl(methyl)amino]methyl]-3-(4-chloro-3-fluoro-phenyl)propanoic acid was replaced with 2-[[tert-butoxycarbonyl(methyl)amino]methyl]-3-(4-chloro-phenyl)propanoic acid.

Peak 1 (R) I-13 $^1$H NMR (400 MHz, DMSO-d$_6$) δ 8.89-8.82 (s, 1H), 8.23-8.14 (d, J=5.3 Hz, 1H), 7.42-7.31 (m, 5H), 7.27-7.23 (s, 1H), 7.19-7.14 (dd, J=5.4, 1.5 Hz, 1H), 7.12-7.07 (s, 1H), 6.31-6.24 (d, J=1.8 Hz, 1H), 6.14-6.07 (s, 1H), 3.94-3.83 (m, 1H), 3.73-3.66 (s, 3H), 3.51-3.44 (dd, J=11.9, 5.1 Hz, 1H), 3.43-3.33 (dd, J=13.8, 5.6 Hz, 1H), 3.11-3.04 (s, 3H), 3.02-2.93 (dd, J=13.9, 8.6 Hz, 1H).

Peak 2 (S) I-13 $^1$H NMR (400 MHz, DMSO-d$_6$) δ 8.89-8.82 (s, 1H), 8.23-8.16 (dd, J=5.2, 0.7 Hz, 1H), 7.42-7.31 (m, 5H), 7.28-7.23 (d, J=1.1 Hz, 1H), 7.20-7.13 (dd, J=5.4, 1.6 Hz, 1H), 7.13-7.07 (dd, J=1.6, 0.8 Hz, 1H), 6.30-6.25 (d, J=1.9 Hz, 1H), 6.14-6.06 (d, J=1.2 Hz, 1H), 3.93-3.83 (tt, J=7.6, 5.5 Hz, 1H), 3.72-3.67 (s, 3H), 3.51-3.44 (dd, J=11.9, 5.1 Hz, 1H), 3.42-3.35 (dd, J=13.9, 5.6 Hz, 1H), 3.10-3.03 (s, 3H), 3.02-2.93 (dd, J=13.9, 8.6 Hz, 1H).

4-(3-(4-methoxybenzyl)-5-methyl-4,5-dihydro-3H-1,2,2a$^1$,5-tetraazaacenaphthylen-7-yl)-N-(1-methyl-1H-pyrazol-5-yl)pyridin-2-amine (I-18) can be prepared analogously except in step 1, 2-[[tert-butoxycarbonyl(methyl)amino]methyl]-3-(4-chloro-3-fluoro-phenyl)propanoic acid was replaced with 2-[[tert-butoxycarbonyl(methyl)amino]methyl]-3-(4-methoxy-phenyl)propanoic acid and in step 2, 4-(2-fluoro-6-hydrazino-4-pyridyl)-N-(2-methylpyrazol-3-yl)pyrimidin-2-amine was replaced with (2'-hydrazino-[4,4']bipyridinyl-2-yl)-(2-methyl-2H-pyrazol-3-yl)-amine.

4-(3-isobutyl-5-methyl-4,5-dihydro-3H-1,2,2a$^1$,5-tetraazaacenaphthylen-7-yl)-N-(1-methyl-1H-pyrazol-5-yl)pyridin-2-amine (I-20) can be prepared analogously except in step 1 was omitted and in step 2, 2-[[tert-butoxycarbonyl(methyl)amino]methyl]-3-(4-chloro-3-fluoro-phenyl)propanoic acid was replaced with N-Boc-N-methyl leucine (CASRN 13734-32-2).

4-(3-(4-fluorobenzyl)-5-methyl-4,5-dihydro-3H-1,2,2a$^1$,5-tetraazaacenaphthylen-7-yl)-N-(1-methyl-1H-I-42pyrazol-5-yl)pyrimidin-2-amine (I-31)) can be prepared analogously except in step 1, 2-[[tert-butoxycarbonyl(methyl)amino]methyl]-3-(4-chloro-3-fluoro-phenyl)propanoic acid was replaced with 2-[[tert-butoxycarbonyl(methyl)amino]methyl]-3-(4-fluoro-phenyl)propanoic acid.

Example 9

4-(9-((5-fluoropyridin-3-yl)oxy)-8,9-dihydro-7H-6-oxa-1,2,2a$^1$-triazabenzo[cd]azulen-4-yl)-N-(1-methyl-1H-pyrazol-5-yl)pyrimidin-2-amine (I-91)

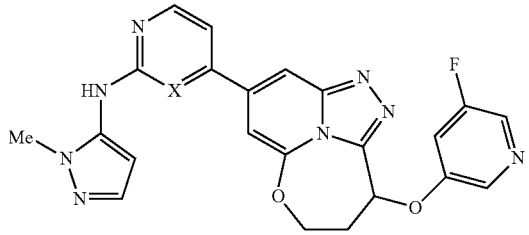

I-91

(SCHEME G) step 1: To a solution of 5-fluoropyridin-3-ol (1.02 g, 9.00 mmol) in DMF (30 mL) was added K$_2$CO$_3$ (1.25 equiv) and the solution was stirred at RT for 5 min. α-Bromo-γ-lactone (1.35 g, 1350 mg, 0.775 mL, 8.18 mmol) was added dropwise and stirred at RT over the week end. The solution was diluted with water (100 mL), extracted with EtOAc (3×80 mL). The combined organic extracts were washed with water, dried (Na$_2$SO$_4$), filtered, and concentrated on CELITE®. The crude product was purified by SiO$_2$ chromatography on an 40 g ISCO column eluting with an EtOAc/DCM gradient (0 to 20% EtOAc) to afford 0.795 g of 3-[(5-fluoro-3-pyridyl)oxy]tetrahydrofuran-2-one as a white solid.

step 2: To a solution of 3-[(5-fluoro-3-pyridyl)oxy]tetrahydrofuran-2-one (795 mg, 4.0323 mmol) in MeOH (12 mL) and THF (4 mL) was added 1 M LiOH (1.2 equiv, 4.84 mL, 4.8387 mmol, 1.00 M) and the solution stirred overnight at RT. The solution was concentrated in vacuo, diluted with water, acidified with 1N HCl and extracted with EtOAc (3×30 mL) Salt was added to the aqueous phase and the brine solution extracted with 10% MeOH/EtOAc (2×30 mL). The combined organic extracts were dried (Na$_2$SO$_4$), filtered and concentrated in to afford 0.47 g of 2-[(5-fluoro-3-pyridyl)oxy]-4-hydroxy-butanoic acid as an off white solid.

step 3. To a solution of 2-[(5-fluoro-3-pyridyl)oxy]-4-hydroxy-butanoic acid (0.47 g, 470 mg, 2.2 mmol) in DMF (8 mL) was added tert-butylchlorodimethylsilane (3 equiv, 1000 mg, 6.6 mmol) and imidazole in H$_2$O (5 equiv, 760 mg, 11 mmol) and the solution stirred at RT overnight. The solution was diluted with water and extracted with EtOAc (3×50 mL). The combined organic extracts were washed with water, dried (Na$_2$SO$_4$), filtered and concentrated in vacuo to afford 1.04 g of 4-[tert-butyl(dimethyl)silyl]oxy-2-[(5-chloro-3-pyridyl)oxy]butanoic acid as a clear syrup which was used without further purification.

step 4: To a solution of 4-[tert-butyl(dimethyl)silyl]oxy-2-[(5-chloro-3-pyridyl)oxy]butanoic acid (1.5 equiv, 863.9 mg, 2.498 mmol) in DMF (10 mL) was added HATU (1.5 equiv, 969.0 mg, 2.498 mmol), 4-(2-fluoro-6-hydrazino-4-pyridyl)-N-(2-methylpyrazol-3-yl)pyrimidin-2-amine (500 mg, 1.665 mmol) and DIPEA (2 equiv, 0.581 mL, 3.330 mmol) in that sequence and the resulting solution was stirred at RT for 2 h. The solution was diluted with water, extracted with EtOAc (3×30 mL). The combined extracts were dried (Na$_2$SO$_4$), filtered and concentrated on CELITE®. The crude product was purified on a 24 g ISCO SiO$_2$ column eluting with MeOH/DCM gradient (0 to 5% MeOH) to afford 637 mg of 4-[tert-butyl(dimethyl)silyl]oxy-N'-[6-fluoro-4-[2-[(2-methylpyrazol-3-yl)amino]pyrimidin-4-yl]-2-pyridyl]-2-[(5-fluoro-3-pyridyl)oxy]butanehydrazide as a light yellow solid.

step 5: To a solution of 4-[tert-butyl(dimethyl)silyl]oxy-N'-[6-fluoro-4-[2-[(2-methylpyrazol-3-yl)amino]pyrimidin-4-yl]-2-pyridyl]-2-[(5-fluoro-3-pyridyl)oxy]butanehydrazide (444 mg, 0.7258 mmol) in MeCN (12 mL) was added Ph$_3$P.Br$_2$ (3 equiv, 937.9 mg, 2.178 mmol) and DIPEA (4 equiv, 0.506 mL, 2.903 mmol). The resulting solution was stirred at RT for 1.5 h. It was diluted with water extracted with EtOAc (3×50 mL). The combined extracts were washed with 5% citric acid, dried (Na$_2$SO$_4$), filtered, concentrated on CELITE® and purified on a 24 g ISCO SiO$_2$ column eluting with a MeOH/DCM gradient to afford 311 mg of 3-[5-fluoro-7-[2-[(2-methylpyrazol-3-yl)amino]pyrimidin-4-yl]-[1,2,4]triazolo[4,3-a]pyridin-3-yl]-3-[(5-fluoro-3-pyridyl)oxy]propan-1-ol yellow solid.

step 6: To a suspension of 4-[3-[3-[tert-butyl(dimethyl)silyl]oxy-1-[(5-fluoro-3-pyridyl)oxy]propyl]-5-fluoro-[1,2,4]triazolo[4,3-a]pyridin-7-yl]-N-(2-methylpyrazol-3-yl)pyrimidin-2-amine (310 mg, 0.5221 mmol) in DCM (10 mL) was added BF$_3$-Et$_2$O (6 equiv, 444.6 mg, 0.3963 mL, 3.133 mmol) and the resulting solution was stirred at RT overnight. The reaction was quenched with sat'd NaHCO$_3$, the phases separation, and the aqueous solution extracted with EtOAc (2×20 mL). The combined extracts were dried, filtered, concentrated in vacuo to afford 198 mg yellow solid of 3-[5-fluoro-7-[2-[(2-methylpyrazol-3-yl)amino]pyrimidin-4-yl]-[1,2,4]triazolo[4,3-a]pyridin-3-yl]-3-[(5-fluoro-3-pyridyl)oxy]propan-1-ol step 7: To a mixture of 3-[5-fluoro-7-[2-[(2-methylpyrazol-3-yl)amino]pyrimidin-4-yl]-[1,2,4]triazolo[4,3-a]pyridin-3-yl]-3-[(5-fluoro-3-pyridyl)oxy]propan-1-ol (198 mg, 0.4130 mmol) in THF (20 mL) was added NaH (8 equiv, 132.2 mg, 3.304 mmol, 60% mineral oil dispersion) and the resulting solution was stirred at RT for 15 min then heated at 65° C. for 1 h. Two additional equiv of NaH were added and heated at 70° C. for 1 h which resulted in complete conversion. The reaction was quenched with few drops of water, concentrated on CELITE® and purified on a 12 g ISCO column eluting with a MeOH/DCM gradient (0 to 8% MeOH) to afford 68 mg yellow solid which was resolved on a chiral SFC column to afford 26.8 mg (S) I-91 and 25.6 mg of (R) I-91.

(S) I-91: 1H NMR (400 MHz, DMSO-d6) δ 9.56 (d, J=4.0 Hz, 1H), 8.61 (d, J=5.2 Hz, 1H), 8.34-8.21 (m, 3H), 7.76 (dt, J=11.0, 2.0 Hz, 1H), 7.68 (d, J=5.6 Hz, 1H), 7.40 (d, J=1.9 Hz, 1H), 7.16 (s, 1H), 6.50 (t, J=4.3 Hz, 1H), 6.29 (d, J=1.9 Hz, 1H), 4.88 (ddd, J=12.6, 6.9, 3.8 Hz, 1H), 4.65 (ddd, J=12.6, 6.9, 3.7 Hz, 1H), 3.71 (s, 3H), 2.78 (qdt, J=11.6, 7.1, 4.1 Hz, 2H); MS: m/z 459.

(R) I-91: $^1$H NMR (400 MHz, DMSO-d6) δ 9.57 (s, 1H), 8.61 (d, J=5.2 Hz, 1H), 8.35-8.21 (m, 3H), 7.82-7.73 (m, 1H), 7.68 (d, J=5.2 Hz, 1H), 7.40 (d, J=1.9 Hz, 1H), 7.17 (s, 1H), 6.51 (t, J=4.3 Hz, 1H), 6.29 (d, J=1.9 Hz, 1H), 4.88 (ddd, J=12.3, 6.9, 3.8 Hz, 1H), 4.65 (ddd, J=12.6, 7.0, 3.7 Hz, 1H), 3.71 (s, 3H), 2.78 (dddd, J=22.4, 18.3, 9.0, 4.9 Hz, 2H); MS: m/z 459.

4-(9-(4-fluorophenoxy)-8,9-dihydro-7H-6-oxa-1,2,2a$^1$-triazabenzo[cd]azulen-4-yl)-N-(1-methyl-1H-pyrazol-5-yl)pyrimidin-2-amine (I-66) can be prepared analogously except in step 1, 5-fluoropyridin-3-ol was replaced with 4-fluoro-phenol.

4-(9-((5-chloropyridin-3-yl)oxy)-8,9-dihydro-7H-6-oxa-1,1,2a$^1$-triazabenzo[cd]azulen-4-yl)-N-(1-methyl-1H-pyrazol-5-yl)pyrimidin-2-amine (I-77) can be prepared analogously except in step 1, 5-fluoropyridin-3-ol was replaced with 3-chloro-5-hydroxypyridine.

(S) I-77 $^1$H NMR (400 MHz, DMSO-d6) δ 9.56 (s, 1H), 8.61 (d, J=5.2 Hz, 1H), 8.38-8.24 (m, 3H), 7.94 (t, J=2.2 Hz, 1H), 7.68 (d, J=5.2 Hz, 1H), 7.40 (d, J=1.9 Hz, 1H), 7.16 (d, J=1.5 Hz, 1H), 6.52 (t, J=4.3 Hz, 1H), 6.29 (d, J=1.9 Hz, 1H), 4.88 (ddd, J=12.6, 7.1, 3.7 Hz, 1H), 4.65 (ddd, J=12.6, 7.0, 3.7 Hz, 1H), 3.71 (s, 3H), 2.78 (dtdt, J=19.6, 11.6, 7.3, 3.9 Hz, 2H); MS: m/z 475.

(R) I-77 $^1$H NMR (400 MHz, DMSO-d6) δ 9.56 (s, 1H), 8.61 (d, J=5.1 Hz, 1H), 8.38-8.24 (m, 3H), 7.94 (t, J=2.3 Hz, 1H), 7.68 (d, J=5.1 Hz, 1H), 7.40 (d, J=1.9 Hz, 1H), 7.16 (d, J=1.5 Hz, 1H), 6.52 (t, J=4.3 Hz, 1H), 6.29 (d, J=1.9 Hz, 1H), 4.88 (ddd, J=12.7, 7.1, 3.9 Hz, 1H), 4.65 (ddd, J=12.7, 7.0, 3.6 Hz, 1H), 3.71 (s, 3H), 2.77 (qdt, J=15.8, 7.9, 4.1 Hz, 2H); MS: m/z 475.

4-(9-((5-chloropyridin-3-yl)oxy)-8,9-dihydro-7H-6-oxa-1,1,2a$^1$-triazabenzo[cd]azulen-4-yl)-N-(1-methyl-1H-pyrazol-5-yl)pyridin-2-amine (I-78) can be prepared analogously except in step 1, 5-fluoropyridin-3-ol was replaced with 3-chloro-5-hydroxypyridine. and in step 4, and (6'-fluoro-2'-hydrazino-[4,4']bipyridinyl-2-yl)-(2-methyl-2H-pyrazol-3-yl)-amine replaced 4-(2-fluoro-6-hydrazino-4-pyridyl)-N-(2-methylpyrazol-3-yl)pyrimidin-2-amine.

4-(9-(4-Fluorophenoxy)-8,9-dihydro-7H-6-oxa-1,2,2a$^1$-triazabenzo[cd]azulen-4-yl)-N-(1-methyl-1H-pyrazol-5-yl)pyrimidin-2-amine (I-108) can be prepared analogously except in step 1, 5-fluoropyridin-3-ol was replaced with 4-fluorophenol.

4-(9-(3-fluorophenoxy)-8,9-dihydro-7H-6-oxa-1,2,2a1-triazabenzo[cd]azulen-4-yl)-N-(1-methyl-1H-pyrazol-5-yl)pyrimidin-2-amine can be prepared analogously except in step 1, 5-fluoropyridin-3-ol was replaced with 3-fluorophenol.

(S)-4-(9-(3-fluorophenoxy)-8,9-dihydro-7H-6-oxa-1,2,2a$^1$-triazabenzo[cd]azulen-4-yl)-N-(1-methyl-1H-pyrazol-5-yl)pyrimidin-2-amine: $^1$H NMR (400 MHz, DMSO-d6) δ 9.57 (s, 1H), 8.61 (d, J=5.2 Hz, 1H), 8.32 (d, J=1.5 Hz, 1H), 7.68 (d, J=5.3 Hz, 1H), 7.43-7.27 (m, 2H), 7.18-7.05 (m, 2H), 6.97 (dd, J=8.3, 2.3 Hz, 1H), 6.82 (td, J=8.5, 2.4 Hz, 1H), 6.39 (t, J=4.2 Hz, 1H), 6.30 (d, J=1.9 Hz, 1H), 4.85 (ddd, J=12.6, 6.7, 4.2 Hz, 1H), 4.63 (ddd, J=12.7, 6.9, 3.9 Hz, 1H), 3.71 (s, 3H), 2.74 (tdd, J=15.3, 7.8, 4.1 Hz, 2H); MS: m/z 458.

(R)-4-(9-(3-fluorophenoxy)-8,9-dihydro-7H-6-oxa-1,2,2a1-triazabenzo[cd]azulen-4-yl)-N-(1-methyl-1H-pyrazol-5-yl)pyrimidin-2-amine: $^1$H NMR (400 MHz, DMSO-d6) δ 9.57 (s, 1H), 8.61 (d, J=5.2 Hz, 1H), 8.32 (d, J=1.5 Hz, 1H), 7.68 (d, J=5.2 Hz, 1H), 7.43-7.27 (m, 2H), 7.18-7.05 (m, 2H), 6.97 (dd, J=8.3, 2.3 Hz, 1H), 6.82 (td, J=8.5, 2.4 Hz, 1H), 6.39 (t, J=4.2 Hz, 1H), 6.30 (d, J=1.9 Hz, 1H), 4.85 (ddd, J=12.6, 6.7, 4.1 Hz, 1H), 4.63 (ddd, J=12.5, 7.0, 4.0 Hz, 1H), 3.71 (s, 3H), 3.28 (d, J=1.4 Hz, 1H), 2.74 (dqt, J=15.0, 7.4, 3.6 Hz, 2H); MS: m/z 458.

4-(3-(3-((tert-butyldimethylsilyl)oxy)-1-(3,4-difluorophenoxy)propyl)-5-fluoro-[1,2,4]triazolo[4,3-a]pyridin-7-yl)-N-(1-methyl-1H-pyrazol-5-yl)pyrimidin-2-amine can be prepared analogously except in step 1, 5-fluoropyridin-3-ol was replaced with 3,4-difluorophenol and in the final step desilylation was accomplished with tetrabutylammonium fluoride (TBAF) which resulted in spontaneous cyclization of the alcohol.

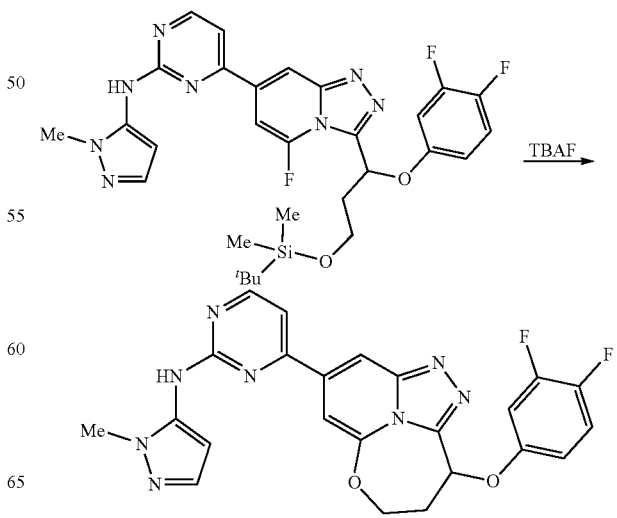

alternate step 6: To a solution of 4-[3-[3-[tert-butyl(dimethyl)silyl]oxy-1-(3,4-difluorophenoxy)propyl]-5-fluoro-[1,2,4]triazolo[4,3-a]pyridin-7-yl]-N-(2-methylpyrazol-3-yl)pyrimidin-2-amine (250 mg, 0.40 mmol) in THF (4 mL) was added) dropwise tetrabutylammonium fluoride in THF (1.0 M, 1.0 mL, 1.02 mmol and the reaction was stirred at RT for 2 h. It was diluted with water, extracted with EtOAc (3×30 ml), dried (Na$_2$SO$_4$), filtered and concentrated on CELITE®. The product was purified by SiO$_2$ chromatography (ISCO 12 g column) eluting with a MeOH/DCM gradient (0 to 8% MeOH) to afford 60 mg (31%) of 4-(3-(3-((tert-butyldimethylsilyl)oxy)-1-(3,4-difluorophenoxy)propyl)-5-fluoro-[1,2,4]triazolo[4,3-a]pyridin-7-yl)-N-(1-methyl-1H-pyrazol-5-yl)pyrimidin-2-amine as light brown solid.

(S)-4-(9-(3,4-difluorophenoxy)-8,9-dihydro-7H-6-oxa-112a1-triazabenzo[cd]azulen-4-yl)-N-(1-methyl-1H-pyrazol-5-yl)pyrimidin-2-amine (24.5 mg): $^1$H NMR (400 MHz, DMSO-d6) δ 9.57 (s, 1H), 8.61 (d, J=5.1 Hz, 1H), 8.31 (d, J=1.4 Hz, 1H), 7.68 (d, J=5.2 Hz, 1H), 7.43-7.27 (m, 3H), 7.15 (d, J=1.5 Hz, 1H), 6.95 (dtd, J=8.8, 3.4, 1.7 Hz, 1H), 6.36-6.27 (m, 2H), 4.85 (ddd, J=12.6, 6.8, 4.1 Hz, 1H), 4.63 (ddd, J=12.5, 6.9, 3.9 Hz, 1H), 3.71 (s, 3H), 2.74 (dddd, J=15.7, 13.4, 7.7, 4.3 Hz, 2H); MS: m/z 476.

(R)-4-(9-(3,4-difluorophenoxy)-8,9-dihydro-7H-6-oxa-1,2,2a$^1$-triazabenzo[cd]azulen-4-yl)-N-(1-methyl-1H-pyrazol-5-yl)pyrimidin-2-amine (24.0 mg): $^1$H NMR (400 MHz, DMSO-d6) δ 9.57 (s, 1H), 8.61 (d, J=5.2 Hz, 1H), 8.31 (d, J=1.4 Hz, 1H), 7.68 (d, J=5.2 Hz, 1H), 7.43-7.27 (m, 3H), 7.15 (d, J=1.6 Hz, 1H), 6.95 (dtd, J=8.8, 3.3, 1.7 Hz, 1H), 6.36-6.27 (m, 2H), 4.85 (ddd, J=12.4, 6.7, 4.1 Hz, 1H), 4.63 (ddd, J=12.5, 6.8, 3.9 Hz, 1H), 3.71 (s, 3H), 3.35-3.25 (m, 1H), 2.81-2.65 (m, 2H); MS: m/z 476.

4-(9-(3,4-difluorophenoxy)-8,9-dihydro-7H-6-oxa-1,2,2a$^1$-triazabenzo[cd]azulen-4-yl)-N-(1-methyl-1H-pyrazol-5-yl)pyridin-2-amine can be prepared analogously except in step 4, 4-(2-fluoro-6-hydrazinylpyridin-4-yl)-N-(1-methyl-1H-pyrazol-5-yl)pyrimidin-2-amine was replaced with 2'-fluoro-6'-hydrazinyl-N-(1-methyl-1H-pyrazol-5-yl)-[4,4'-bipyridin]-2-amine. The racemic product was purified by SFC chromatography on a chiral column.

(S)-4-(9-(3,4-difluorophenoxy)-8,9-dihydro-7H-6-oxa-1,2,2a$^1$-triazabenzo[cd]azulen-4-yl)-N-(1-methyl-1H-pyrazol-5-yl)pyridin-2-amine: $^1$H NMR (400 MHz, DMSO-d6) δ 8.87 (s, 1H), 8.22 (dd, J=5.3, 0.7 Hz, 1H), 7.86 (d, J=1.5 Hz, 1H), 7.42-7.15 (m, 4H), 7.11 (dd, J=1.6, 0.7 Hz, 1H), 6.95 (dtd, J=9.2, 3.4, 1.7 Hz, 1H), 6.80 (d, J=1.5 Hz, 1H), 6.36-6.26 (m, 2H), 4.85 (ddd, J=12.5, 6.7, 4.2 Hz, 1H), 4.63 (ddd, J=12.5, 6.8, 4.0 Hz, 1H), 3.69 (s, 3H), 2.73 (ddd, J=11.5, 7.3, 4.2 Hz, 2H); MS: m/z 475.

(R)-4-(9-(3,4-difluorophenoxy)-8,9-dihydro-7H-6-oxa-1,2,2a$^1$-triazabenzo[cd]azulen-4-yl)-N-(1-methyl-1H-pyrazol-5-yl)pyridin-2-amine: $^1$H NMR (400 MHz, DMSO-d6) δ 8.88 (s, 1H), 8.22 (d, J=5.3 Hz, 1H), 7.85 (d, J=1.5 Hz, 1H), 7.42-7.26 (m, 3H), 7.23 (dd, J=5.4, 1.6 Hz, 1H), 7.14-7.08 (m, 1H), 7.00-6.91 (m, 1H), 6.80 (d, J=1.5 Hz, 1H), 6.36-6.26 (m, 2H), 4.85 (ddd, J=12.5, 6.7, 4.2 Hz, 1H), 4.63 (ddd, J=12.5, 6.8, 4.0 Hz, 1H), 3.69 (s, 3H), 3.39-3.24 (m, 2H), 2.81-2.65 (m, 2H); MS: m/z 475.

(S)-4-(9-((1-methyl-1H-pyrazol-4-yl)oxy)-8,9-dihydro-7H-6-oxa-1,2,2a$^1$-triazabenzo[cd]azulen-4-yl)-N-(1-methyl-1H-pyrazol-5-yl)pyrimidin-2-amine can be prepared analogously except in step 1, 5-fluoropyridin-3-ol was replaced with 1-methyl-1H-pyrazol-4-ol.

(S)-4-(9-((1-methyl-1H-pyrazol-4-yl)oxy)-8,9-dihydro-7H-6-oxa-1,2,2a$^1$-triazabenzo[cd]azulen-4-yl)-N-(1-methyl-1H-pyrazol-5-yl)pyrimidin-2-amine: $^1$H NMR (400 MHz, DMSO-d6) δ 9.57 (s, 1H), 8.61 (d, J=5.2 Hz, 1H), 8.31 (d, J=1.4 Hz, 1H), 7.68 (d, J=5.2 Hz, 1H), 7.53 (d, J=0.9 Hz, 1H), 7.40 (d, J=1.9 Hz, 1H), 7.20 (d, J=0.9 Hz, 1H), 7.14 (d, J=1.5 Hz, 1H), 6.29 (d, J=1.9 Hz, 1H), 5.81 (t, J=4.0 Hz, 1H), 4.81 (ddd, J=12.5, 6.5, 4.2 Hz, 1H), 4.60 (ddd, J=12.5, 7.1, 4.1 Hz, 1H), 3.72 (d, J=4.8 Hz, 6H), 2.77-2.61 (m, 2H); MS: m/z 444.

(R)-4-(9-((1-methyl-1H-pyrazol-4-yl)oxy)-8,9-dihydro-7H-6-oxa-1,2,2a$^1$-triazabenzo[cd]azulen-4-yl)-N-(1-methyl-1H-pyrazol-5-yl)pyrimidin-2-amine: $^1$H NMR (400 MHz, DMSO-d6) δ 9.57 (s, 1H), 8.61 (d, J=5.2 Hz, 1H), 8.31 (d, J=1.4 Hz, 1H), 7.68 (d, J=5.2 Hz, 1H), 7.53 (d, J=0.9 Hz, 1H), 7.40 (d, J=1.9 Hz, 1H), 7.20 (d, J=0.9 Hz, 1H), 7.14 (d, J=1.4 Hz, 1H), 6.29 (d, J=1.9 Hz, 1H), 5.81 (t, J=4.0 Hz, 1H), 4.81 (ddd, J=12.5, 6.6, 4.3 Hz, 1H), 4.60 (ddd, J=12.5, 7.1, 4.1 Hz, 1H), 3.72 (d, J=4.8 Hz, 6H), 2.79-2.58 (m, 2H); MS: m/z 444.

Example 10

3-benzyl-5-methyl-7-(2-((1-methyl-1H-pyrazol-5-yl)amino)pyrimidin-4-yl)-3H-1,1,2a$^1$,3,5-pentaazaacenaphthylen-4(5H)-one (I-28)

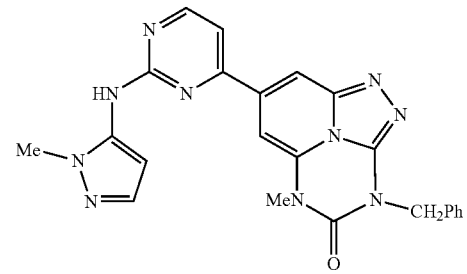

(SCHEME E) step 1: To a solution of 6-fluoro-4-[2-[(2-methylpyrazol-3-yl)amino]pyrimidin-4-yl]-1H-pyridin-2-one hydrazone (500 mg, 1.665 mmol) in DMF (12 mL) was added benzyl isocyanate (0.0268 mL, 1.00 equiv, 1.665 mmol) in two portions. The mixture was stirred for 30 min then concentrated in vacuo. The residue was triturated with Et$_2$O and the resulting solid 1-benzyl-3-[(Z)-[6-fluoro-4-[2-[(2-methylpyrazol-3-yl)amino]pyrimidin-4-yl]-1H-pyridin-2-ylidene]amino]urea was used in the next step without further purification.

step 2: To a solution of 1-benzyl-3-[(Z)-[6-fluoro-4-[2-[(2-methylpyrazol-3-yl)amino]pyrimidin-4-yl]-1H-pyridin-2-ylidene]amino]urea (701 mg, 1.617 mmol) and DIPEA (2.82 mL, 16.17 mmol, 10.0 equiv) in MeCN (30 mL) was added PPh$_3$.Br$_2$ (3.483 g, 8.087 mmol, 5.0 equiv). The mixture was heated at 70° C. for 2 h. The mixture was cooled, diluted with water, stirred for 30 min then concentrated in vacuo. The residue was extracted with MeTHF and the combined organic extracts were washed sequentially with water, 1% aq. citric acid and water. The resulting solution was dried ((MgSO$_4$), filtered and concentrated. The crude product was purified by SiO$_2$ chromatography eluting with a MeOH/DCM gradient (0 to 9% MeOH) to afford 522 mg of N-benzyl-5-fluoro-7-[2-[(2-methylpyrazol-3-yl)amino]pyrimidin-4-yl]-[1,2,4]triazolo[4,3-a]pyridin-3-amine.

step 3: A mixture of N-benzyl-5-fluoro-7-[2-[(2-methylpyrazol-3-yl)amino]pyrimidin-4-yl]-[1,2,4]triazolo[4,3-a]

pyridin-3-amine (132 mg, 0.3178 mmol) and 8M ethanolic solution of methylamine (8 mol/L) in EtOH (5 mL, 40 mmol) was stirred for 2 h at RT. The mixture was concentrated in vacuo and the residue partitioned between MeTHF and water. The pH of the aqueous phase was adjusted to ca. 5 by careful addition of 1% aq. citric acid. The aqueous phase was extracted with MeTHF and the combined extracts washed with water and brine, dried ($Na_2SO_4$), filtered and concentrated. The residue was used in the next step without further purification.

step 4: A mixture of $N^3$-benzyl-$N^5$-methyl-7-[2-[(2-methylpyrazol-3-yl]amino]pyrimidin-4-yl]-[1,2,4]triazolo[4,3-a]pyridine-3,5-diamine (130 mg, 0.3048 mmol) and 1,1'-carbonyldiimidazole (0.2471 g, 1.524 mmol) was heated at 80° C. for 4 h. The reaction was cooled and partitioned between water and MeTHF. The combined organic extracts were washed sequentially with 1% aq citric acid, water, brine, dried ($MgSO_4$), filtered and concentrated in vacuo. After standing for 2 d the resulting precipitate was collected, washed with cold MeOH. The crude product (72 mg) was dissolved in DMF and submitted for RP HPLC purification which afforded 42 mg of I-28. $^1$H NMR (400 MHz, DMSO-$d_6$) δ 9.54 (s, 1H), 8.58 (d, J=5.2 Hz, 1H), 7.64 (s, 1H), 7.56 (d, J=5.3 Hz, 1H), 7.48 (d, J=7.2 Hz, 2H), 7.40-7.25 (m, 4H), 6.36 (s, 1H), 6.27 (d, J=1.9 Hz, 1H), 4.99 (s, 2H), 3.70 (s, 3H), 3.20 (s, 3H).

3-(4-chlorobenzyl)-5-methyl-7-(2-((1-methyl-1H-pyrazol-5-yl)amino)pyrimidin-4-yl)-3H-1,2,2a$^1$,3,5-pentaazaacenaphthylen-4(5H)-one (I-98) can be prepared analogously except in step 1, 4-chlorobenzyl isocyanate replaced benzyl isocyanate.

3-(3,5-difluorobenzyl)-5-methyl-7-(2-((1-methyl-1H-pyrazol-5-yl)amino)pyrimidin-4-yl)-3H-1,2,2a$^1$,3,5-pentaazaacenaphthylen-4(5H)-one (I-99) can be prepared analogously except in step 1, 3,5-difluorobenzyl isocyanate replaced benzyl isocyanate.

3-(3-chlorobenzyl)-5-methyl-7-(2-((1-methyl-1H-pyrazol-5-yl)amino)pyrimidin-4-yl)-3H-1,2,2a$^1$,3,5-pentaazaacenaphthylen-4(5H)-one (I-100) can be prepared analogously except in step 1, 4-chlorobenzyl isocyanate replaced benzyl isocyanate.

Example 11

(S)-9-(4-chlorobenzyl)-6-methyl-4-(2-((1-methyl-1H-pyrazol-5-yl)amino)pyrimidin-4-yl)-8,9-dihydro-1,2,2a$^1$,6-tetraazabenzo[cd]azulen-7(6H)-one (I-22)

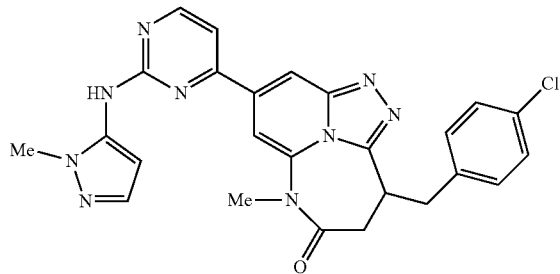

I-22 step 1: To a mixture of 4-tert-butoxy-2-[(4-chlorophenyl)methyl]-4-oxo-butanoic acid (165.3 mg, 0.5531 mmol), 6-fluoro-4-[2-[(2-methylpyrazol-3-yl)amino]pyrimidin-4-yl]-1H-pyridin-2-one hydrazone (151 mg, 0.5028 mmol) and TEA (0.168 mL, 2.4 equiv, 1.207 mmol) in DMF (3 mL) was added HATU (2.10 mg, 0.5531 mmol). The mixture was stirred for 2 h. The mixture was concentrated in in vacuo and the residue partitioned between EtOAc and water. The organic extracts were washed sequentially with water, aq. citric acid, water and brine, dried ($Na_2SO_4$), filtered and concentrated to afford 338 mg of tert-butyl 3-[(4-chlorophenyl)methyl]-4-[(2Z)-2-[6-fluoro-4-[2-[(2-methylpyrazol-3-yl)amino]pyrimidin-4-yl]-1H-pyridin-2-ylidene]hydrazino]-4-oxo-butanoate which was used without further purification.

step 2: To a mixture of tert-butyl 3-[(4-chlorophenyl)methyl]-4-[(2Z)-2-[6-fluoro-4-[2-[(2-methylpyrazol-3-yl)amino]pyrimidin-4-yl]-1H-pyridin-2-ylidene]hydrazino]-4-oxo-butanoate (338 mg, 0.4945 mmol) and DIPEA (9.0 equiv, 4.450 mmol) in MeCN was added portionwise $Ph_3P.Br_2$ (4.0 equiv, 1.978 mmol). The mixture was heated at 80° C. for 2 h which afforded a mixture of two new compounds. Water was added and the mixture was stirred for 15 min then was extracted with EtOAc. The organic extracts were washed sequentially with water, aq. citric acid, water and brine, dried ($MgSO_4$) and concentrated. The residue was purified on a 40 g $SiO_2$ column eluting with an EtOAc/heptane gradient (0 to 100% EtOAc) to afford 177 mg of tert-butyl 4-(4-chlorophenyl)-3-[5-fluoro-7-[2-[(2-methylpyrazol-3-yl)amino]pyrimidin-4-yl]-[1,2,4]triazolo[4,3-a]pyridin-3-yl]butanoate.

step 3 (steps 3 to 5 correspond to steps 1 to 3 depicted in SCHEME D.: A mixture of tert-butyl 4-(4-chlorophenyl)-3-[5-fluoro-7-[2-[(2-methylpyrazol-3-yl)amino]pyrimidin-4-yl]-[1,2,4]triazolo[4,3-a]pyridin-3-yl]butanoate and $MeNH_2$ in THF (2M, 3 mL, 6 mmol) was heated in a sealed vial at 80° C. for 4 h. The mixture was concentrated, the residue partitioned between EtOAc and 5% aq citric acid. The organic extracts were washed with water, brine, dried ($Na_2SO_4$), filtered and concentrated to afford 138 mg of tert-butyl 4-(4-chlorophenyl)-3-[5-(methylamino)-7-[2-[(2-methylpyrazol-3-yl)amino]pyrimidin-4-yl]-[1,2,4]triazolo[4,3-a]pyridin-3-yl]butanoate which was used without additional purification.

step 4: A solution of tert-butyl 4-(4-chlorophenyl)-3-[5-(methylamino)-7-[2-[(2-methylpyrazol-3-yl)amino]pyrimidin-4-yl]-[1,2,4]triazolo[4,3-a]pyridin-3-yl]butanoate (138 mg, 0.2404 mmol), DCM (2 mL) and TFA (8 mL) was stirred for 2 h. The mixture was concentrated in vacuo, the residue dissolved in MeCN and concentrated again. The resulting pyrazol-3-yl)amino]pyrimidin-4-yl]-[1,2,4]triazolo[4,3-a]pyridin-3-yl]butanoic acid was a red oil which was used without further work-up.

step 5: To a solution of the crude product from step 4 (0.24 mmol), TEA and DMF (4 mL) was added in one portion HATU (110 mg, 0.2893 mmol) and the mixture was stirred for 1 h. The mixture was concentrated in vacuo and the residue partitioned between EtOAc and water. The combined organic extracts were washed sequentially with water, aq. citric acid, water and brine, dried ($MgSO_4$), filtered and concentrated. The residue was purified on a 4 g $SiO_2$ column eluting with a MeOH/DCM gradient (0 to 8% MeOH) to afford 84 mg of I-22 which was resolved on a chiral SFC column to afford 30 mg (S)-I-22 and 30 mg of (R)-I-22.

9-(4-Chlorobenzyl)-6-methyl-4-(2-((1-methyl-1H-pyrazol-5-yl)amino)pyrimidin-4-yl)-8,9-dihydro-1,2,2a$^1$,6-tetraazabenzo[cd]azulen-7(6H)-one (I-40) can be prepared analogously except in step 1, 6-fluoro-4-[2-[(2-methylpyrazol-3-yl)amino]pyrimidin-4-yl]-1H-pyridin-2-one hydrazine was replaced with 4-(2-fluoro-6-hydrazino-4-pyridyl)-N-(2-methylpyrazol-3-yl)pyridin-2-amine.

9-Benzyl-6-methyl-4-(2-((1-methyl-1H-pyrazol-5-yl)amino)pyridin-4-yl)-8,9-dihydro-1,2,2a$^1$,6-tetraazabenzo[cd]azulen-7(6H)-one (I-61) can be prepared analogously except in step 1, 4-tert-butoxy-2-[(4-chlorophenyl)methyl]-4-oxo-butanoic acid was replaced with 4-tert-butoxy-2-[(phenyl)methyl]-4-oxo-butanoic acid and 6-fluoro-4-[2-[(2-methylpyrazol-3-yl)amino]pyrimidin-4-yl]-1H-pyridin-2-one hydrazine was replaced with 4-(2-fluoro-6-hydrazino-4-pyridyl)-N-(2-methylpyrazol-3-yl)pyridin-2-amine.

9-(4-Methoxybenzyl)-6-methyl-4-(2-((1-methyl-1H-pyrazol-5-yl)amino)pyrimidin-4-yl)-8,9-dihydro-1,2,2a$^1$,6-tetraazabenzo[cd]azulen-7(6H)-one (I-62) can be prepared analogously except in step 1, 4-tert-butoxy-2-[(4-chlorophenyl)methyl]-4-oxo-butanoic acid was replaced with 4-tert-butoxy-2-[(4-methoxyphenyl)methyl]-4-oxo-butanoic acid.

9-(4-Methoxybenzyl)-6-methyl-4-(2-((1-methyl-1H-pyrazol-5-yl)amino)pyridin-4-yl)-8,9-dihydro-1,2,2a$^1$,6-tetraazabenzo[cd]azulen-7(6H)-one (I-63) can be prepared analogously except in step 1, 4-tert-butoxy-2-[(4-chlorophenyl)methyl]-4-oxo-butanoic acid was replaced with 4-tert-butoxy-2-[(4-methoxyphenyl)methyl]-4-oxo-butanoic acid and 6-fluoro-4-[2-[(2-methylpyrazol-3-yl)amino]pyrimidin-4-yl]-1H-pyridin-2-one hydrazine was replaced with 4-(2-fluoro-6-hydrazino-4-pyridyl)-N-(2-methylpyrazol-3-yl)pyridin-2-amine.

6-Methyl-4-(2-((1-methyl-1H-pyrazol-5-yl)amino)pyrimidin-4-yl)-9-propyl-8,9-dihydro-1,2,2a$^1$,6-tetraazabenzo[cd]azulen-7(6H)-one (I-64) can be prepared analogously except-fluoro-4-[2-[(2-methylpyrazol-3-yl)amino]pyrimidin-4-yl]-1H-pyridin-2-one hydrazine was replaced with 2-(2-(tert-butoxy)-2-oxoethyl)pentanoic acid.

9-Cyclopropyl-6-methyl-4-(2-((1-methyl-1H-pyrazol-5-yl)amino)pyrimidin-4-yl)-8,9-dihydro-1,2,2a$^1$,6-tetraazabenzo[cd]azulen-7(6H)-one (I-65) can be prepared analogously except in step 1, 4-tert-butoxy-2-[(4-chlorophenyl)methyl]-4-oxo-butanoic acid was replaced with 4-tert-butoxy-2-(cyclopropyl)-4-oxo-butanoic acid.

9-Benzyl-6-methyl-4-(2-((1-methyl-1H-pyrazol-5-yl)amino)pyrimidin-4-yl)-8,9-dihydro-1,2,2a$^1$,6-tetraazabenzo[cd]azulen-7(6H)-one (I-67) can be prepared analogously except in step 1, 4-tert-butoxy-2-[(4-chlorophenyl)methyl]-4-oxo-butanoic acid was replaced with 4-tert-butoxy-2-[(phenyl)methyl]-4-oxo-butanoic acid.

9-Isobutyl-6-methyl-4-(2-((1-methyl-1H-pyrazol-5-yl)amino)pyrimidin-4-yl)-8,9-dihydro-1,2,2a$^1$,6-tetraazabenzo[cd]azulen-7(6H)-one (I-68) can be prepared analogously except in step 1, 4-tert-butoxy-2-[(4-chlorophenyl)methyl]-4-oxo-butanoic acid was replaced with 2-(2-(tert-butoxy)-2-oxoethyl)-4-methylpentanoic acid.

9-Isopropyl-6-methyl-4-(2-((1-methyl-1H-pyrazol-5-yl)amino)pyrimidin-4-yl)-8,9-dihydro-1,2,2a$^1$,6-tetraazabenzo[cd]azulen-7(6H)-one (I-69) can be prepared analogously except in step 1, 4-tert-butoxy-2-[(4-chlorophenyl)methyl]-4-oxo-butanoic acid was replaced with 4-(tert-butoxy)-2-isopropyl-4-oxobutanoic acid.

(S)-9-(4-Fluorobenzyl)-6-methyl-4-(2-((1-methyl-1H-pyrazol-5-yl)amino)pyridin-4-yl)-8,9-dihydro-1,2,2a$^1$,6-tetraazabenzo[cd]azulen-7(6H)-one (I-70) can be prepared analogously except in step 1, 4-tert-butoxy-2-[(4-chlorophenyl)methyl]-4-oxo-butanoic acid was replaced with 4-tert-butoxy-2-[(4-fluorophenyl)methyl]-4-oxo-butanoic acid and 6-fluoro-4-[2-[(2-methylpyrazol-3-yl)amino]pyrimidin-4-yl]-1H-pyridin-2-one hydrazine was replaced with 4-(2-fluoro-6-hydrazino-4-pyridyl)-N-(2-methylpyrazol-3-yl)pyridin-2-amine.

6-Methyl-4-(2-((1-methyl-1H-pyrazol-5-yl)amino)pyrimidin-4-yl)-9-(2,2,2-trifluoroethyl)-8,9-dihydro-1,2,2a$^1$,6-tetraazabenzo[cd]azulen-7(6H)-one (I-71) can be prepared analogously except in step 1, 4-tert-butoxy-2-[(4-chlorophenyl)methyl]-4-oxo-butanoic acid was replaced with 2-((tert-butoxycarbonyl)amino)-4,4,4-trifluorobutanoic acid.

9-(2-Fluoro-4-methoxybenzyl)-6-methyl-4-(2-((1-methyl-1H-pyrazol-5-yl)amino)pyridin-4-yl)-8,9-dihydro-1,2,2a$^1$,6-tetraazabenzo[cd]azulen-7(6H)-one (I-74) can be prepared analogously except in step 1, 4-tert-butoxy-2-[(4-chlorophenyl)methyl]-4-oxo-butanoic acid was replaced with 4-tert-butoxy-2-[(2-fluoro-4-methoxyphenyl)methyl]-4-oxo-butanoic acid and 6-fluoro-4-[2-[(2-methylpyrazol-3-yl)amino]pyrimidin-4-yl]-1H-pyridin-2-one hydrazine was replaced with 4-(2-fluoro-6-hydrazino-4-pyridyl)-N-(2-methylpyrazol-3-yl)pyridin-2-amine.

9-Isobutyl-6-methyl-4-(2-((1-methyl-1H-pyrazol-5-yl)amino)pyridin-4-yl)-8,9-dihydro-1,2,2a$^1$,6-tetraazabenzo[cd]azulen-7(6H)-one (I-75) can be prepared analogously except in step 1, 4-tert-butoxy-2-[(4-chlorophenyl)methyl]-4-oxo-butanoic acid was replaced with 2-(2-(tert-butoxy)-2-oxoethyl)-4-methylpentanoic acid and 6-fluoro-4-[2-[(2-methylpyrazol-3-yl)amino]pyrimidin-4-yl]-1H-pyridin-2-one hydrazine was replaced with 4-(2-fluoro-6-hydrazino-4-pyridyl)-N-(2-methylpyrazol-3-yl)pyridin-2-amine.

9-(4-Fluorobenzyl)-6-methyl-4-(2-((1-methyl-1H-pyrazol-5-yl)amino)pyrimidin-4-yl)-8,9-dihydro-1,2,2a$^1$,6-tetraazabenzo[cd]azulen-7(6H)-one (I-79) can be prepared analogously except in step 1, 4-tert-butoxy-2-[(4-chlorophenyl)methyl]-4-oxo-butanoic acid was replaced with 4-tert-butoxy-2-[(4-fluorophenyl)methyl]-4-oxo-butanoic acid.

9-(3-Chlorobenzyl)-6-methyl-4-(2-((1-methyl-1H-pyrazol-5-yl)amino)pyrimidin-4-yl)-8,9-dihydro-1,2,2a$^1$,6-tetraazabenzo[cd]azulen-7(6H)-one (I-80) can be prepared analogously except in step 1, 4-tert-butoxy-2-[(4-chlorophenyl)methyl]-4-oxo-butanoic acid was replaced with 4-tert-butoxy-2-[(3-chlorophenyl)methyl]-4-oxo-butanoic acid.

9-((5-Chloropyridin-2-yl)methyl)-6-methyl-4-(2-((1-methyl-1H-pyrazol-5-yl)amino)pyrimidin-4-yl)-8,9-dihydro-1,2,2a$^1$,6-tetraazabenzo[cd]azulen-7(6H)-one (I-84) can be prepared analogously except in step 1, 4-tert-butoxy-2-[(4-chlorophenyl)methyl]-4-oxo-butanoic acid was replaced with 4-(tert-butoxy)-2-((5-chloropyridin-2-yl)methyl)-4-oxobutanoic acid.

9-(2-Fluoro-4-methoxybenzyl)-6-methyl-4-(2-((1-methyl-1H-pyrazol-5-yl)amino)pyrimidin-4-yl)-8,9-dihydro-1,2,2a$^1$,6-tetraazabenzo[cd]azulen-7(6H)-one (I-85) can be prepared analogously except in step 1, 4-tert-butoxy-2-[(4-chlorophenyl)methyl]-4-oxo-butanoic acid was replaced with 4-tert-butoxy-2-[(2-fluoro4-methoxyphenyl)methyl]-4-oxo-butanoic acid.

6-Methyl-4-(2-((1-methyl-1H-pyrazol-5-yl)amino)pyridin-4-yl)-9-(2,2,2-trifluoroethyl)-8,9-dihydro-1,2,2a$^1$,6-tetraazabenzo[cd]azulen-7(6H)-one (I-86) can be prepared analogously except in step 1, 4-tert-butoxy-2-[(4-chlorophenyl)methyl]-4-oxo-butanoic acid was replaced with 2-((tert-butoxycarbonyl)amino)-4,4,4-trifluorobutanoic acid and 6-fluoro-4-[2-[(2-methylpyrazol-3-yl)amino]pyrimidin-4-yl]-1H-pyridin-2-one hydrazine was replaced with 4-(2-fluoro-6-hydrazino-4-pyridyl)-N-(2-methylpyrazol-3-yl)pyridin-2-amine.

9-Isopropyl-6-methyl-4-(2-((1-methyl-1H-pyrazol-5-yl)amino)pyridin-4-yl)-8,9-dihydro-1,2,2a$^1$,6-tetraazabenzo[cd]azulen-7(6H)-one (I-87) can be prepared analogously except in step 1, 4-tert-butoxy-2-[(4-chlorophenyl)methyl]-4-oxo-butanoic acid was replaced with 4-(tert-butoxy)-2-isopropyl-4-oxobutanoic acid and 6-fluoro-4-[2-[(2-methylpyrazol-3-yl)amino]pyrimidin-4-yl]-1H-pyridin-2-one hydrazine was replaced with 4-(2-fluoro-6-hydrazino-4-pyridyl)-N-(2-methylpyrazol-3-yl)pyridin-2-amine.

9-((5-chloropyridin-2-yl)methyl)-6-methyl-4-(2-((1-methyl-1H-pyrazol-5-yl)amino)pyridin-4-yl)-8,9-dihydro-1,2,2a¹,6-tetraazabenzo[cd]azulen-7(6H)-one (I-94) can be prepared analogously except in step 1, 4-tert-butoxy-2-[(4-chlorophenyl)methyl]-4-oxo-butanoic acid was replaced with 4-(tert-butoxy)-2-((5-chloropyridin-2-yl)methyl)-4-oxobutanoic acid and 6-fluoro-4-[2-[(2-methylpyrazol-3-yl)amino]pyrimidin-4-yl]-1H-pyridin-2-one hydrazine was replaced with 4-(2-fluoro-6-hydrazino-4-pyridyl)-N-(2-methylpyrazol-3-yl)pyridin-2-amine.

Example 12

9-(4-chlorobenzyl)-4-(2-((1-methyl-1H-pyrazol-5-yl)amino)pyrimidin-4-yl)-8,9-dihydro-1,2,2a¹,6-tetraazabenzo[cd]azulen-7(6H)-one (I-34)

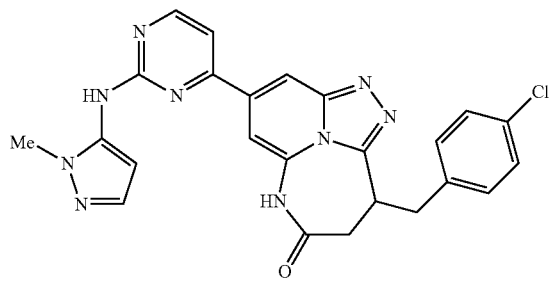

I-34 step 1: Ammonia was passed through a solution of 4-(4-chlorophenyl)-3-[5-fluoro-7-[2-[(2-methylpyrazol-3-yl)amino]pyrimidin-4-yl]-[1,2,4]triazolo[4,3-a]pyridin-3-yl]butanoic acid bis-TFA salt (90 mg, 0.1224 mmol) in DMSO (2 mL) for 30 min. The vial was sealed and kept overnight. The mixture was mixed with water and concentrated to remove ammonia. The residual solution was diluted with water and acidified to pH 4 with 1 N HCl. A precipitate was collected, washed with water and dried in high vacuum to afford 45 mg of 3-[5-amino-7-[2-[(2-methylpyrazol-3-yl)amino]pyrimidin-4-yl]-[1,2,4]triazolo[4,3-a]pyridin-3-yl]-4-(4-chlorophenyl)butanoic acid.

step 2: To a mixture of 3-[5-amino-7-[2-[(2-methylpyrazol-3-yl)amino]pyrimidin-4-yl]-[1,2,4]triazolo[4,3-a]pyridin-3-yl]-4-(4-chlorophenyl)butanoic acid (45 mg, 0.08930 mmol) and DIPEA (2.0 equiv, 0.1786 mmol) in DMF (2 mL) was added HATU (33.65 mg, 1.05 equiv, 0.09377 mmol). The mixture was stirred overnight, concentrated in vacuo and the residue partitioned between water and MeTHF. The organic extracts were washed sequentially with water, sat'd. aq. NaHCO₃, aq. citric acid, water and brine, dried (Na₂SO₄), filtered and concentrated. The residue was dry loaded on a 4 g SiO₂ column eluting with a MeOH/DCM gradient (0 to 8% MeOH) to afford 33 mg of material which contained an impurity. The product was repurified on a reverse phase HPLC column to afford 13.5 mg of product which was resolved on a chiral SFC column.

Example 13

4-(3-((6-methoxypyridin-3-yl)methyl)-4,5-dihydro-3H-1,2,2a¹,5-tetraazaacenaphthylen-7-yl)-N-(1-methyl-1H-pyrazol-5-yl)pyrimidin-2-amine (I-24)

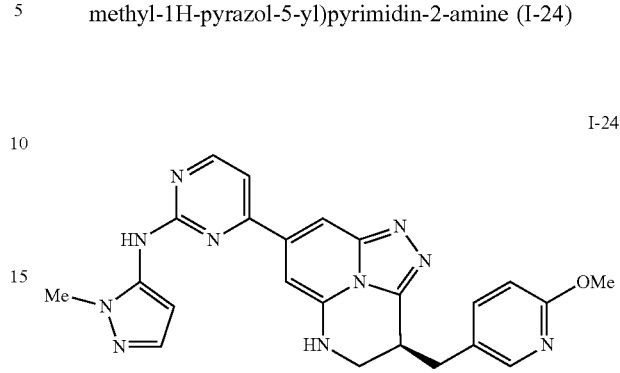

I-24 step 1: To a solution of 6-methoxypyridine-3-carbaldehyde (1 g, 7.28 mmol) and methyl cyanoacetate (1.2 equiv, 867 mg, 8.75 mmol) in MeOH was added dropwise piperidine (1.08 mL, 931 mg, 1.5 equiv). The resulting reaction stirred overnight at RT. The precipitate was filtered, washed with a small amount of EtOAc/heptane (ca. 1:5) and dried to afford 1.54 g of methyl (Z)-2-cyano-3-(6-methoxy-pyridin-3-yl)-acrylate as a white crystalline solid.

step 2: To a solution of (E)-2-cyano-3-(6-methoxy-2-pyridyl)prop-2-enoate (710 mg, 3.254 mmol) in MeOH (20 mL) and THF (10 mL) was added C(II)Cl₂ (871.1 mg, 6.507 mmol, 2 equiv) and the resulting solution stirred for several minutes. The solution was cooled in an ice bath and NaBH₄ (738.6 mg 19.522 mmol, 6 equiv.) was added in portions. The mixture was stirred for 4 h at RT then acidified with 1N HCl. The volatile solvents were removed in vacuo and the aqueous phase was twice extracted with EtOAc. The aqueous phase was made basic with sat'd. aq. NaHCO₃, salted with NaCl and concentrated in vacuo to afford methyl 2-(aminomethyl)-3-(6-methoxy-2-pyridyl)propanoate as gray solid which was used without additional purification.

step 3: To a solution of methyl 2-(aminomethyl)-3-(6-methoxy-2-pyridyl)propanoate (287 mg, 1.28 mmol) in THF (8 mL) and water (2 mL) was added NaHCO₃ (169.75 mg 1.92 mmol, 1.5 equiv) followed by tert-butoxycarbonyl tert-butyl carbonate (279.31 mg, 1.28 mmol). The resulting solution was stirred for 1 h at RT. The solution was diluted with EtOAc (20 mL) and the organic phase washed with sat'd. NH₄Cl, dried (Na₂SO₄), filtered and concentrated in vacuo to afford 408 mg of methyl 2-[(tert-butoxycarbonylamino)methyl]-3-(6-methoxy-3-pyridyl)propanoate which used without additional purification.

step 4: To a solution of methyl 2-[(tert-butoxycarbonylamino)methyl]-3-(6-methoxy-3-pyridyl)propanoate (406 mg, 1.258 mmol) in THF (7 mL) and water (2 mL) was added LiOH (1.3 equiv. 0.282 mL, 0.635 mmol) and the reaction was stirred overnight at RT. An additional 20 mg of LiOH was added and stirring continues for another 4 h. The solvents were removed in vacuo and the resulting 2-[(tert-butoxycarbonylamino)methyl]-3-(6-methoxy-3-pyridyl)propanoic acid was used without additional purification.

step 5: To a mixture of 2-[(tert-butoxycarbonylamino)methyl]-3-(6-methoxy-3-pyridyl)propanoic acid (310 mg, 0-999 mmol) in DMF (3 mL) was added HATU 387.6 mg 0.999 mmol) and 4-(2-fluoro-6-hydrazino-4-pyridyl)-N-(2-methylpyrazol-3-yl)pyrimidin-2-amine (200 mg, 0.666 mmol) then DIPEA (172.2 mg 0.232 mL, 1.332 mmol) was added. The resulting solution was stirred at RT for 2.5 h. The solution was diluted with water and extracted with EtOAc (2×20 mL). The combined extracts were dried (Na$_2$SO$_4$), filtered and concentrated on CELITE® in vacuo. The crude product was purified by SiO$_2$ chromatography eluting with a MeOH/DCM gradient (0 to 5% MeOH) to afford 137 mg of tert-butyl N-[3-[2-[6-fluoro-4-[2-[(2-methylpyrazol-3-yl)amino]pyrimidin-4-yl]-2-pyridyl]hydrazino]-2-[(6-methoxy-3-pyridyl)methyl]-3-oxo-propyl]carbamate as a yellow solid.

step 6: To a solution of tert-butyl N-[3-[2-[6-fluoro-4-[2-[(2-methylpyrazol-3-yl)amino]pyrimidin-4-yl]-2-pyridyl]hydrazino]-2-[(6-methoxy-3-pyridyl)methyl]-3-oxo-propyl]carbamate (135 mg, 0.2278 mmol) in THF (3 mL) was added Ph$_3$P.Br$_2$ (294.4 mg, 0.6834 mmol) followed by the slow addition of DIPEA (0.199 mL, 147.2 mg, 1.139 mmol). The resulting mixture was heated at 70° C. for 1.5 h. The reaction was diluted with water and extracted with EtOAc (2×15 mL). The combined extracts were washed with 5% citric acid, dried (Na$_2$SO$_4$), filtered and concentrated on CELITE®. The crude product was purified by SiO$_2$ chromatography (ISCO 12 g column) eluting with a MeOH/DCM gradient (0 to 5% MeOH) to afford 83 mg of tert-butyl N-[2-[5-fluoro-7-[2-[(2-methylpyrazol-3-yl)amino]pyrimidin-4-yl]-[1,2,4]triazolo[4,3-a]pyridin-3-yl]-3-(6-methoxy-3-pyridyl)propyl]carbamate The title compound can be prepared from tert-butyl N-[2-[5-fluoro-7-[2-[(2-methylpyrazol-3-yl)amino]pyrimidin-4-yl]-[1,2,4]triazolo[4,3-a]pyridin-3-yl]-3-(6-methoxy-3-pyridyl)propyl]carbamate utilizing the procedure in steps 3 and 4 of Example 3.

4-(3-((6-methoxypyridin-2-yl)methyl)-4,5-dihydro-3H-1,2,2a$^1$,5-tetraazaacenaphthylen-7-yl)-N-(1-methyl-1H-pyrazol-5-yl)pyrimidin-2-amine (I-27) can be prepared analogously except 6-methoxypyridine-2-carbaldehyde replaced 6-methoxypyridine-3-carbaldehyde in step 1.

(S)-4-(3-((2-methoxypyridin-3-yl)methyl)-5-methyl-4,5-dihydro-3H-1,2,2a$^1$,5-tetraazaacenaphthylen-7-yl)-N-(1-methyl-1H-pyrazol-5-yl)pyrimidin-2-amine (I-43) can be prepared analogously except 2-methoxypyridine-3-carbaldehyde replaced 6-methoxypyridine-3-carbaldehyde in step 1.

Example 14

(R)-9-(4-chlorobenzyl)-6-methyl-4-(2-((1-methyl-1H-pyrazol-5-yl)amino)pyrimidin-4-yl)-8,9-dihydro-1,2,2a$^1$,6,8-pentaazabenzo[cd]azulen-7(6H)-one
(I-6)

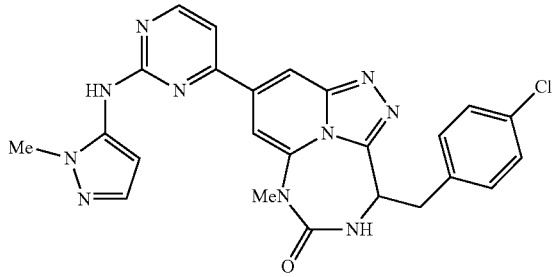

I-6 step 1: HATU (153 mg, 0.40 mmol) was added to a mixture of 6-fluoro-4-[2-[(2-methylpyrazol-3-yl)amino]pyrimidin-4-yl]-1H-pyridin-2-one hydrazone (104 mg, 0.33 mmol), (2R)-2-(tert-butoxycarbonylamino)-3-(4-chlorophenyl)propanoic acid (125 mg, 0.4 mmol) and TEA (0.138 mL, 1.0 mmol) in DMF (1.5 mL). The mixture was stirred for 2 h and partitioned between water and EtOAc. The organic extracts were washed sequentially with water, aq. NaHCO$_3$, 1% aq. citric acid, water and brine, dried (MgSO$_4$), filtered and concentrated in vacuo to afford 195 mg (89%) of (R)-tert-butyl (3-(4-chlorophenyl)-1-(2-(6-fluoro-4-(2-((1-methyl-1H-pyrazol-5-yl)amino)pyrimidin-4-yl)pyridin-2(1H)-ylidene)hydrazinyl)-1-oxopropan-2-yl)carbamate which was used in the next step without further purification. MS: m/z 582.

step 2: A mixture of (R)-tert-butyl (2-(4-chlorophenyl)-1-(5-fluoro-7-(2-((1-methyl-H-pyrazol-5-yl)amino)pyrimidin-4-yl)-[1,2,4]triazolo[4,3-a]pyridin-3-yl)ethyl)carbamate (195 mg, 0.3 mmol), Ph$_3$P.Br$_2$ (506 mg 1.2 mmol) and DIPEA (0.46 mL, 2.644 mmol) in MeCN (5 mL) was heated at 80° C. for 40 min in a sealed vial. The mixture was cooled to RT, mixed with water (1 mL) and stirred for 20 min. The mixture was partitioned between EtOAc and H$_2$O, the organic extracts were washed sequentially with aq. NaHCO$_3$, 1% aq citric acid, water and brine then dried (MgSO$_4$), filtered and concentrated in vacuo. The residue was purified on a 12 g SiO$_2$ column eluting with a MeOH/DCM gradient (0 to 7% MeOH) to afford 120 mg (72%) of (R)-tert-butyl (2-(4-chlorophenyl)-1-(5-fluoro-7-(2-((1-methyl-H-pyrazol-5-yl)amino)pyrimidin-4-yl)-[1,2,4]triazolo[4,3-a]pyridin-3-yl)ethyl)carbamate as a yellow foam. MS: m/z 564.

step 6 (SCHEME E): A mixture of tert-butyl N-[(2S)-3-(4-chlorophenyl)-2-[5-fluoro-7-[2-[(2-methylpyrazol-3-yl)amino]pyrimidin-4-yl]-[1,2,4]triazolo[4,3-a]pyridin-3-yl]propyl]carbamate (44 mg, 0.078 mmol) and MeNH$_2$ (2 M, 3.0 mL, 66.0 mmol) in THF was stirred at RT for 30 min. The mixture was concentrated in vacuo, the residue was dissolved in TEA containing MeOH and concentrated. The residue was triturated with a mixture of hexane and Et$_2$O (2:1) and filtered to afford 43 mg (99%) of (R)-tert-butyl (2-(4-chlorophenyl)-1-(7-(2-((1-methyl-1H-pyrazol-5-yl)amino)pyrimidin-4-yl)-5-(methylamino)-[1,2,4]triazolo[4,3-a]pyridin-3-yl)ethyl)carbamate. MS: m/z 575 step 7: To a solution of HCl in dioxane (4 mL) was added to a solution of (R)-tert-butyl (2-(4-chlorophenyl)-1-(7-(2-((1-methyl-1H-pyrazol-5-yl)amino)pyrimidin-4-yl)-5-(methylamino)-[1,2,4]triazolo[4,3-a]pyridin-3-yl)ethyl)carbamate (43 mg, 0.075 mmol) in DCM (6 mL). The mixture was stirred for 4 h and concentrated in vacuo. The residue was triturated with Et$_2$O and filtered to afford of (R)-3-(1-amino-2-(4-chlorophenyl)ethyl)-N-methyl-7-(2-((1-methyl-1H-pyrazol-5-yl)amino)pyrimidin-4-yl)-[1,2,4]triazolo[4,3-a]pyridin-5-amine tetrahydrochloride which was used in the next step without further purification. MS: m/z 475.

step 8: 1,1'-Carbonyldiimidazole (65 mg, 0.4 mmol) was added to 3-[(1R)-1-amino-2-(4-chlorophenyl)ethyl]-N-methyl-7-[2-[(2-methylpyrazol-3-yl)amino]pyrimidin-4-yl]-[1,2,4]triazolo[4,3-a]pyridin-5-amine tetrahydrochloride (46 mg, 0.074 mmol) in MeCN (3 mL). The mixture was irradiated in a microwave at 140° C. for 2 h. The mixture was concentrated cooled and concentrated in vacuo. The residue purified on a 4 g SiO$_2$ column eluting with a MeOH/DCM gradient (0 to 7% MeOH) to afford 12 mg of (R)-9-(4-chlorobenzyl)-6-methyl-4-(2-((1-methyl-1H-pyrazol-5-yl)amino)pyrimidin-4-yl)-8,9-dihydro-1,2,2a$^1$,6,8-pentaazabenzo[cd]azulen-7(6H)-one (I-6) as a yellow foam. $^1$H NMR (400 MHz, DMSO-d6) δ 9.59 (s, 1H), 8.62 (d, J=5.2 Hz, 1H), 8.38 (d, J=5.8 Hz, 1H), 8.21 (d, J=1.2 Hz, 1H), 7.71 (d, J=5.2 Hz, 1H), 7.44-7.33 (m, 5H), 7.06 (d, J=1.2 Hz, 1H), 6.31 (d, J=1.9 Hz, 1H), 5.22 (dt, J=9.1, 5.7 Hz, 1H), 3.72 (s, 3H), 3.51-3.45 (m, 2H), 3.21 (s, 3H). MS: m/z 501.

(R)-9-isobutyl-6,8-dimethyl-4-(2-((1-methyl-1H-pyrazol-5-yl)amino)pyrimidin-4-yl)-8,9-dihydro-1,2,2a$^1$,6,8-pentaazabenzo[cd]azulen-7(6H)-one (I-19) can be prepared analogously except in step 1, 2-(tert-butoxycarbonyl-methyl-amino)-4-methyl-pentanoic acid replaced (2R)-2-(tert-butoxycarbonylamino)-3-(4-chlorophenyl)propanoic acid. MS: m/z 447.

(R)-9-isobutyl-8-methyl-4-(2-((1-methyl-1H-pyrazol-5-yl)amino)pyrimidin-4-yl)-8,9-dihydro-1,2,2a$^1$,6,8-pentaazabenzo[cd]azulen-7(6H)-one (I-23) can be prepared analogously except in step 1, 2-(tert-butoxycarbonyl-methyl-amino)-4-methyl-pentanoic acid replaced (2R)-2-(tert-butoxycarbonylamino)-3-(4-chlorophenyl)propanoic acid and in step 5 methylamine was replaced with ammonia. $^1$H NMR (400 MHz, DMSO-d$_6$) δ 10.36 (s, 1H), 9.54 (s, 1H), 8.60 (d, J=5.2 Hz, 1H), 8.02 (d, J=1.3 Hz, 1H), 7.47 (d, J=5.2 Hz, 1H), 7.39 (d, J=1.9 Hz, 1H), 7.04 (d, J=1.4 Hz, 1H), 6.35 (d, J=1.9 Hz, 1H), 5.01 (dd, J=9.2, 6.8 Hz, 1H), 3.73 (s, 3H), 3.06 (s, 3H), 1.96 (dt, J=13.4, 7.3 Hz, 1H), 1.83 (ddd, J=13.4, 9.2, 5.8 Hz, 1H), 1.41 (dt, J=13.5, 6.7 Hz, 1H), 1.01 (d, J=6.6 Hz, 3H), 0.85 (d, J=6.6 Hz, 3H). MS: m/z 433

9-isobutyl-6-methyl-4-(2-((1-methyl-1H-pyrazol-5-yl)amino)pyridin-4-yl)-8,9-dihydro-1,2,2a$^1$,6,8-pentaazabenzo[cd]azulen-7(6H)-one (I-25) can be prepared analogously except in step 1, (2R)-2-(tert-butoxycarbonylamino)-3-(4-chlorophenyl)propanoic acid was replaced with 2-((tert-butoxycarbonyl)amino)-4-methylpentanoic acid.

(R)-9-(4-methoxybenzyl)-6-methyl-4-(2-((1-methyl-1H-pyrazol-5-yl)amino)pyridin-4-yl)-8,9-dihydro-1,2,2a$^1$,6,8-pentaazabenzo[cd]azulen-7(6H)-one (I-26) can be prepared analogously except in step 1, (2R)-2-(tert-butoxycarbonylamino)-3-(4-chlorophenyl)propanoic acid was replaced with (2R)-2-(tert-butoxycarbonylamino)-3-(4-methoxyphenyl)propanoic acid and 6-fluoro-4-[2-[(2-methylpyrazol-3-yl)amino]pyrimidin-4-yl]-1H-pyridin-2-one hydrazone was replaced with 4-(2-fluoro-6-hydrazino-4-pyridyl)-N-(2-methylpyrazol-3-yl)pyridin-2-amine.

(R)-9-(4-fluorobenzyl)-6-methyl-4-(2-((1-methyl-1H-pyrazol-5-yl)amino)pyrimidin-4-yl)-8,9-dihydro-1,2,2a$^1$,6,8-pentaazabenzo[cd]azulen-7(6H)-one (I-35) can be prepared analogously except in step 1, (2R)-2-(tert-butoxycarbonylamino)-3-(4-chlorophenyl)propanoic acid was replaced with (2R)-2-(tert-butoxycarbonylamino)-3-(4-fluorophenyl)propanoic acid.

(R)-9-(3-fluorobenzyl)-6-methyl-4-(2-((1-methyl-1H-pyrazol-5-yl)amino)pyrimidin-4-yl)-8,9-dihydro-1,2,2a$^1$,6,8-pentaazabenzo[cd]azulen-7(6H)-one (I-39) can be prepared analogously except in step 1, (2R)-2-(tert-butoxycarbonylamino)-3-(4-chlorophenyl)propanoic acid was replaced with (2R)-2-(tert-butoxycarbonylamino)-3-(3-fluorophenyl)propanoic acid.

(R)-9-(cyclopropylmethyl)-6-methyl-4-(2-((1-methyl-1H-pyrazol-5-yl)amino)pyrimidin-4-yl)-8,9-dihydro-1,2,2a$^1$,6,8-pentaazabenzo[cd]azulen-7(6H)-one (I-51) can be prepared analogously except in step 1, (2R)-2-(tert-butoxycarbonylamino)-3-(4-chlorophenyl)propanoic acid was replaced with (R)-2-((tert-butoxycarbonyl)amino)-3-cyclopropylpropanoic acid.

Example 15

4-(9-((4-chloro-1H-pyrazol-1-yl)methyl)-8,9-dihydro-7H-6-oxa-1,2,2a$^1$-triazabenzo[cd]azulen-4-yl)-N-(tetrahydro-2H-pyran-4-yl)pyrimidin-2-amine (I-110)

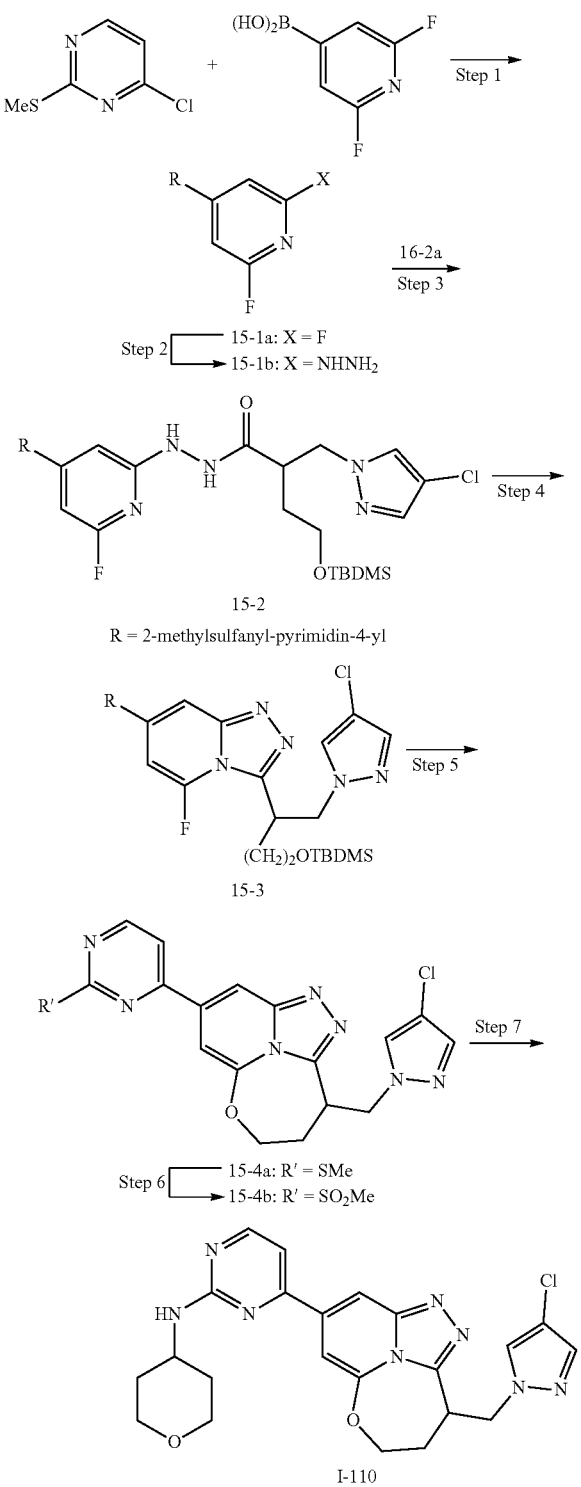

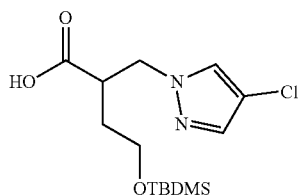

15-2a step 1: A mixture of 4-chloro-2-(methylsulfanyl)pyrimidine (2 g, 12.45 mmol), (2,6-difluoro-4-pyridyl)boronic acid (3.95 g, 24.90 mmol), Cs₂CO₃ (8.11 g, 24.90 mmol) and (dppf)PdCl₂.DCM (1.07 g, 1.24 mmol) in water (15 mL) and MeCN (45 mL) was degassed with N₂, capped in a glass reaction tube (150 mL), heated at 95° C. for 2.5 h. After cooled, it was filtered through a short pad of CELITE®, diluted with water, extracted with EtOAc (2×80 mL), dried (Na₂SO₄), filtered and concentrated on CELITE®. The crude product was purified by SiO₂ chromatography (ISCO 40 g column) and eluded with an EtOAc/heptane gradient (0 to 15% EtOAc) to afford 2.66 g (89%) of 4-(2,6-difluoropyridin-4-yl)-2-(methylthio)pyrimidine as white solid. MS: m/z 239.

step 2: To a suspension of 4-(2,6-difluoro-4-pyridyl)-2-methylsulfanyl-pyrimidine (2.66 g, 11.1 mmol) in EtOH (70 mL) was added hydrazine (1.11 mL, 33.4 mmol) and heated at 70° C. for 5.5 h. After cooling, the solution was concentrated in vacuo and triturated with water. The solid was collected by filtration, washed with water, dried under high vacuum to afford 2.69 g (96%) of 4-(2-fluoro-6-hydrazinylpyridin-4-yl)-2-(methylthio)pyrimidine (15-1b) as off white solid. MS: m/z 251.

step 3: To a solution of 4-[tert-butyl(dimethyl)silyl]oxy-2-[(4-chloropyrazol-1-yl)methyl]butanoic acid (1.34 g, 4.04 mmol) in DMF (20 mL) was added HATU (1.70 g, 4.37 mmol), [6-fluoro-4-(2-methylsulfanylpyrimidin-4-yl)-2-pyridyl]hydrazine (0.845 g, 3.36 mmol) and DIPEA (0.88 mL, 5.04 mmol) in that order and the resulting mixture was stirred at RT for 2.5 h. The solution was diluted with water and extracted with EtOAc (3×50 mL). The combined extracts were washed with 5% citric acid, brine then dried (Na₂SO₄), filtered and concentrated on CELITE®. The crude product was purified by SiO₂ chromatography ((ISCO 24 g column) and eluted with a MeOH/DCM gradient (0 to 5% MeOH) to afford 1.37 g (72%) of 4-((tert-butyldimethylsilyl)oxy)-2-((4-chloro-1H-pyrazol-1-yl)methyl)-N'-(6-fluoro-4-(2-(methylthio)pyrimidin-4-yl)pyridin-2-yl)butanehydrazide (15-2) as brown solid. MS: m/z 566.

step 4: To a solution of 4-[tert-butyl(dimethyl)silyl]oxy-2-[(4-chloropyrazol-1-yl)methyl]-N'-[6-fluoro-4-(2-methylsulfanylpyrimidin-4-yl)-2-pyridyl]butanehydrazide (2.04 g, 3.60 mmol) in MeCN (30 mL) and DIPEA (3.14 mL, 18.0 mmol) was added Ph₃P.Br₂ (4.56 g, 10.8 mmol) in portions and the solution stirred at RT for 1 h. The solution was diluted with water, extracted with EtOAc (3×80 mL). The combined extracts were washed with 5% citric acid, brine, dried (Na₂SO₄), filtered and concentrated on CELITE®. The crude product was purified by SiO₂ chromatography (ISCO 40 g column) eluting with a MeOH/DCM gradient (0 to 5% MeOH) to afford 1.38 g (70%) of 3-(4-((tert-butyldimethylsilyl)oxy)-1-(4-chloro-1H-pyrazol-1-yl)butan-2-yl)-5-fluoro-7-(2-(methylthio)pyrimidin-4-yl)-[1,2,4]triazolo[4,3-a]pyridine (15-3) as red-brown gum. MS: m/z 548.

step 5: To a solution of tert-butyl-[4-(4-chloropyrazol-1-yl)-3-[5-fluoro-7-(2-methylsulfanylpyrimidin-4-yl)-[1,2,4]triazolo[4,3-a]pyridin-3-yl]butoxy]-dimethyl-silane (658 mg, 1.20 mmol) in THF (15 mL) was added tetrabutylammonium fluoride in THF ((1.0 M, 3 30 mL, 2.96 mmol). The resulting solution was stirred at RT for 1.5 h, diluted with water and extracted with EtOAc (2×50 mL). The combined extracts were washed with brine, dried (Na₂SO₄), filtered and concentrated on CELITE®. The crude product was purifies by SiO₂ chromatography (ISCO 12 g column) eluting with a MeOH/DCM gradient (0 to 5% MeOH) to afford 278 mg (56%) of 15-4a as yellow solid. MS: m/z 413.

step 6: To a solution of 9-((4-chloro-1H-pyrazol-1-yl)methyl)-4-(2-(methylthio)pyrimidin-4-yl)-8,9-dihydro-7H-6-oxa-1,2,2a1-triazabenzo[cd]azulene (278 mg, 0.67 mmol) in DCM (7 mL) cooled in ice bath was added mCPBA (451.6 mg, 2.01 mmol) in portions and stirred at RT for 1.5 h. It was washed with sat. aq. Na₂S₂O₃, sat, NaHCO₃, dried (Na₂SO₄), filtered and concentrated in vacuo to afford 279 mg (93%) of 15-4b as brown solid, which was used in the next step without further purification. MS: m/z 445.

step 7: To a solution of 9-((4-chloro-1H-pyrazol-1-yl)methyl)-4-(2-(methylsulfonyl)pyrimidin-4-yl)-8,9-dihydro-7H-6-oxa-1,2,2a1-triazabenzo[cd]azulene (279 mg, 0.62 mmol) in DMSO (2.5 mL) was added 4-aminotetrahydropyran (0.40 mL, 3.75 mmol) and DIPEA (0.65 mL, 3.75 mmol). The solution was heated at 80° C. for 1 h, diluted with water and extracted with EtOAc (3×20 mL). The combined extracts were washed with 5% citric acid, dried (Na₂SO₄), filtered and concentrated on CELITE®. The crude product was purified by SiO₂ chromatography (ISCO, 12 g column) eluting with MeOH/DCM gradient (0 to 8% MeOH) to afford 187 mg (64%) of racemic I-110 as yellow solid. MS: m/z 466.

The racemic mixture was resolved by SFC chromatography on a chiral support:

(R) I-110 (38.7 mg)$^1$H NMR (400 MHz, DMSO-d6) δ 8.41 (d, J=5.2 Hz, 1H), 8.22 (d, J=1.4 Hz, 1H), 8.04 (d, J=0.8 Hz, 1H), 7.56 (d, J=1.0 Hz, 1H), 7.32 (t, J=6.4 Hz, 2H), 7.05 (d, J=1.5 Hz, 1H), 4.91 (dd, J=13.8, 5.3 Hz, 1H), 4.69-4.57 (m, 2H), 4.50 (ddd, J=12.1, 8.0, 3.6 Hz, 1H), 4.12 (tt, J=8.6, 5.6 Hz, 1H), 4.03 (s, 1H), 3.89 (dt, J=11.3, 3.4 Hz, 2H), 3.43 (t, J=11.4 Hz, 2H), 2.25-2.02 (m, 2H), 1.88 (d, J=12.5 Hz, 2H), 1.55 (qd, J=11.6, 4.3 Hz, 2H); MS: m/z 466.

(S) I-110 (38.2 mg)$^1$H NMR (400 MHz, DMSO-d6) δ 8.41 (d, J=5.1 Hz, 1H), 8.22 (d, J=1.4 Hz, 1H), 8.04 (s, 1H), 7.56 (s, 1H), 7.38-7.28 (m, 2H), 7.05 (d, J=1.5 Hz, 1H), 4.91 (dd, J=13.8, 5.4 Hz, 1H), 4.69-4.57 (m, 2H), 4.50 (ddd, J=12.1, 8.0, 3.6 Hz, 1H), 4.12 (tt, J=8.6, 5.6 Hz, 1H), 4.03 (s, 1H), 3.89 (dt, J=11.3, 3.4 Hz, 2H), 3.43 (t, J=11.3 Hz, 2H), 2.25-2.02 (m, 2H), 1.88 (d, J=12.3 Hz, 2H), 1.63-1.48 (m, 2H); MS: m/z 466.

4-(9-((4-chloro-1H-pyrazol-1-yl)methyl)-8,9-dihydro-7H-6-oxa-1,2,2a[1]-triazabenzo[cd]azulen-4-yl)-N-(oxetan-3-yl)pyrimidin-2-amine was prepared analogously except in step 7, 4-amino tetrahydropyran was replaced with 3-aminooxetane. The racemic mixture was resolved by SFC chromatography on a chiral column to afford:

(R)-4-(9-((4-chloro-1H-pyrazol-1-yl)methyl)-8,9-dihydro-7H-6-oxa-1,2,2a[1]-triazabenzo[cd]azulen-4-yl)-N-(oxetan-3-yl)pyrimidin-2-amine: $^1$H NMR (400 MHz, DMSO-d6) δ 8.44 (d, J=5.1 Hz, 1H), 8.24 (d, J=1.4 Hz, 1H), 8.10-8.01 (m, 2H), 7.56 (s, 1H), 7.41 (d, J=5.2 Hz, 1H), 7.06 (d, J=1.4 Hz, 1H), 5.03 (s, 1H), 4.91 (dd, J=13.8, 5.3 Hz, 1H), 4.82 (t, J=6.7 Hz, 2H), 4.69-4.44 (m, 5H), 4.12 (tt, J=8.4, 5.6 Hz, 1H), 3.31 (d, J=19.9 Hz, 1H), 2.25-2.03 (m, 2H); MS: m/z 438.

(S)-4-(9-((4-chloro-1H-pyrazol-1-yl)methyl)-8,9-dihydro-7H-6-oxa-1,2,2a[1]-triazabenzo[cd]azulen-4-yl)-N-

(oxetan-3-yl)pyrimidin-2-amine: $^1$H NMR (400 MHz, DMSO-d6) δ 8.44 (d, J=5.1 Hz, 1H), 8.24 (d, J=1.4 Hz, 1H), 8.10-8.01 (m, 2H), 7.56 (s, 1H), 7.41 (d, J=5.2 Hz, 1H), 7.06 (d, J=1.4 Hz, 1H), 5.03 (s, 1H), 4.91 (dd, J=13.8, 5.4 Hz, 1H), 4.82 (t, J=6.7 Hz, 2H), 4.69-4.44 (m, 5H), 4.12 (tt, J=8.5, 5.6 Hz, 1H), 3.31 (d, J=19.9 Hz, 1H), 2.25-2.03 (m, 2H); MS: m/z 438.

4-(9-((4-chloro-1H-pyrazol-1-yl)methyl)-8,9-dihydro-7H-6-oxa-1,2,2a$^1$-triazabenzo[cd]azulen-4-yl)-N-isopropylpyrimidin-2-amine was prepared analogously except in step 7, 4-amino tetrahydropyran was replaced with iso-propylamine. The racemic mixture was resolved by SFC chromatography on a chiral column to afford:

(R)-4-(9-((4-chloro-1H-pyrazol-1-yl)methyl)-8,9-dihydro-7H-6-oxa-1,2,2a$^1$-triazabenzo[cd]azulen-4-yl)-N-isopropylpyrimidin-2-amine: $^1$H NMR (400 MHz, DMSO-d$_6$) δ 8.40 (d, J=5.1 Hz, 1H), 8.21 (d, J=1.4 Hz, 1H), 8.04 (d, J=0.7 Hz, 1H), 7.56 (s, 1H) 7.30 (d, J=5.2 Hz, 1H), 7.14 (d, J=7.8 Hz, 1H), 7.06 (d, J=1.4 Hz, 1H), 4.91 (dd, J=13.8, 5.3 Hz, 1H), 4.68-4.58 (m, 2H), 4.49 (ddd, J=12.1, 8.0, 3.7 Hz, 1H), 4.12 (tt, J=8.6, 5.9 Hz, 2H), 2.23-2.04 (m, 2H), 1.20 (d, J=6.5 Hz, 6H; MS: m/z 424

(S)-4-(9-((4-chloro-1H-pyrazol-1-yl)methyl)-8,9-dihydro-7H-6-oxa-1,2,2a$^1$-triazabenzo[cd]azulen-4-yl)-N-isopropylpyrimidin-2-amine: $^1$H NMR (400 MHz, DMSO-d$_6$) δ 8.40 (d, J=5.1 Hz, 1H), 8.22 (d, J=1.4 Hz, 1H), 8.04 (d, J=0.7 Hz, 1H), 7.56 (s, 1H), 7.30 (d, J=5.2 Hz, 1H), 7.15 (d, J=7.8 Hz, 1H), 7.06 (d, J=1.4 Hz, 1H), 4.91 (dd, J=13.8, 5.4 Hz, 1H), 4.70-4.57 (m, 2H), 4.49 (ddd, J=12.1, 8.0, 3.6 Hz, 1H), 4.12 (tt, J=8.5, 6.1 Hz, 2H), 2.25-2.02 (m, 2H), 1.20 (d, J=6.5 Hz, 6H); MS: m/z 424.

Example 16

4-(9-((4-chloro-1H-pyrazol-1-yl)methyl)-8,9-dihydro-7H-6-oxa-1,2,2a$^1$-triazabenzo[cd]azulen-4-yl)-N-(1,3-dimethyl-1H-pyrazol-5-yl)pyrimidin-2-amine

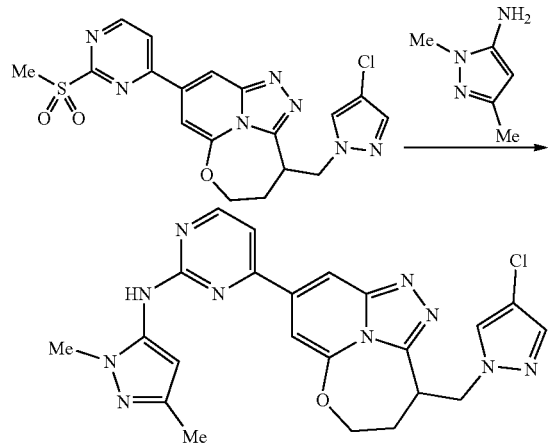

To a solution of 9-((4-chloro-1H-pyrazol-1-yl)methyl)-4-(2-(methylsulfonyl)pyrimidin-4-yl)-8,9-dihydro-7H-6-oxa-1,2,2a1-triazabenzo[cd]azulene (15-4b, 200 mg, 0.44 mmol), 2,5-dimethylpyrazol-3-amine (149.5 mg, 1.34 mmol) in DMSO (2 mL) was added NaH (35.80 mg, 28 mmol, 60% mineral oil dispersion). The reaction was stirred at RT for 45 min, quenched with water and extracted with EtOAc (3×20 mL). The combined extracts were washed with 5% citric acid, brine, dried (Na$_2$SO$_4$), filtered and concentrated in vacuo. The crude product was purified by SiO$_2$ chromatography (ISCO 12 g column) eluting with a MeOH/DCM gradient (0 to 8% MeOH) to afford 95 mg (88.5%) of the title compound as yellow solid.

The racemic mixture was resolved by SFC chromatography on a chiral column to afford:

(R)-4-(9-((4-chloro-1H-pyrazol-1-yl)methyl)-8,9-dihydro-7H-6-oxa-1,2,2a$^1$ triazabenzo[cd]azulen-4-yl)-N-(1,3-dimethyl-1H-pyrazol-5-yl)pyrimidin-2-amine: $^1$H NMR (400 MHz, DMSO-d6) δ 9.51 (s, 1H), 8.58 (d, J=5.2 Hz, 1H), 8.27 (d, J=1.4 Hz, 1H), 8.05 (d, J=0.7 Hz, 1H), 7.65 (d, J=5.2 Hz, 1H), 7.57 (d, J=0.7 Hz, 1H), 7.05 (d, J=1.2 Hz, 1H), 6.06 (s, 1H), 4.91 (dd, J=13.8, 5.4 Hz, 1H), 4.68-4.59 (m, 2H), 4.50 (ddd, J=12.1, 8.1, 3.6 Hz, 1H), 4.12 (tt, J=8.7, 5.6 Hz, 1H), 3.61 (s, 3H), 2.22-2.06 (m, 5H); MS: m/z 476.

(S)-4-(9-((4-chloro-1H-pyrazol-1-yl)methyl)-8,9-dihydro-7H-6-oxa-1,2,2a$^1$-triazabenzo[cd]azulen-4-yl)-N-(1,3-dimethyl-1H-pyrazol-5-yl)pyrimidin-2-amine: $^1$H NMR (400 MHz, DMSO-d6) δ 9.51 (s, 1H), 8.58 (d, J=5.2 Hz, 1H), 8.27 (d, J=1.5 Hz, 1H), 8.05 (s, 1H), 7.65 (d, J=5.2 Hz, 1H), 7.04 (d, J=1.6 Hz, 1H), 6.06 (s, 1H), 4.91 (dd, J=13.8, 5.4 Hz, 1H), 4.68-4.59 (m, 2H), 4.50 (ddd, J=12.0, 8.1, 3.6 Hz, 1H), 4.12 (tt, J=8.5, 5.5 Hz, 1H), 3.61 (s, 3H), 2.21-2.07 (m, 6H); MS: m/z 476.

Example 17

N-(1-methyl-1H-pyrazol-5-yl)-4-(9-phenoxy-8,9-dihydro-7H-6-oxa-1,2,2a$^1$-triazabenzo[cd]azulen-4-yl)pyrimidin-2-amine (I-90)

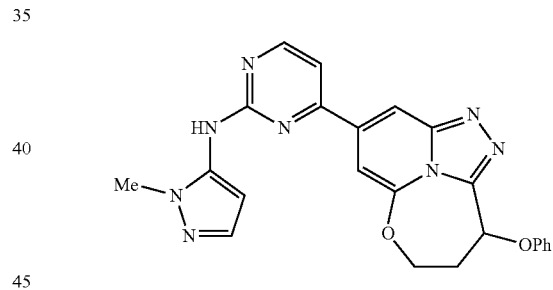

step 1: To a solution of phenol (1.25 g, 13.33 mmol) in DMF (35 mL) was added K$_2$CO$_3$ (2.09 g, 15.15 mmol), stirred for 10 min then α-bromo-γ-butyrolactone (1.14 mL, 12.12 mmol) was added dropwise and the resulting solution was stirred at RT for 18 h. The mixture was diluted with water and extracted with EtOAc (3×80 mL). The combined extracts were washed with water, dried (Na$_2$SO$_4$), filtered and concentrated on CELITE®. The product was purified by SiO$_2$ chromatography (ISCO 40 g column) and eluted with an EtOAc/heptane gradient (0 to 20% EtOAc) to afford 1.03 g (47.7%) of 3-phenoxytetrahydrofuran-2-one as clear liquid. MS: m/z 178 step 2: To a solution of 3-phenoxytetrahydrofuran-2-one (1.03 g, 5.78 mmol) in THF (20 mL) and water (10 mL) was added LiOH (208 mg, 8.67 mmol) and the resulting solution stirred at RT for 18 h. It was acidified with 1N HCl, extracted with EtOAc (3×50 mL). The combined extracts were dried (Na$_2$SO$_4$), filtered and concentrated in vacuo, to afford 1.05 g (92.6%) of 4-hydroxy-2-phenoxy-butanoic acid as clear syrup which was used without additional purification: MS m/z 196.

step 3: To a solution of 4-hydroxy-2-phenoxy-butanoic acid (1.0 g, 5.1 mmol) in DMF (20 mL) was added tert-butyl-chloro-dimethyl-silane (2.30 g, 15 mmol) and imidazole (1.40 g, 20 mmol). The solution was stirred at RT for 18 h, then diluted with water and extracted with EtOAc (3×80 mL). The combined extracts were washed with water, dried ($Na_2SO_4$), filtered and concentrated in vacuo, and dried under high vacuum to give 1.38 g (87%) of 4-[tert-butyl(dimethyl)silyl]oxy-2-phenoxy-butanoic acid as clear syrup. MS: m/z 310, step 4 (SCHEME G): To a solution of 4-[tert-butyl(dimethyl)silyl]oxy-2-phenoxy-butanoic acid (672.1 mg, 2.16 mmol) in DMF (8 mL) was added HATU (969.0 mg, 2.49 mmol), 4-(2-fluoro-6-hydrazino-4-pyridyl)-N-(2-methylpyrazol-3-yl)pyrimidin-2-amine (500 mg, 1.66 mmol) and DIPEA (0.58 mL, 3.33 mmol) in that order, and the reaction was stirred at RT for 2 h. It was diluted with water, extracted with EtOAc (3×20 mL). The combined extracts were washed with water, dried ($Na_2SO_4$), filtered and concentrated on CELITE®. The crude product was purified by $SiO_2$ chromatography (ISCO 24 g column) eluting with a MeOH/DCM gradient (0 to 5% MeOH) to afford 763 mg (77.3%) of 4-((tert-butyldimethylsilyl)oxy)-N'-(6-fluoro-4-(2-((1-methyl-1H-pyrazol-5-yl)amino)pyrimidin-4-yl)pyridin-2-yl)-2-phenoxybutanehydrazide as yellow solid. MS: m/z 592 step 5: To a solution of 4-[tert-butyl(dimethyl)silyl]oxy-N'-[6-fluoro-4-[2-[(2-methylpyrazol-3-yl)amino]pyrimidin-4-yl]-2-pyridyl]-2-phenoxy-butanehydrazide (763 mg, 1.28 mmol) in MeCN (15 mL) was added DIPEA (0.89 mL, 5.14 mmol), followed by $Ph_3P.Br_2$ (1.63 g, 3.86 mmol) in small portions and the solution was stirred at RT for 2 h. The solution was diluted with water and extracted with EtOAc (3×50 mL). The combined extracts were washed with water, dried ($Na_2SO_4$), filtered and concentrated on CELITE®. The crude product was purified by $SiO_2$ chromatography (ISCO 24 g column) eluting with MeOH/DCM gradient (0 to 5% MeOH) to afford 470 mg (63.5%) of 4-(3-(3-((tert-butyldimethylsilyl)oxy)-1-phenoxypropyl)-5-fluoro-[1,2,4]triazolo[4,3-a]pyridin-7-yl)-N-(1-methyl-1H-pyrazol-5-yl)pyrimidin-2-amine compound as yellow solid. MS: m/z 574 step 6: To a suspension of 4-[3-[3-[tert-butyl(dimethyl)silyl]oxy-1-phenoxy-propyl]-5-fluoro-[1,2,4]triazolo[4,3-a]pyridin-7-yl]-N-(2-methylpyrazol-3-yl)pyrimidin-2-amine (470 mg, 0.61 mmol) in DCM (15 mL) was added $BF_3.OEt_2$ (0.46 mL, 3.68 mmol) and the resulting solution stirred at RT for 18 h. The reaction was quenched with sat. $NaHCO_3$, diluted with water, extracted with DCM (2×20 mL). The combined extracts were dried ($Na_2SO_4$), filtered and concentrated on CELITE®. The crude product was purified by $SiO_2$ (ISCO 12 g column) and eluded with a MeOH/DCM gradient (0 to 8% MeOH) to give 130 mg (46%) 3-(5-fluoro-7-(2-((1-methyl-1H-pyrazol-5-yl)amino)pyrimidin-4-yl)-[1,2,4]triazolo[4,3-a]pyridin-3-yl)-3-phenoxypropan-1-ol.

step 7: To a mixture of 3-(5-fluoro-7-(2-((1-methyl-H-pyrazol-5-yl)amino)pyrimidin-4-yl)-[1,2,4]triazolo[4,3-a]pyridin-3-yl)-3-phenoxypropan-1-ol ol (130 mg, 0.28 mmol) in THF (10 mL) was added NaH (90.33 mg, 2.25 mmol, 60% mineral oil dispersion)), stirred for 15 min then heated in oil bath at 65° C. for 60 min. The reaction was quenched with few drops of water, concentrated on CELITE®. The crude product was purified by $SiO_2$ chromatography (ISCO 4 g column) and eluted with a MeOH/DCM gradient (0 to 8% MeOH) to give 61 mg (49%) of N-(1-methyl-1H-pyrazol-5-yl)-4-(9-phenoxy-8,9-dihydro-7H-6-oxa-1,2,2a$^1$-triazabenzo[cd]azulen-4-yl)pyrimidin-2-amine as a yellow solid. MS: m/z 440

The racemic mixture was resolved by SFC chromatography on a chiral support:

(S)—N-(1-methyl-1H-pyrazol-5-yl)-4-(9-phenoxy-8,9-dihydro-7H-6-oxa-1,2,2a$^1$-triazabenzo[cd]azulen-4-yl)pyrimidin-2-amine (S) I-90: $^1$H NMR (400 MHz, DMSO-d6) δ 9.55 (s, 1H), 8.61 (d, J=5.2 Hz, 1H), 8.30 (d, J=1.5 Hz, 1H), 7.67 (d, J=5.2 Hz, 1H), 7.40 (d, J=1.9 Hz, 1H), 7.35-7.25 (m, 2H), 7.17-7.10 (m, 3H), 7.03-6.94 (m, 1H), 6.36-6.27 (m, 2H), 4.91-4.81 (m, 1H), 4.63 (ddd, J=12.7, 7.0, 4.3 Hz, 1H), 3.71 (d, J=1.3 Hz, 4H), 3.28 (d, J=2.4 Hz, 12H), 2.73 (dq, J=6.7, 4.4 Hz, 2H); MS: m/z 440.

(R)—N-(1-methyl-1H-pyrazol-5-yl)-4-(9-phenoxy-8,9-dihydro-7H-6-oxa-1,2,2a$^1$-triazabenzo[cd]azulen-4-yl)pyrimidin-2-amine (R) I-90: $^1$H NMR (400 MHz, DMSO-d6) δ 9.55 (s, 1H), 8.60 (d, J=5.2 Hz, 1H), 8.30 (d, J=1.5 Hz, 1H), 7.67 (d, J=5.3 Hz, 1H), 7.40 (d, J=2.0 Hz, 1H), 7.35-7.26 (m, 2H), 7.13 (d, J=8.6 Hz, 3H), 6.98 (t, J=7.4 Hz, 1H), 6.35-6.26 (m, 2H), 4.86 (ddd, J=11.6, 6.5, 4.5 Hz, 1H), 4.63 (ddd, J=12.0, 6.7, 4.3 Hz, 1H), 3.71 (s, 3H), 2.73 (dq, J=9.1, 4.8 Hz, 2H); MS: m/z 440.

N-(1-methyl-1H-pyrazol-5-yl)-4-(9-phenoxy-8,9-dihydro-7H-6-oxa-1,2,2a$^1$-triazabenzo[cd]azulen-4-yl)pyridin-2-amine was prepared analogously except in step 4-(2-fluoro-6-hydrazino-4-pyridyl)-N-(2-methylpyrazol-3-yl)pyrimidin-2-amine was replaced with 2'-fluoro-6'-hydrazinyl-N-(1-methyl-1H-pyrazol-5-yl)-[4,4'-bipyridin]-2-amine and the racemic product resolved by SFC on a chiral column by chiral separation.

(S)—N-(1-methyl-1H-pyrazol-5-yl)-4-(9-phenoxy-8,9-dihydro-7H-6-oxa-1,2,2a$^1$-triazabenzo[cd]azulen-4-yl)pyridin-2-amine: $^1$H NMR (400 MHz, DMSO-d6) δ 8.86 (s, 1H), 8.22 (d, J=5.3 Hz, 1H), 7.84 (t, J=1.5 Hz, 1H), 7.38-7.19 (m, 4H), 7.17-7.08 (m, 3H), 6.98 (t, J=7.3 Hz, 1H), 6.78 (t, J=1.6 Hz, 1H), 6.35-6.26 (m, 2H), 4.86 (dt, J=11.8, 5.5 Hz, 1H), 4.63 (dt, J=11.7, 5.5 Hz, 1H), 3.69 (d, J=1.6 Hz, 3H), 2.73 (dt, J=6.9, 4.3 Hz, 2H); MS: m/z 439.

(R)—N-(1-methyl-1H-pyrazol-5-yl)-4-(9-phenoxy-8,9-dihydro-7H-6-oxa-1,2,2a$^1$-triazabenzo[cd]azulen-4-yl)pyridin-2-amine: $^1$H NMR (400 MHz, DMSO-d6) δ 8.86 (s, 1H), 8.22 (dd, J=5.3, 1.6 Hz, 1H), 7.84 (t, J=1.7 Hz, 1H), 7.38-7.19 (m, 4H), 7.17-7.08 (m, 3H), 6.98 (t, J=7.3 Hz, 1H), 6.78 (t, J=1.6 Hz, 1H), 6.35-6.26 (m, 2H), 4.92-4.81 (m, 1H), 4.69-4.58 (m, 1H), 3.69 (d, J=1.6 Hz, 3H), 2.80-2.68 (m, 2H): MS m/z 439.

Biological Example 1

ERK-2 Enzymatic Assay

Compounds were tested in an enzymatic assay using human ERK-2 (Mitogen Activated Kinase 1), recombinantly expressed as an n-terminal 6-His fusion protein in *E. coli* and corresponding to aa 8-360. The substrate used was the fluorescent Omnia peptide S/T17 (Invitrogen of Carlsbad, Calif.; Cat. KNZ1171C). Test compounds were diluted in DMSO in 3-fold serial dilutions at 100× final concentrations. In addition to compound, the assay contained 50 mM HEPES [pH 7.3], 10 mM $MgCl_2$, 2 mM DTT, 0.005% Triton-X100, 5 nM ERK-2 enzyme, 6.25 µM S/T17 peptide substrate and 25 µM ATP (corresponding to the observed $K_m$) for a total reaction volume of 25 µL. The assay was run at ambient temperature in a white 384-well polypropylene plate (Nunc, Inc of Naperville, Ill.; Cat. 267462) collecting data every 50 seconds for approximately 30 minutes on an Envision plate reader (PerkinElmer, Inc. of Waltham, Mass.); Excitation 340 nm/Emission 495 nm. The data collected from each well was fit to a straight line, and the resulting rates were used to calculate percent of control.

Percent of control was plotted against compound concentration, and IC$_{50}$ values were determined using a four-parameter fit. Table 1 contains representative data for compounds disclosed herein. Representative data is in TABLE 1 (supra).

Biological Example 2

Cellular P90RSK(Ser380) Phosphorylation Assay

Inhibition of PMA-stimulated P90RSK(Ser380) phosphorylation was determined by the following in vitro cellular mechanistic assay, which comprises incubating cells with a compound for 1.5 hours and quantifying fluorescent pP90RSK(Ser380) signal on fixed cells and normalizing to GAPDH signal.

Materials and Methods: HepG2 cells were obtained from ATCC and grown in DMEM supplemented with 10% fetal bovine serum. Cells were plated in 96-well plates at 35,000 cells/well and allowed to attach overnight at 37° C./5% CO$_2$. Diluted compounds were then added at a final concentration of 0.5% DMSO. After 1.5 hour compound incubation, cells were stimulated with the addition of PMA (phorbol 12-myristate 13-acetate) at a final concentration of 100 ng/mL; the PMA stimulation was a 30-minute incubation at 37° C./5% CO$_2$. After the 30-minute PMA stimulation, cells were washed with PBS and fixed in 3.7% formaldehyde in PBS at room temperature for 15-20 minutes. This was followed by another wash in PBS and then permeabilization in 100% MeOH at room temperature for 10-15 minutes. Following the permeabilization incubation, cells were washed in PBS/0.05% Tween-20, followed by a block in Odyssey blocking buffer (LI-COR Biosciences) for at least 1 hour. Antibodies to phosphorylated P90RSK(Ser380) (Cell Signaling #9335, rabbit monoclonal) and GAPDH (Fitzgerald 10R-G109a, mouse monoclonal) were added to the cells and incubated overnight at 4° C. pP90RSK(Ser380) antibody was used at a 1:250 dilution; GAPDH was used at a 1:10,000 dilution. After washing with PBS/0.05% Tween-20, the cells were incubated with fluorescently-labeled secondary antibodies (Anti-rabbit-Alexa Flour680, Invitrogen Cat #A21109; Anti-mouse-IRDye800CW, Rockland Inc. Cat #610-131-121) for 1 hour. Both secondary antibodies were used at a 1:1000 dilution. Cells were then washed and analyzed for fluorescence at both wavelengths using the Odyssey Infrared Imaging System (LI-COR Biosciences). Phosphorylated P90RSK(Ser380) signal was normalized to GAPDH signal. Representative date is in TABLE II (infra).

TABLE II

| Compound | P-P90RSK (S380) IC$_{50}$ (μM) | Compound | P-P90RSK (S380) IC$_{50}$ (μM) |
| --- | --- | --- | --- |
| (S)-I-7 | 0.00387 | (S) I-36 | 0.00245 |
| (S) I-21 | 0.00432 | (R) I-48 | 0.00173 |
| (R) I-15 | 0.00291 | (R) I-66 | 0.001 |
| (S) I-22 | 0.00141 | (R) I-73 | 0.00447 |
| I-28 | 0.00505 | (S) I-29 | 0.00794 |

Formulation Example 1

Pharmaceutical compositions of the subject Compounds for administration via several routes were prepared as described in this Example.

Composition for Oral Administration (A)

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each.

Composition for Oral Administration (B)

| Ingredient | % wt./wt. |
| --- | --- |
| Active ingredient | 20.0% |
| Magnesium stearate | 0.5% |
| Croscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration (C)

| Ingredient | % wt./wt. |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 mL |
| Colorings | 0.5 mg |
| Distilled water | q.s. to 100 mL |

The ingredients are mixed to form a suspension for oral administration.

Parenteral Formulation (D)

| Ingredient | % wt./wt. |
| --- | --- |
| Active ingredient | 0.25 g |
| Sodium Chloride | qs to make isotonic |
| Water for injection to | 100 mL |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation (E)

| Ingredient | % wt./wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation (F)

| Ingredients | grams |
|---|---|
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually.

We claim:
1. A compound of formula I:

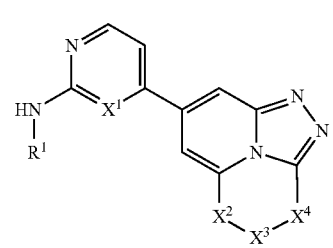

or a pharmaceutically acceptable salt thereof;
wherein
$X^1$ is N or CH;
$X^2$ is $NR^a$;
$X^3$ is C(=O);
$X^4$ is $NR^3$;
$R^1$ is (i) a 4 to 7 membered saturated or partially unsaturated heterocyclyl containing an oxygen atom; or, (ii) a heteroaryl selected from the group consisting of 1-methyl-H-pyrazol-4-yl, 1-methyl-1H-pyrazol-3-yl, 2-ethyl-2H-pyrazol-3-yl, 2-methyl-2H-pyrazol-3-yl, 2-isopropyl-2H-pyrazol-3-yl, 1-methyl-1H-pyrazol-5-yl, 1-ethyl-1H-pyrazol-5-yl, 4-methylthiazol-2-yl, 1-methyl-1H-[1,2,4]triazol-3-yl, 2-methyl-2H-[1,2,3]-triazol-4-yl, 1-methyl-H-[1,2,4]-triazol-5-yl, 1,3-dimethyl-1H-pyrazol-4-yl, 1,3,5-trimethyl-1H-pyrazol-4-yl, 1-methyl-1H-tetrazol-5-yl, 2-methyl-2H-tetrazol-5-yl, 5-methyl-1,3,4-thiadizol-2-yl, oxetan-3-yl, 3-methyloxetan-3-yl, tetrahydropyran-4-yl, tetrahydro-2H-pyran-4-yl, tetrahydropyran-3-yl, 2-methyl-tetrahydropyran-4-yl, 2,2-dimethyl-tetrahydropyran-4-yl, 2-hydroxymethyltetrahydropyran-4-yl, 3-fluorotetrahydropyran-4-yl and tetrahydrofuran-3-yl;
$R^a$ is hydrogen or $C_{1-3}$ alkyl; and
$R^3$ is benzyl, optionally substituted with one or more groups selected from fluoro, chloro, cyclopropyl, $C_{1-3}$ alkoxy, and $C_{1-3}$ alkyl.

2. The compound according to claim 1 selected from:
3-benzyl-5-methyl-7-(2-((1-methyl-1H-pyrazol-5-yl)amino)pyrimidin-4-yl)-3H-1,2,2a¹,3,5-pentaazaacenaphthylen-4(5H)-one;
3-(4-chlorobenzyl)-5-methyl-7-(2-((1-methyl-1H-pyrazol-5-yl)amino)pyrimidin-4-yl)-3H-1,2,2a¹,3,5-pentaazaacenaphthylen-4(5H)-one;
3-(3,5-difluorobenzyl)-5-methyl-7-(2-((1-methyl-1H-pyrazol-5-yl)amino)pyrimidin-4-yl)-3H-1,2,2a¹,3,5-pentaazaacenaphthylen-4(5H)-one; and
3-(3-chlorobenzyl)-5-methyl-7-(2-((1-methyl-1H-pyrazol-5-yl)amino)pyrimidin-4-yl)-3H-1,2,2a¹,3,5-pentaazaacenaphthylen-4(5H)-one.

3. The compound of claim 1 wherein $R^1$ is selected from the group consisting of 1-methyl-1H-pyrazol-4-yl, 1-methyl-1H-pyrazol-3-yl, 2-ethyl-2H-pyrazol-3-yl, 2-methyl-2H-pyrazol-3-yl, 2-isopropyl-2H-pyrazol-3-yl, 1-methyl-1H-pyrazol-5-yl, 1-ethyl-H-pyrazol-5-yl, 1,3-dimethyl-1H-pyrazol-4-yl, and 1,3,5-trimethyl-1H-pyrazol-4-yl.

4. The compound of claim 3 wherein $R^1$ is 1-methyl-H-pyrazol-5-yl.

5. The compound of claim 1 wherein $R^a$ is methyl.

6. The compound of claim 1 wherein $R^3$ is selected from the group consisting of benzyl, 3-chlorobenzyl, 4-chlorobenzyl, and 3,5-difluorobenzyl.

7. A pharmaceutical composition comprising a compound according to claim 1, or a pharmaceutically acceptable salt thereof, and at least one pharmaceutically acceptable excipient.

8. A method of treating or ameliorating the severity of a hyperproliferative disorder in a patient in need thereof comprising administering to said patient a compound according to claim 1, or a pharmaceutically acceptable salt thereof, wherein said hyperproliferative disorder is selected from the group consisting of adenoma, bladder cancer, brain cancer, breast cancer, colon cancer, epidermal carcinoma, follicular carcinoma, cancer of the genitourinary tract, glioblastoma, Hodgkin's disease, head and neck cancers, hepatoma, keratoacanthoma, kidney cancer, large cell carcinoma, leukemias, lung adenocarcinoma, lung cancer, lymphoid disorders, melanoma and non-melanoma skin cancer, myelodysplastic syndrome, neuroblastoma, non-Hodgkins lymphoma, ovarian cancer, papillary carcinoma, pancreatic cancer, prostate cancer, rectal cancer, sarcoma, small cell carcinoma, testicular cancer, tetracarcinomas, thyroid cancer, and undifferentiated carcinoma.

9. The method according to claim 8 wherein said hyperproliferative disorder is selected from the group consisting of melanoma, pancreatic cancer, thyroid cancer, colorectal cancer, lung cancer, breast cancer and ovarian cancer.

10. The method according to claim 8 wherein said hyperproliferative disorder is selected from the group consisting of acute myelogenous leukemia, chronic myelomonocytic leukemia, chronic myelogenous leukemia, multiple myeloma and myeloid leukemia.

11. The method according to claim 8 wherein the compound, or a-pharmaceutically acceptable salt thereof, is co-administered with at least one other chemotherapeutic agent used to treat or ameliorate a hyperproliferative disorder; wherein the chemotherapeutic agent is selected from the group consisting of erlotinib, bortezomib, fulvestrant, sunitinib, letrozole, imatinib mesylate, vatalanib, oxaliplatin, 5-fluorouracil, leucovorin, rapamycin, lapatinib, lonafarnib, sorafenib, gefitinib, AG1478, thiotepa, cyclophosphamide, busulfan, improsulfan, piposulfan, benzodepa, carboquone, meturedepa, uredepa, altretamine, triethylenemelamine, triethylenephosphoramide, triethylenethiophosphoramide, bullatacin, bullatacinone, camptothecin, topotecan, bryostatin, callystatin, CC-1065, adozelesin, carzelesin, bizelesin, cryptophycin 1, cryptophycin 8, dolastatin, duocarmycin, KW-2189, eleutherobin, pancratistatin, sarcodictyin, spongistatin, chlorambucil, chlornaphazine, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, calicheamicin yl, dynemicin A, clodronate, esperamicin, neocarzinostatin chromophore, aclacinomycin, actinomycin, anthramycin, azaserine, bleomycin, carubicin, carzinophilin, chromomycin, dactinomycin, daunorubicin, detorubicin, 6-diazo-5-oxo-L-norleucine, doxorubicin, morpholino-doxorubicin, cyanomorpholino-doxorubicin, 2-pyrrolino-doxorubicin, deoxydoxorubicin, epirubicin, esorubicin, idarubicin, marcellomycin, mitomycin C, mycophenolic acid, nogalamycin, olivomycin, peplomycin, porfiromycin, puromycin, quelamycin, rodorubicin, streptonigrin, streptozocin, tubercidin, ubenimex, zinostatin, zorubicin, methotrexate, denopterin, pteropterin, trimetrexate, fludarabine, 6-mercaptopurine, thiamiprine-ancitabine, azacitidine, 6-azauridine, carmofur, cytarabine, dideoxyuridine, doxifluridine, enocitabine, floxuridine, calusterone, dromostanolone propionate, epitiostanol, mepitiostane, testolactone, aminoglutethimide, mitotane, trilostane, folinic acid, aceglatone, aldophosphamide glycoside, aminolevulinic acid, eniluracil, amsacrine, bestrabucil, bisantrene, edatrexate, demecolcine, diaziquone, elfornithine, elliptinium acetate, epothilone, etoglucid, gallium nitrate, hydroxyurea, lentinan, lonidamine, maytansine, ansamitocin, mitoguazone, mitoxantrone, nitracrine, pentostatin, phenamet, pirarubicin, losoxantrone, podophyllinic acid, 2-ethylhydrazide, procarbazine, razoxane, rhizoxin, sizofuran, spirogermanium, tenuazonic acid, triaziquone, 2,2',2"-trichlorotriethylamine, T-2 toxin, roridin A, anguidine, urethane, vindesine, dacarbazine, mannomustine, mitobronitol, mitolactol, pipobroman, paclitaxel, docetaxel, gemcitabine, 6-thioguanine, cisplatin, carboplatin, vinblastine, etoposide, vincristine, vinorelbine, novantrone, teniposide, daunomycin, aminopterin, capecitabine, ibandronate, CPT-11, difluoromethylornithine, retinoic acid, tamoxifen, raloxifene, droloxifene, 4-hydroxytamoxifen, trioxifene, LY117018, onapristone, toremifene citrate, megestrol acetate, exemestane, formestane, fadrozole, vorozole, letrozole, anastrozole, flutamide, nilutamide, bicalutamide, leuprolide, goserelin, troxacitabine, and bevacizumab; or a pharmaceutically acceptable salt thereof.

* * * * *